US011319298B2

(12) United States Patent
Bao et al.

(10) Patent No.: US 11,319,298 B2
(45) Date of Patent: May 3, 2022

(54) HETEROARYL PIPERIDINE ETHER ALLOSTERIC MODULATORS OF THE M4 MUSCARINIC ACETYLCHOLINE RECEPTOR

(71) Applicants: Merck Sharp & Dohme Corp., Rahway, NJ (US); MSD R&D (China) Co., Ltd., Shanghai (CN)

(72) Inventors: Jianming Bao, San Mateo, CA (US); Ronald Ferguson, Scotch Plains, NJ (US); Xiaolei Gao, Bridgewater, NJ (US); Scott Harrison, Elkins Park, PA (US); Sandra L. Knowles, Princeton, NJ (US); Michael Man-Chu Lo, Bedminster, NJ (US); Robert D. Mazzola, Jr., Stewartsville, NJ (US); Jeffrey W. Shubert, North Wales, PA (US)

(73) Assignees: Merck Sharp & Dohme Corp., Rahway, NJ (US); MSD R&D (China) Co., Ltd., Shanghai (CN)

(*) Notice: Subject to any disclaimer, the term of this patent is extended or adjusted under 35 U.S.C. 154(b) by 0 days.

(21) Appl. No.: 16/471,679

(22) PCT Filed: Dec. 18, 2017

(86) PCT No.: PCT/US2017/066917
§ 371 (c)(1),
(2) Date: Jun. 20, 2019

(87) PCT Pub. No.: WO2018/118734
PCT Pub. Date: Jun. 28, 2018

(65) Prior Publication Data
US 2019/0315708 A1 Oct. 17, 2019

(30) Foreign Application Priority Data
Dec. 22, 2016 (WO) ................ PCT/CN2016/111530

(51) Int. Cl.
*C07D 401/02* (2006.01)
*C07D 401/04* (2006.01)
*C07D 401/14* (2006.01)
*C07D 405/14* (2006.01)
*C07D 413/14* (2006.01)
*C07D 417/14* (2006.01)
*C07D 491/107* (2006.01)
*C07D 498/08* (2006.01)
*C07D 513/04* (2006.01)

(52) U.S. Cl.
CPC ......... *C07D 401/04* (2013.01); *C07D 401/14* (2013.01); *C07D 405/14* (2013.01); *C07D 413/14* (2013.01); *C07D 417/14* (2013.01); *C07D 491/107* (2013.01); *C07D 498/08* (2013.01); *C07D 513/04* (2013.01)

(58) Field of Classification Search
CPC ................................................... C07D 401/02
See application file for complete search history.

(56) References Cited

U.S. PATENT DOCUMENTS

| 5,574,044 | A | 11/1996 | Thompson et al. |
| 5,691,323 | A | 11/1997 | Thompson et al. |
| 6,699,880 | B1 | 3/2004 | Yamakawa et al. |
| 6,900,224 | B2 | 5/2005 | Ledoussal et al. |
| 7,074,801 | B1 | 7/2006 | Yoshida et al. |
| 7,858,635 | B2 | 12/2010 | Makings et al. |
| 7,964,602 | B2 | 6/2011 | MacDonald et al. |
| 7,994,094 | B2 | 8/2011 | Endo |
| 8,071,776 | B2 | 12/2011 | Rubio Esteban et al. |
| 8,168,639 | B2 | 5/2012 | Kogan |
| 8,349,850 | B2 | 1/2013 | Tworowski et al. |
| 8,614,319 | B2 | 12/2013 | Tworowski et al. |
| 9,034,872 | B2 | 5/2015 | Tworowski et al. |
| 9,056,875 | B2 | 6/2015 | Lindsley et al. |
| 9,056,876 | B2 | 6/2015 | Conn et al. |
| 9,493,481 | B2 | 11/2016 | Lindsley et al. |
| 9,593,106 | B2 | 3/2017 | Livermore et al. |
| 9,637,498 | B2 | 5/2017 | Lindsley et al. |

(Continued)

FOREIGN PATENT DOCUMENTS

| EP | 1932844 A1 | 6/2008 |
| JP | 2013237634 | 11/2013 |

(Continued)

OTHER PUBLICATIONS

American Chemical Society Chemical Abstract Service. RN 1643120-01-7. Entered into STN/first public availability date: Jan. 15, 2015. (Year: 2015).*

(Continued)

*Primary Examiner* — John S Kenyon
(74) *Attorney, Agent, or Firm* — Eric A. Meade; John C. Todaro

(57) ABSTRACT

The present invention is directed to heteroarylpiperidine ether compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

20 Claims, No Drawings

(56) References Cited

U.S. PATENT DOCUMENTS

| | | |
|---|---|---|
| 9,670,183 B2 | 6/2017 | Brown et al. |
| 9,758,506 B2 | 9/2017 | Brown et al. |
| 9,868,746 B2 | 1/2018 | Lindsley et al. |
| 10,329,289 B2 | 6/2019 | Bao et al. |
| 10,351,564 B2 | 7/2019 | Gao et al. |
| 10,512,638 B2 | 12/2019 | Rudd et al. |
| 2007/0004763 A1 | 1/2007 | Baindur et al. |
| 2008/0306107 A1 | 12/2008 | Griffin et al. |
| 2009/0247584 A1 | 10/2009 | Holzemann et al. |
| 2016/0200733 A1 | 7/2016 | Lindsley et al. |
| 2017/0096437 A1 | 4/2017 | Congreve et al. |
| 2017/0369505 A1 | 12/2017 | Lindsley et al. |

FOREIGN PATENT DOCUMENTS

| | | | |
|---|---|---|---|
| JP | 2014047192 | 3/2014 | |
| JP | 2014062063 | 4/2014 | |
| WO | 1998006697 A1 | 2/1998 | |
| WO | 1999032481 A1 | 7/1999 | |
| WO | 2005100351 A1 | 10/2005 | |
| WO | 2006125180 A1 | 11/2006 | |
| WO | 2006135649 A2 | 12/2006 | |
| WO | 2007040280 A1 | 4/2007 | |
| WO | 2007045462 A2 | 4/2007 | |
| WO | 2007065669 A1 | 6/2007 | |
| WO | 2008026658 A1 | 3/2008 | |
| WO | WO-2008076779 A2 * | 6/2008 | ........... C07D 401/12 |
| WO | 2008132502 A1 | 11/2008 | |
| WO | WO-2008132502 A1 * | 11/2008 | .............. A61P 35/00 |
| WO | 2011087776 A1 | 7/2011 | |
| WO | 2012020813 A1 | 2/2012 | |
| WO | 2012154731 A1 | 11/2012 | |
| WO | 2013056015 A1 | 4/2013 | |
| WO | 2013122107 A1 | 8/2013 | |
| WO | 2014035829 A1 | 3/2014 | |
| WO | 2014101373 A1 | 7/2014 | |
| WO | 2014122474 A1 | 8/2014 | |
| WO | 2015027214 A1 | 2/2015 | |
| WO | 2015090232 A1 | 6/2015 | |
| WO | 2016147011 A1 | 9/2016 | |
| WO | 2017021728 A1 | 2/2017 | |
| WO | 2017077292 A1 | 5/2017 | |
| WO | 2017107087 A1 | 6/2017 | |
| WO | 2017112556 A1 | 6/2017 | |
| WO | 2017112719 A1 | 6/2017 | |

OTHER PUBLICATIONS

American Chemical Society. Chemical Abstract Service. RN 1643120-00-6. Entered into STN/first made available to the public on Jan. 15, 2015. (Year: 2015).*

Bewley, Blake R., et al., Discovery of a novel, CNS penetrant M4PAM chemotype based on a 6-fluoro-4-(piperiden-1-yl)quinoline-3-carbonitrile core, Bioorganic and Med Chem Letters, 2017, 4274-4279, 27.

Byun, Nellie B, et al., Antipsychotic Drug-like Effects of the Selective M4 Muscarinic Acetylcholine Receptor Positive Allosteric Modulator VU02552100, Neuropsychopharmacology, 2014, 1578-1593, 39.

Eglen, Richard M., Muscarinic receptor ligands and their therapeutic potential, Current Opinion in Chemical Biology, 1999, 426-432, 3.

Kargbo, Robert B., Allosteric Modulators of the M4 Muuscarinic Acetylcholine Receptor, ACS Medicinal Chemistry Letters, 2017, 903-904, 8.

Lindsley, Craig W., et al., Discovery of the mAChR subtype selective M4 positive allosteric modulators, Current Topics in Medicinal Chemistry, 2008, 531, 8-6.

Long, Madeline F., Discovery of a nove 2,4-dimethylquinoline-6-carboxamide M4 positive allosteric modulator (PAM) Chemotype via scaffold hopping, Bioorganic and Med Chem Letters, 2017, 4999-5001, 27.

Melancon, Bruce J., et al., Optimization of M4 Positive Allosteric Modulators (PAMs): The discovery of VUO476406, a non-human primate in vivo tool compound for translational pharmacology, Bioorganic and Med Chem Letters, 2017, 2296-2301, 27.

Salovich, James M., et al., Discovery of N-(4-methoxy-7-methylbenzo[d]thiazol-2-yl) . . . , Bioorganic and Med Chem Letters, 2012, 5084-5088, 22.

Tarr, James C., Challenges in the development of an M4PAM preclinical candidate: The discovery, SAR and in vivo characterization of a . . . , Bioorganic and Med Chem Letters, 2017, 2990-2995, 27.

Tarr, James C., et al., Challenges in the development of an M4PAM Preclinical candidate: . . . , Bioorganic and Med Chem Letters, 2017, 5179-5184, 27.

Utley, Thomas, Synthesis and SAR of a novel metabotropic glutamate receptor 4 . . . , Bioorganic and Med Chem Letters, 2011, 6955-6959, 21.

Wood, Michael R., et al., Discovery and Optimization of a novel series of highly CNS penetrant M4PAMS based on a 5,6-dimethul-4-(piperidin-1-yl)thieno[2,3-d]pyrimidine core, Bioorganic and Med Chem Letters, 2016, 3029-3033, 26.

Wood, Michael R., et al., Discovery of VU0467485/AZ13713945: An M4PAM evaluated as a Preclinical candidate for the Treatment of Schizophrenia, ACS Medicinal Chemistry Letters, 2017, 233-238, 8.

PCT Search Report and Written Opinion for PCT/US2017/066917 dated Apr. 16, 2018; 9 pages.

European Search Report, Application EP178845533, dated Apr. 17, 2020, 6 pages.

Kim, MS et al., 2-(3-Fluoro-4-methylsulfonylaminophenyl) Propanamides as Potent Transient Receptor Potential Vanilloid 1 (TRPV1) Antagonists: Structure Activity Relationships of 2-Amino Derivatives in the N-(6-trifluoromethyl-pyridin-3-ylmethyl) C-region, J Med Chem, 2012, 8392-8408, 55(19).

* cited by examiner

HETEROARYL PIPERIDINE ETHER ALLOSTERIC MODULATORS OF THE M4 MUSCARINIC ACETYLCHOLINE RECEPTOR

CROSS REFERENCE TO RELATED APPLICATIONS

This application is a U.S. National Phase application under 35 U.S.C. § 371 of PCT Application No. PCT/US2017/066917, filed Dec. 18, 2017, which claims priority under 35 U.S.C. § 119(e) from PCT/CN2016/111530, filed Dec. 22, 2016.

BACKGROUND OF THE INVENTION

Acetylcholine (ACh) is a key neurotransmitter that modulates neuronal function in the peripheral nervous system (PNS) and central nervous system (CNS). ACh mediates its actions via two families of receptors, termed the muscarinic ACh receptors (mAChRs) and the nicotinic ACh receptors (nAChRs). A large body of evidence suggests that basal forebrain cholinergic neurons and basalo-cortical cholinergic pathways are selectively vulnerable to degeneration in Alzheimer's disease. It has therefore been hypothesized that cholinergic hypofunction contributes to the cognitive deficits of patients suffering from Alzheimer's disease. Consequently, acetylcholinesterase inhibitors, which inhibit ACh hydrolysis and potentiate cholinergic signaling have been demonstrated to not only provide improvements in cognitive symptoms associated with Alzheimer's disease, but also show efficacy in treating the psychiatric symptoms. Acetylcholinesterase inhibitors, however, have not been shown to change the underlying disease pathology.

Another potential pharmacotherapeutic target to counteract cholinergic hypofunction is the activation of muscarinic acetylcholine receptors (mAChRs). Muscarinic acetylcholine receptors are members of the G protein-coupled receptor superfamily which mediate the actions of the neurotransmitter acetylcholine in both the central and peripheral nervous system. Muscarinic acetylcholine receptors are prevalent throughout the body and five distinct muscarinic receptors (M1-M5) have been identified in mammals. The muscarinic receptors are known to contain one or more allosteric sites which may alter the affinity with which muscarinic ligands bind to the primary binding or orthosteric sites. In the central nervous system, muscarinic receptors are involved in cognitive, behavior, sensory, motor and autonomic functions. The M4 muscarinic acetylcholine receptor is predominantly expressed in the striatum, but also in the hippocampus and cortex.

Muscarinic receptors in the central nervous system play a critical role in mediating higher cognitive processing and control of dopamine release. Administration of nonselective muscarinic antagonists can induce cognitive deficits and psychosis in humans suggesting that mAChR activation may provide pro-cognitive and antipsychotic efficacy. Accordingly, several mAChR agonists have been developed and entered clinical studies for the treatment of cognitive and psychiatric symptoms associated with Alzheimer's and neuropsychiatric diseases such as schizophrenia. (Carruthers, Neuroscience & Biobehavioral Rev., 2015, 55: 393-402; Jones, et al. Neuropsychopharmacology, 2012, 37: 16-42).

One of these, the M1/M4 preferring mAChR agonist xanomeline was assessed in patients with Alzheimer's disease, and while showing a trend for improving cognitive deficits, did produce robust and dose-dependent reductions in hallucinations, delusions, vocal outbursts, and other behavioral disturbances in these patients. A subsequent study in patients with schizophrenia demonstrated that xanomeline produced robust improvements in positive, negative and cognitive symptoms. (Bodick, et al., Arch Neurol. 1997; 54: 465-73). Xanomeline, in addition to other mAChR agonists have been demonstrated to produce robust antipsychotic-like effects in a number of preclinical paradigms. For instance, xanomeline, reverses a number of dopamine driven behaviors, including amphetamine induced locomotion in rats, apomorphine induced climbing in mice, dopamine agonist driven turning in unilateral 6-OH-DA lesioned rats and amphetamine induced motor unrest in monkeys (without EPS liability). It also has been shown to inhibit A10, but not A9, dopamine cell firing and conditioned avoidance and induces c-fos expression in prefrontal cortex and nucleus accumbens, but not in striatum in rats. These data are all suggestive of an atypical antipsychotic-like profile. Subsequent studies with M4 knockout mice have demonstrated that the antipsychotic-like effects of xanomeline are mediated by the M4 receptor. Despite these promising clinical and preclinical effects, xanomeline, like other muscarinic agonists, ultimately failed in clinical development due to lack of adequate receptor subtype selectivity resulting in dose-limiting side effects including disturbed gastrointestinal motility, bradycardia, nausea and vomiting.

The development of selective M4 positive allosteric modulators (PAMs) is a strategy to overcome the challenges of developing selective orthosteric muscarinic agonists. Indeed, studies with M4 PAMs have shown that selective activation of M4 mAChRs can reverse both hyperdopaminergic and hypoglutamatergic behaviors in preclinical models. Accordingly, the compounds of the present invention, which are allosteric modulators of the M4 muscarinic acetylcholine receptor, are believed to be useful in the treatment of Alzheimer's disease and other diseases mediated by the muscarinic M4 muscarinic acetylcholine receptor.

SUMMARY OF THE INVENTION

The present invention is directed to heteroarylpiperidine ether compounds which are allosteric modulators of the M4 muscarinic acetylcholine receptor. The present invention is also directed to uses of the compounds described herein in the potential treatment or prevention of neurological and psychiatric disorders and diseases in which M4 muscarinic acetylcholine receptors are involved. The present invention is also directed to compositions comprising these compounds. The present invention is also directed to uses of these compositions in the potential prevention or treatment of such diseases in which M4 muscarinic acetylcholine receptors are involved.

DETAILED DESCRIPTION OF THE INVENTION

The present invention is directed to compounds of the formula I:

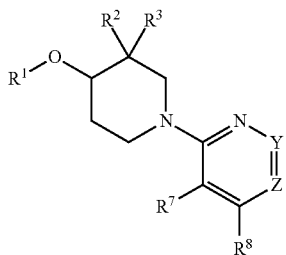

wherein:

Y is selected from the group consisting of:
(1) N, and
(2) (CR$^{11}$);

Z is selected from the group consisting of:
(1) N, and
(2) (CR$^{10}$), with the proviso that if Y is N, then Z is (CR$^{10}$);

R$^1$ is selected from the group consisting of:
(1) —C$_{1-6}$alkyl, which is unsubstituted or substituted with substituents selected from the group consisting of: hydroxy, fluoro, —CN, —O—C$_{1-6}$alkyl, and C$_{3-6}$cycloalkyl, wherein the C$_{1-6}$alkyl or C$_{3-6}$cycloalkyl is unsubstituted or substituted with substituents selected from the group consisting of: fluoro, cyano, CF$_3$, or —O—C$_{1-6}$alkyl;
(2) a phenyl, heteroaryl or heterocyclyl ring, wherein the phenyl, heteroaryl or heterocyclyl ring is substituted with one or more R$^{1a}$, R$^{1b}$ and R$^{1c}$, wherein R$^{1a}$, R$^{1b}$ and R$^{1c}$ are independently selected from the group consisting of:
(a) hydrogen,
(b) halogen,
(c) C$_{1-6}$alkyl, which is unsubstituted or substituted with substituents selected from the group consisting of: hydroxyl, fluoro and —NH$_2$,
(d) —O—C$_{1-6}$alkyl, which is unsubstituted or substituted with substituents selected from the group consisting of: fluoro and —NH$_2$,
(e) C$_{3-6}$cycloalkyl,
(f) —SO$_2$—C$_{1-6}$ alkyl, and
(g) —CN;

R$^2$ and R$^3$ are independently selected from the group consisting of:
(1) hydrogen, and
(2) fluoro;

R$^7$ is selected from the group consisting of:
(1) halogen,
(2) C$_{1-6}$alkyl, which is unsubstituted or substituted with hydroxy, methoxy, fluoro or —(C=O)O—C$_{1-6}$alkyl,
(3) —CN, and
(4) —(C=O)O—C$_{1-6}$ alkyl;

R$^8$ is selected from the group consisting of:
(1) hydrogen,
(2) halogen,
(3) —C$_{1-6}$alkyl, which is unsubstituted or substituted with substituents selected from the group consisting of: hydroxy, methoxy, fluoro, —C(C=O)O—C$_{1-6}$alkyl, —NH$_2$, —NH(C$_{1-6}$ alkyl), —N(C$_{1-6}$alkyl)$_2$, —C(C=O)NH$_2$, —C(C=O)OH, oxetanyl, phenyl, or pyridyl,
(4) —C$_{2-4}$alkenyl,
(5) —C$_{3-6}$cycloalkyl, which is unsubstituted or substituted with fluoro,
(6) a phenyl or heteroaryl ring, wherein the phenyl or heteroaryl ring is independently substituted with one or more R$^{1a}$, R$^{1b}$ and R$^{1c}$,
(7) —NH$_2$, —NH(C$_{1-6}$alkyl), or —N(C$_{1-6}$alkyl)$_2$, which is unsubstituted or substituted with fluoro, hydroxyl or pyridinyl,
(8) azetidinyl, furanyl, oxadiazolyl, pyrrolidinyl, or piperidinyl, which is unsubstituted or substituted with fluoro, or which is fused with oxetanyl, tetrahydrofuranyl, thiazolyl, or pyridinyl, which is unsubstituted or substituted with fluoro, and
(9) —CN;

each of R$^{10}$ and R$^{11}$ is independently selected from the group consisting of:
(1) hydrogen,
(2) halogen,
(3) hydroxy,
(4) —C$_{1-6}$alkyl, which is unsubstituted or substituted with substituents selected from the group consisting of: hydroxy, methoxy, or fluoro,
(5) —C$_{2-4}$ alkenyl,
(6) —O—C$_{1-6}$alkyl, which is unsubstituted or substituted with substituents selected from the group consisting of: methoxy or fluoro,
(7) —C$_{3-6}$cycloalkyl, which is unsubstituted or substituted with fluoro,
(8) —(C=O)O—C$_{1-6}$ alkyl,
(9) —(C=O)NH$_2$,
(10) —(C=O)—NH—C$_{3-6}$cycloalkyl, which is unsubstituted or substituted with phenyl, pyridinyl, fluoro, chloro, —C$_{1-6}$alkyl or —O—C$_{1-6}$alkyl,
(11) —(C=O)—NH—C$_{1-6}$alkyl, which is unsubstituted or substituted with benzodioxolyl, benzofuranyl, bicyclopentyl, imidazolyl, imidazolopyridinyl, indenyl, isothiazolyl, oxoisoindolinyl, oxopyrrolidinyl, phenyl, pyrrolidinonyl, pyrazolyl, pyridyl, pyridinyl, pyridazinyl, pyrimidinyl, tetrahydroquinolinyl, tetrahydroisoquinolinyl, thiadiazolyl, thiazolyl, triazolyl, which is unsubstituted or substituted with fluoro, chloro, —C$_{1-6}$ alkyl, —CF$_3$, —CN, —(SO$_2$)—C$_{1-6}$alkyl, —O—C$_{1-6}$ alkyl, phenyl, or pyridyl;
(12) —(C=O)—NH-heteroaryl or —(C=O)—NH-heterocyclyl, wherein the heteroaryl or heterocyclyl is selected from the group consisting of benzodioxolyl, benzofuranyl, bicyclopentyl, imidazolyl, imidazolopyridinyl, indenyl, isothiazolyl, oxoisoindolinyl, oxopyrrolidinyl, pyrrolidinonyl, pyrazolyl, pyridyl, pyridinyl, pyridazinyl, pyrimidinyl, tetrahydroquinolinyl, tetrahydroisoquinolinyl, thiadiazolyl, thiazolyl, triazolyl, which is unsubstituted or substituted with fluoro, chloro, —C$_{1-6}$alkyl, —CF$_3$, —CN, —(SO$_2$)—C$_{1-6}$alkyl, —O—C$_{1-6}$alkyl, phenyl, or pyridyl;
(13) —(C=O)—NH—O—C$_{1-6}$alkyl,
(14) —(C=O)—NH—NH—C$_{1-6}$alkyl,
(15) pyridyl,
(16) oxadiazolyl,
(17) —NH$_2$,
(18) —NH—C$_{1-6}$alkyl or —N(C$_{1-6}$alkyl)$_2$, which is unsubstituted or substituted with fluoro, hydroxyl, phenyl, or pyridyl,
(19) —CN,
(20) —S—C$_{1-6}$alkyl, and
(21) —(SO$_2$)—C$_{1-6}$alkyl;

or a pharmaceutically acceptable salt thereof.

An embodiment of the present invention includes compounds of the formula Ia:

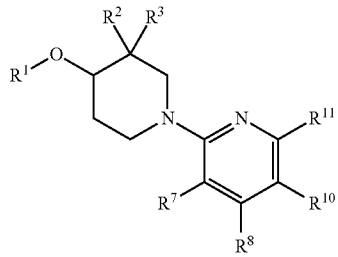

Ia wherein $R^1$, $R^2$, $R^3$, $R^7$, $R^8$, $R^{10}$ and $R^{11}$ are defined herein; or a pharmaceutically acceptable salt thereof.

An embodiment of the present invention includes compounds of the formula Ib:

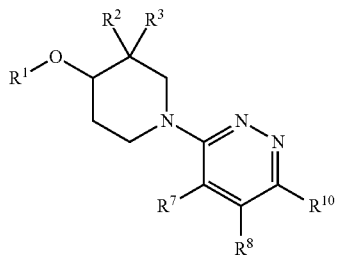

Ib wherein $R^1$, $R^2$, $R^3$, $R^7$, $R^8$ and $R^{10}$ are defined herein; or a pharmaceutically acceptable salt thereof.

An embodiment of the present invention includes compounds of the formula Ic:

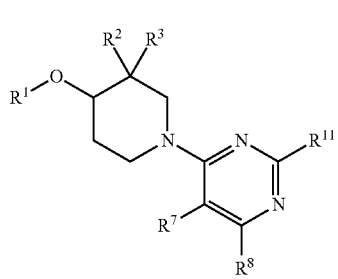

Ic wherein $R^1$, $R^2$, $R^7$, $R^8$, $R^{10}$ and $R^{11}$ are defined herein; or a pharmaceutically acceptable salt thereof.

An embodiment of the present invention includes compounds of the formula I, or a pharmaceutically acceptable salt thereof, wherein the group:

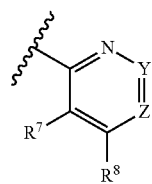

is selected from the group consisting of:

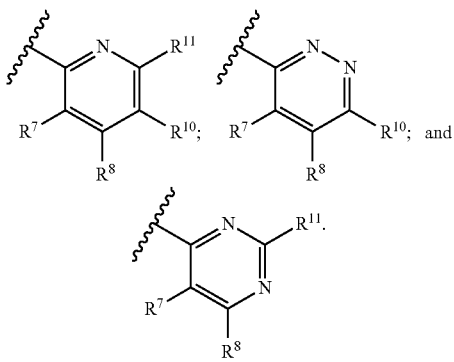

An embodiment of the present invention includes compounds wherein $R^1$ is selected from the group consisting of: benzodioxolyl, benzoimidazolyl, benzoxazolyl, benzooxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with one or more of $R^{1a}$, $R^{1b}$ and $R^{1c}$.

An embodiment of the present invention includes compounds wherein $R^1$ is selected from the group consisting of:
(a) $C_{1-6}$alkyl, which is unsubstituted or substituted with cyclopropyl which is unsubstituted or substituted with substituents selected from the group consisting of: fluoro and $C_{1-6}$alkyl,
(b) phenyl, which is unsubstituted or substituted with $C_{1-3}$alkyl or —CN, and
(c) pyridyl, which is unsubstituted or substituted with $C_{1-3}$alkyl or —O—$C_{1-3}$alkyl.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of:
(a) hydrogen,
(b) hydroxyl,
(c) halogen,
(d) $C_{1-6}$alkyl, which is unsubstituted or substituted with substituents selected from the group consisting of: hydroxy, fluoro, and —$OCH_3$,
(e) —O—$C_{1-6}$alkyl, which is unsubstituted or substituted with substituents selected from the group consisting of: hydroxy, fluoro, and —$OCH_3$,
(f) $C_{3-6}$cycloalkyl, which is unsubstituted or substituted with a substituent selected from the group consisting of: $C_{1-6}$alkyl and hydroxy; and
(g) —CN.

An embodiment of the present invention includes compounds wherein $R^1$ is phenyl or pyridyl, which is substituted with $R^{1a}$, $R^{1b}$ and $R^{1c}$, wherein $R^{1a}$, $R^{1b}$ and $R^{1c}$ are independently selected from the group consisting of
(a) hydrogen,
(b) hydroxyl,
(c) halogen, (d) $C_{1-3}$alkyl, which is unsubstituted or substituted with a substituent selected from the group consisting of: hydroxy, 1-3 fluoro, and —$OCH_3$,
(e) —O—$C_{1-3}$alkyl, which is unsubstituted or substituted with a substituent selected from the group consisting of: 1-3 fluoro, and —$OCH_3$, and
(g) —CN.

An embodiment of the present invention includes compounds wherein $R^1$ is selected from the group consisting of:
(a) phenyl, which is unsubstituted or substituted with $C_{1-3}$alkyl or —CN, and
(b) pyridyl, which is unsubstituted or substituted with $C_{1-3}$alkyl or —O—$C_{1-3}$alkyl.

An embodiment of the present invention includes compounds wherein $R^1$ is phenyl, which is unsubstituted or substituted with —CN. An embodiment of the present invention includes compounds wherein $R^1$ is 3-cyanophenyl. An embodiment of the present invention includes compounds wherein $R^1$ is pyridyl, which is unsubstituted or substituted with —$OCH_3$.

An embodiment of the present invention includes compounds wherein $R^1$ is pyridyl, which is substituted with —$OCH_3$. An embodiment of the present invention includes compounds wherein $R^1$ is 6-methoxypyridin-3-yl.

An embodiment of the present invention includes compounds wherein $R^2$ is fluoro and $R^3$ is hydrogen. An embodiment of the present invention includes compounds wherein $R^2$ is fluoro and $R^3$ is hydrogen. An embodiment of the present invention includes compounds wherein $R^2$ is hydrogen and $R^3$ is hydrogen. An embodiment of the present invention includes compounds wherein $R^2$ is fluoro and $R^3$ is fluoro.

An embodiment of the present invention includes compounds wherein $R^7$ is selected from the group consisting of:
(1) methyl,
(2) ethyl,
(3) —$CHF_2$,
(4) -fluoro,
(5) -chloro,
(6) -bromo,
(7) —CN,
(8) —(C=O)O-methyl, and
(9) —$CH_2$(C=O)O-methyl.

An embodiment of the present invention includes compounds wherein $R^7$ is —$CH_3$. An embodiment of the present invention includes compounds wherein $R^8$ is selected from the group consisting of:
(1) hydrogen,
(2) methyl,
(3) ethyl,
(4) -fluoro, and
(5) -chloro.

An embodiment of the present invention includes compounds wherein $R^8$ is hydrogen. An embodiment of the present invention includes compounds wherein $R^8$ is —$CH_3$.

An embodiment of the present invention includes compounds wherein each of $R^{10}$ and $R^{11}$ is independently selected from the group consisting of:
(1) hydrogen,
(2) fluoro,
(3) chloro,
(4) hydroxy,
(5) —$CH_3$,
(6) —$CF_3$,
(7) —$CH_2OH$,
(8) —$CH_2CH_2OH$,
(9) —$C(CH_3)_2OH$,
(10) —S—$CH_3$,
(11) —$CH_2OCH_3$,
(12) cyclopropyl,
(13) —(C=O)O—$CH_3$,
(14) —(C=O)O—$CH_2CH_3$,
(15) —(C=O)—NH-tetrahydroquinolinyl,
(16) —(C=O)—NH—$CH_2$-pyridyl, and
(17) —(C=O)—NH—$CH_2$-tetrahydroquinolinyl.

An embodiment of the present invention includes compounds wherein each of $R^{10}$ and $R^{11}$ is independently selected from the group consisting of:
(1) hydrogen, and
(2) —$C_{1-6}$alkyl, which is unsubstituted or substituted with hydroxy, methoxy, 1-3 fluoro.

An embodiment of the present invention includes compounds wherein $R^{10}$ is hydrogen. An embodiment of the present invention includes compounds wherein $R^{10}$ is —$CH_3$. An embodiment of the present invention includes compounds wherein $R^{10}$ is —$CH_2OH$.

An embodiment of the present invention includes compounds wherein $R^{11}$ is hydrogen. An embodiment of the present invention includes compounds wherein $R^{11}$ is —$CH_3$. An embodiment of the present invention includes compounds wherein $R^{11}$ is —$CH_2OH$.

Certain embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. Substituents (such as $R^{1a}$, $R^{1b}$ and $R^{1c}$) may be absent if the valency of the group to which they are attached does not permit such substitution. The value of a variable (such as $R^9$) at a particular position is independent of its value at a different position. A group which is designated as being independently substituted with substituents may be independently substituted with multiple numbers of such substituents.

The term "heteroaryl" as used herein represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5-to 14-ring atoms of carbon and from one to four heteroatoms selected from O, N, or S. As with the definition of heterocyclyl below, "heteroaryl" is also understood to include the N-oxide derivative of any nitrogen-containing heteroaryl. In cases where the heteroaryl substituent is bicyclic and one ring is non-aromatic, in one embodiment, the attachment is via a carbon atom of the aromatic ring. Examples of heteroaryl include but are not limited to benzodioxolyl, benzofuranyl, benzofurazanyl, benzoimidazolyl, benzimidazolonyl, benzopyrazolyl, benzothiazolyl, benzotriazolyl, benzothiophenyl, benzoxazepinyl, benzooxazinonyl, benzooxazolonyl, benzoxazolyl, carbazolyl, carbolinyl, chromanyl, cinnolinyl, cyclopentapyridinyl, dihydrobenzo[1,4]dioxinyl, dihydrobenzofuranyl, dihydrobenzo[1,4]oxazinyl, dihydrofuropyridinyl, dihydroindolyl, dihydroisobenzofuranyl, dihydroisoquinolinonyl, dihydropyranopyridinyl, dihydroimidazopyridinyl, dihydropyrido[1,4]oxazinyl, dihydroquinolinone, furanyl, imidazolyl, indolinyl, indolyl, indanyl, indolazinyl, indazolyl, isobenzofuranyl, isobenzofuranonyl, isochromanonyl, isochromanyl, isoindolinyl, isoindolyl, isoxazolinyl, isoxazolyl, isoquinolyl, isothiazolyl, isoxazolyl, naphthpyridinyl, oxadiazolyl, oxazolyl, oxazolinyl, oxetanyl, oxoisoindolinyl, pyrazinyl, pyrazolopyridinyl, pyrazolyl, pyridazinyl, pyridopyridinyl, pyridazinyl, pyridyl, pyrimidinyl, pyrimidyl, pyrrolopyridinyl, pyrrolyl, quinazolinyl, quinolyl, quinoxalinyl, tetrahydrobenzooxepinyl, tetrahydroisoquinolinyl, tetrahydropyranyl, tetrahydroquinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. In one embodiment, the heterocyclyls contain about 5 to about 6 ring atoms. The heterocyclyl may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydropyran, chromenone, tetrahydrothiophenyl, lactam, lactone, and the like. "Heterocyclyl" also includes heterocyclyl rings as described above wherein =O replaces two available hydrogens on the same ring carbon atom.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes that can be incorporated into the compounds of the invention include isotopes of hydrogen such as $^2$H and $^3$H, carbon such as $^{11}$C, $^{13}$C and $^{14}$C, nitrogen such as $^{13}$N and $^{15}$N, oxygen such as $^{15}$O, $^{17}$O and $^{18}$O, phosphorus such as $^{32}$P, sulfur such as $^{35}$S, fluorine such as $^{18}$F, iodine such as $^{123}$I and $^{125}$I, and chlorine such as $^{36}$Cl. Certain isotopically-labelled compounds of Formula I, for example those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}$C isotope. An embodiment of the present invention includes compounds that are substituted with an $^{18}$F isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual enantiomers or diastereomers thereof.

As used herein, the term "M4 muscarinic acetylcholine receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno, et al., *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to augment the response produced by the endogenous ligand at the orthosteric binding site. The compounds of the invention are allosteric modulators of the M4 muscarinic acetylcholine receptor, including as positive allosteric modulators of the M4 muscarinic acetylcholine receptor and silent allosteric modulators of the M4 muscarinic acetylcholine receptor. Some of the compounds of the invention are agonists of the M4 muscarinic acetylcholine receptor. Some of the compounds of the invention are allosteric modulators of the M1 muscarinic acetylcholine receptor, or may be agonists of the M1 muscarinic acetylcholine receptor. For example, a modulator or potentiator may directly or indirectly augment the response produced by the endogenous ligand (such as acetylcholine or xanomeline) at the orthosteric site of the M4 muscarinic acetylcholine receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the M4 muscarinic acetylcholine receptor, thereby augmenting the response produced by the endogenous ligand acetylcholine at the orthosteric site of the M4 muscarinic acetylcholine receptor. It is also believed that the compounds of the invention bind to an allosteric site which is distinct from the xanomeline site of the M4 muscarinic acetylcholine receptor, thereby augmenting the response produced by the endogenous ligand xanomeline at the orthosteric site of the M4 muscarinic acetylcholine receptor.

The present invention is also directed to the use of the compounds disclosed herein as modulators of M4 muscarinic acetylcholine receptor activity. The subject compounds and pharmaceutically acceptable salts thereof are useful in a method of M4 modulating muscarinic acetylcholine receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for modulating M4 muscarinic acetylcholine receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to modulate the M4 muscarinic acetylcholine receptor in the subject. In an embodiment, the amount of compound can be an "effective amount" or "therapeutically effective amount", wherein the subject compound or pharmaceutical composition is administered in an amount that will elicit the biological or medical response of a tissue, system, animal or human that is being sought by the researcher, veterinarian, medical doctor or other clinician, or otherwise inhibiting the noted disease and thus producing the desired therapeutic, ameliorative, inhibitory or preventative effect. An effective amount does not necessarily include considerations of toxicity and safety related to the administration of the compound. It is recognized that one skilled in the art may affect neurological and psychiatric disorders associated with M4 muscarinic acetylcholine receptor modulation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and "administering" a compound should be understood to mean providing a compound of the invention or a prodrug of a compound of the invention to the subject. The term "dysfunction" refers to abnormality or impairment in the function of the noted system.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof. The utility of the compounds in accordance with the present invention as modulators of M4 muscarinic acetylcholine receptors may be readily determined without undue experimentation by methodology well known in the art, including monitoring the mobilization of intracellular Ca++, determining the levels of intracellular cAMP, or quantiting the exchange of GDP for [35S]γGTP.

In a typical experiment the M4 muscarinic acetylcholine receptor modulating activity of the compounds of the present invention was determined in accordance with the following experimental method. CHO-K1 cells stably transfected with human M4 receptor and chimeric G-protein Gαqi5 (Coward P, et al., Analytical Biochemistry, 270:242-248 (1999)) are thawed from liquid $N_2$ storage, resuspended in growth medium, plated in black, clear bottom 384 well plates, and incubated 16-20 hours at 37° C., 5% $CO_2$. On the day of assay, growth medium is removed, the cells are washed 2 times with wash buffer, and cells are incubated in dye loading buffer at 37° C., 5% $CO_2$ for ~1 hour. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed. The resulting dose response curves are fit to a 4 parameter logistic equation and the final result is determined as the inflection point (IP) of the curve The intrinsic M4 muscarinic acetylcholine receptor modulating activity of a compound which may be used in the present invention may be determined by these assays.

All of the final compounds of the following examples had activity in the human FLIPR-based M4 PAM assay with an IP of about 5 nM to 15000 nM against the human M4 muscarinic acetylcholine receptor. Additional data is provided in the following Examples. Such a result is indicative of the intrinsic activity of the compounds in use as a modulating the human M4 muscarinic acetylcholine receptor. In general, one of ordinary skill in the art would appreciate that a substance is considered to effectively modulate the human M4 muscarinic acetylcholine receptor if it has an IP of less than about 50 µM, or more specifically less than about 15000 nM.

The M4 muscarinic acetylcholine receptor has been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with M4 muscarinic acetylcholine receptors, including one or more of the following conditions or diseases, and other diseases related to general M4 muscarinic acetylcholine receptor system dysfunction.

Potential conditions or disorders for which the compounds of the invention may be useful further include one or more of the following conditions or diseases: Alzheimer's disease (including mild Alzheimer's disease, moderate Alzheimer's disease and severe Alzheimer's disease), olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, cognitive disorders (including mild cognitive impairment), glaucoma, amyloidosis, type II diabetes, diabetes-associated amyloidogenesis, scrapie, bovine spongiform encephalitis, traumatic brain injury, Creutzfeld-Jakob disease, schizophrenia, sleep disorders, pain disorders (including acute pain, inflammatory pain and neuropathic pain), pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism, atherosclerosis, tolerance and/or dependence to opioid treatment of pain, and for treatment of withdrawal syndrome of e.g., alcohol, opioids, and cocaine, Huntington's disease, drug-induced dyskinesias.

Potential conditions or disorders for which the compounds of the invention may be useful further include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Levodopa induced dyskinesia, other drug induced dyskinesia (e.g. tardive dyskinesias), Huntington's disease, Pick's disease, Creutzfeldt-Jacob disease, perinatal hypoxia, other general medical conditions or substance abuse); delirium, amnestic disorders or age related cognitive decline; delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder; major depressive disorder, affective disorder, bipolar disorder, electrolyte disorder, neurological disorder, hypoglycemia, AIDS, lupus, and post-traumatic stress disorder; brain tumor, dementia with Lewy bodies, multiple sclerosis, sarcoidosis, Lyme disease, syphilis, Alzheimer's disease, Parkinson's disease, and anti-NMDA receptor encephalitis. Thus, in another specific embodiment, the present invention provides a method for treating schizophrenia or psychosis comprising administering to a patient in need thereof an effective amount of a compound of the present invention. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Potential conditions or disorders for which the compounds of the invention may be useful further include one or more of the following conditions or diseases: mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, *cannabis*, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Generally, dosage levels of between 0.0001 to 10 mg/kg of body weight daily are administered to the subject, e.g., humans and elderly humans, to obtain effective modulation of M4 muscarinic acetylcholine receptors. The dosage range will generally be about 0.5 mg to 1.0 g per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered before bedtime. For example, the compounds may be administered about 1 hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be used in combination with one or more other drugs in the treatment of diseases or conditions for which the compounds of the present invention have utility, where the combination of the drugs together are safer or more effective than either drug alone. In a embodiment, the subject compound may be employed in combination with other compounds which are known in the art, either administered separately or in the same pharmaceutical compositions, including, but are not limited to: anti-Alzheimer's agents; beta-secretase inhibitors, such as verubecestat; alpha 7 nicotinic agonists, such as ABT089, SSR180711 and MEM63908; HT2a modulators, such as pimavaserin; ADAM 10 ligands or activators; gamma-secretase inhibitors, such as LY450139 and TAK 070; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1α antagonists, such as lecozotan; p25/CDK5 inhibitors; NK1/ NK3 receptor antagonists; COX-2 inhibitors; HMG-CoA reductase inhibitors; NSAID's including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; CB-1 receptor antagonists or CB-1 receptor inverse agonists; antibiotics such as doxycycline and rifampin; N-methyl-D-aspartate (NMDA) receptor antagonists, such as memantine, neramexane and EVT101; recombinant growth hormone; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; neuronal nicotinic agonists; muscarinic antagonists (e.g., M1 agonists (such as acetylcholine, oxotremorine, carbachol, or McNa343), or $M_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5, 6-dimethoxy-2-[[1-(phenylmethyl)-4-piperidinyl]methyl]-1H-inden-1-one hydrochloride), tacrine, phenserine, ladostigil, ABT-089, galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; anti-inflammatory agents that can reduce neuroinflammation; glycogen synthase kinase beta inhibitors; promoters of alpha secretase activity; PDE IV inhibitors, including MEM1414, HT0712 and AVE8112; PDE-10 inhibitors; Tau kinase inhibitors (e.g., GSK3beta inhibitors, cdk5 inhibitors, or ERK inhibitors); GSK3β inhibitors, including AZD1080, SAR502250 and CEP16805; neuronal nicotinic agonists; selective M1 agonists; HDAC inhibitors; and microtubule affinity regulating kinase (MARK) ligands; Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer); or other drugs that affect receptors or enzymes that either increase the efficacy, safety, convenience, or reduce unwanted side effects or toxicity of the compounds of the present invention.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NM antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, filorexant, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, suvorexant, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The subject or patient to whom the compounds of the present invention is administered is generally a human being, male or female, but may also encompass other mammals, such as dogs, cats, mice, rats, cattle, horses, sheep, rabbits, monkeys, chimpanzees or other apes or primates, for which treatment of the above noted disorders is desired.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. Pharmaceutical compositions of the present compounds in the form of a sterile injectable aqueous or oleagenous suspension may be formulated by known techniques for depo administration and thereby provide a sustained action over a longer period. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; aq: aqueous; BINAP: 2,2'-bis(diphenylphosphino)-1,1'-binaphthyl; Bn: benzyl; Ac: acetyl; Boc: tert-butyloxy carbonyl; BSA: bovine serum albumin; CAN: acetonitrile; Cbz: carboxylbenzyl; CbzCl: benzylchloroformate; CDI: carbonyl diimidazole; DABCO: 1,4-diazabicyclo[2.2.2]octane; DAST: diethylaminosulfur trifluoride; DBAD: di-tert-butyl azodicarboxylate; DCM: dichloromethane; DCE: dichloroethane; DEA: diethylamine; DEAD: diethylazodicarboxylate; DIAD: diisopropyl azodicarboxylate; DIBAL: diisobutylaluminium hydride; DIPEA: N,N-diisopropylethylamine; DMAP: 4-dimethylaminopyridine; DMF: N,N-dimethylformamide; DMP: Dess-Martin periodinane; DMS: dimethylsulfide; DMSO: dimethylsulfoxide; dppf: 1,1'-bis(diphenyl-phosphino)ferrocene; $CH_2Cl_2$: dichloromethane; EDC: N-(3-Dimethylaminopropyl)-N'-ethylcarbodiimide; $Et_3N$: triethylamine; EtOAc: ethyl acetate; EtOH: ethanol; F-TEDA: Selectfluor®; HATU: (1-[bis(dimethylamino)methylene]-1H-1,2,3-triazolo[4,5-b]pyridinium 3-oxid hexafluorophosphate); HCl: hydrogen chloride; HOAt: 1-hydroxy-7-aza-benzotriazole; HOBT: hydroxybenzotriazole hydrate; HPLC: high performance liquid chromatography; Hunig's base: N,N-diisopropylethylamine; LDA: diisopropylamine; LHMDS: lithium bis(trimethylsilyl)amide; mCPBA: meta-chloroperbenzoic acid; MeOH: methanol; MgSO4: magnesium sulfate; Ms: methanesulfonyl; MTBE: methyl tert-butyl ether; MS: Mass spectra; $NaHCO_3$: sodium bicarbonate; NaOH: sodium hydroxide; NBS: N-bromosuccinimide; NCS: N-chlorosuccinimide; NMM: N-methylmorpholine; NMR: nuclear magnetic resonance; PG: protecting group; PtO2: platinum oxide; PCC: pyridinium chlorochromate; rt: room temperature; SEM: 2-(Trimethylsilyl)ethoxylmethyl; SFC: supercritical fluid chromatography; $SOCl_2$: thionyl chloride; T3P: 2,4,6-tripropyl-1,3,5,2,4,6-trioxatriphosphorinane-2,4,6-trioxide; TBAF: tetra-n-butylammonium fluoride; TBS: tert-Butyldimethylsilyl; TEA: triethylamine; TES: Triethylsilyl; TFA: trifluoracetic acid; Tf: triflate; TFAA: trifluoroacetic anhydride; THF: tetrahydrofuran; TIPS: tri-isopropylsilyl; TLC: thin layer chromatography; Ts: toluenesulfonyl; X-Phos: 2-(dicyclohexyl-phosphino)-2',4',6'-triisopropyl-biphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. Because the schemes are an illustration, the invention should not be construed as being limited by the chemical reactions and conditions expressed. The preparation of the various starting materials used herein is well within the skill of a person versed in the art. The following examples are provided so that the invention might be more fully understood. These examples are illustrative only and should not be construed as limiting the invention in any way. Absolute stereochemistry of separate stereoisomers in the examples and intermediates are not determined unless stated otherwise in an example or explicitly in the nomenclature.

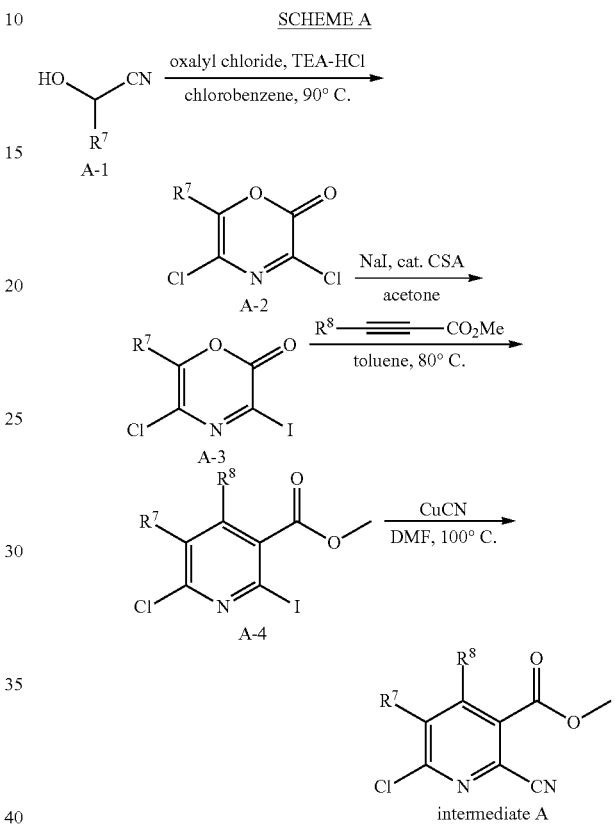

Intermediate A is prepared according to Scheme A via condensation of commercially available hydroxynitrile A-1 with oxalyl chloride to yield adduct A-2. A Finkelstein reaction of chloride A-2 with sodium iodide, catalyzed by camphorsulfonic acid (CSA), results in iodide product A-3. A hetero-Diels-Alder reaction of diene A-3 with a commercially available ynone gives pyridine A-4. A subsequent copper-meditated cyanation provides intermediate A.

INTERMEDIATE A1

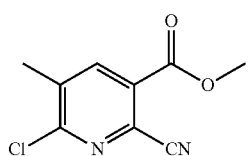

Methyl 6-chloro-2-cyano-5-methylnicotinate
(Scheme A)

Step 1: 3,5-Dichloro-6-methyl-2H-1,4-oxazin-2-one

Into a 10 L 4-necked round-bottom flask was charged oxalic dichloride (3.32 kg, 26.2 mol) and chlorobenzene (3.5

L) under an inert atmosphere of nitrogen. A solution of 2-hydroxypropanenitrile (464.8 g, 6.54 mol) in chlorobenzene (500 mL) was added dropwise to the flask at 0° C. The system was heated to 90° C. and triethylamine hydrochloride (66.2 g, 481 mmol) was added in portions at 90° C. The resulting solution was stirred for 3 h before concentrating the mixture under reduced pressure. The resulting solution was diluted with ether (5 L) and the solids were filtered out. The filtrate concentrated and was then applied purified by silica gel column chromatography (0:1-1:4 EtOAc:petroleum ether) to yield the title compound.

Step 2:
5-Chloro-3-iodo-6-methyl-2H-1,4-oxazin-2-one

Into a 10 L 4-necked round-bottom flask was added 3,5-dichloro-6-methyl-2H-1,4-oxazin-2-one (470.8 g, 2.62 mol), acetone (10 L), NaI (1568 g, 10.5 mol) and camphorsulfonic acid (40 g, 172.2 mmol) under an atmosphere of nitrogen. The resulting solution was stirred for 3 h at 25° C. The mixture was concentrated and then diluted with water (20 L) and dichloromethane (3×5 L). The organic layers were combined and washed with brine (5 L). The mixture was dried over anhydrous sodium sulfate, filtered and was concentrated under reduced pressure to yield the title compound.

Step 3: Methyl 6-chloro-2-iodo-5-methylnicotinate

Into a 5 L 3-necked round-bottom flask was placed 5-chloro-3-iodo-6-methyl-2H-1,4-oxazin-2-one (638 g, 2.35 mol), toluene (2.3 L), and methyl prop-2-ynoate (592.8 g, 7.05 mol) under an atmosphere of nitrogen. The resulting solution was stirred for 2 days at 80° C. The reaction was cooled and the volatiles were removed under reduced pressure. The residue was purified by silica gel column chromatography (0:1-1:50 EtOAc:petroleum ether) to provide the major regioisomeric product as the title compound.

Step 4: Methyl 6-chloro-2-cyano-5-methylnicotinate

Into a 20-mL microwave tube was added methyl 6-chloro-2-iodo-5-methylpyridine-3-carboxylate (2 g, 6.42 mmol), DMF (15 mL), and CuCN (850 mg, 9.60 mmol). The resulting solution was stirred for 5 min at 100° C. by microwave irradiation. The mixture was diluted with water (20 mL) and a saturated, aqueous solution of $NH_4Cl$ (100 mL). Dichloromethane (2×20 mL) was used to extract the crude material and the organic layers were combined and dried over anhydrous sodium sulfate. The residue was purified by silica gel chromatography (0:1-1:8 ethyl acetate:petroleum ether) to provide the title compound. MS: 211 (M+1). $^1$H NMR (500 MHz, $CDCl_3$): δ 7.87 (s, 1H), 3.95 (s, 4H), 2.37 (s, 3H).

The following intermediates in table A were prepared according to scheme A using the procedure outlined in the synthesis of intermediate A1 using commercially available hydroxynitriles in step 1 and using commercially available ynones for step 3.

TABLE A

| Intermediate | Structure | Name | MS (M + 1) |
|---|---|---|---|
| A2 | 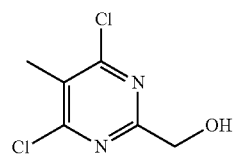 | dimethyl 2-chloro-6-cyanopyridine-3,5-dicarboxylate | 356 |

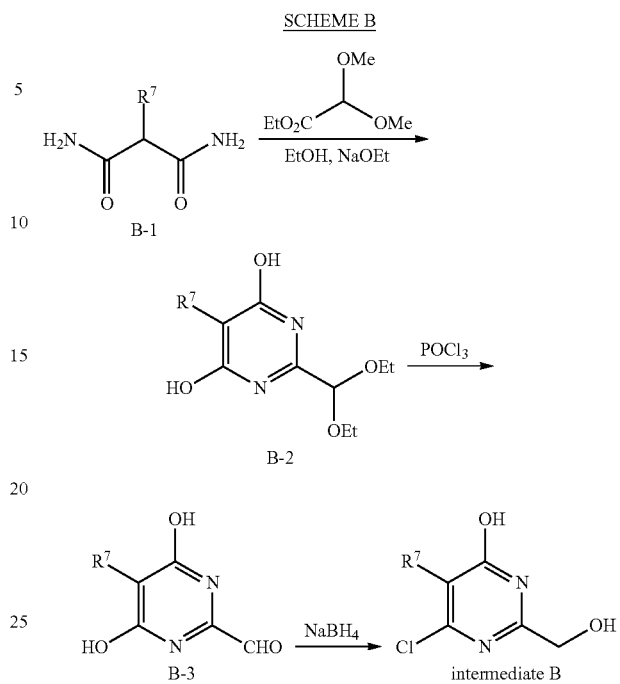

SCHEME B

Intermediate B is prepared according to Scheme B via condensation of known or commercially available 2-substituted malonamide B-1 with ethyl 2,2-diethoxyacetate to form pyrimidine adduct B-2. Reaction with $POCl_3$ concomitantly provides the dichloride as well as unmasks the acetal to the corresponding aldehyde B-3. Subsequent reduction with borohydride provides provides intermediate B.

INTERMEDIATE B (4,6-Dichloro-5-methylpyrimidin-2-yl)methanol (Scheme B)

Step 1:
2-(Diethoxymethyl)-5-methylpyrimidine-4,6-diol

A mixture of 2-methylpropanediamide (300 g, 2.58 mol), ethanol (8 L), NaOEt/EtOH (2000 g, 5.29 mol), ethyl 2,2-diethoxyacetate (560 g, 3.18 mol) was stirred for 15 h at reflux under an inert atmosphere of nitrogen. Upon cooling to RT, aqueous HCl (6 M) was added to adjust the pH-3 and the resulting solution was extracted with ethyl acetate (4×6 L). The combined organics were washed with brine (5 L), dried over anhydrous sodium sulfate and concentrated under reduced pressure to afford the title compound.

Step 2: 4,6-Dichloro-5-methylpyrimidine-2-carbaldehyde

A solution of 2-(diethoxymethyl)-5-methylpyrimidine-4,6-diol (500 g, 2.19 mol) in POCl$_3$ (3 L) was stirred for 3 h at 90° C. The resulting mixture was concentrated under reduced pressure and was quenched by pouring into ice water (2 L). The resulting solution was extracted with ethyl acetate (3×1 L) and the combined organic layers were washed with brine (1.5 L), dried over anhydrous sodium sulfate and concentrated. The residue was purified by silica gel chromatography (1:10 EtOAc: petroleum ether to yield the title compound.

Step 3: (4,6-Dichloro-5-methylpyrimidin-2-yl)methanol

To a solution of 4,6-dichloro-5-methylpyrimidine-2-carbaldehyde (130 g, 681 mmol) in THF (2 L) was added NaBH$_4$ (13 g, 343.64 mmol) followed by the dropwise addition of water (200 mL) with stirring at −10° C. The reaction was stirred for 1 h at −10° C. before being quenched by the addition of aqueous NH$_4$Cl (saturated, 1 L). The mixture was extracted with EtOAc (3×500 mL) and the organic combined organics were washed with brine (500 mL), dried anhydrous sodium sulfate and concentrated. The residue was applied onto a silica gel chromatography (1:10 EtOAc: petroleum ether) to afford the title compound. MS: 293 (M+1).

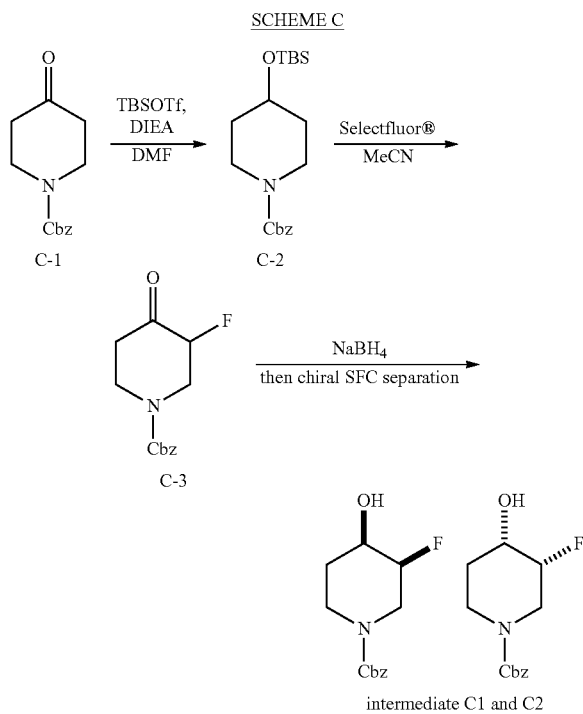

SCHEME C intermediate C1 and C2

Intermediate C is prepared from protected piperidone C-1 which was converted to the enol silane C-2 under the action of TBSOTf in the presence of base. Electrophilic fluorination by Selectfluor® on C-2 provided the corresponding alpha-fluorinated product C-3. Reduction by sodium borohydride and subsequent chiral SFC separation provided intermediate C1 and intermediate C2 as single enantiomers.

INTERMEDIATE C1 And C2

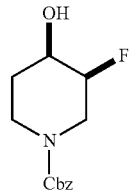

intermediate C1

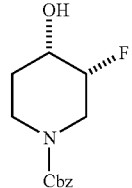

intermediate C2

Benzyl (3S,4R)-3-fluoro-4-hydroxypiperidine-1-carboxylate and benzyl (3R,4S)-3-fluoro-4-hydroxypiperidine-1-carboxylate (Scheme C)

Step 1: Benzyl 4-((tert-butyldimethylsilyl)oxy)-3,6-dihydropyridine-1(2H)-carboxylate To a solution of benzyl 4-oxopiperidine-1-carboxylate (260 g, 1.11 mmol) in DMF (700 mL) and was added DIPEA (216 g, 1.67 mol) and TBSOTf (83 g, 1.45 mol) at RT under an atmosphere of nitrogen. The reaction mixture was stirred for 16 h. After diluting with water (1.5 L) and extracting with EtOAc (1.5 L×3), the organic layers were combined and washed with brine (2 L×3) and concentrated. The residue was purified by silica gel column chromatography (50:1-20:1 petroleum ether:ethyl acetate) to obtain the title compound.

Step 2: Benzyl 3-fluoro-4-oxopiperidine-1-carboxylate

To a solution of benzyl 4-((tert-butyldimethylsilyl)oxy)-3,6-dihydropyridine-1(21-1)-carboxylate (200 g, 0.58 mol) in MeCN (1.6 L) was added Selectfluor® (224 g, 0.63 mol) at 25° C. The reaction mixture was stirred for 10 h. The volatiles were removed under reduced pressure and the residue was diluted with EtOAc (2 L) and then washed with brine (1.5 L×3). The organic was concentrated in vacuo to give the title compound which was carried forward without further purification.

Step 3: Benzyl(3S,4R)-3-fluoro-4-hydroxypiperidine-1-carboxylate and Benzyl (3R,4S)-3-fluoro-4-hydroxypiperidine-1-carboxylate To a solution of benzyl 3-fluoro-4-oxopiperidine-1-carboxylate (300 g, 1.19 mol) in MeOH (2.5 L) was added NaBH$_4$ (50 g, 1.31 mol) at 0° C. After stirring for 4 h at RT, the volatiles were removed under reduced pressure and the residue was diluted with EtOAc (2 L) and washed with water (2 L) and then brine (2 L×2). The organic was concentrated in vacuo and was purified on silica gel by column chromatography (10:1-2:1 petroleum ether:ethyl acetate) to obtain the racemic product. The material was then purified by chiral SFC (AD column, 30%/70% EtOH with 0.1% ammonium hydroxide modifier/CO$_2$) to afford intermediate C1 (faster eluting 3S,4R isomer): MS: 254 (M+1). $^1$H NMR (400 MHz, CDCl$_3$): δ 7.41-7.29 (m, 1H), 5.15 (s, 1H), 4.74-4.52 (m, 1H), 4.11-3.76 (m, 3H), 3.62-3.17 (m, 2H), 2.07 (br s, 1H), 1.93-1.70 (m, 2H). Intermediate C2 (slower eluting 3R,4S isomer): MS: 254 (M+1). $^1$H NMR (400 MHz, CDCl$_3$): δ 7.40-7.30 (m, 5H), 5.15 (s, 2H), 4.75-4.51 (m, 1H), 4.09-3.69 (m, 3H), 3.62-3.18 (m, 2H), 2.08 (br s, 1H), 1.93-1.71 (m, 2H).

SCHEME D

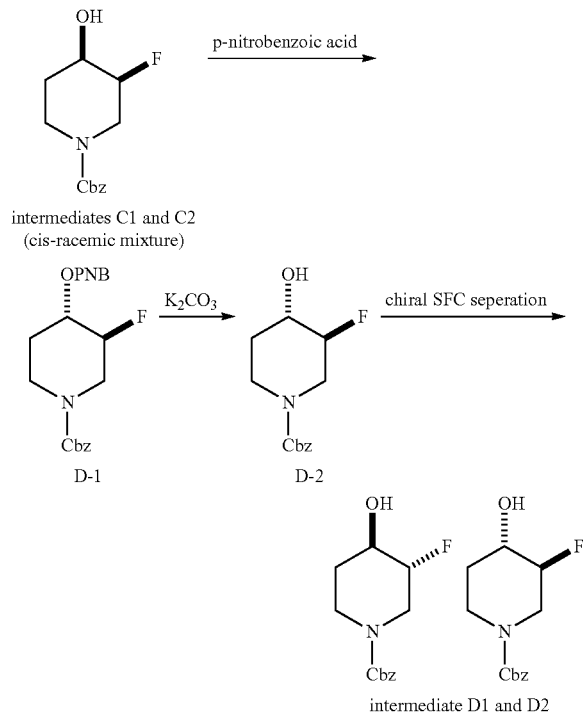

intermediates C1 and C2
(cis-racemic mixture)

D-1

D-2 intermediate D1 and D2

Intermediate D is prepared from a racemic mixture of intermediate C1 and intermediate C2 which is carried through a Mitsunobu reaction with p-nitrobenzoic acid to provide trans-racemic adduct D-1. Subsequent saponification reveals alcohol D-2. Chiral separation to resolve the enantiomers is carried out to provide intermediate D1 and intermediate D2 as single enantiomers.

INTERMEDIATE D1 AND D2

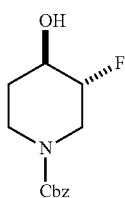

intermediate D1

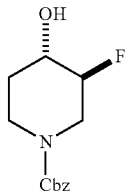

intermediate D2

Benzyl (3R,4R)-3-fluoro-4-hydroxypiperidine-1-carboxylate and benzyl (3S,4S)-3-fluoro-4-hydroxypiperidine-1-carboxylate (Scheme D)

Step 1: Benzyl trans-3-fluoro-4-((4-nitrobenzoyl)oxy)piperidine-1-carboxylate

To a stirred solution of benzyl cis-3-fluoro-4-hydroxypiperidine-1-carboxylate (60 g, 0.24 mol, intermediate C1 and C2) in THF (400 mL) was added p-nitrobenzoic acid (60 g, 0.36 mol) and Ph$_3$P (92 g, 0.35 mol) at RT. After cooling the mixture to −0-5° C., DIAD (78 g, 0.39 mol) was added dropwise. The reaction was stirred 15 h at RT and was quenched with an aqueous, saturated NH$_4$Cl solution (600 mL) and was then extracted with EtOAc (500 mL×3). The combined organic layers were washed with brine (1 L), dried over anhydrous sodium sulfate and concentrated under reduced pressure. The residue was purified on silica gel by column chromatography (10:1 petroleum ether:ethyl acetate) to yield the title compound.

Step 2: Benzyl trans-3-fluoro-4-hydroxypiperidine-1-carboxylate

To a solution of benzyl cis-3-fluoro-4-((4-nitrobenzoyl)oxy)piperidine-1-carboxylate (90 g, 0.22 mol) in MeOH (900 mL) was added potassium carbonate (90 g, 0.65 mol). The resulting mixture was stirred at RT for 15 h and then the volatiles were removed under reduced pressure. The residue was partitioned between EtOAc (200 mL) and saturated NH$_4$Cl(aq) (200 mL). The aqueous layer was extracted with EtOAc (200 mL×2) and the combined organic layers were washed with brine (500 mL), dried over anhydrous sodium sulfate, filtered and concentrated. The residue was purified by silica gel column chromatography (1:1 petroleum ether: ethyl acetate) to afford the title compound.

Step 3: Benzyl (3R,4R)-3-fluoro-4-hydroxypiperidine-1-carboxylate and benzyl (3S,4S)-3-fluoro-4-hydroxypiperidine-1-carboxylate Benzyl trans-3-fluoro-4-hydroxypiperidine-1-carboxylate was resolved into single enantiomers via chiral SFC (AD column, 5-40% EtOH with 0.05% diethylamine modifier/CO$_2$) to afford intermediate D1 (faster eluting 3R,4R isomer): MS: 254 (M+1). $^1$H NMR (400 MHz, CDCl$_3$): δ 7.31-7.56 (m, 5H), 5.19 (s, 2H), 4.17-4.37 (m, 2H), 3.84-3.95 (m, 2H), 3.06-3.28 (m, 2H), 2.28 (s, 1H), 2.01 (s, 1H), 1.57 (s, 1H). Intermediate D2 (slower eluting 3S,4S isomer): MS: 254 (M+1). $^1$H NMR (400 MHz, CDCl$_3$): δ 7.31-7.56 (m, 5H), 5.19 (s, 2H), 4.17-4.37 (m, 2H), 3.84-3.95 (m, 2H), 3.06-3.28 (m, 2H), 2.28 (s, 1H), 2.01 (s, 1H), 1.57 (s, 1 H).

SCHEME E

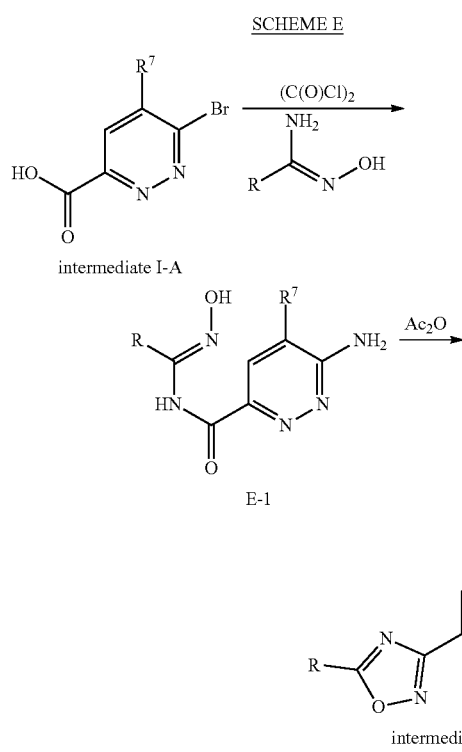

intermediate I-A

E-1 intermediate E

Intermediate E is prepared according to scheme E from prepared intermediate I-A with oxalyl chloride to form the corresponding acyl chloride, which is intercepted by a commercial N-hydroxyacetamide to form adduct E-1. Reaction with acetic anhydride provides cyclized product intermediate E.

INTERMEDIATE E

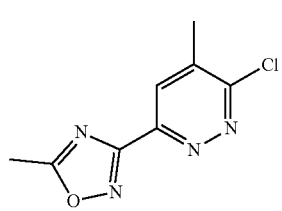

3-(6-Chloro-5-methylpyridazin-3-yl)-5-methyl-1,2,4-oxadiazole (Scheme E)

Step 1: (Z)-6-Chloro-N-(1-(hydroxyimino)ethyl)-5-methylpyridazine-3-carboxamide

To a solution of 6-bromo-5-methylpyridazine-3-carboxylic acid (intermediate IA, 120 mg, 0.553 mmol) in DCM (4 mL) was added oxalyl dichloride (211 mg, 1.66 mmol) at 0° C. The resulting mixture was stirred at RT for 2 h before the volatiles were removed in vacuo. The resultant residue dissolved in DCM (2 mL) and was added dropwise to a solution of (Z)—N'-hydroxyacetimidamide (45.1 mg, 0.61 mmol), DIPEA (0.39 mL, 2.21 mmol) in DCM (2 mL) at 0° C. The resulting suspension was stirred at RT for 8 h before the mixture was diluted with water (10 mL) and extracted with EtOAc (10 mL×3). The combined organic phases were dried over anhydrous sodium sulfate, filtered and the filtrate was concentrated. The residue was purified by prep-TLC (1:20 MeOH: DCM) to yield the title compound.

Step 2: (Z)-6-Chloro-N-(1-(hydroxyimino)ethyl)-5-methylpyridazine-3-carboxamide

A mixture of (Z)—N'-hydroxy-6-(4-((6-methoxypyridin-3-yl)oxy)piperidin-1-yl)-5-methylpyridazine-3-carboximidamide (23 mg, 0.064 mmol), Ac$_2$O (0.012 mL, 0.128 mmol) in pyridine (2 mL) was stirred for 8 h at 100 C under an atmosphere of nitrogen. After cooling the reaction to RT, it was diluted with water (7 mL), extracted with EtOAc (8 mL×3) and the combined organic layers were washed with brine (8 mL), dried over anhydrous Na$_2$SO$_4$, filtered and concentrated under reduced pressure. The residue was purified by reverse phase HPLC (ACN/water with 0.1% ammonium hydroxide modifier) to yield the title compound. MS: 383 (M+1).

SCHEME F

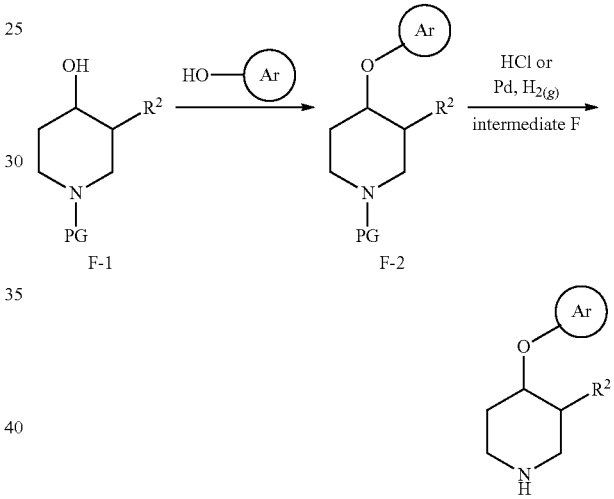

Intermediate F is prepared according to scheme F via Mitsunobu reaction of commercially available N-protected piperdine F-1 with known or prepared phenols (wherein Ar is an aromatic or heteroaromatic ring of R$^1$) to yield adduct F-2. Subsequent deprotection of ether F-2 provides intermediate F.

INTERMEDIATE F1

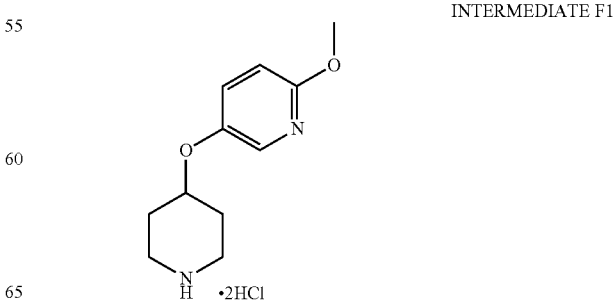

2-Methoxy-5-(piperidin-4-yloxy)pyridine Dihydrochloride (Scheme F)

Step 1: tert-Butyl 4-((6-methoxypyridin-3-yl)oxy)piperidine-1-carboxylate

Into a 5-L 4-necked round-bottom flask purged and maintained with an inert atmosphere of nitrogen was placed a solution of 6-methoxypyridin-3-ol (200 g, 1.60 mol) in THF (1.5 L). tert-Butyl 4-hydroxypiperidine-1-carboxylate (386 g, 1.92 mol) and triphenylphosphine (545 g, 2.08 mol) were added followed by the dropwise addition of DIAD (420 g, 2.08 mol) at RT. After stirring for 1 h at 40° C., the resulting solution was diluted with water (2 L) and was partitioned with EtOAc (4 L). The organic layers were combined, washed with brine (2 L), dried over anhydrous sodium sulfate, filtered and concentrated. The residue was purified by silica gel column chromatography (1/10 ethyl acetate/petroleum ether) to yield the title compound.

Step 2: 2-Methoxy-5-(piperidin-4-yloxy)pyridine Dihydrochloride

A solution of tert-butyl 4-((6-methoxypyridin-3-yl)oxy)piperidine-1-carboxylate (270 g, 875.6 mmol) in methanol (2 L) was bubbled slowly with HCl(g). The resulting solution was stirred for 2 h at RT. The volatiles were removed and the crude material was diluted with hot EtOAc:MeOH (8:1) and was then cooled to obtain a precipitate that was collected by filtration to yield the title compound. MS: 236 (M-2 HCl+H). $^1$H NMR (300 MHz, D$_2$O): δ 7.79-7.98 (m, 2 H), 7.24-7.23 (m, 1H), 4.0 (s, 3H), 3.36-3.40 (m, 2H), 3.15-3.26 (m, 2H), 1.97-2.14 (m, 4H).

The following intermediates in table F were prepared according to scheme F using the procedure outlined in the synthesis of intermediate F1 using commercially available, known or prepared phenols in step 1 and employing various azodicarboxylates with TBAD being the preferred reagent. In cases where additional chemical manipulation are to be carried out on the intermediate, the second step may be omitted.

TABLE F

| Intermediate | Structure | Name | MS (M + 1) |
|---|---|---|---|
| F2 | 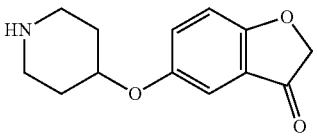 [SMILES: O=C1COc2ccc(OC3CCNCC3)cc21] | 5-(piperidin-4-yloxy)benzofuran-3(2H)-one | 234 |
| F3 | 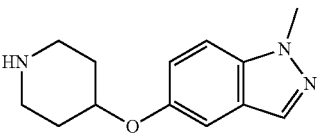 [SMILES: Cn1ncc2cc(OC3CCNCC3)ccc21] | 1-methyl-5-(piperidin-4-yloxy)-1H-indazole | 232 |
| F4 | 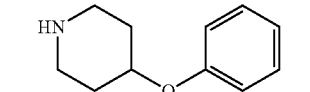 | 4-phenoxypiperidine | 178 |
| F5 | 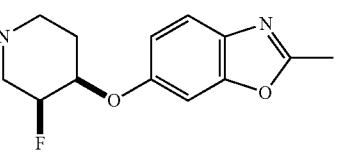 | 6-(((3S,4R)-3-fluoropiperidin-4-yl)oxy)-2-methylbenzo[d]oxazole | 251 |
| F6 | 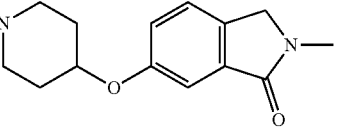 | 2-methyl-6-(piperidin-4-yloxy)isoindolin-1-one | 247 |
| F7 | 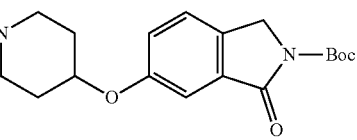 | tert-butyl 1-oxo-6-(piperidin-4-yloxy)isoindoline-2-carboxylate | 333 |
| F8 | 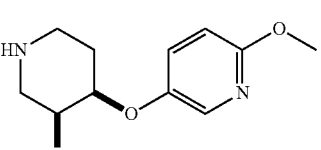 | 5-(((3S,4R)-3-fluoropiperidin-4-yl)oxy)-2-methoxypyridine | 227 |

TABLE F-continued

| Intermediate | Structure | Name | MS (M + 1) |
|---|---|---|---|
| F9 | 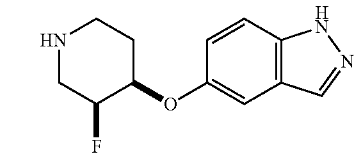 [SMILES: F[C@H]1CNCC[C@H]1Oc1ccc2[nH]ncc2c1] | 5-(((3S,4R)-3-fluoropiperidin-4-yl)oxy)-1H-indazole | 236 |
| F10 | 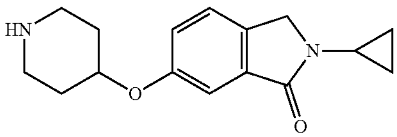 [SMILES: O=C1c2cc(OC3CCNCC3)ccc2CN1C1CC1] | 2-cyclopropyl-6-(piperidin-4-yloxy)isoindolin-1-one | 273 |
| F11 | 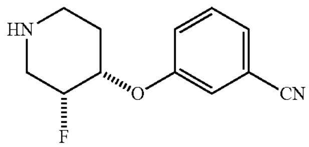 [SMILES: N#Cc1cccc(O[C@H]2CCNC[C@H]2F)c1] | 3-(((3R,4S)-3-fluoropiperidin-4-yl)oxy)benzonitrile | 221 |
| F12 | 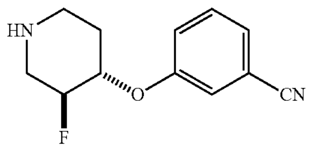 [SMILES: N#Cc1cccc(O[C@H]2CCNC[C@@H]2F)c1] | 3-(((3S,4S)-3-fluoropiperidin-4-yl)oxy)benzonitrile | 221 |
| F13 | 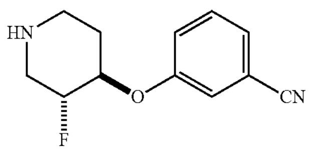 [SMILES: N#Cc1cccc(O[C@@H]2CCNC[C@H]2F)c1] | 3-(((3R,4R)-3-fluoropiperidin-4-yl)oxy)benzonitrile | 221 |
| F14 | 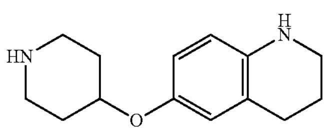 [SMILES: c1cc2c(cc1OC1CCNCC1)CCCN2] | 6-(piperidin-4-yloxy)-1,2,3,4-tetrahydroquinoline | 233 |
| F15 | 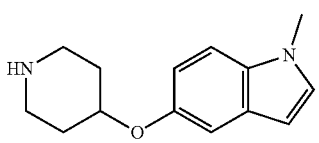 [SMILES: Cn1ccc2cc(OC3CCNCC3)ccc21] | 1-methyl-5-(piperidin-4-yloxy)-1H-indole | 231 |
| F16 | 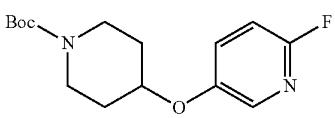 [SMILES: CC(C)(C)OC(=O)N1CCC(Oc2ccc(F)nc2)CC1] | tert-butyl 4-((6-fluoropyridin-3-yl)oxy)piperidine-1-carboxylate | 241* |
| F17 | 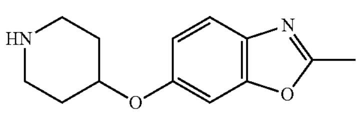 [SMILES: Cc1nc2ccc(OC3CCNCC3)cc2o1] | 2-methyl-6-(piperidin-4-yloxy)benzo[d]oxazole | 233 |
| F18 | 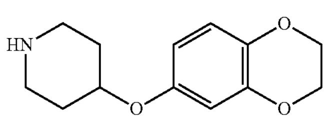 [SMILES: c1cc2c(cc1OC1CCNCC1)OCCO2] | 4-((2,3-dihydrobenzo[b][1,4]-dioxin-6-yl)oxy)piperidine | 236 |
| F19 | 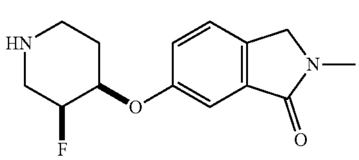 [SMILES: CN1Cc2ccc(O[C@@H]3CCNC[C@@H]3F)cc2C1=O] | 6-(((3S,4R)-3-fluoropiperidin-4-yl)oxy)-2-methylisoindolin-1-one | 265 |

TABLE F-continued

| Intermediate | Name | MS (M + 1) |
|---|---|---|
| F20 | 7-(piperidin-4-yloxy)-2H-chromen-2-one | 246 |
| F21 | 5-(piperidin-4-yloxy)benzo[c][1,2,5]-oxadiazole | 220 |
| F22[1] | 3-methyl-6-(piperidin-4-yloxy)quinazolin-4(3H)-one | 260 |
| F23 | 4-(4-(methylsulfonyl)-phenoxy)piperidine | 256 |
| F24[2] | 2-methyl-7-(piperidin-4-yloxy)isoquinolin-1(2H)-one | 259 |
| F25 | cis-3-fluoro-4-(4-methoxyphenoxy)-piperidine | 226 |
| F26 | 6-(piperidin-4-yloxy)chroman-4-one | 248 |
| F27[3] | 6-(piperidin-4-yloxy)isobenzofuran-1(3H)-one | 234 |

TABLE F-continued

| Intermediate | Structure | Name | MS (M + 1) |
|---|---|---|---|
| F28 | | 5-(((cis)-3-fluoropiperidin-4-yl)oxy)-1-methyl-1H-indazole | 250 |
| F28 | | 6-(piperidin-4-yloxy)-2,3-dihydro-1H-inden-1-one | 232 |
| F29 | 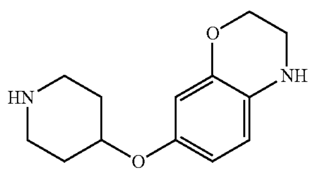 [SMILES: c1cc2c(cc1OC1CCNCC1)OCCN2] | 7-(piperidin-4-yloxy)-3,4-dihydro-2H-benzo[b][1,4]oxazine | 235 |
| F30 | 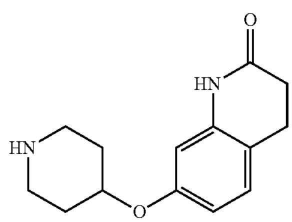 [SMILES: O=C1CCc2ccc(OC3CCNCC3)cc2N1] | 7-(piperidin-4-yloxy)-3,4-dihydroquinolin-2(1H)-one | 247 |
| F31 | 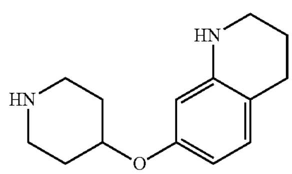 [SMILES: c1cc2c(cc1OC1CCNCC1)NCCC2] | 7-(piperidin-4-yloxy)-1,2,3,4-tetrahydroquinoline | 233 |
| F32 | 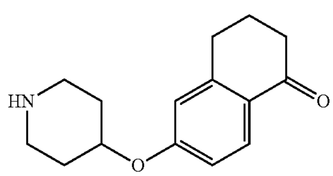 [SMILES: O=C1CCCc2cc(OC3CCNCC3)ccc21] | 6-(piperidin-4-yloxy)-3,4-dihydronaphthalen-1(2H)-one | 247 |
| F33 | 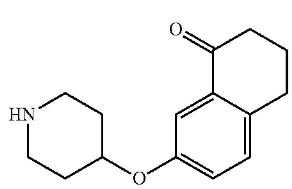 [SMILES: O=C1CCCc2ccc(OC3CCNCC3)cc21] | 7-(piperidin-4-yloxy)-3,4-dihydronaphthalen-1(2H)-one | 247 |
| F34 | 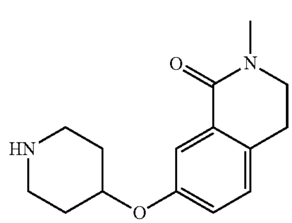 [SMILES: CN1CCc2ccc(OC3CCNCC3)cc2C1=O] | 2-methyl-7-(piperidin-4-yloxy)-3,4-dihydroisoquinolin-1(2H)-one | 261 |

TABLE F-continued

| Intermediate | Structure | Name | MS (M + 1) |
|---|---|---|---|
| F35 | 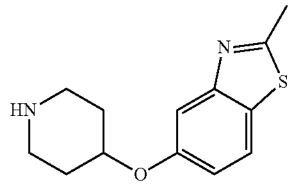 [SMILES: Cc1nc2cc(OC3CCNCC3)ccc2s1] | 2-methyl-5-(piperidin-4-yloxy)benzo[d]thiazole | 249 |
| F36 | 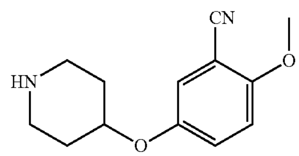 [SMILES: COc1ccc(OC2CCNCC2)cc1C#N] | 2-methoxy-5-(piperidin-4-yloxy)benzonitrile | 233 |
| F37 | 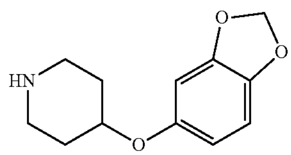 [SMILES: c1cc2c(cc1OC1CCNCC1)OCO2] | 4-(benzo[d][1,3]dioxol-5-yloxy)piperidine | 222 |
| F38[4] | 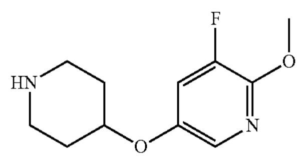 [SMILES: COc1ncc(OC2CCNCC2)cc1F] | 3-fluoro-2-methoxy-5-(piperidin-4-yloxy)pyridine | 227 |
| F39 | 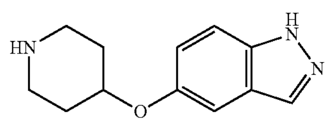 [SMILES: c1cc2[nH]ncc2cc1OC1CCNCC1] | 1-methyl-5-(piperidin-4-yloxy)-1H-indazole | 218 |
| F40[5] | 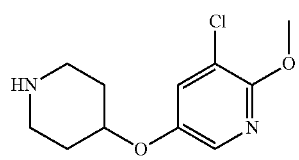 | 3-chloro-2-methoxy-5-(piperidin-4-yloxy)pyridine | 243 |
| F41 | 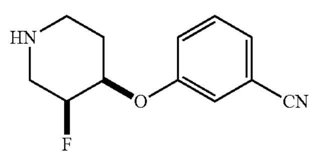 [SMILES: N#Cc1cccc(O[C@@H]2CCNC[C@@H]2F)c1] | 3-(((3S,4R)-3-fluoropiperidin-4-yl)oxy)benzonitrile | 221 |
| F42 | 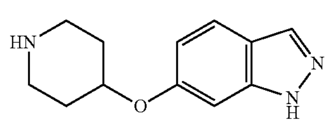 [SMILES: c1cc2cn[nH]c2cc1OC1CCNCC1] | 6-(piperidin-4-yloxy)-1H-indazole | 218 |
| F43[6] | 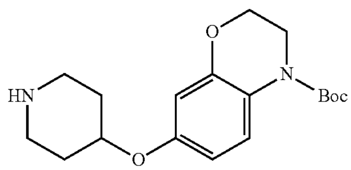 [SMILES: CC(C)(C)OC(=O)N1CCOc2cc(OC3CCNCC3)ccc21] | tert-butyl 7-(piperidin-4-yloxy)-2,3-dihydro-4H-benzo[b][1,4]oxazine-4-carboxylate | 335 |

TABLE F-continued

| Intermediate | Structure | Name | MS (M + 1) |
|---|---|---|---|
| F44 | 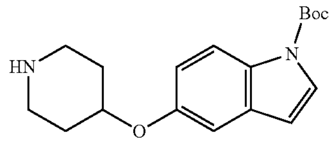 [SMILES: CC(C)(C)OC(=O)n1ccc2cc(OC3CCNCC3)ccc21] | tert-butyl 5-(piperidin-4-yloxy)-1H-indole-1-carboxylate | 317 |

*MS Data is for (M + 1-tBu)

[1] Phenol starting materials may be prepared according to literature procedures, see e.g.: Aquila, B., et al. Quinazolin-4-one derivatives as B-Raf inhibitors, process for their preparation and pharmaceutical compositions containing them for treating cancer. AstraZeneca AB, PCT Patent Publication WO 2007119055, 25 Oct. 2007.
[2] Phenol starting materials may be prepared according to literature procedures, see e.g.: Oshima, K., et al. Nitrogen-containing heterocyclic compounds as potassium channel blockers and their preparation, pharmaceutical compositions and us in the treatment of arrhythmia. Otsuka Pharmaceutical Co., Ltd., PCT Patent Publication WO 2011021726, 24 Feb. 2011.
[3] Phenol starting materials may be prepared according to literature procedures, see e.g.: Teixeira, R. R., et al. J. Mol. Struct. 2013, 1061, 61-68.
[4] Phenol starting materials may be prepared according to literature procedures, see e.g.: Behke, M. L., et al. Preparation of isoxazoline derivatives for use as fatty acid amide hydrolase inhibitors. Infinity Pharmaceuticals, Inc., PCT Patent Publication WO 2010135360, 25 Nov. 2010.
[5] Phenol starting materials may be prepared according to literature procedures, see e.g.: Brown, A., et al. Preparation of sulfonamide derivatives as Nav1.7 inhibitors. Pfizer Limited, PCT Patent Publication WO 2012007869, 19 Jan. 2012.
[6] Phenol starting materials may be prepared according to literature procedures, see e.g.: Machinaga, N., et al. Preparation of heteroarylamide derivatives as immunosuppressants with S1P agonist activity. Daiichi Sankyo Company, Ltd., Japan, PCT Patent Publication WO 2007129745, 15 Nov. 2007.

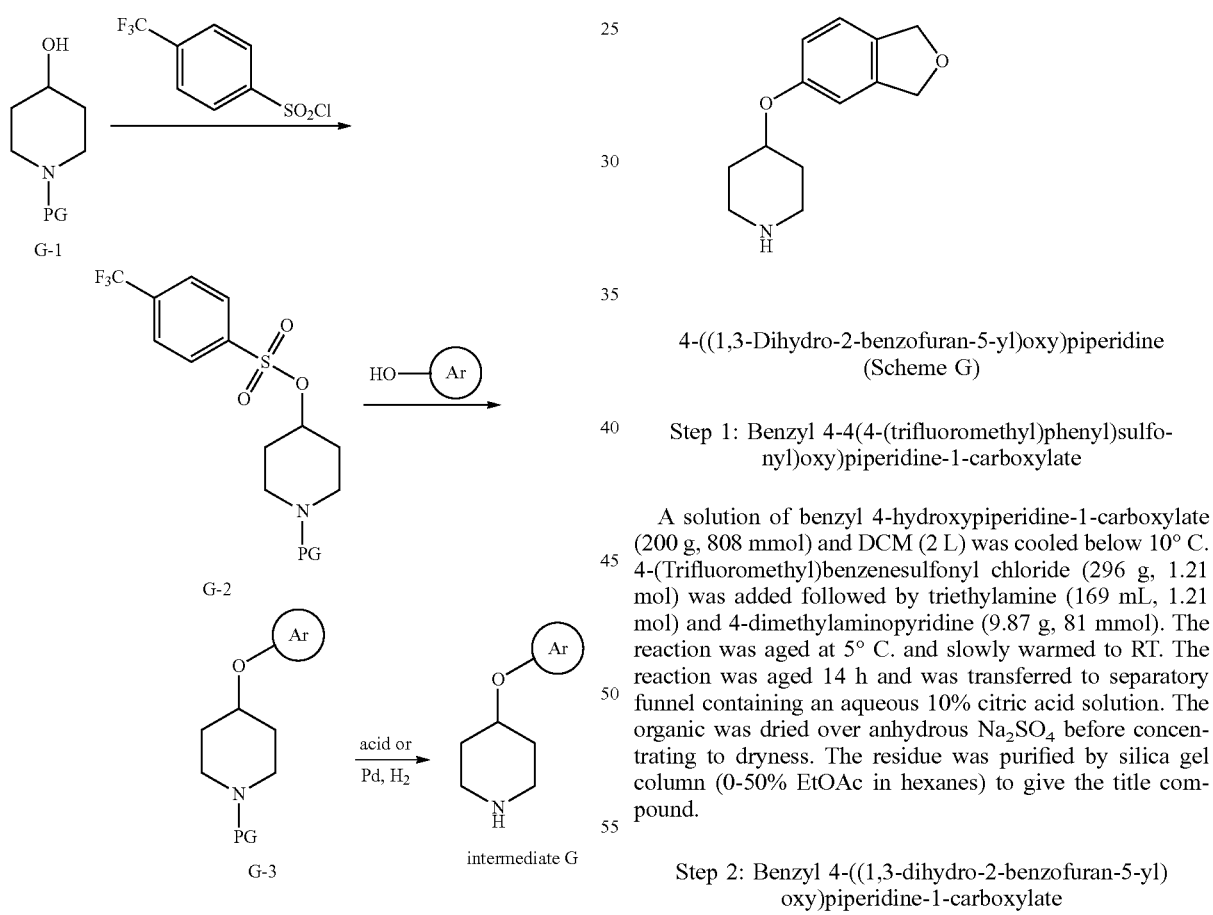

4-((1,3-Dihydro-2-benzofuran-5-yl)oxy)piperidine (Scheme G)

Step 1: Benzyl 4-4(4-(trifluoromethyl)phenyl)sulfonyl)oxy)piperidine-1-carboxylate A solution of benzyl 4-hydroxypiperidine-1-carboxylate (200 g, 808 mmol) and DCM (2 L) was cooled below 10° C. 4-(Trifluoromethyl)benzenesulfonyl chloride (296 g, 1.21 mol) was added followed by triethylamine (169 mL, 1.21 mol) and 4-dimethylaminopyridine (9.87 g, 81 mmol). The reaction was aged at 5° C. and slowly warmed to RT. The reaction was aged 14 h and was transferred to separatory funnel containing an aqueous 10% citric acid solution. The organic was dried over anhydrous $Na_2SO_4$ before concentrating to dryness. The residue was purified by silica gel column (0-50% EtOAc in hexanes) to give the title compound.

Step 2: Benzyl 4-((1,3-dihydro-2-benzofuran-5-yl)oxy)piperidine-1-carboxylate

Intermediate G is prepared from a commercial alcohol G-1 (wherein PG is an amine protecting group), which after reaction with 4-(trifluoromethyl)benzenesulfonyl chloride forms adduct G-2. Displacement of sulfone G-2 by a known or prepared phenol or alcohol (wherein Ar is an aromatic or heteroaromatic ring of $R^1$) is carried out under the action of $K_3PO_4$ or $Cs_2CO_3$ to provide ether G-3. Deprotection under acidic or reductive conditions provides intermediate G.

To a flask was added benzyl 4-(((4(trifluoromethyl)phenyl)sulfonyl)oxy)piperidine-1-carboxylate (73.3 g, 165 mmol) and 1,3-dihydro-2-benzofuran-5-ol (15 g, 110 mmol), a fine powder of potassium tribasic phosphate (35.1 g, 165 mmol) and MeCN (150 mL). After being stirred at 60° C. for an appropriate period, the mixture was cooled and poured into water and then extracted with EtOAc. The organic layer was dried over anhydrous $Na_2SO_4$ before concentrating to dryness. The residue was purified by silica gel column (0-50% EtOAc in hexanes) to give the title compound.

Step 3: 4-((1,3-Dihydro-2-benzofuran-5-yl)oxy)piperidine

To a solution of benzyl 4-((1,3-dihydro-2-benzofuran-5-yl)oxy)piperidine-1-carboxylate (9.7 g, 27.4 mmol) in methanol (194 mL) was added Pd/C (10 wt %, 0.877 g, 2.74 mmol) under an atmosphere of $N_2(g)$. The system was purged and was placed under a balloon of $H_2(g)$ with stirring at RT. Upon completion, the reaction was filtered and the filtrate was concentrated to provide the title compound, which was carried forward without further purification. MS: 220 (M+1).

The following intermediates in table G were prepared according to scheme G using the procedure outlined in the synthesis of intermediate G1. Alternative conditions are: (1) using tert-butyl 4-hydroxypiperidine-1-carboxylate in step 1, (2) using the combination of cesium carbonate as a base and DMF as the solvent in step 2, and (3) using TFA or HCl for N-Boc deprotection. In some cases, step 3 may be omitted to furnish the N-protected piperidine intermediate.

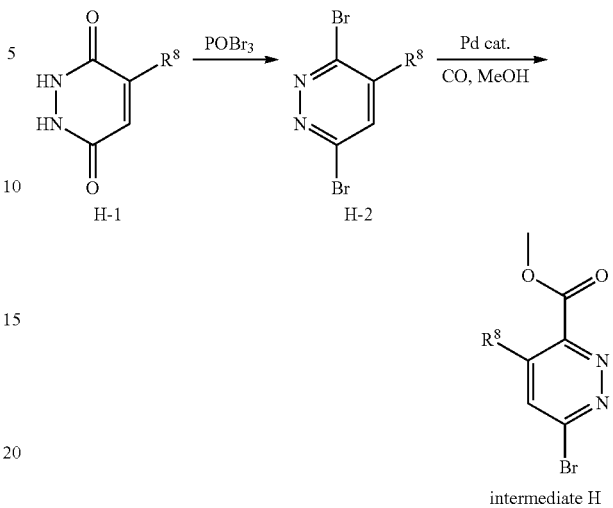

SCHEME H

Intermediate H is prepared from a commercial pyrazine which is transformed to the corresponding dibromide after reaction with phosphoryl tribromide. A palladium-catalyzed carbonylation provided intermediate H.

TABLE G

| Intermediate | Structure | Name | MS (M + 1) |
|---|---|---|---|
| G2 | 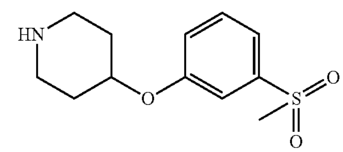 [SMILES: CS(=O)(=O)c1cccc(OC2CCNCC2)c1] | 4-(3-(methylsulfonyl)-phenoxy)piperidine | 256 |
| G3 | 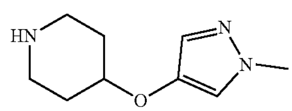 | 4-((1-methyl-1H-pyrazol-4-yl)oxy)piperidine | 182 |
| G4 | 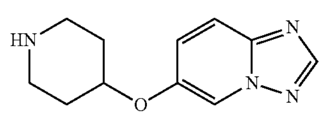 [SMILES: c1nc2ccc(OC3CCNCC3)cn2n1] | 6-(piperidin-4-yloxy)-[1,2,4]triazolo[1,5-a]pyridine | 219 |
| G5 | 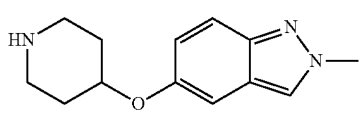 [SMILES: Cn1cc2cc(OC3CCNCC3)ccc2n1] | 2-methyl-5-(piperidin-4-yloxy)-2H-indazole | 232 |
| G6 | 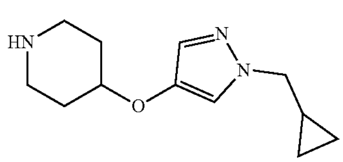 [SMILES: c1nn(CC2CC2)cc1OC1CCNCC1] | 4-((1-(cyclopropylmethyl)-1H-pyrazol-4-yl)oxy)piperidine | 222 |

INTERMEDIATE H

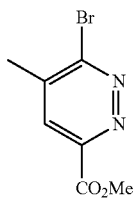

Methyl 6-bromo-5-methylpyridazine-3-carboxylate
(Scheme H)

Step 1: 3,6-Dibromo-4-methylpyridazine

A solution of 4-methylpyridazine-3,6-dione (150 g, 1.21 mol) and phosphoryl tribromide (694 g, 2.42 mol) in 1,4-dioxane (2 L) heated to reflux for 5 h with stirring. The reaction was cooled to RT and was then quenched by addition of water (2.5 L). The resulting solution was extracted with ethyl acetate (3×2 L) and the combined organic layer was washed with aqueous sodium bicarbonate (saturated, 2×1.5 L) and brine (2×1.5 L) before being dried over anhydrous sodium sulfate and concentrated. The residue was purified by a silica gel chromatography (1:5 EtOAc/petroleum ether) to afford the title compound.

Step 2: Methyl 6-bromo-5-methylpyridazine-3-carboxylate

To a pressure tank reactor (10 atm) was charged with a solution of 3,6-dibromo-4-methylpyridazine (70 g, 278 mmol) in methanol (1 L), Pd(dppf)Cl$_2$ (700 mg, 0.96 mmol) and triethylamine (83.8 g, 829.7 mmol). The reaction was stirred under a CO atmosphere for 15 h at 60° C. The resulting mixture was concentrated under vacuo and purified by silica gel chromatography (20:1-7:1 EtOAc/petroleum ether) to yield the title compound. $^1$H NMR (300 MHz, DMSO-d$_6$): δ 2.45-2.51 (s, 3H), 3.96 (s, 3H), 8.24 (s, 1H).

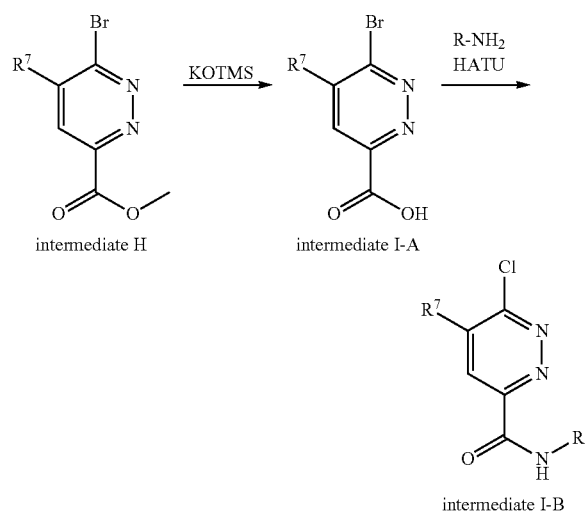

Intermediate I is prepared from intermediate H which is saponified to carboxylic acid intermediate I-A and is then coupled to commercial amines in the presence of a coupling agent such as HATU to yield amide intermediate I-B.

INTERMEDIATE IA

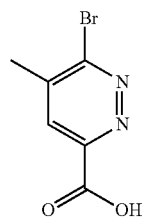

6-Bromo-5-methylpyridazine-3-carboxylic acid (Scheme I) To a solution of methyl methyl 6-bromo-5-methylpyridazine-3-carboxylate (2 g, 8.66 mmol) in DCM (10 mL) and THF (20 mL) was added potassium trimethylsilanolate (2.22 g, 17.3 mmol). The mixture was stirred at 27° C. for 12 h and the volatiles were removed under reduced pressure. Aqueous citric acid (1 M) was added to adjust the pH-2 and the mixture was extracted with dichloromethane (30 mL×3), dried over anhydrous sodium sulfate, filtered and the filtrate was concentrated in vacuo to give the title compound. MS: 217, 219 (M+1).

INTERMEDIATE IB

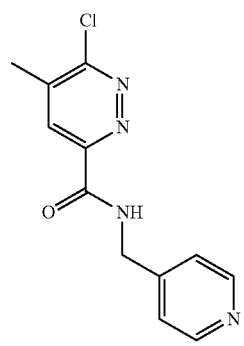

6-Chloro-5-methyl-N-(pyridin-4-ylmethyl)pyridazine-3-carboxamide (Scheme I)

To a solution of 6-bromo-5-methylpyridazine-3-carboxylic acid (intermediate IA, 1.3 g, 5.99 mmol) in DCM (12 mL) was added oxalyl dichloride (1.52 g, 11.9 mmol) at 0° C. The resulting mixture was stirred at RT for 30 min and was then concentrated to dryness. This residue was dissolved in DCM (5 mL) and was added to a solution of pyridin-4-ylmethanamine (0.713 g, 6.59 mmol) and triethylamine (2.43 g, 24 mmol) in DCM (12 mL) at 0° C. The resulting suspension was stirred for 8 h at RT before quenching with water (17 mL) and extracting with EtOAc (17 mL×3). The combined organic layers were washed with water (20 mL) and brine (20 mL), dried over anhydrous sodium sulfate, filtered and concentrated. The crude material was purified by silica gel chromatography (30:1-10:1 petroleum ether:EtOAc) to yield the title compound. MS: 263 (M+1).

SCHEME J

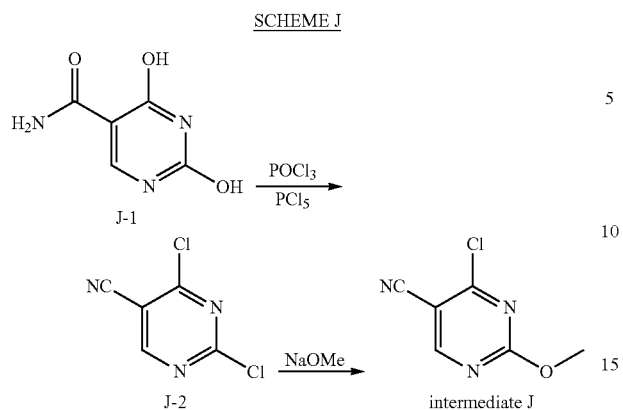

Intermediate J is prepared according to Scheme J from intermediate B after treatment with base followed by an alkyl halide. Depending on the reagents and conditions utilized the mono-, bis- and tris-adducts maybe obtained.

INTERMEDIATE J1

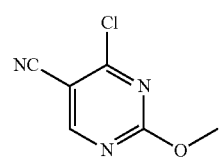

4-Chloro-2-methoxypyrimidine-5-carbonitrile
(Scheme J)

Step 1: 2,4-Dichloropyrimidine-5-carbonitrile

A mixture of 2,4-dihydroxypyrimidine-5-carboxamide (1.1 kg, 7.1 mol) was added into POCl$_3$ (9 L) under an inert nitrogen atmosphere and was heated to 100° C. After 15 h, the reaction was concentrated and the residue was diluted with EtOAc and ice water. Aqueous ammonium hydroxide was used to adjust the pH-5 and the mixture was extracted with EtOAc (1 L×3), washed with brine (600 mL×3), dried over anhydrous sodium sulfate, and concentrated. The residue was purified by silica gel column chromatography (30:1 petroleum ether:EtOAc) to yield the title compound.

Step 2: 4-Chloro-2-methoxypyrimidine-5-carbonitrile 2,4-Dichloropyrimidine-5-carbonitrile (180 g, 1.04 ml) was added to THF (2.7 L) followed by the batchwise addition of NaOMe (58.9 g, 1.09 mol) at 0° C. The reaction was aged for 6 h at 10° C. and the volatiles were removed under reduced pressure. The residue was diluted with water (1.2 L) and extracted with EtOAc (300 mL×3), washed with brine (200 mL×3), dried over anhydrous sodium sulfate, filtered and concentrated. The residue was purified by silica gel chromatography (30:1 petroleum ether:EtOAc) to afford the title compound. $^1$H NMR (400 MHz, DMSO-d$_6$): δ 9.05 (s, 1H), 4.10 (s, 3H).

SCHEME K

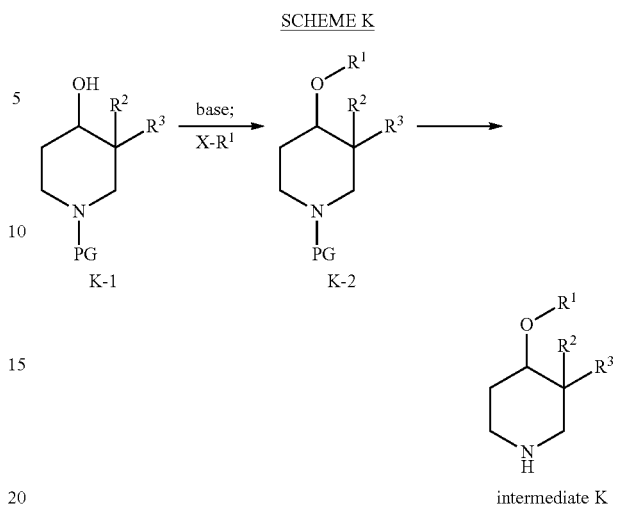

Intermediate K is prepared according to Scheme K from N-protected piperidine alcohol K-1 in a two-step procedure involving base-mediated alkylation to form adduct K-2 and subsequent deprotection to reveal the piperidine amine.

INTERMEDIATE K

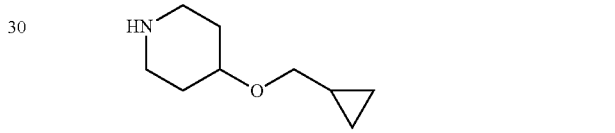

4-(Cyclopropylmethoxy)piperidine (Scheme K)

Step 1: tert-Butyl 4-(cyclopropylmethoxy)piperidine-1-carboxylate

To a solution of tert-butyl 4-hydroxypiperidine-1-carboxylate (400 mg, 1.987 mmol) in DMF (4 mL) was added sodium hydride (95 mg, 2.39 mmol, 60%) at 0° C. The reaction was stirred for 1 h before (bromomethyl)cyclopropane (322 mg, 2.39 mmol) and sodium iodide (14.9 mg, 0.099 mmol) were added. The reaction was stirred for 20 h at RT and then the mixture was treated with water (25 mL) and extracted with DCM (25 mL×3). The combined organic layers were dried over anhydrous sodium sulfate, filtered and concentrated. The residue was purified by flash silica gel chromatography (0-25% THF in petroleum ether) to give the title compound.

Step 2: 4-(Cyclopropylmethoxy)piperidine

A solution of tert-butyl 4-(cyclopropylmethoxy)piperidine-1-carboxylate (290 mg, 1.136 mmol) in 4 M HCl in EtOAc (3 mL) was stirred at RT for 1 h. Volatiles were removed from the reaction under reduced pressure. The residue was dissolved in MeOH (2 mL) and basified by saturated aqueous NaHCO$_3$ to pH 8. The mixture was concentrated and the residue was treated with EtOAc (5 mL), filtered and concentrated to afford the title compound. $^1$H NMR (400 MHz, CDCl$_3$): δ 3.50-3.53 (1H, m), 3.28 (2H, d, J=6.8 Hz), 3.17-3.21 (2H, m), 2.87-2.90 (2H, m), 1.99-

2.04 (2H, m), 1.67-1.71 (2H, m), 1.06-1.03 (1H, m), 0.52-0.57 (2H, m), 0.17-0.21 (2H, m).

SCHEME L

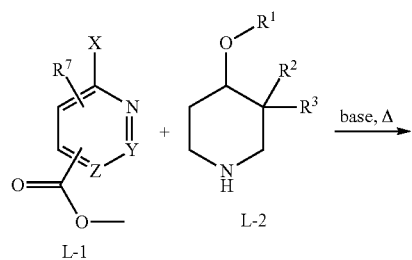

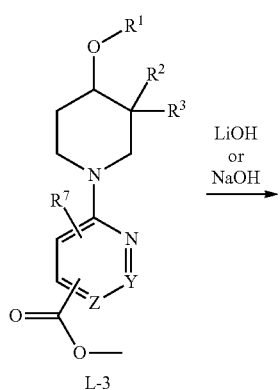

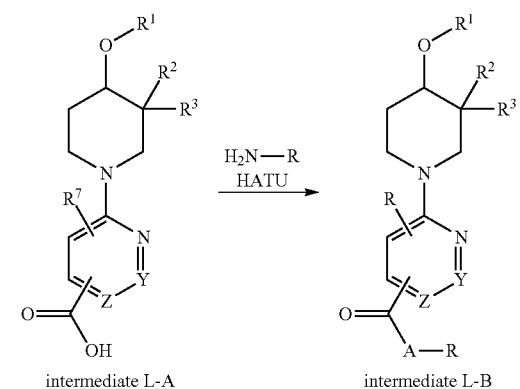

Intermediate L is prepared according to Scheme L from ester L-1 via a S$_N$Ar reaction with a known or prepared piperdine L-2 to provide adduct L-3. Saponification of ester L-3 to the corresponding acid intermediate L-A is followed by an amide coupling reaction carried out with a commercially available amine to afford intermediate L-B.

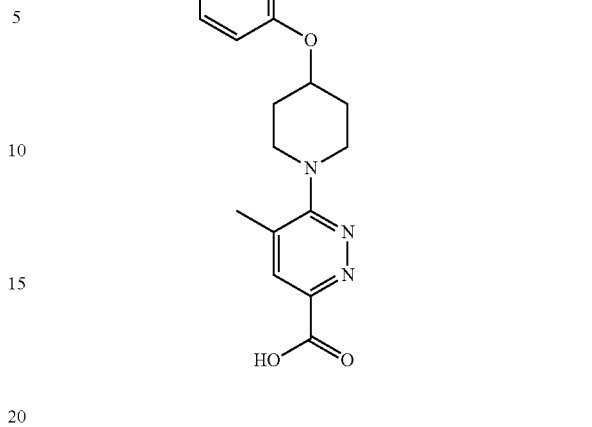

INTERMEDIATE LA1

6-(4-((6-Methoxypyridin-3-yl)oxy)piperidin-1-yl)-5-methylpyridazine-3-carboxylic Acid (Scheme L)

Step 1: Methyl 6-(4-((6-methoxypyridin-3-yl)oxy)piperidin-1-yl)-5-methylpyridazine-3-carboxylate To a solution of methyl 6-bromo-5-methylpyridazine-3-carboxylate (500 mg, 2.164 mmol) in dioxanes (15 mL) was added 2-methoxy-5-(piperidin-4-yloxy)pyridine hydrochloride (583 mg, 2.38 mmol) and DIPEA (1.13 mL, 6.49 mmol). The reaction was stirred for 18 h at 120° C. before the volatiles were removed under reduced pressure. The resultant residue was purified by silica gel chromatography (0-30% EtOAc/petroleum ether) to afford the title compound.

Step 2: 6-(4-((6-Methoxypyridin-3-yl)oxy)piperidin-1-yl)-5-methylpyridazine-3-carboxylic Acid To a solution of methyl 6-(4-((6-methoxypyridin-3-yl)oxy)piperidin-1-yl)-5-methylpyridazine-3-carboxylate (800 mg, 2.232 mmol) in MeOH (10 mL) and water (1 mL) was added sodium hydroxide (179 mg, 4.46 mmol). The reaction was stirred for 4 h at RT before aqueous HCl (4 N) was added to adjust the pH-5-6. The mixture was concentrated under reduced pressure and the material was partitioned in water (30 mL) and extracted with EtOAc (15 mL×3). The combined organic layers were dried over anhydrous sodium sulfate, filtered and the filtrate was concentrated in vacuo to afford the title compound. MS: 345 (M+1).

The following intermediates in table LA were prepared according to scheme L using the procedure outlined in the synthesis of intermediate LA1 using known or prepared 2-fluoro-, 2-chloro-, or 2-bromoheterocycles.

TABLE LA

| Intermediate | Structure | Name | MS (M + 1) |
|---|---|---|---|
| LA2 | 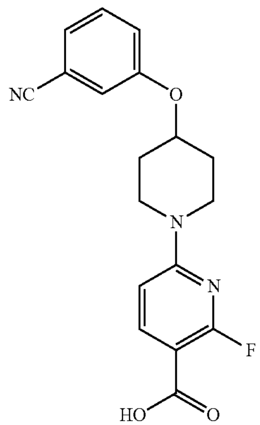 [SMILES: N#Cc1cccc(OC2CCN(c3ccc(C(=O)O)c(F)n3)CC2)c1] | 6-(4-(3-cyanophenoxy)piperidin-1-yl)-2-fluoronicotinic acid | 342 |

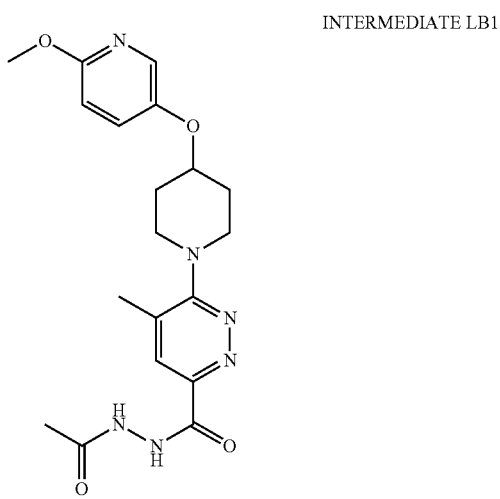 [SMILES: COc1ccc(OC2CCN(c3nnc(C(=O)NNC(C)=O)cc3C)CC2)cn1]

INTERMEDIATE LB1

N-Acetyl-6-(4-(((6-methoxypyridin-3-yl)oxy)piperidin-1-yl)-5-methylpyridazine-3-carbohydrazide (Scheme L)

To a solution of 6-(4-(((6-methoxypyridin-3-yl)oxy)piperidin-1-yl)-5-methylpyridazine-3-carboxylic acid (intermediate LA1.50 mg, 0.145 mmol) in DMF (4 mL) was added acetohydrazide (12.9 mg, 0.174 mmol), TBTU (69.9 mg, 0.218 mmol), TEA (0.101 mL, 0.726 mmol). The mixture was stirred at RT for 8 h before the reaction was diluted with water (50 mL, and extracted with EtOAc (50 mL×3). The combined organics were dried over anhydrous sodium sulfate, filtered and the filtrate was concentrated. The resultant residue was purified by silica gel chromatography (8/1 DCM/MeOH=8:1) to afford the title compound. MS: 401 (M+1).

The following intermediates in table LB were prepared according to scheme L using the procedure outlined in the synthesis of intermediate LB1 using commercially available amines or ammonium chloride in the amide coupling procedure.

TABLE LB

| Intermediate | Structure | Name | MS (M + 1) |
|---|---|---|---|
| LB2 | 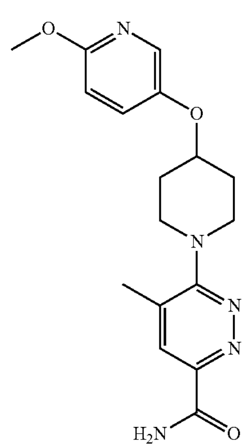 [SMILES: COc1ccc(OC2CCN(c3nnc(C(N)=O)cc3C)CC2)cn1] | 6-(4-((6-methoxypyridin-3-yl)oxy)piperidin-1-yl)-5-methylpyridazine-3-carboxamide | 344 |

TABLE LB-continued

| Intermediate | Structure | Name | MS (M + 1) |
|---|---|---|---|
| LB3 | 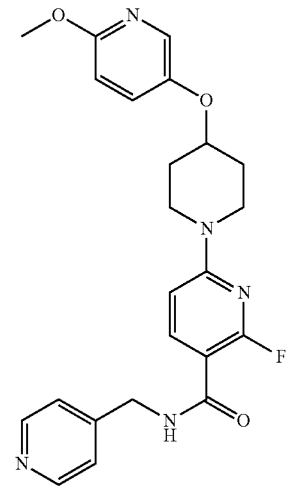 [SMILES: COc1ccc(OC2CCN(c3ccc(C(=O)NCc4ccncc4)c(F)n3)CC2)cn1] | 2-fluoro-6-(4-((6-methoxypyridin-3-yl)oxy)piperidin-1-yl)-N-(pyridin-4-ylmethyl)nicotinamide | 432 |

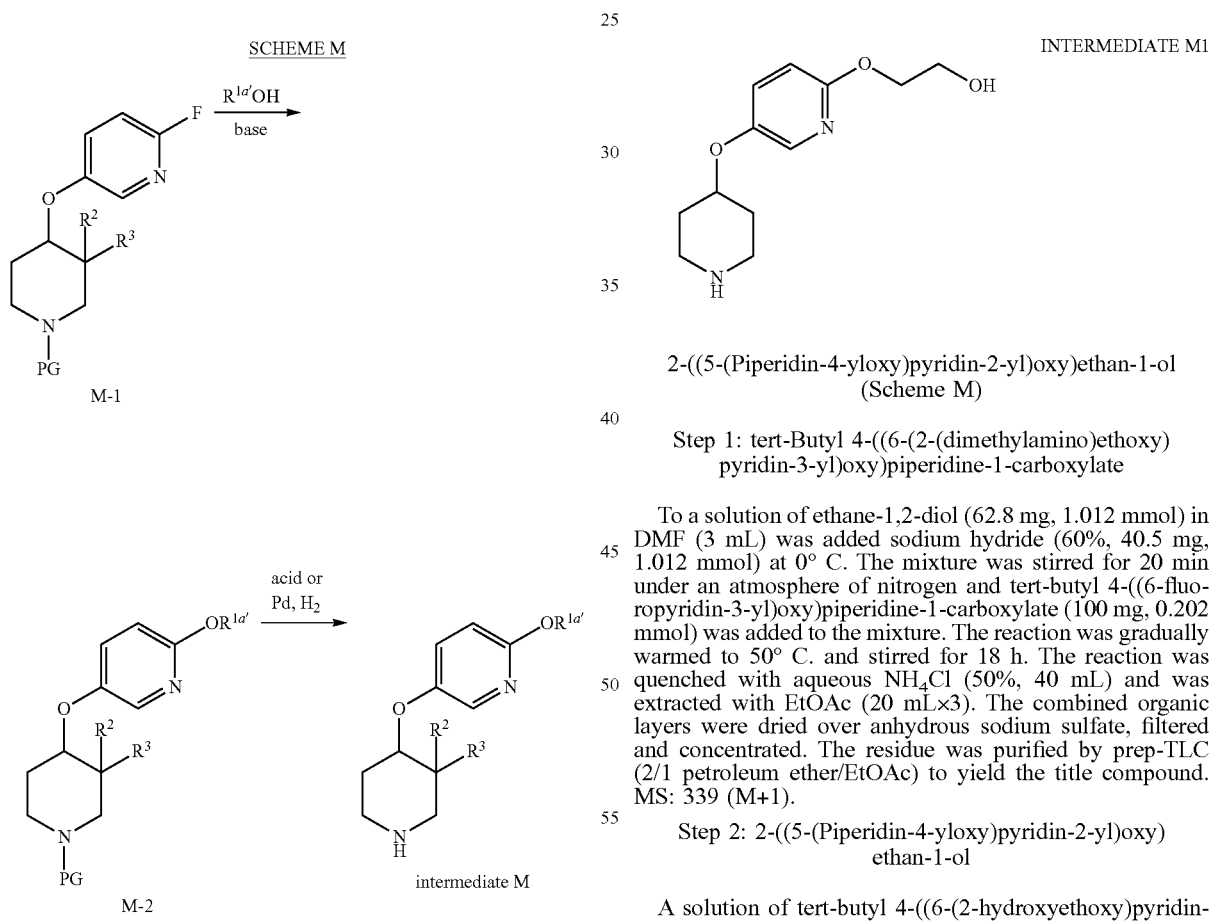

2-((5-(Piperidin-4-yloxy)pyridin-2-yl)oxy)ethan-1-ol (Scheme M)

Step 1: tert-Butyl 4-((6-(2-(dimethylamino)ethoxy)pyridin-3-yl)oxy)piperidine-1-carboxylate To a solution of ethane-1,2-diol (62.8 mg, 1.012 mmol) in DMF (3 mL) was added sodium hydride (60%, 40.5 mg, 1.012 mmol) at 0° C. The mixture was stirred for 20 min under an atmosphere of nitrogen and tert-butyl 4-((6-fluoropyridin-3-yl)oxy)piperidine-1-carboxylate (100 mg, 0.202 mmol) was added to the mixture. The reaction was gradually warmed to 50° C. and stirred for 18 h. The reaction was quenched with aqueous NH$_4$Cl (50%, 40 mL) and was extracted with EtOAc (20 mL×3). The combined organic layers were dried over anhydrous sodium sulfate, filtered and concentrated. The residue was purified by prep-TLC (2/1 petroleum ether/EtOAc) to yield the title compound. MS: 339 (M+1).

Step 2: 2-((5-(Piperidin-4-yloxy)pyridin-2-yl)oxy)ethan-1-ol

A solution of tert-butyl 4-((6-(2-hydroxyethoxy)pyridin-3-yl)oxy)piperidine-1-carboxylate (50 mg, 0.148 mmol) in HCl (4 M in MeOH, 2 mL) was stirred at 20° C. for 1 h. The reaction was concentrated to give the title compound as the bis-HCl salt. MS: 239 (M+1).

The following intermediates in table M were prepared according to scheme M using the procedure outlined in the synthesis of intermediate M1 using commercially available alcohols in step 1. In cases where additional chemical manipulations are required, step 2 may be omitted.

Intermediate M is prepared according to scheme M from ether M-1, which is prepared using 6-fluoropyridin-3-ol in step 1 of the procedure outlined in the synthesis of intermediate F. S$_N$Ar with an alcohol or amine in the presence of base provides adduct M-2. Deprotection of piperidine amine M-2 provides intermediate M.

TABLE M

| Intermediate | Structure | Name | MS (M + 1) |
|---|---|---|---|
| M2 | 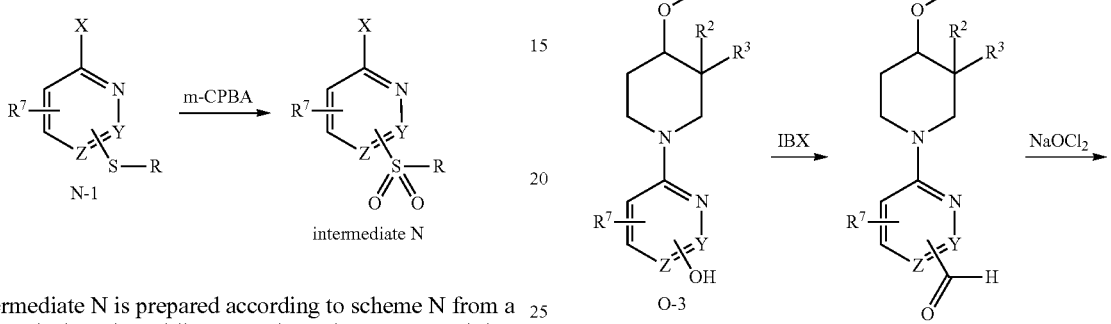 | 2-methyl-1-((5-(piperidin-4-yloxy)pyridin-2-yl)oxy)propan-2-amine | 266 |

SCHEME N

intermediate N

Intermediate N is prepared according to scheme N from a 2-halo substituted pyridine or other nitrogen containing heterocycle (Y or Z=N or C) N-1, which is oxidized to the corresponding sulfone after reaction with m-CPBA.

INTERMEDIATE N 4,6-Dichloro-5-methyl-2-(methylsulfonyl)pyrimidine (Scheme N)

To a solution of 4,6-dichloro-5-methyl-2-(methylthio)pyrimidine (pyrimidine may be prepared according to literature procedures, see e.g.: Shipe, William D.; et al. *J. Med. Chem.* 2015, 58, 7888-7894) (6.3 g, 30.1 mmol) in DCM (100 mL) was added 3-chloroperoxybenzoic acid (14.9 g, 66.3 mmol). The resulting suspension was stirred at RT for 15 h before being partitioned with water and DCM. The organic phase was washed with aqueous sodium bicarbonate and brine, dried over anhydrous sodium sulfate, and concentrated. The resultant material was purified by silica gel chromatography (EtOAc/hexanes) to provide the title compound. MS: 241 (M+1).

SCHEME O

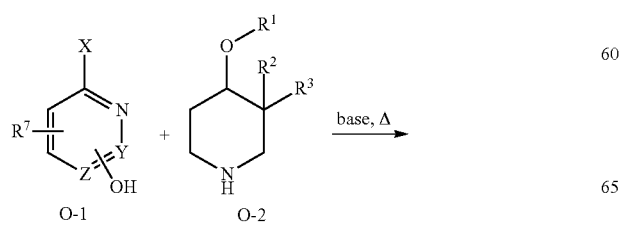

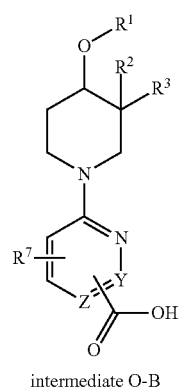

intermediate O-B

Intermediate O is prepared according to scheme O from an S$_N$Ar reaction of prepared or known compounds O-1 and O-2. Adduct O-3 is oxidized by 2-iodoxybenzoic acid (IBX) to the corresponding aldehyde intermediate O-A. A second oxidation reaction of intermediate O-A under Pinnick reaction conditions provides intermediate O—B.

INTERMEDIATE OA1

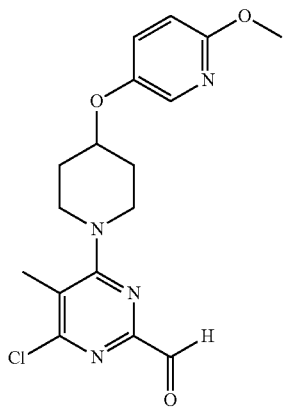

4-Chloro-6-(4-(((6-methoxypyridin-3-yl)oxy)piperidin-1-yl)-5-methylpyrimidine-2-carbaldehyde (Scheme O)

Step 1: 4-Chloro-6-(4-((6-methoxypyridin-3-yl)oxy)piperidin-1-yl)-5-methylpyrimidin-2-yl)methanol To (4,6-dichloro-5-methylpyrimidin-2-yl)methanol (intermediate B, 3 g, 15.5 mmol) and 2-methoxy-5-(piperidin-4-yloxy)pyridine hydrochloride (3.80 g, 15.5 mmol) in DMF (38.9 mL) was added DIPEA (5.43 mL, 31.1 mmol). The reaction was heated to 70° C. for 6 h before cooling to RT. The mixture was quenched with water and was diluted with DCM. The organic phase was separated, dried over anhydrous sodium sulfate, filtered, and concentrated under reduced pressure. The residue was purified by column chromatography on silica gel (0-40% 3:1 EtOAc:EtOH in hexanes) to give the title compound. MS: 365 (M+1).

Step 2: 4-Chloro-6-(4-((6-methoxypyridin-3-yl)oxy)piperidin-1-yl)-5-methylpyrimidine-2-carbaldehyde To (4-chloro-6-(4-(((6-methoxypyridin-3-yl)oxy)piperidin-1-yl)-5-methylpyrimidin-2-yl)methanol (0.45 g, 1.23 mmol) in DCM (12.3 mL) and THF (12.3 mL) was added IBX polystyrene (4.49 g, 4.93 mmol). The reaction was stirred for 24 h at RT before the heterogenous mixture was filtered. The filtrate was concentrated to afford the title compound. MS: 363 (M+1).

INTERMEDIATE OB1

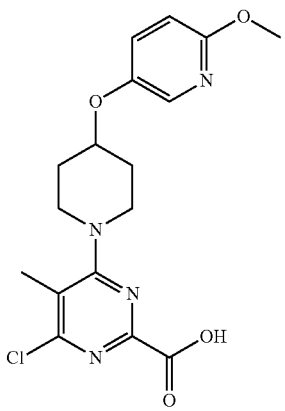

N-(2-(benzyloxy)ethyl)-5-(piperidin-4-yloxy)pyridin-2-amine (Scheme O)

4-Chloro-6-(4-(((6-methoxypyridin-3-yl)oxy)piperidin-1-yl)-5-methylpyrimidine-2-carbaldehyde (vide supra for preparation of intermediate OA) (0.397 g, 1.10 mmol) was dissolved in tert-butanol (5 mL) and MeCN (1.7 mL). To this solution was added 2-methyl-2-butene (0.921 mL, 11.0 mmol) followed by a solution of sodium chloride (80%, 0.620 g, 5.48 mmol) and potassium dihydrogen phosphate (0.746 g, 5.48 mmol) in water (4.5 mL). The reaction was stirred at RT for 2 h before quenching with aqueous sodium thiosulfate (saturated). The mixture was diluted with 1:9 MeOH:DCM and the organic was separated, dried over anhydrous sodium sulfate, filtered, and concentrated under reduced pressure to obtain the title compound. MS: 379 (M+1).

The following intermediates in table 0 were prepared according to scheme 0 using the procedure outlined in the synthesis of intermediate OB1.

TABLE O

| Intermediate | Structure | Name | MS (M + 1) |
|---|---|---|---|
| OB2 | (structure shown) | 4-bromo-6-(4-(((6-methoxypyridin-3-yl)oxy)piperidin-1-yl)-5-methylpyrimidine-2-carboxylic acid | 423, 425 |

SCHEME P

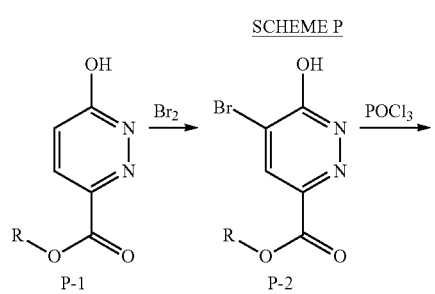

Intermediate P is prepared from known phenol P-1 which is reacted with NBS to yield bromide P-2. Reaction of phenol P-2 with phosphoryl chloride provide intermediate P.

INTERMEDIATE P1

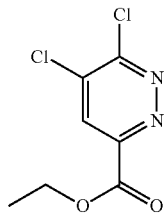

Ethyl 5,6-dichloropyridazine-3-carboxylate (Scheme P)

Step 1: Ethyl 5-bromo-6-oxo-1,6-dihydropyridazine-3-carboxylate

To a mixture of compound ethyl 6-oxo-1,6-dihydropyridazine-3-carboxylate (41 g, 244 mmol) and potassium acetate (71.8 g, 731 mmol) in acetic acid (400 mL) was added bromine (50.2 mL, 975 mmol) dropwise at 0° C. The reaction was then stirred for 24 h at 80° C. before cooling to RT and quenching with aqueous Na$_2$S$_2$O$_3$ (saturated, 500 mL). The mixture was extracted with ethyl acetate (500 mL×3) and DCM/MeOH (10%, 500 mL×2). The organic layers were washed with aqueous NaHCO$_3$ (saturated, 600 mL) and brine (500 mL), dried over anhydrous sodium sulfate, filtered and concentrated to afford the title compound.

Step 2: Ethyl 5,6-dichloropyridazine-3-carboxylate

A mixture of ethyl 5-bromo-6-hydroxypyridazine-3-carboxylate (1.7 g, 6.88 mmol) in DCM (10 mL) was added phosphorous oxychloride (52.8 g, 344 mmol) dropwise RT. The reaction was stirred at 90° C. for 18 h before the reaction was cooled to RT and treated with ice water. The mixture was extracted with ethyl acetate (15 mL×3) and the combined organic layers were washed with water and brine, dried over anhydrous sodium sulfate, filtered and concentrated. The crude was purified by silical gel chromatography (30:1-10:1 petroleum ether/EtOAc) to afford the title compound. MS: 221 (M+1).

The following intermediates in table P were prepared according to scheme P using the procedure outlined in the synthesis of intermediate P 1.

TABLE P

| Intermediate | Structure | Name | MS (M + 1) |
| --- | --- | --- | --- |
| P2 | 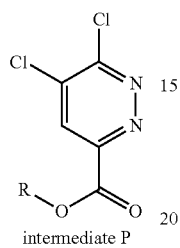 | methyl 5,6-dichloropyridazine-3-carboxylate | 207 |

SCHEME Q

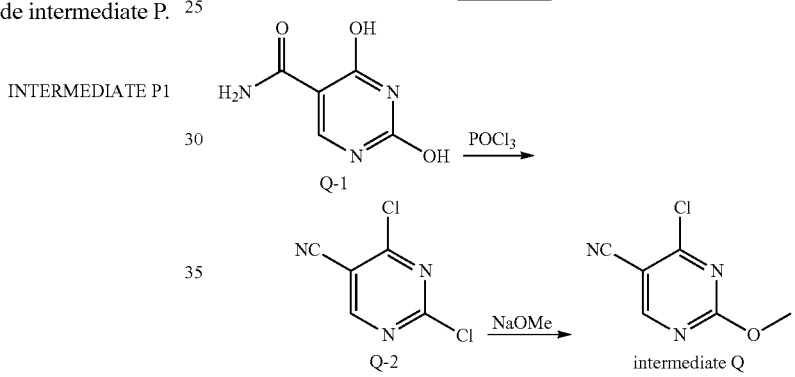

Intermediate Q is prepared from a product from pyrimidine Q-1 which is exposed to phosphoryl chloride to afford the corresponding nitrile product Q-2 with subsequent S$_N$Ar reaction with sodium methoxide.

INTERMEDIATE Q

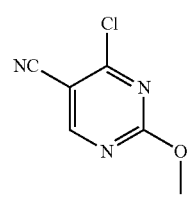

4-Chloro-2-methoxypyrimidine-5-carbonitrile (Scheme Q)

Step 1: 2,4-Dichloropyrimidine-5-carbonitrile 2,4-Dihydroxypyrimidine-5-carboxamide (1.10 kg, 7.1 mol) was added into POCl$_3$ (9 L) and the reaction was heated to 100° C. and stirred for 15 under an inert nitrogen atmosphere. After concentration, the residue was taken up in EtOAc and ice water, and aqueous ammonium hydroxide was added until pH-5. The mixture was filtered and extracted with EtOAc (3×1 L), washed with brine (3×600 mL), dried over anhydrous sodium sulfate, filtered and concentrated to dryness. The residue was purified by silica gel column chromatography (30:1 petroleum ether:EtOAc) to afford the title compound.

Step 2:
4-Chloro-2-methoxypyrimidine-5-carbonitrile 2,4-Dichloropyrimidine-5-carbonitrile (180 g, 1.04 mol) was added to THF (2.7 L) followed by the batchwise addition of MeONa (58.9 g, 1.09 mol) at 0° C. The reaction was stirred for 6 h at 10° C. before concentration under reduced pressure. The mixture was quenched by water (1.2 L) and extracted with EtOAc (3×300 mL), washed with brine (3×200 mL), dried over anhydrous sodium sulfate, filtered and concentrated. The residue was purified by silica gel column chromatography (30:1 petroleum ether:EtOAc) to afford the title compound. $^1$H NMR (400 MHz, DMSO-$d_6$) δ: 4.10 (3H, s), 9.05 (1H, s).

SCHEME R

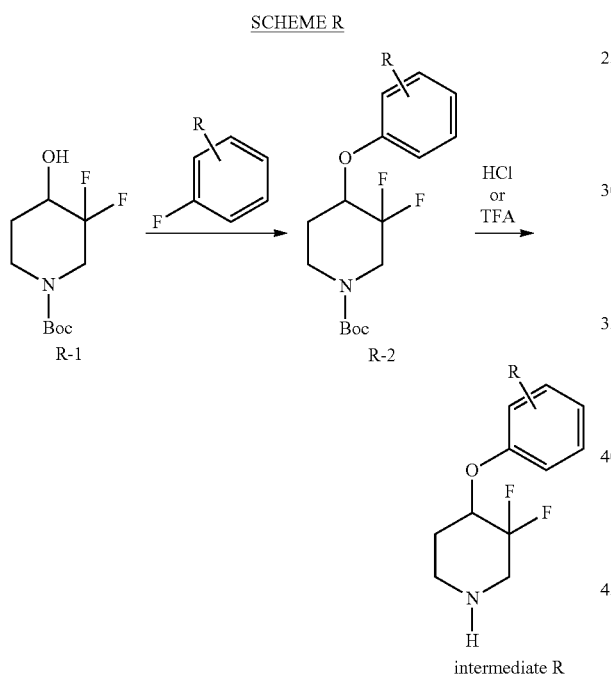

Intermediate R is prepared via $S_NAr$ reaction of commercially available piperidine R-1 and an electronically deficient substituted fluorobenzene followed by an acid-mediated deprotection provides intermediate R.

INTERMEDIATE R1

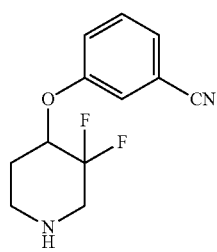

3-((3,3-Difluoropiperidin-4-yl)oxy)benzonitrile (Scheme R)

Step 1: tert-Butyl 4-(3-cyanophenoxy)-3,3-difluoropiperidine-1-carboxylate

To a solution of tert-butyl 3,3-difluoro-4-hydroxypiperidine-1-carboxylate (50 mg, 0.211 mmol) in THF (2 mL) was added potassium 2-methylpropan-2-olate (23.65 mg, 0.211 mmol). A solution of 3-fluorobenzonitrile (38.3 mg, 0.316 mmol) in DMF (0.5 mL) was added to the mixture and the resulting mixture was stirred at 50° C. for 1 h. The reaction was quenched with water (2 mL) and extracted with EtOAc (30 mL×3). The combined organic layers were washed with brine (50 m×3), dried over sodium sulfate, filtered, and concentrated in vacuo. The residue was purified by silica gel chromatography (50:1 to 1:1 petroleum ether:EtOAc) to give the title compound.

Step 2:
3-((3,3-Difluoropiperidin-4-yl)oxy)benzonitrile

To a solution of tert-butyl 4-(3-cyanophenoxy)-3,3-difluoropiperidine-1-carboxylate (30 mg, 0.089 mmol) in DCM (5 mL) was added TFA (0.020 mL, 0.266 mmol). The resulting mixture was stirred at 0° C. for 1 h. The volatiles were removed under reduced pressure and the residue was purified by silica gel chromatography (5:1 petroleum ether: EtOAc) to provide the title compound. MS: 239 (M+1).

SCHEME S

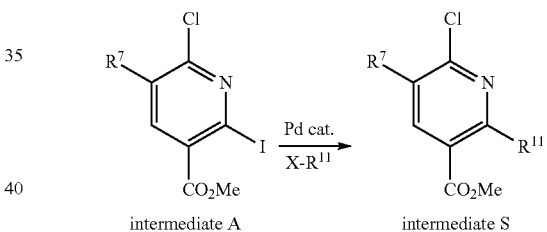

Intermediate S is prepared according to scheme S from intermediate A after a palladium-merdiated coupling reaction.

INTERMEDIATE S

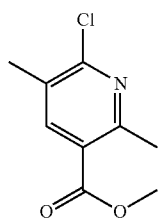

Methyl 6-chloro-2,5-dimethylnicotinate (Scheme S)

To a solution of methyl 6-chloro-2-iodo-5-methylnicotinate (300 mg, 0.963 mmol) in THF (10 mL) was added $PdCl_2(dppf)$ (70.5 mg, 0.096 mmol) and dry trimethylaluminium (2 M, 0.58 mL, 1.16 mmol) under an inert nitrogen atmosphere. The reaction was stirred at 80° C. for 16 h before the volatiles were removed under reduced pressure.

The residue was purified by silica gel chromatography (100:1-7:1 petroleum ether/EtOAc) to give the title compound. MS: 200 (M+1).

SCHEME T

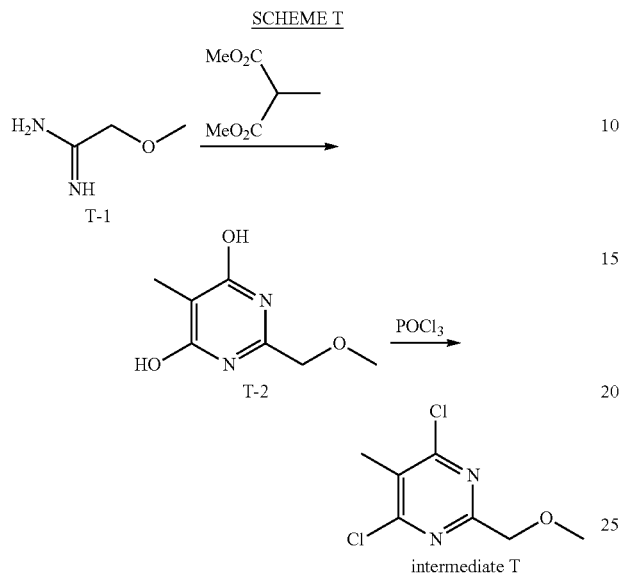

intermediate T

Intermediate T is prepared according to scheme T beginning with 2-methoxyethanimidamide T-1, which is condensed with dimethyl 2-methylmalonate to form pyrimidine T-2. Exposure to refluxing phosphoryl chloride converts T-2 to intermediate T.

INTERMEDIATE T 4,6-Dichloro-2-(methoxymethyl)-5-methylpyrimidine (Scheme T)

Step 1:
2-(Methoxymethyl)-5-methylpyrimidine-4,6-diol

A mixture of 2-methoxyacetimidamide (850 mg, 9.65 mmol), dimethyl 2-methylmalonate (2.12 g, 14.5 mmol) and sodium methoxide (30% in MeOH, 5.5 mL, 28.9 mmol) were stirred at reflux. The volatiles were removed and the title compound was carried forward without further purification.

Step 2:
4,6-Dichloro-2-(methoxymethyl)-5-methylpyrimidine 2-(Methoxymethyl)-5-methylpyrimidine-4,6-diol in a solution of excess phosphoryl chloride was stirred at reflux. After cooling to RT and removing the volatiles the crude material was purified by silica gel chromatography (EtOAc/hexanes) to afford the title compound. MS: 208 (M+1).

SCHEME U

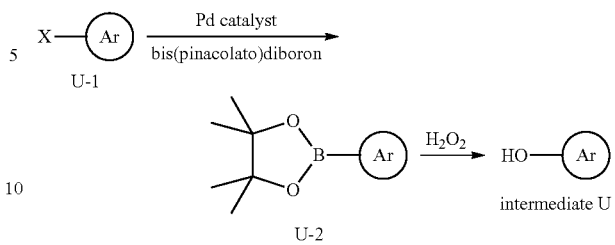

Intermediate U is prepared according to scheme U beginning with commercially available aryl halide U-1. A Miyaura borylation reaction provides boronic ester U-2 which is subsequently transformed by an oxidative hydroxylation to provide intermediate U.

INTERMEDIATE U1

1-(Cyclopropylmethyl)-1H-pyrazol-4-ol (Scheme U)

Step 1: Methyl 2-(1-methyl-5-(4,4,5,5-tetramethyl-1,3,2-dioxaborolan-2-yl)-1H-indazol-3-yl)acetate To a solution of methyl 2-(5-bromo-1-methyl-1H-indazol-3-yl)acetate (200 mg, 0.706 mmol) in dioxane (5 mL) was added [1,1'-bis(diphenylphosphino)ferrocene]dichloro palladium(II) (51.7 mg, 0.071 mmol), 4,4,4',4',5,5,5',5'-octamethyl-2,2'-bi(1,3,2-dioxaborolane) (359 mg, 1.413 mmol) and potassium acetate (139 mg, 1.413 mmol). The reaction mixture was degassed and purged with nitrogen. The reaction was stirred 2 h at 80° C. and the mixture was filtered and concentrated to give the title compound.

Step 2: 1-(Cyclopropylmethyl)-1H-pyrazol-4-ol

To a solution of 1-(cyclopropylmethyl)-4-(4,4,5,5-tetramethyl-1,3,2-dioxaborolan-2-yl)-1H-pyrazole (500 mg, 2.02 mmol) and NaOH (161 mg, 4.03 mmol) in THF (5 mL) at 0° C. was added hydrogen peroxide (30%, 457 mg, 4.03 mmol). After 30 min at 0° C., the mixture was diluted with aqueous $NaHSO_3$ (saturated, 20 mL) and extracted with EtOAc (70 mL×3). The combined organic layers were washed with water (40 mL) and brine (50 mL), dried over anhydrous sodium sulfate, filtered and concentrated. The residue was purified by silica gel chromatography (100:0-5:1 petroleum ether/EtOAc) to give the title compound. $^1$H NMR (400 MHz, $CDCl_3$): δ 6.89 (1H, s), 6.87 (1H, s), 3.55 (2H, d, J=6.8 Hz), 2.15 (1H, br s), 0.30 (2H, d, J=7.2 Hz), 0.21 (2H, d, J=5.2 Hz).

The following intermediates in table U were prepared according to scheme U using the procedure outlined in the synthesis of intermediate U1 using known or prepared halides. In cases where the boronic ester or acid is commercially available, the first step is omitted.

TABLE U

| Intermediate | Structure | Name | MS (M + 1) |
|---|---|---|---|
| U2 | 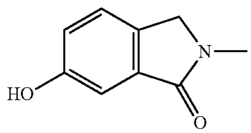 | 6-hydroxy-2-methylisoindolin-1-one | 164 |
| U3 | 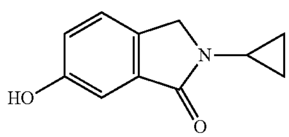 [SMILES: O=C1c2cc(O)ccc2CN1C1CC1] | 2-cyclopropyl-6-hydroxyisoindolin-1-one | 190 |
| U4[1] | 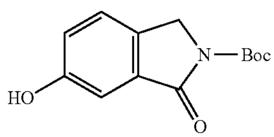 [SMILES: CC(C)(C)OC(=O)N1Cc2ccc(O)cc2C1=O] | tert-butyl 6-hydroxy-1-oxoisoindoline-2-carboxylate | NMR data[2] |
| U5[3] | 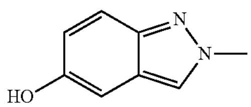 | 2-methyl-2H-indazol-5-ol | 149 |

[1] Starting bromide compound may be prepared according to literature procedures, see e.g.: Schwink, L., et al. Preparation of isoindolinone compounds as GPR119 modulators for the treatment of diabetes, obesity, dyslipidemia and related disorders. Sanofi, PCT Patent Publication WO WO 201515065, 8 Oct. 2015.
[2] $^1$H NMR (400 MHz, CDCl$_3$): δ 7.36 (1 H, s), 7.24 (1 H, d, J = 8.4 Hz), 7.11 (1 H, d, J = 6.8 Hz), 4.61 (2 H, s), 1.18 (9 H, s).
[3] Starting bromide compound may be prepared according to literature procedures, see e.g.: Wang, B. N-(1-Hydroxy-3-(pyrrolidinyl)propan-2-yl)pyrrolidine-3-carboxamide derivatives as glucosylceramide synthase inhibitirs. BioMarin Pharmaceutical Inc., PCT Patent Publication WO 2015065937, 7 May 2015.

SCHEME V

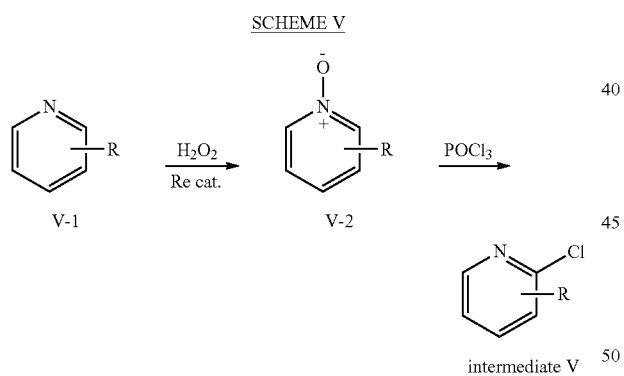

Intermediate V is prepared according to scheme V beginning with known or commercial pyridine V-1. Oxidation with a peroxide provides N-oxide V-2 which is reacted with phosphoryl chloride to provide intermediate V.

4,6-Dichloro-5-methylnicotinonitrile (Scheme V)

Step 1: 4-Chloro-3-cyano-5-methylpyridine 1-oxide

Hydrogen peroxide (50%, 0.803 mL, 13.1 mmol) was added to a DCM (10 mL) solution of methyltrioxorhenium (VII) (0.065 g, 0.261 mmol) and 4-chloro-5-methylnicotinonitrile (1 g, 6.55 mmol) at 0° C. The reaction was warmed to RT and was stirred for 15 h before the mixture was filtered and partitioned between dichloromethane and aqueous NaHSO$_3$ (saturated, 50 mL). The organic layer was dried over anhydrous MgSO$_4$ and concentrated to afford the title compound.

Step 2: 4,6-Dichloro-5-methylnicotinonitrile

POCl$_3$ (7 mL, 75 mmol) was added to 4-chloro-3-cyano-5-methylpyridine 1-oxide (0.7 g, 4.15 mmol) and the reaction was heated to 90° C. for 15 h. The mixture was cooled to RT and concentrated to dryness before purification by silica gel chromatography (0-100% iPrOAc/hexanes) to afford the title compound as the minor regioisomeric product. MS: 187 (M+1)

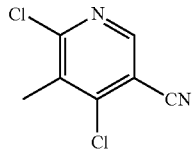

INTERMEDIATE V1

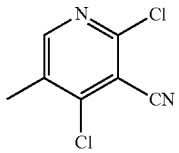

INTERMEDIATE V2

2,4-Dichloro-5-methylnicotinonitrile (Scheme V)

Vide supra for procedure that led to the synthesis of the title compound as the major regioisomeric product. MS: 187 (M+1).

SCHEME W

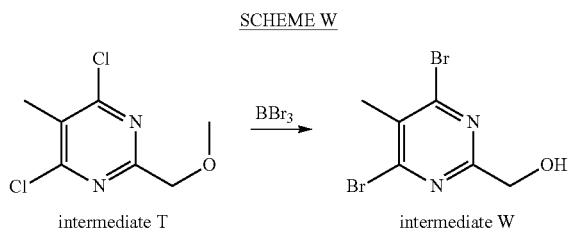

intermediate T → intermediate W

Intermediate W is prepared according to scheme W from intermediate T after treatment with boron tribromide to cleave the methyl ether to the alcohol product.

INTERMEDIATE W

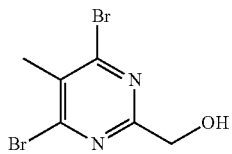

(4,6-Dibromo-5-methylpyrimidin-2-yl)methanol (Scheme W)

To 4,6-dichloro-2-(methoxymethyl)-5-methylpyrimidine (5 g, 24.15 mmol) in DCM (48 mL) was added BBr$_3$ (85 mL, 85 mmol) at 0° C. dropwise via addition funnel. After stirring for 1 h at 0° C., the reaction was quenched with ice at 0° C. and neutralized with aqueous NaOH (1 M) to pH-7. The organic was separated, dried over anhydrous sodium sulfate, filtered, and concentrated under reduced pressure. The residue was purified on a silica gel column (40% EtOAc/hexanes) to afford the title compound. MS: 283 (M+1)

SCHEME X

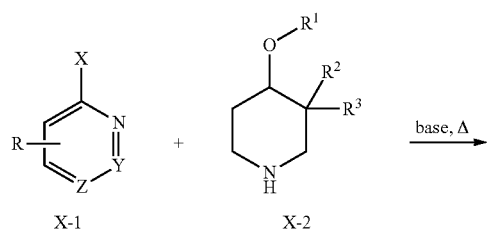

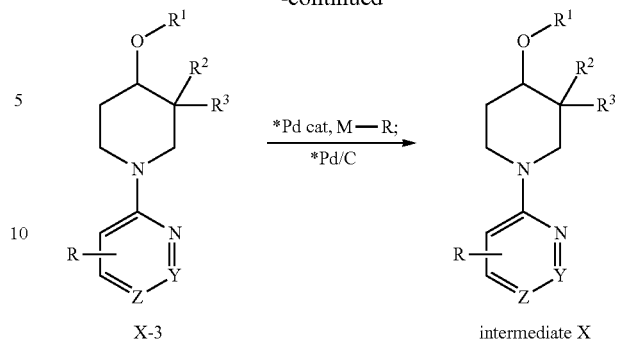

Intermediate X is prepared according to scheme X from an S$_N$Ar reaction of a prepared or known halogenated N-containing heterocycle 1-1, and commercially available piperidinol 1-2. In cases where the heterocycle contains a chloro, bromo, or iodo substituent (=R), an additional palladium-mediated cross-coupling step may be carried out with or without an additional reduction step as necessary.

INTERMEDIATE X1

1-(2,5-Dimethylpyrimidin-4-yl)piperidin-4-ol (Scheme X)

Step 1: 1-(6-Chloro-2,5-dimethylpyrimidin-4-yl)piperidin-4-ol

A mixture of 4,6-dichloro-2,5-dimethylpyrimidine (5 g, 28.2 mmol), piperidin-4-ol (3.5 g, 34.6 mmol) and DIPEA (10 mL, 57.3 mmol) in dioxane (100 mL) was stirred for 8 h at 110° C. The solvent was concentrated in vacuo and the residue was taken up in DCM (200 mL) and water (100 mL). The organic phase was washed with brine (150 mL), dried over anhydrous sodium sulfate, filtered and concentrated in vacuo. The residue was suspended in petroleum ether (100 mL) and after stirring for 15, the title compound was isolated by filtration. MS: 242 (M+1).

Step 2: 1-(2,5-Dimethylpyrimidin-4-yl)piperidin-4-ol

To a solution of 1-(6-chloro-2,5-dimethylpyrimidin-4-yl)piperidin-4-ol (3 g, 12.4 mmol) in MeOH (40 mL) was added Pd/C (10%, 3.96 g, 3.72 mmol). The reaction was stirred under a hydrogen atmosphere at RT for 30 min after which time the mixture was filtered and concentrated to yield the title compound. MS: 208 (M+1).

INTERMEDIATE X2

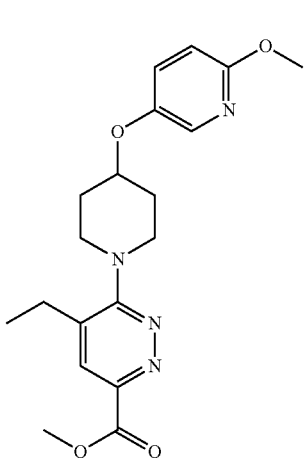

mL×3). The combined organic layers were washed with brine (20 mL), dried over anhydrous sodium sulfate, filtered, and concentrated in vacuo. The residue was purified by flash chromatography (10:1 to 1:1 petroleum ether/EtOAc) to give the title compound. MS: 371 (M+1).

Step 3: Methyl 5-ethyl-6-(4-((6-methoxypyridin-3-yl)oxy)piperidin-1-yl)pyridazine-3-carboxylate To a solution of methyl 6-(4-((6-methoxypyridin-3-yl)oxy)piperidin-1-yl)-5-vinylpyridazine-3-carboxylate (28 mg, 0.076 mmol) in DMF (2 mL) was added Pd/C (10 wt %, 10 mg, 9.40 µmol) at RT for 16 h under an atmosphere of hydrogen. The resulting mixture was filtered, the filtrate was concentrated and the residue was purified by prep-TLC (EtOAc) to afford the title compound. MS: 373 (M+1).

The following intermediates in table X were prepared according to scheme X using the procedure outlined in the synthesis of intermediate X1 or X2 using known or prepared halides in step 1. Steps 2 and 3 are optional and may be omitted when appropriate.

TABLE X

| Intermediate | Structure | Name | MS (M + 1) |
|---|---|---|---|
| X3 | 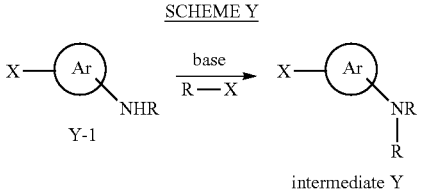 | 6-(4-hydroxypiperidin-1-yl)-5-methyl-N-(pyridin-4-ylmethyl)pyridazine-3-carboxamide | 328 |

Methyl 5-ethyl-6-(4-((6-methoxypyridin-3-yl)oxy)piperidin-1-yl)pyridazine-3-carboxylate (Scheme X)

Step 1: Methyl 5-chloro-6-(4-((6-methoxypyridin-3-yl)oxy)piperidin-1-yl)pyridazine-3-carboxylate To a solution of methyl 5,6-dichloropyridazine-3-carboxylate (intermediate P2, 50 mg, 0.242 mmol) and 2-methoxy-5-(piperidin-4-yloxy)pyridine (503 mg, 2.415 mmol) in DMF (1 mL) was stirred at 110° C. for 16 h. The mixture was diluted with water (10 mL), extracted with EtOAc (10 mL×3) and the combined organic layers were dried over anhydrous sodium sulfate, filtered. The filtrate was concentrated and purified by silica gel chromatography (0-100% EtOAc/petroleum ether) to give the title compound. MS: 379 (M+1).

Step 2: Methyl 6-(4-((6-methoxypyridin-3-yl)oxy)piperidin-1-yl)-5-vinylpyridazine-3-carboxylate To a solution of methyl 5-chloro-6-(4-((6-methoxypyridin-3-yl)oxy)piperidin-1-yl)pyridazine-3-carboxylate (50 mg, 0.132 mmol), potassium vinyltrifluoroborate (17.68 mg, 0.132 mmol) and Cs₂CO₃ (43.0 mg, 0.132 mmol) in toluene (2 mL) and water (0.4 mL) was added 1,1'-bis(di-tert-butylphosphino)ferrocene palladium dichloride (86 mg, 0.132 mmol) under an inert nitrogen atmosphere. The resulting mixture was stirred at 80° C. for 16 h before being diluted with water (10 mL) and extracted with EtOAc (10

SCHEME Y $$X-\text{Ar}\overset{\text{NHR}}{\underset{Y-1}{}} \xrightarrow[R-X]{\text{base}} X-\text{Ar}\overset{\text{NR}}{\underset{R}{}}$$

intermediate Y

Intermediate Y is prepared according to scheme Y from a base-mediated alkylation of a commercial heterocycle Y-1 (wherein Ar is an aromatic or heteroaromatic ring of R¹).

INTERMEDIATE Y

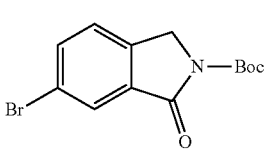

tert-Butyl 6-bromo-1-oxoisoindoline-2-carboxylate (Scheme Y)

To a solution of compound 5-chloro-3-methyl-1H-pyrazolo[3,4-b]pyridine (200 mg, 1.193 mmol) in THF (3 mL) was added NaH (60%, 52.5 mg, 1.31 mmol) at 0° C. After 30 min, SEM-Cl (0.254 mL, 1.432 mmol) was added to the mixture at 0° C. and the reaction was allowed to warm and stir at RT for 16 h. The mixture was diluted with saturated NH$_4$Cl(aq) and extracted with EtOAc (3×10 mL). The combined organic layers were washed with brine and dried over anhydrous Na$_2$SO$_4$ before being concentrated to dryness. The residue was purified by silica gel chromatography (0-10% EtOAc in petroleum ether) give the title compound. $^1$H NMR (400 MHz, CDCl$_3$) δ: 8.03 (1H, s), 7.74 (1H, d, J=8.0), 7.36 (1H, d, J=8.4), 4.71 (2H, s), 1.59 (9H, s).

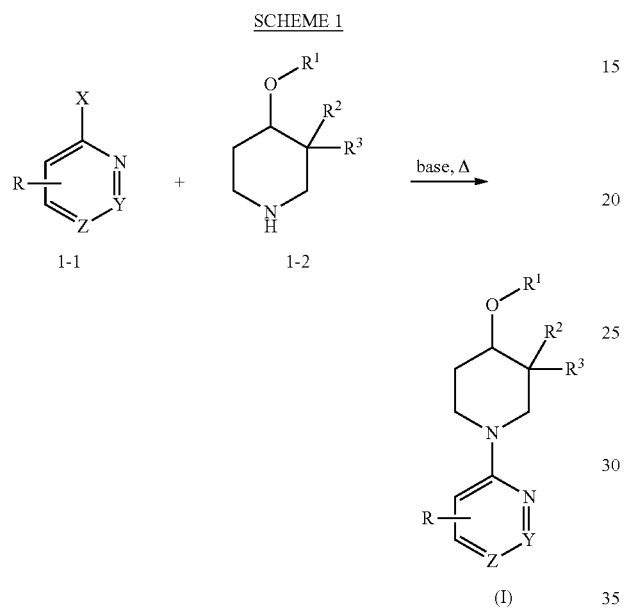

Compounds of formula (I) are synthesized from an S$_N$Ar reaction of prepared or known 2-halo N-containing heterocycles 1-1, and commercially available or prepared piperidines 1-2.

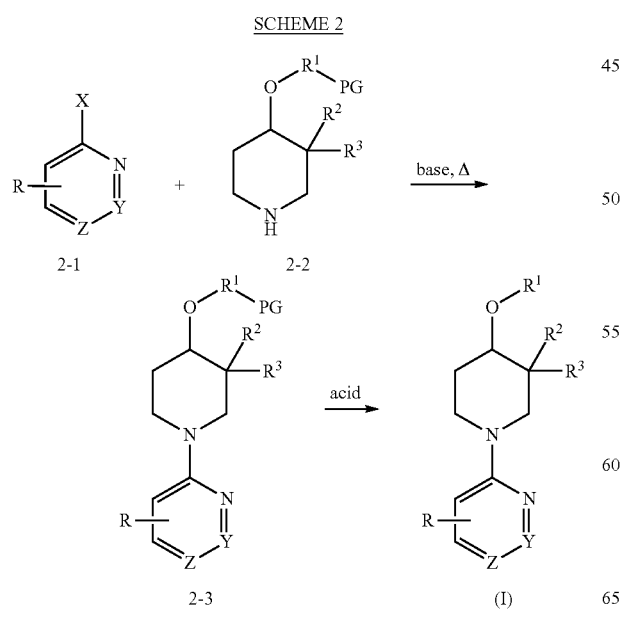

Compounds of formula (I) are synthesized from an S$_N$Ar reaction of prepared or known 2-halo N-containing heterocycles 1-1 and commercially available or prepared N-protected piperidines 1-2, followed by a deprotection step mediated by an acid.

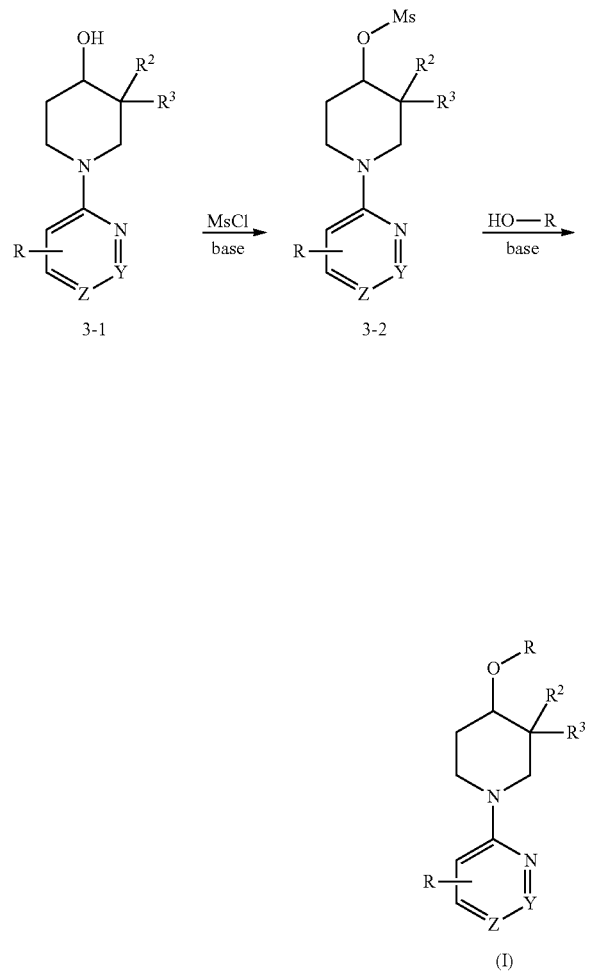

Compounds of formula (I) are synthesized from a prepared alcohol 3-1 which is alkylated with MSCl for the formation of the corresponding activated alcohol 3-2. Subsequent S$_N$2 displacement by a preformed alkoxide yield adducts having the formula (I).

SCHEME 4

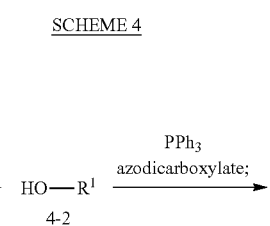

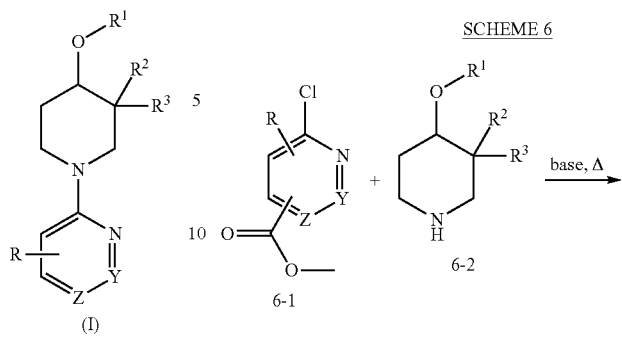

Compounds of formula (I) are synthesized from a Mitsunobu reaction using triphenyl phosphine and an azodicarboxylate with a known or prepared phenol 4-2 and prepared alcohol 4-1.

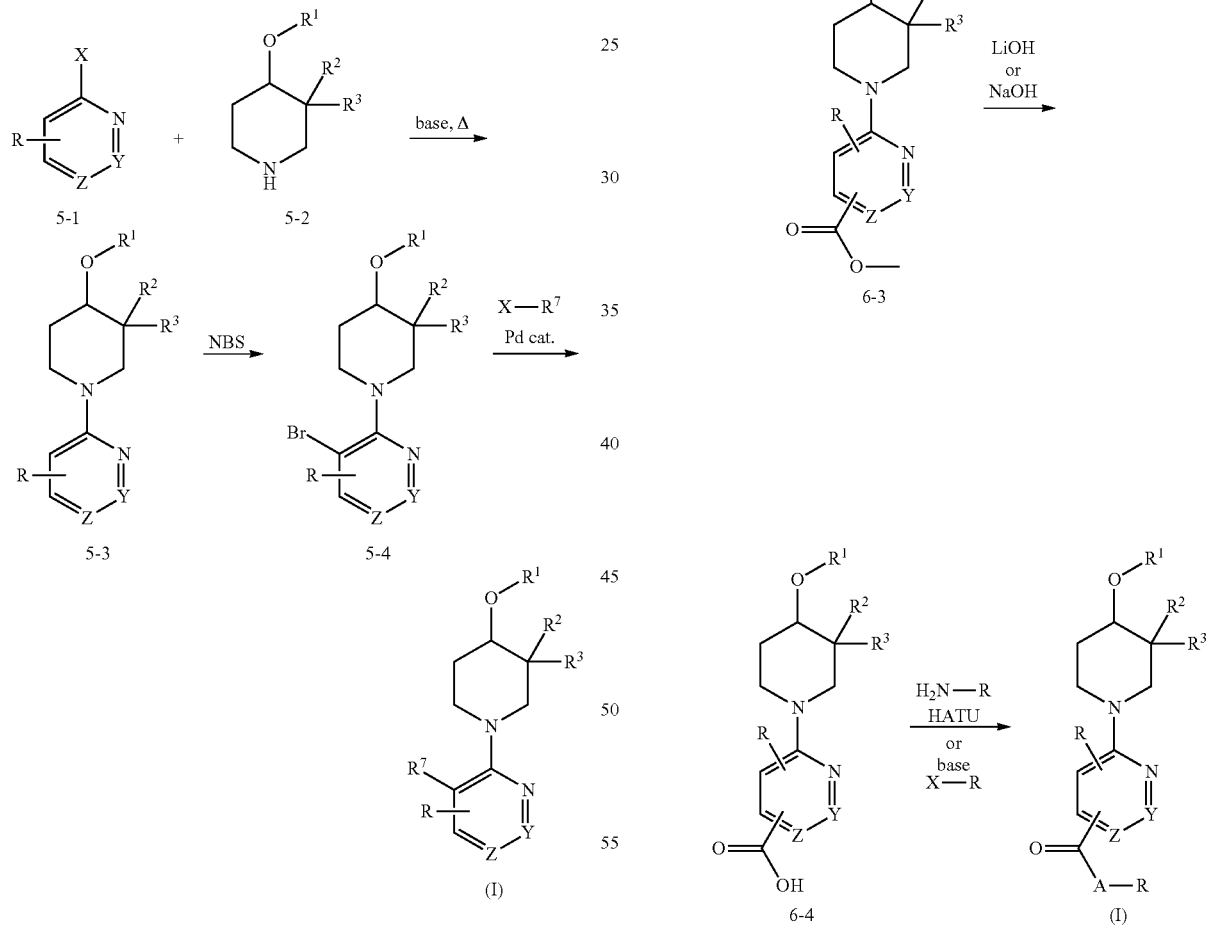

Compounds of formula (I) are synthesized from an $S_NAr$ reaction of prepared or known 2-halo N-containing heterocycle 5-1 and commercially available or prepared N-protected piperidine 5-2. Adduct 5-3 is functionalized in a two-step procedure, first with an electrophilic bromination followed by a palladium-catalyzed coupling procedure. In cases where heterocycle 5-2 has an existing bromide or chloride at the 3-position, the second step may be omitted.

Compounds of formula (I) are synthesized from prepared intermediate 6-1 via a $S_NAr$ reaction with a known or prepared piperdine 6-2 to provide adduct 6-3. Saponification of ester 6-3 to the corresponding acid 6-4 is followed by an amide coupling reaction carried out with a commercially available amine for the amide product or else via and alkylation with an alkyl halide to yield an ester product.

SCHEME 7

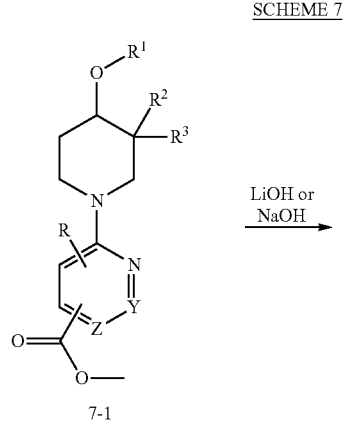

7-1

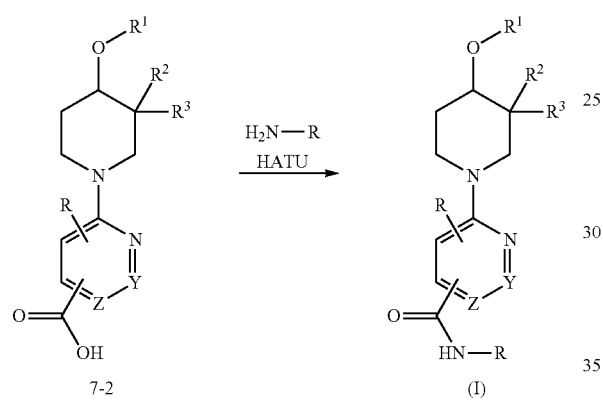

7-2 (I)

Compounds of formula (I) are synthesized from prepared intermediate 7-1 via a saponification of ester to the corresponding acid 7-2 followed by an amide coupling reaction carried out with a commercially available amine.

SCHEME 8

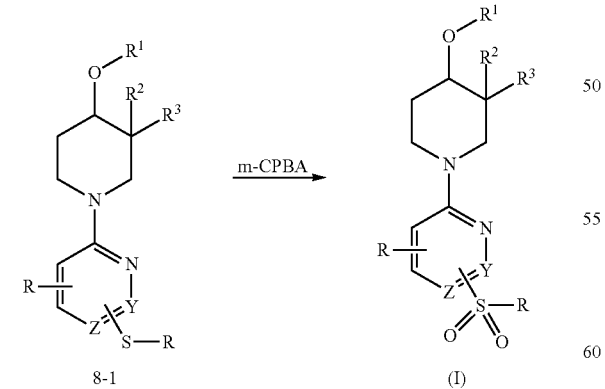

8-1 (I)

Compounds of the formula (i) are prepared according to scheme 9 from a prepared thioether containing a nitrogen-based heterocycle (Y or Z=N or C) 8-1, which is oxidized to the corresponding sulfone after reaction with m-CPBA.

SCHEME 9

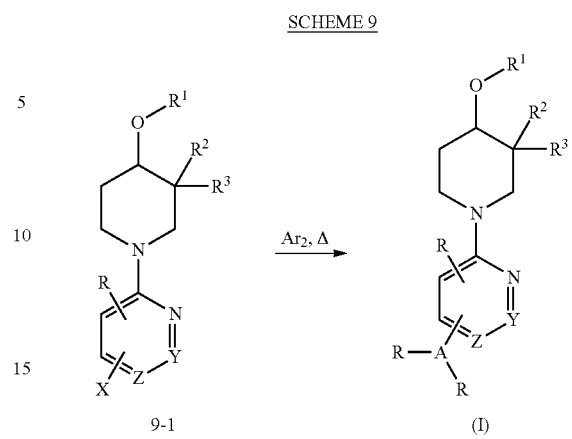

9-1 (I)

Compounds of formula (I) are synthesized from prepared intermediate 9-1 functionalized with a halogen or mesylate (X=Cl, I, OMs), which is displaced via an $S_NAr$ reaction with a commercial amine or alcohol (Y or Z=N or O).

SCHEME 10

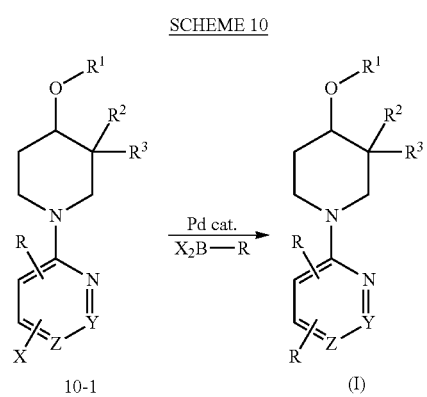

10-1 (I)

Compounds of formula (I) are synthesized from prepared intermediate 10-1 functionalized with a halogen (X=Cl or Br), which is functionalized in a palladium-catalyzed Suzuki coupling reaction with commercially available boronic esters and acids.

SCHEME 11

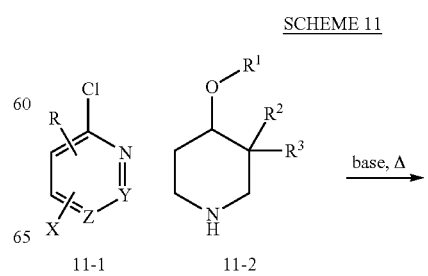

11-1    11-2

-continued

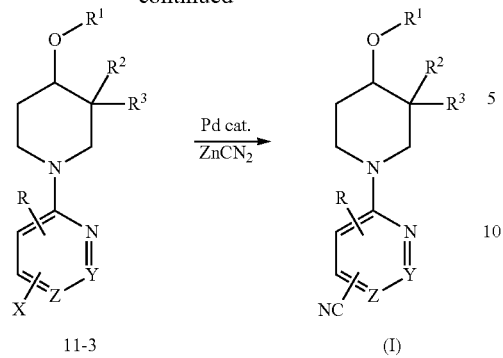

11-3 → (I)

Compounds of formula (I) are synthesized from known or prepared intermediate 11-2 via a S$_N$Ar reaction with a known or prepared heterocycle 11-1 to provide adduct 11-3. Intermediate 11-3 being functionalized with a halogen (X=Cl or Br) is carried forward in a palladium-catalyzed cyanation reaction.

SCHEME 12

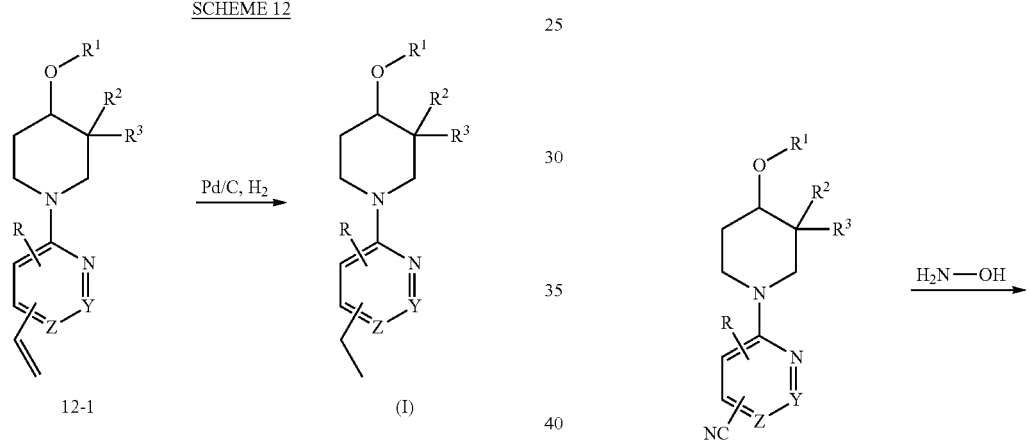

12-1 → (I)

Compounds of formula (I) are synthesized via a palladium-catalyzed reduction of prepared olefin 12-1.

SCHEME 13

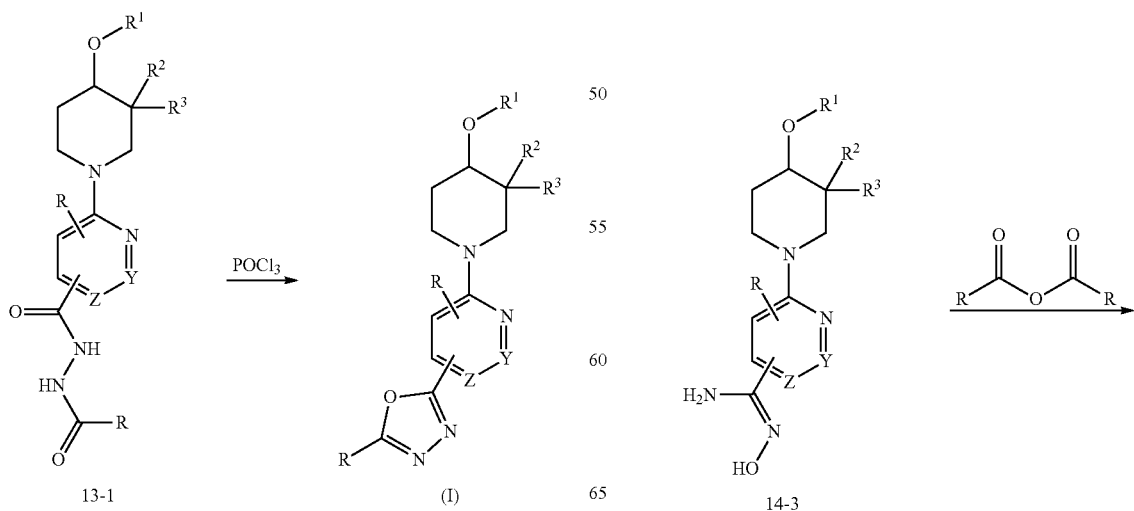

13-1 → (I)

Compounds of formula (I) are prepared via cyclization of hydrazide 13-1 after reaction with phosphoryl chloride.

SCHEME 14

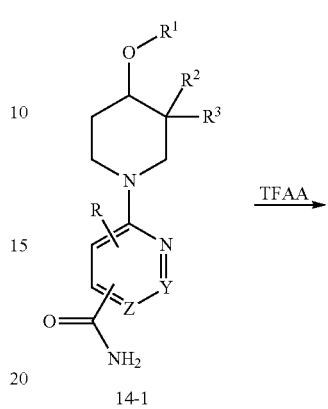

14-1 → 14-2 → 14-3

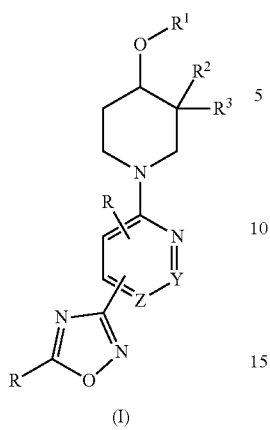

Compounds of formula (I) are synthesized from a prepared carboxamide 14-1 after dehydration to form nitrile 14-2 and subsequent condensation with hydroxylamine to afford adduct 14-3. Reaction with a commercial anhydride yield compounds with the formula (I).

SCHEME 15

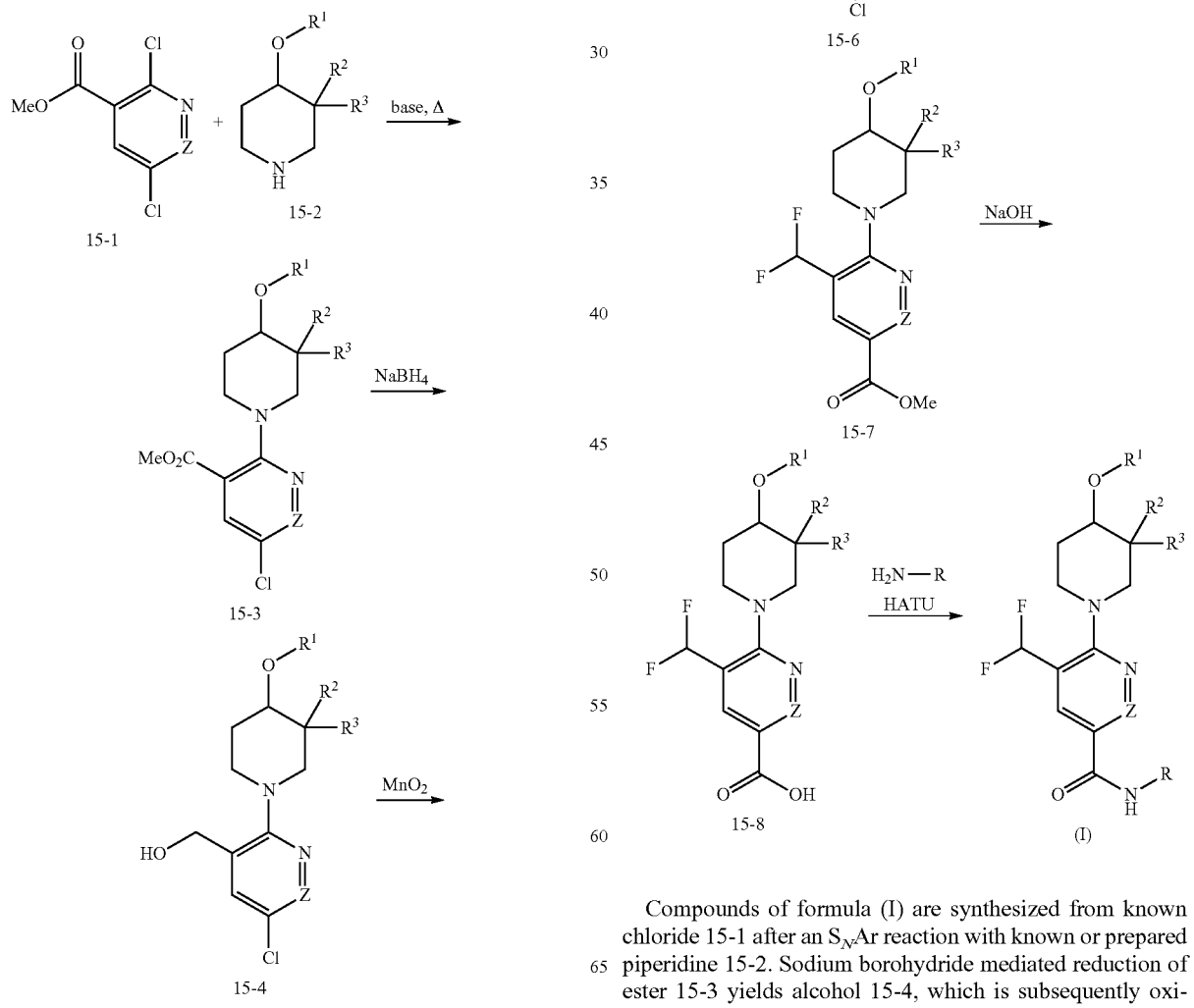

Compounds of formula (I) are synthesized from known chloride 15-1 after an $S_NAr$ reaction with known or prepared piperidine 15-2. Sodium borohydride mediated reduction of ester 15-3 yields alcohol 15-4, which is subsequently oxidized by manganese oxide to afford aldehyde 15-5 for the installation of the difluoromethylene moeity in 15-6. A palladium-catalyzed carbonylation reaction provides ester 15-7 and a two-step saponification and amide coupling reaction yields compounds with the formula (I).

SCHEME 16

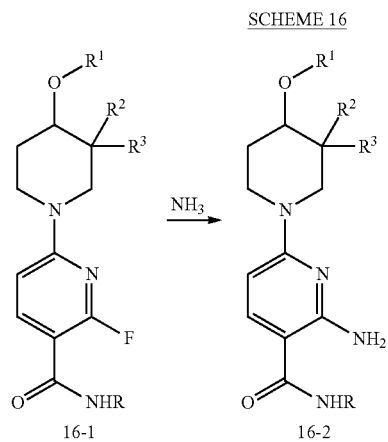

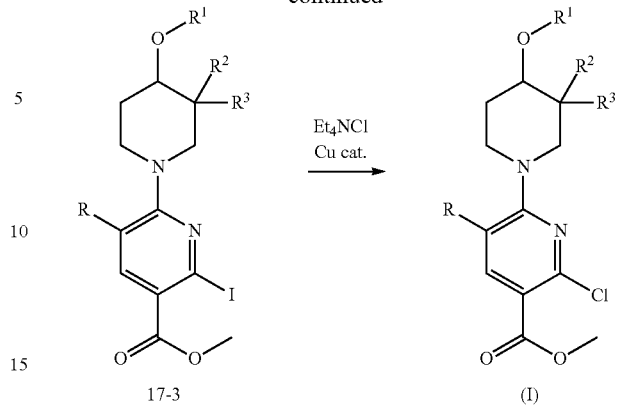

Compounds of formula (I) are synthesized from prepared pyridine 17-1 and known or prepared piperidine 17-2 to yield adduct 17-3. A copper-mediated halogen exchange reaction of iodide 17-3 yields compounds with the formula (I).

Example 1

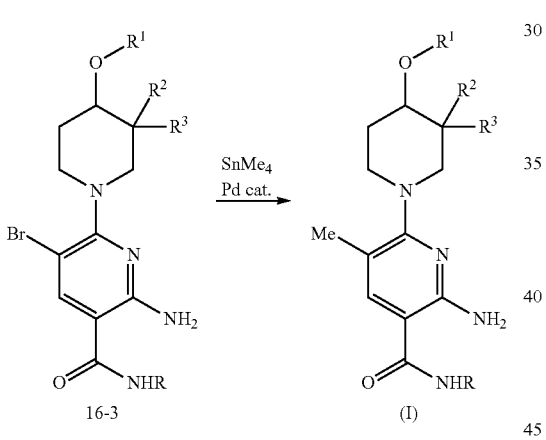

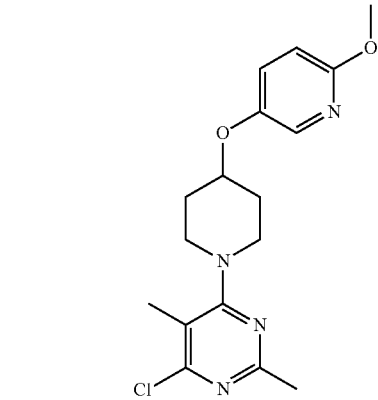

4-Chloro-6-(4-((6-methoxypyridin-3-yl)oxy)piperidin-1-yl)-2,5-dimethylpyrimidine (Scheme 1)

4,6-Dichloro-2,5-dimethylpyrimidine (2.12 g, 12 mmol) and 2-methoxy-5-(piperidin-4-yloxy)pyridine hydrochloride (2.45 g, 10 mmol) were suspended in 1,4-dioxane (50 mL). DIPEA (8.73 mL, 50 mmol) was added to the mixture and the reaction was stirred at 60° C. for 15 h. The reaction was cooled to RT and partitioned between ethyl acetate and aqueous NH$_4$Cl (saturated). The organic was washed a second time with aqueous NH$_4$Cl, then with brine, dried over sodium sulfate, filtered and concentrated. The residue was purified by silica gel chromatography (15-50% EtOAc/hexanes) to afford the title compound. MS: 349 (M+1). $^1$H NMR (500 MHz, CD$_3$OD): δ 7.94 (d, 1H), 7.69 (dd, 1H), 7.02 (d, 1H), 4.66 (m, 1H), 3.96 (s, m, 5H), 3.75 (m, 2H), 2.51 (s, 3H), 2.33 (s, 3H), 2.12 (m, 2H), 1.93 (m, 2H).

Compounds of formula (I) are synthesized from prepared pyridine 16-1 after exposure to ammonia to yield aniline 16-2. Electrophilic bromination with NBS provides bromo adduct 16-3, which is subsequently methylated in a palladium-mediated Stille reaction to afford compounds with the formula (I).

The following examples in table 1 were prepared according to scheme 1 using the procedure outlined in the synthesis of Example 1 using known or prepared piperidines and halogenated heteroaromatic compounds. Alternative conditions can be used in this reaction, such that the base is DIPEA, sodium bicarbonate, or tributylamine as appropriate for each substrate.

SCHEME 17

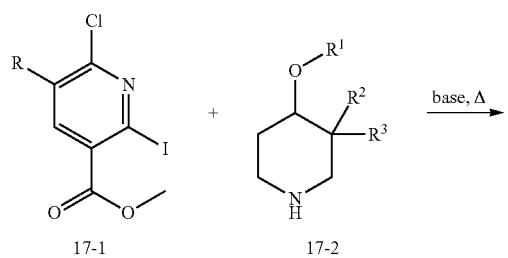

TABLE 1

| Example | Structure | Name | MS (M + 1) |
|---|---|---|---|
| 2 | 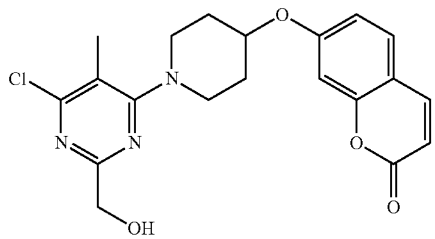 [SMILES: Cc1c(Cl)nc(CO)nc1N1CCC(Oc2ccc3ccc(=O)oc3c2)CC1] | 7-((1-(6-chloro-2-(hydroxymethyl)-5-methylpyrimidin-4-yl)piperidin-4-yl)oxy)-2H-chromen-2-one | 402 |
| 3 | 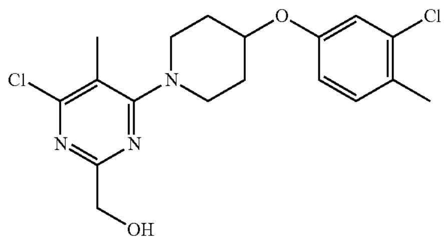 [SMILES: Cc1ccc(OC2CCN(c3nc(CO)nc(Cl)c3C)CC2)cc1Cl] | (4-chloro-6-(4-(3-chloro-4-methylphenoxy)piperidin-1-yl)-5-methylpyrimidin-2-yl)methanol | 382 |
| 4 | 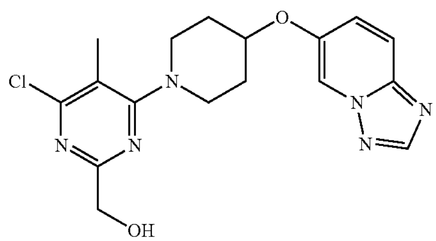 [SMILES: Cc1c(Cl)nc(CO)nc1N1CCC(Oc2ccc3ncnn3c2)CC1] | (4-(4-([1,2,4]triazolo[1,5-a]pyridin-6-yloxy)piperidin-1-yl)-6-chloro-5-methylpyrimidin-2-yl)methanol | 375 |
| 5 | 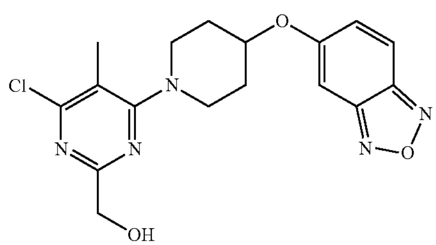 [SMILES: Cc1c(Cl)nc(CO)nc1N1CCC(Oc2ccc3nonc3c2)CC1] | (4-(4-(benzo[c][1,2,5]oxadiazol-5-yloxy)piperidin-1-yl)-6-chloro-5-methylpyrimidin-2-yl)methanol | 376 |
| 6 | 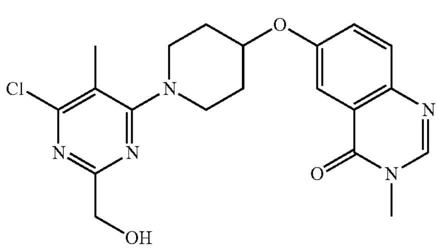 [SMILES: Cc1c(Cl)nc(CO)nc1N1CCC(Oc2ccc3ncn(C)c(=O)c3c2)CC1] | 6-((1-(6-chloro-2-(hydroxymethyl)-5-methylpyrimidin-4-yl)piperidin-4-yl)oxy)-3-methylquinazolin-4(3H)-one | 416 |
| 7 | 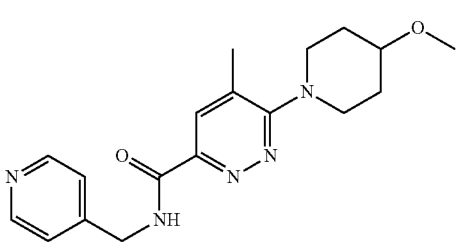 [SMILES: COC1CCN(c2nnc(C(=O)NCc3ccncc3)cc2C)CC1] | 6-(4-methoxypiperidin-1-yl)-5-methyl-N-(pyridin-4-ylmethyl)pyridazine-3-carboxamide | 342 |

TABLE 1-continued

| Example | Structure | Name | MS (M + 1) |
|---|---|---|---|
| 8 | 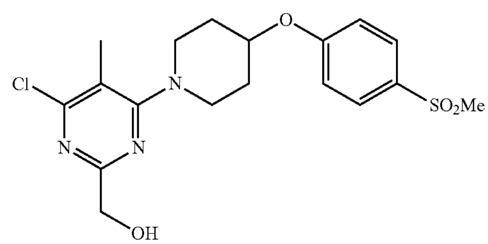 [SMILES: Cc1c(Cl)nc(CO)nc1N1CCC(Oc2ccc(S(C)(=O)=O)cc2)CC1] | (4-chloro-5-methyl-6-(4-(4-(methylsulfonyl)phenoxy)piperidin-1-yl)pyrimidin-2-yl)methanol | 412 |
| 9 | 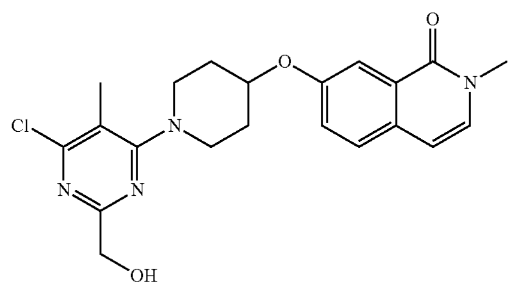 [SMILES: Cc1c(Cl)nc(CO)nc1N1CCC(Oc2ccc3ccn(C)c(=O)c3c2)CC1] | 7-((1-(6-chloro-2-(hydroxymethyl)-5-methylpyrimidin-4-yl)piperidin-4-yl)oxy)-2-methylisoquinolin-1(2H)-one | 415 |
| 10 | 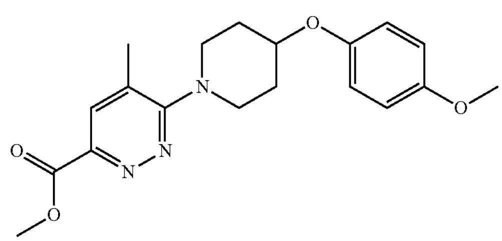 [SMILES: COC(=O)c1cc(C)c(N2CCC(Oc3ccc(OC)cc3)CC2)nn1] | methyl 6-(4-(4-methoxyphenoxy)piperidin-1-yl)-5-methylpyridazine-3-carboxylate | 358 |
| 11[1] | 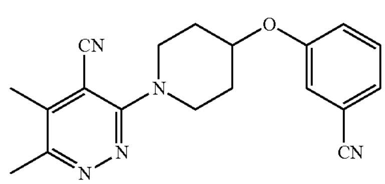 [SMILES: Cc1nnc(N2CCC(Oc3cccc(C#N)c3)CC2)c(C#N)c1C] | 3-(4-(3-cyanophenoxy)piperidin-1-yl)-5,6-dimethylpyridazine-4-carbonitrile | 334 |
| 12 | 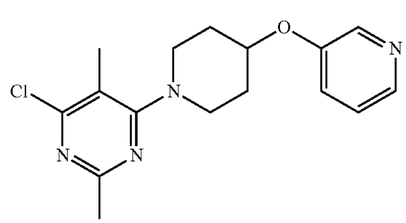 [SMILES: Cc1nc(Cl)c(C)c(N2CCC(Oc3cccnc3)CC2)n1] | 4-chloro-2,5-dimethyl-6-(4-(pyridin-3-yloxy)piperidin-1-yl)pyrimidine | 319 |
| 13 | 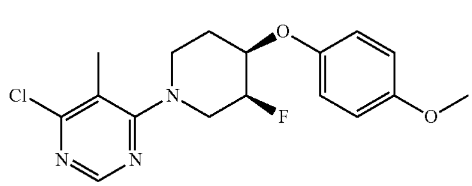 [SMILES: COc1ccc(O[C@@H]2CCN(c3ncnc(Cl)c3C)C[C@@H]2F)cc1] | 4-chloro-6-((cis)-3-fluoro-4-(4-methoxyphenoxy)piperidin-1-yl)-5-methylpyrimidine | 352 |

TABLE 1-continued

| Example | Structure | Name | MS (M + 1) |
|---|---|---|---|
| 14 | 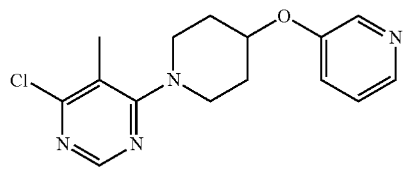 [SMILES: Cc1c(Cl)ncnc1N1CCC(Oc2cccnc2)CC1] | 4-chloro-5-methyl-6-(4-(pyridin-3-yloxy)piperidin-1-yl)pyrimidine | 305 |
| 15 | 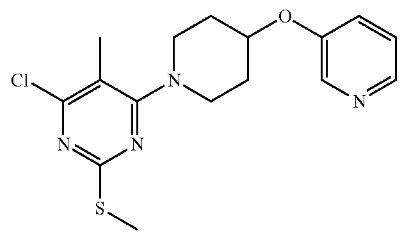 [SMILES: CSc1nc(Cl)c(C)c(N2CCC(Oc3cccnc3)CC2)n1] | 4-chloro-5-methyl-2-(methylthio)-6-(4-(pyridin-3-yloxy)piperidin-1-yl)pyrimidine | 351 |
| 16 | 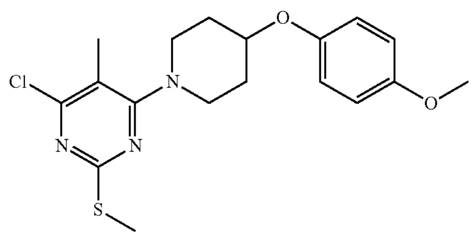 [SMILES: COc1ccc(OC2CCN(c3nc(SC)nc(Cl)c3C)CC2)cc1] | 4-chloro-6-(4-(4-methoxyphenoxy)piperidin-1-yl)-5-methyl-2-(methylthio)pyrimidine | 380 |
| 17 | 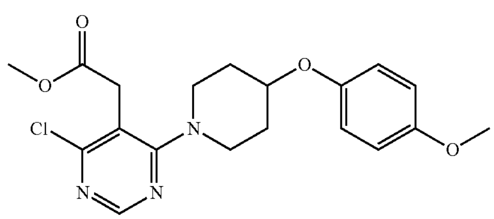 | methyl 2-(4-chloro-6-(4-(4-methoxyphenoxy)piperidin-1-yl)pyrimidin-5-yl)acetate | 392 |
| 18 | 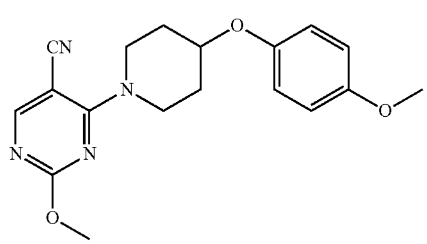 [SMILES: COc1ccc(OC2CCN(c3nc(OC)ncc3C#N)CC2)cc1] | 2-methoxy-4-(4-(4-methoxyphenoxy)piperidin-1-yl)pyrimidine-5-carbonitrile | 341 |
| 19 | 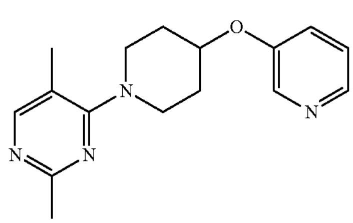 [SMILES: Cc1ncc(C)c(N2CCC(Oc3cccnc3)CC2)n1] | 2,5-dimethyl-4-(4-(pyridin-3-yloxy)piperidin-1-yl)pyrimidine | 285 |

TABLE 1-continued

| Example | Structure | Name | MS (M + 1) |
|---|---|---|---|
| 20 | 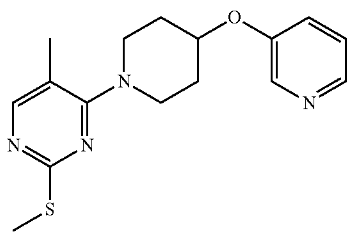 [SMILES: CSc1ncc(C)c(N2CCC(Oc3cccnc3)CC2)n1] | 5-methyl-2-(methylthio)-4-(4-(pyridin-3-yloxy)piperidin-1-yl)pyrimidine | 317 |
| 21 | 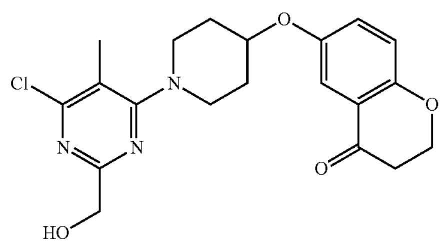 [SMILES: Cc1c(Cl)nc(CO)nc1N1CCC(Oc2ccc3c(c2)C(=O)CCO3)CC1] | 6-((1-(6-chloro-2-(hydroxymethyl)-5-methylpyrimidin-4-yl)piperidin-4-yl)oxy)chroman-4-one | 404 |
| 22 | 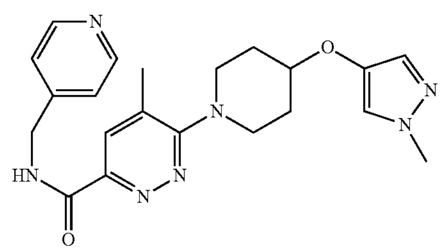 [SMILES: Cc1cc(C(=O)NCc2ccncc2)nnc1N1CCC(Oc2cnn(C)c2)CC1] | 5-methyl-6-(4-((1-methyl-1H-pyrazol-4-yl)oxy)piperidin-1-yl)-N-(pyridin-4-ylmethyl)pyridazine-3-carboxamide | 408 |
| 23 | 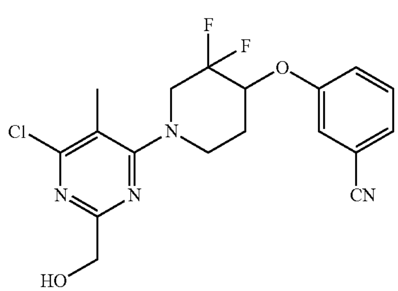 [SMILES: Cc1c(Cl)nc(CO)nc1N1CCC(Oc2cccc(C#N)c2)C(F)(F)C1] | 3-((1-(6-chloro-2-(hydroxymethyl)-5-methylpyrimidin-4-yl)-3,3-difluoropiperidin-4-yl)oxy)benzonitrile | 395 |
| 24 | 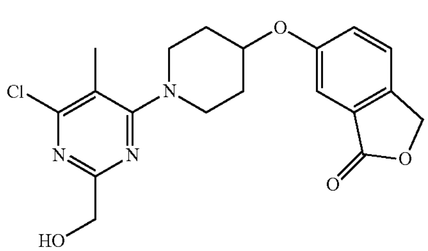 [SMILES: Cc1c(Cl)nc(CO)nc1N1CCC(Oc2ccc3c(c2)C(=O)OC3)CC1] | 6-((1-(6-chloro-2-(hydroxymethyl)-5-methylpyrimidin-4-yl)piperidin-4-yl)oxy)isobenzofuran-1(3H)-one | 390 |
| 25 | 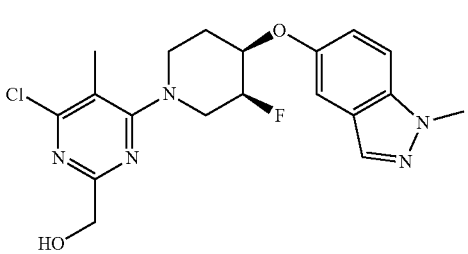 [SMILES: Cc1c(Cl)nc(CO)nc1N1CC[C@@H](Oc2ccc3c(cnn3C)c2)[C@@H](F)C1] | (4-chloro-6-((cis)-3-fluoro-4-((1-methyl-1H-indazol-5-yl)oxy)piperidin-1-yl)-5-methylpyrimidin-2-yl)methanol | 406 |

TABLE 1-continued

| Example | Structure | Name | MS (M + 1) |
|---|---|---|---|
| 26 | 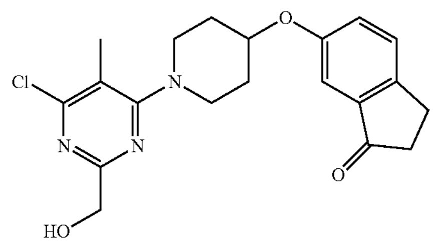 [SMILES: Cc1c(Cl)nc(CO)nc1N1CCC(Oc2ccc3c(c2)C(=O)CC3)CC1] | 6-((1-(6-chloro-2-(hdyroxymethyl)-5-methylpyrimidin-4-yl)piperidin-4-yl)oxy)-2,3-dihydro-1H-inden-1-one | 388 |
| 27 | 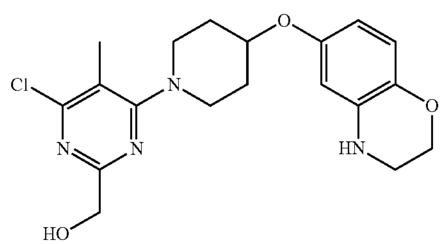 [SMILES: Cc1c(Cl)nc(CO)nc1N1CCC(Oc2ccc3c(c2)NCCO3)CC1] | (4-chloro-6-(4-((3,4-dihydro-2H-benzo[b][1,4]oxazin-6-yl)oxy)piperidin-1-yl)-5-methylpyrimidin-2-yl)methanol | 391 |
| 28 | 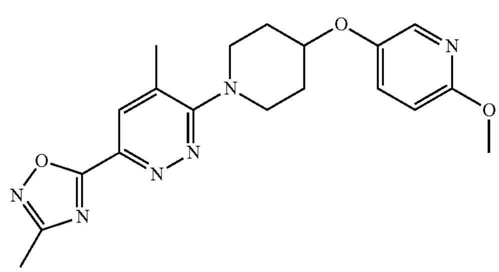 [SMILES: COc1ccc(OC2CCN(c3nnc(-c4nc(C)no4)cc3C)CC2)cn1] | 5-(6-(4-((6-methoxypyridin-3-yl)oxy)piperidin-1-yl)-5-methylpyridazin-3-yl)-3-methyl-1,2,4-oxadiazole | 383 |
| 29 | 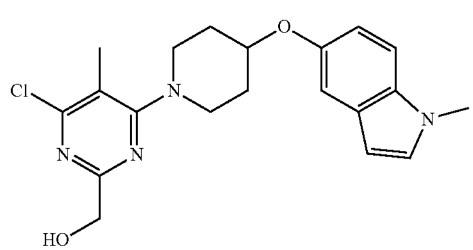 [SMILES: Cc1c(Cl)nc(CO)nc1N1CCC(Oc2ccc3c(ccn3C)c2)CC1] | (4-chloro-5-methyl-6-(4-((1-methyl-1H-indol-5-yl)oxy)piperidin-1-yl)pyrimidin-2-yl)methanol | 387 |
| 30 | 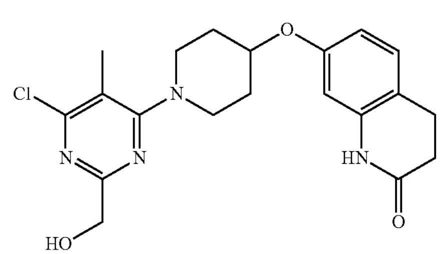 [SMILES: Cc1c(Cl)nc(CO)nc1N1CCC(Oc2ccc3c(c2)NC(=O)CC3)CC1] | 7-((1-(6-chloro-2-(hydroxymethyl)-5-methylpyrimidin-4-yl)piperidin-4-yl)oxy)-3,4-dihydroquinolin-2(1H)-one | 403 |
| 31 | 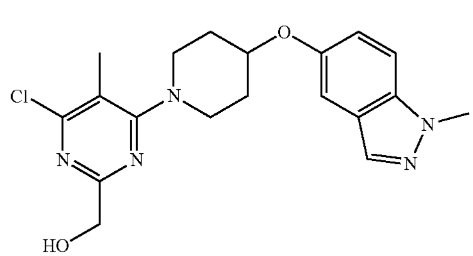 [SMILES: Cc1c(Cl)nc(CO)nc1N1CCC(Oc2ccc3c(cnn3C)c2)CC1] | (4-chloro-5-methyl-6-(4-((1-methyl-1H-indazol-5-yl)oxy)piperidin-1-yl)pyrimidin-2-yl)methanol | 387 |

TABLE 1-continued

| Example | Structure | Name | MS (M + 1) |
|---|---|---|---|
| 32 | 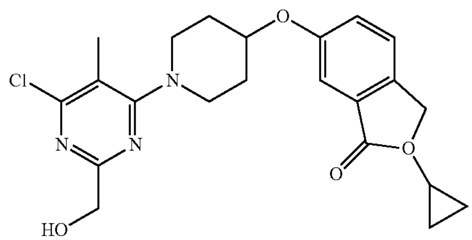 | 6-((1-(6-chloro-2-(hydroxymethyl)-5-methylpyrimidin-4-yl)piperidin-4-yl)oxy)-2-cyclopropylisoindolin-1-one | 387 |
| 33 | 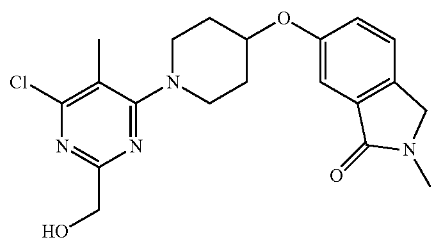 [SMILES: Cc1c(Cl)nc(CO)nc1N1CCC(Oc2ccc3c(c2)C(=O)N(C)C3)CC1] | 6-((1-(6-chloro-2-(hydroxymethyl)-5-methypyrimidin-4-yl)piperidin-4-yl)oxy)-2-methylisoindolin-1-one | 403 |
| 34 | 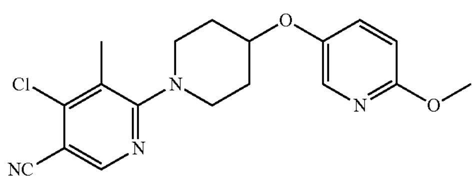 [SMILES: COc1ccc(OC2CCN(c3ncc(C#N)c(Cl)c3C)CC2)cn1] | 4-chloro-5-(4-((6-methoxypyridin-3-yl)oxy)piperidin-1-yl)-5-methylnicotinonitrile | 359 |
| 35 | 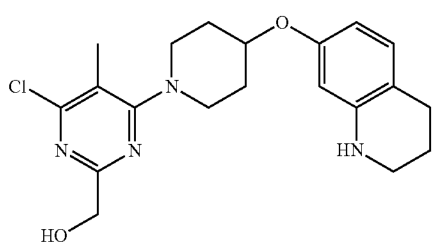 [SMILES: Cc1c(Cl)nc(CO)nc1N1CCC(Oc2ccc3c(c2)NCCC3)CC1] | (4-chloro-5-methyl-6-(4-((1,2,3,4-tetrahydroquinolin-7-yl)oxy)piperidin-1-yl)pyrimidin-2-yl)methanol | 389 |
| 36 | 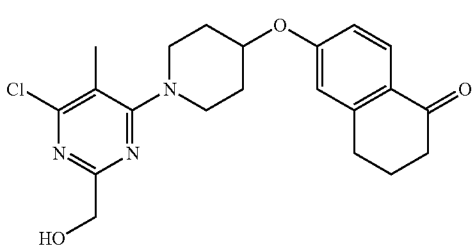 [SMILES: Cc1c(Cl)nc(CO)nc1N1CCC(Oc2ccc3c(c2)CCCC3=O)CC1] | 6-((1-(6-chloro-2-(hydroxymethyl)-5-methylpyrimidin-4-yl)piperidin-4-yl)oxy)-3,4-dihydronaphthalen-1(2H)-one | 402 |
| 37 | 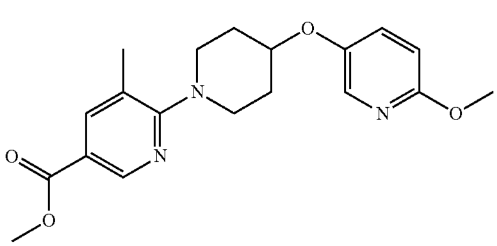 [SMILES: COC(=O)c1cnc(N2CCC(Oc3ccc(OC)nc3)CC2)c(C)c1] | methyl 6-(4-((6-methoxypyridin-3-yl)oxy)piperidin-1-yl)-5-methylnicotinate | 358 |

TABLE 1-continued

| Example | Structure | Name | MS (M + 1) |
|---|---|---|---|
| 38 | 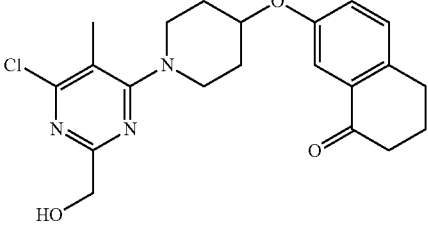 | 7-((1-(6-chloro-2-(hydroxymethyl)-5-methylpyrimidin-4-yl)piperidin-4-yl)oxy)-3,4-dihydronaphthalen-1(2H)-one | 402 |
| 39 | 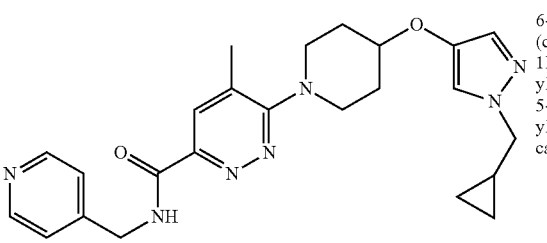 | 6-(4-((1-(cyclopropylmethyl)-1H-pyrazol-4-yl)oxy)piperidin-1-yl)-5-methyl-N-(pyridin-4-ylmethyl)pyridazine-3-carboxamide | 342 |
| 40 | 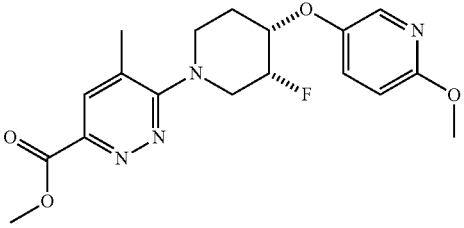 [SMILES: COC(=O)c1cc(C)c(N2CC[C@H](Oc3ccc(OC)nc3)[C@H](F)C2)nn1] | methyl 6-((3R,4S)-3-fluoro-4-((6-methoxypyridin-3-yl)oxy)piperidin-1-yl)-5-methylpyridazine-3-carboxylate | 417 |
| 41 | 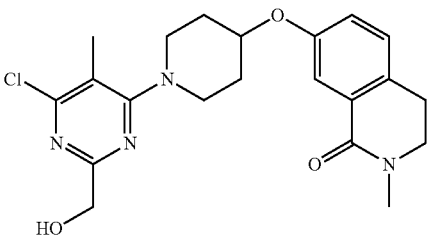 [SMILES: Cc1c(Cl)nc(CO)nc1N1CCC(Oc2ccc3c(c2)C(=O)N(C)CC3)CC1] | 7-((1-(6-chloro-2-(hydroxymethyl)-5-methylpyrimidin-4-yl)piperidin-4-yl)oxy)-2-methyl-3,4-dihdyroisoquinolin-1(2H)-one | 417 |
| 42 | 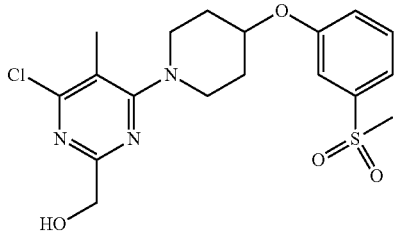 [SMILES: Cc1c(Cl)nc(CO)nc1N1CCC(Oc2cccc(S(C)(=O)=O)c2)CC1] | (4-chloro-5-methyl-6-(4-(3-(methylsulfonyl)phen-oxy)piepridin-1-yl)pyrimidin-2-yl)methanol | 412 |
| 43 | 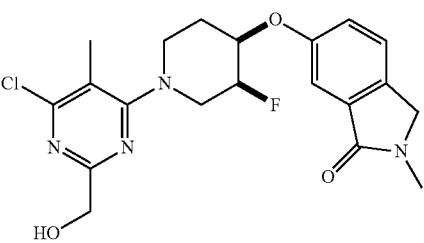 [SMILES: Cc1c(Cl)nc(CO)nc1N1CC[C@@H](Oc2ccc3c(c2)C(=O)N(C)C3)[C@@H](F)C1] | 6-(((3S,4R)-1-(6-chloro-2-(hydroxymethyl)-5-methylpyrimidin-4-yl)-3-fluoropiperidin-4-yl)oxy)-2-methylisoindolin-1-one | 421 |

TABLE 1-continued

| Example | Structure | Name | MS (M + 1) |
|---|---|---|---|
| 44 | 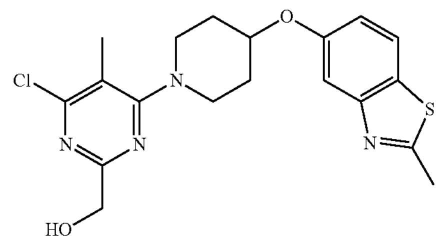 [SMILES: Cc1nc2cc(OC3CCN(c4nc(CO)nc(Cl)c4C)CC3)ccc2s1] | 4(4-chloro-5-methyl-6-(4-((2-methylbenzo[d]thiazol-5-yl)oxy)piperidin-1-yl)pyrimidin-2-yl)methanol | 405 |
| 45 | 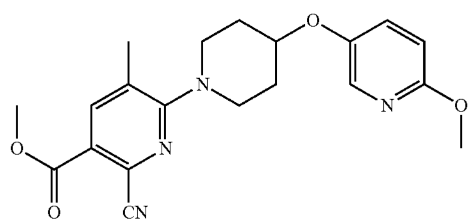 [SMILES: COC(=O)c1cc(C)c(N2CCC(Oc3ccc(OC)nc3)CC2)nc1C#N] | methyl 2-cyano-6-(4-((6-methoxypyridin-3-yl)oxy)piperidin-1-yl)-5-methylnicotinate | 383 |
| 46 | 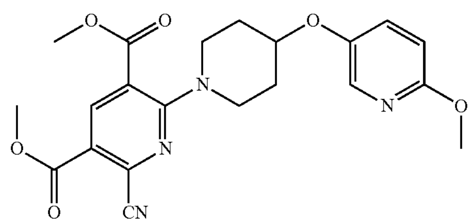 [SMILES: COC(=O)c1cc(C(=O)OC)c(N2CCC(Oc3ccc(OC)nc3)CC2)nc1C#N] | dimethyl 2-cyano-6-(4-((6-methoxypyridin-3-yl)oxy)piperidin-1-yl)pyridine-3,5-dicarboxylate | 427 |
| 47 | 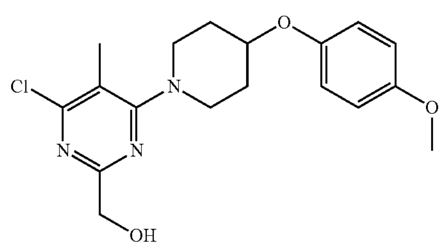 | (4-chloro-6-(4-(4-methoxyphenoxy)piperidin-1-yl)-5-methypyrimidin-2-yl)methanol | 364 |
| 48 | 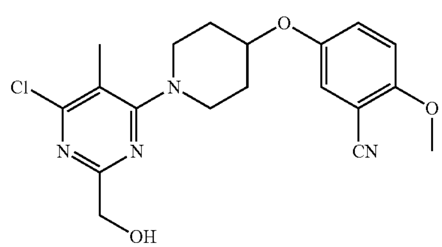 [SMILES: COc1ccc(OC2CCN(c3nc(CO)nc(Cl)c3C)CC2)cc1C#N] | 5-((1-(6-chloro-2-(hydroxymethyl)-5-methylpyrimidin-4-yl)piperidin-4-yl)oxy)-2-methoxybenzonitrile | 389 |
| 49 | 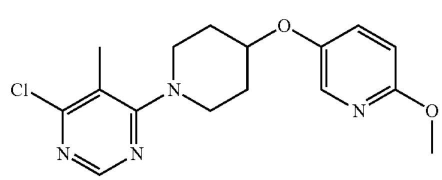 [SMILES: COc1ccc(OC2CCN(c3ncnc(Cl)c3C)CC2)cn1] | 4-chloro-6-(4-((6-methoxypyridin-3-yl)oxy)piperidin-1-yl)-5-methylpyrimidine | 335 |
| 50 | 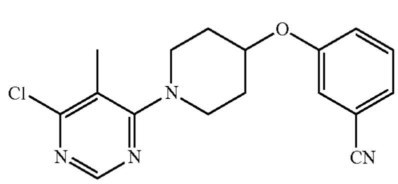 [SMILES: Cc1c(Cl)ncnc1N1CCC(Oc2cccc(C#N)c2)CC1] | 3-((1-(6-chloro-5-methypyrimidin-4-yl)piperidin-4-yl)oxy)benzonitrile | 329 |

TABLE 1-continued

| Example | Name | MS (M + 1) |
|---|---|---|
| 51 | 3-((1-(6-chloro-2-(hydroxymethyl)-5-methylpyrimidin-4-yl)piperidin-4-yl)oxy)benzonitrile | 359 |
| 52 | (4-chloro-6-((3S,4R)-3-fluoro-4-((2-methylbenzo[d]oxazol-6-yl)oxy)piperidin-1-yl)-5-methylpyrimidin-2-yl)methanol | 407 |
| 53 | (4-(4-(benzo[d][1,3]dioxol-5-yloxy)piperidin-1-yl)-6-chloro-4-methylpyrimidin-2-yl)methanol | 328 |
| 54 | (4-chloro-6-(4-((5-fluoro-6-methoxypyridin-3-yl)oxy)piperidin-1-yl)-5-methylpyrimidin-2-yl)methanol | 383 |
| 55 | 3-((1-(6-chloro-2,5-dimethylpyrimidin-4-yl)piperidin-4-yl)oxy)benzonitrile | 343 |
| 56 | 5-((1-(6-chloro-2,5-dimethypyrimidin-4-yl)piperidin-4-yl)oxy)-1-methyl-1H-indazole | 372 |

TABLE 1-continued

| Example | Structure | Name | MS (M + 1) |
|---|---|---|---|
| 57 | 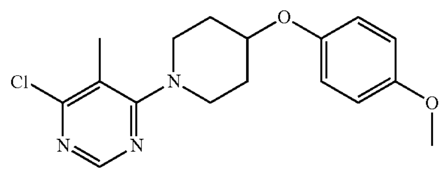 [SMILES: COc1ccc(OC2CCN(c3ncnc(Cl)c3C)CC2)cc1] | 4-chloro-6-(4-(4-methoxyphenoxy)piperidin-1-yl)-5-methypyrimidine | 334 |
| 58 | 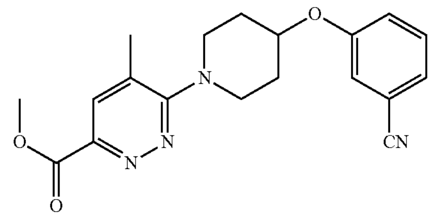 [SMILES: COC(=O)c1cc(C)c(N2CCC(Oc3cccc(C#N)c3)CC2)nn1] | methyl 6-(4-(3-cyanophenoxy)piperidin-1-yl)-5-methylpyridazine-3-carboxylate | 353 |
| 59 | 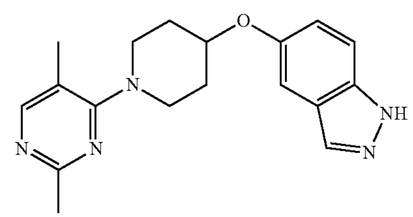 [SMILES: Cc1ncc(C)c(N2CCC(Oc3ccc4[nH]ncc4c3)CC2)n1] | 5-((1-(2,5-dimethylpyrimidin-4-yl)piperidin-4-yl)oxy)-1H-indazole | 324 |
| 60 | 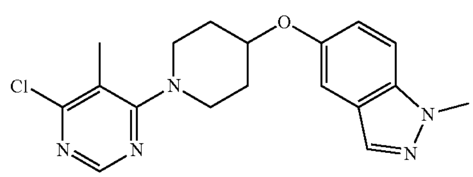 [SMILES: Cc1c(Cl)ncnc1N1CCC(Oc2ccc3c(cnn3C)c2)CC1] | 5-((1-(6-chloro-5-methylpyrimidin-4-yl)piperidin-4-yl)oxy)-1-methyl-1H-indazole | 358 |
| 61 | 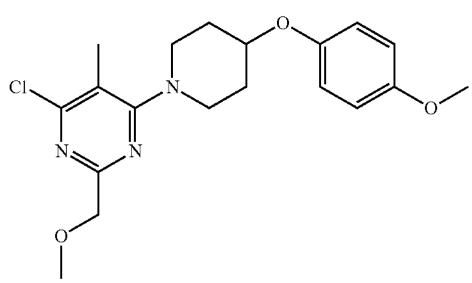 [SMILES: COCc1nc(Cl)c(C)c(N2CCC(Oc3ccc(OC)cc3)CC2)n1] | 4-chloro-2-(methoxymethyl)-6-(4-(4-methoxyphenoxy)piperidin-1-yl)-5-methylpyrimidine | 378 |
| 62 | 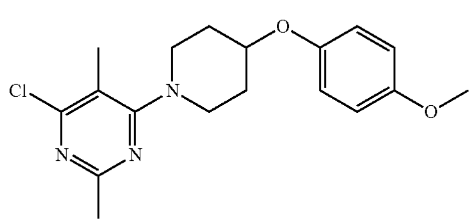 [SMILES: COc1ccc(OC2CCN(c3nc(C)nc(Cl)c3C)CC2)cc1] | 4-chloro-6-(4-(4-methoxyphenoxy)piperidin-1-yl)-2,5-dimethylpyrimidine | 348 |
| 63 | 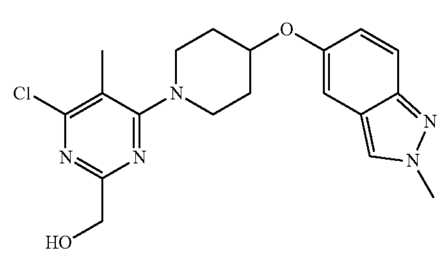 [SMILES: Cc1c(Cl)nc(CO)nc1N1CCC(Oc2ccc3nn(C)cc3c2)CC1] | 5-((1-(6-chloro-5-methylpyrimidin-4-yl)piperidin-4-yl)oxy)-1-methyl-1H-indazole | 388 |

TABLE 1-continued

| Example | Structure | Name | MS (M + 1) |
|---|---|---|---|
| 64 | 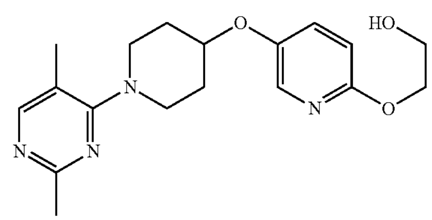 [SMILES: Cc1ncc(C)c(N2CCC(Oc3ccc(OCCO)nc3)CC2)n1] | 2-((5-((1-(2,5-dimethylpyrimidin-4-yl)piperidin-4-yl)oxy)pyridin-2-yl)oxy)ethan-1-ol | 345 |
| 65 | 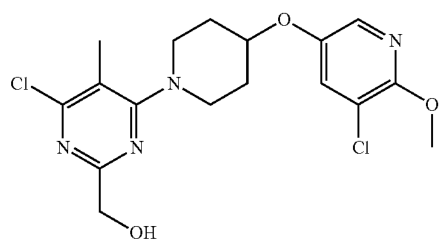 [SMILES: COc1ncc(OC2CCN(c3nc(CO)nc(Cl)c3C)CC2)cc1Cl] | (4-chloro-6-(4-((5-chloro-6-methoxypyridin-3-yl)oxy)piperidin-1-yl)-5-methylpyrimidin-2-yl)methanol | 399 |
| 66 | 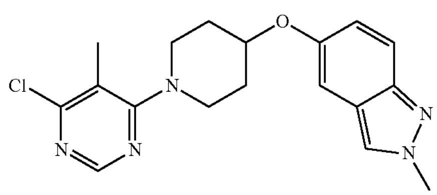 [SMILES: Cc1c(Cl)ncnc1N1CCC(Oc2ccc3nn(C)cc3c2)CC1] | 5-((1-(6-chloro-5-methylpyrimidin-4-yl)piperidin-4-yl)oxy)-2-methyl-2H-indazole | 358 |
| 67 | 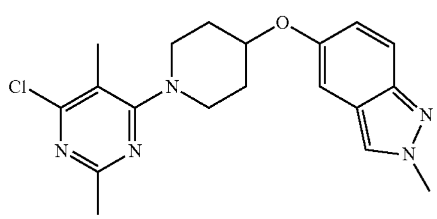 [SMILES: Cc1nc(Cl)c(C)c(N2CCC(Oc3ccc4nn(C)cc4c3)CC2)n1] | 5-((1-(6-chloro-2,5-dimethypyrimidin-4-yl)piperidin-4-yl)oxy)-2-methyl-2H-indazole | 372 |
| 68 | 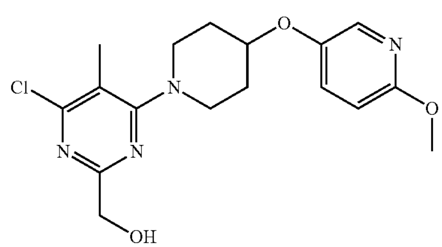 [SMILES: COc1ccc(OC2CCN(c3nc(CO)nc(Cl)c3C)CC2)cn1] | (4-chloro-6-(4-((6-methoxypyridin-3-yl)oxy)piperidin-1-yl)-5-methylpyrimidin-2-yl)methanol | 365 |
| 69 | 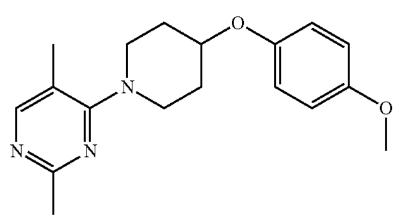 [SMILES: COc1ccc(OC2CCN(c3nc(C)ncc3C)CC2)cc1] | 4-(4-(4-methoxyphenoxy)piperidin-1-yl)-2,5-dimethylpyrimidine | 314 |

TABLE 1-continued

| Example | Structure | Name | MS (M + 1) |
|---|---|---|---|
| 70 | 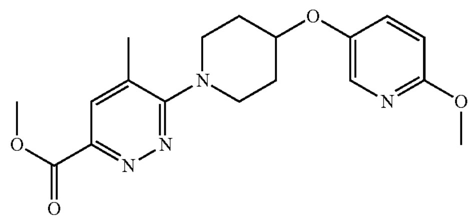 [SMILES: COC(=O)c1cc(C)c(N2CCC(Oc3ccc(OC)nc3)CC2)nn1] | methyl 6-(4-((6-methoxypyridin-3-yl)oxy)piperidin-1-yl)-5-methylpyridazine-3-carboxylate | 359 |
| 71 | 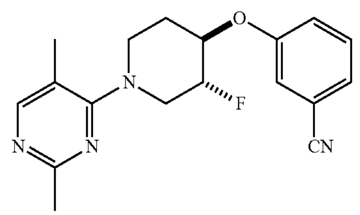 [SMILES: Cc1ncc(C)c(N2CC[C@@H](Oc3cccc(C#N)c3)[C@H](F)C2)n1] | 3-(((3R,4R)-1-(2,5-dimethylpyrimidin-4-yl)-3-fluoropiperidin-4-yl)oxy)benzonitrile | 327 |
| 72 | 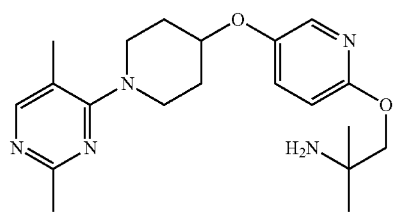 [SMILES: Cc1ncc(C)c(N2CCC(Oc3ccc(OCC(C)(C)N)nc3)CC2)n1] | 1-((5-((1-(2,5-dimethylpyrimidin-4-yl)piperidin-4-yl)oxy)pyridin-2-yl)oxy)-2-methylpropan-2-amine | 372 |
| 73 | 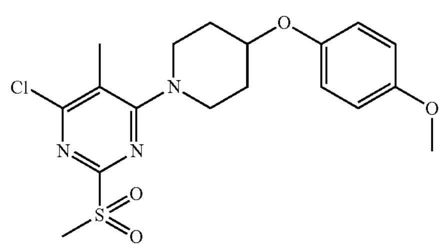 [SMILES: COc1ccc(OC2CCN(c3nc(S(C)(=O)=O)nc(Cl)c3C)CC2)cc1] | 4-chloro-6-(4-(4-methoxyphenoxy)piperidin-1-yl)-5-methyl-2-(methylsulfonyl)pyrimidine | 412 |
| 74 | 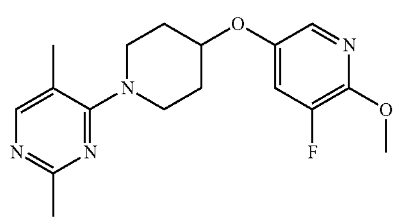 [SMILES: COc1ncc(OC2CCN(c3nc(C)ncc3C)CC2)cc1F] | 4-(4-((5-fluoro-6-methoxypyridin-3-yl)oxy)piperidin-1-yl)-2,5-dimethylpyrimidine | 333 |
| 75 | 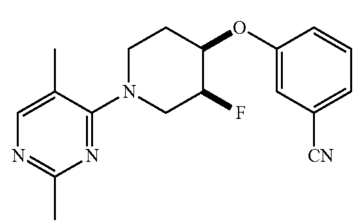 [SMILES: Cc1ncc(C)c(N2CC[C@@H](Oc3cccc(C#N)c3)[C@@H](F)C2)n1] | 3-(((3S,4R)-1-(2,5-dimethylpyrimidin-4-yl)-3-fluoropiperidin-4-yl)oxy)benzonitrile | 327 |

TABLE 1-continued

| Example | Name | MS (M + 1) |
|---|---|---|
| 76 | 3-((1-(2,5-dimethylpyrimidin-4-yl)piperidin-4-yl)oxy)benzonitrile | 309 |
| 77 | 2,4-dichloro-6-(4-(4-methoxyphenoxy)piperidin-1-yl)-5-methylpyrimidine | 368 |
| 78 | 4-chloro-2-(methoxymethyl)-6-(4-((6-methoxypyridin-3-yl)oxy)piperidin-1-yl)-5-methylpyrimidine | 379 |
| 79 | 4-(4-((6-methoxypyridin-3-yl)oxy)piperidin-1-yl)-2,5-dimethylpyrimidine | 315 |
| 80 | 6-((1-(2,5-dimethylpyrimidin-4-yl)piperidin-4-yl)oxy)-1H-indazole | 324 |
| 81 | 3-(((3R,4S)-1-(2,5-dimethylpyrimidin-4-yl)-3-fluoropiperidin-4-yl)oxy)benzonitrile | 327 |

TABLE 1-continued

| Example | Name | MS (M + 1) |
|---|---|---|
| 82 | 4-chloro-6-(4-((6-methoxypyridin-3-yl)oxy)piperidin-1-yl)-5-methyl-2-(methylthio)pyrimidine | 381 |
| 83 | 3-(((3S,4S)-1-(2,5-dimethylpyrimidin-4-yl)-3-fluoropiperidin-4-yl)oxy)benzonitrile | 327 |
| 84 | 4-((3S,4R)-3-fluoro-4-((6-methoxypyridin-3-yl)oxy)piperidin-1-yl)-2,5-dimethylpyrimidine | 333 |
| 85 | 4-(4-((6-methoxypyridin-3-yl)oxy)piperidin-1-yl)-2-(methylthio)pyrimidine-5-carbonitrile | 358 |
| 86 | 3-(4-((6-methoxypyridin-3-yl)oxy)piperidin-1-yl)-5,6-dimethylpyridazine-4-carbonitrile | 340 |
| 87 | 6-(4-((6-methoxypyridin-3-yl)oxy)piperidin-1-yl)-2,5-dimethylpyrimidin-4-amine | 330 |

TABLE 1-continued

| Example | Structure | Name | MS (M + 1) |
|---|---|---|---|
| 88 | 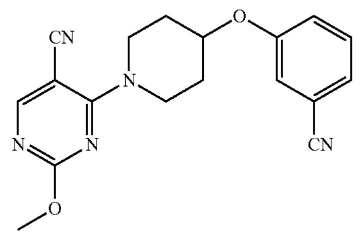 [SMILES: COc1ncc(C#N)c(N2CCC(Oc3cccc(C#N)c3)CC2)n1] | 4-(4-(3-cyanophenoxy)piperidin-1-yl)-2-methoxypyrimidine-5-carbonitrile | 336 |
| 89[2] | 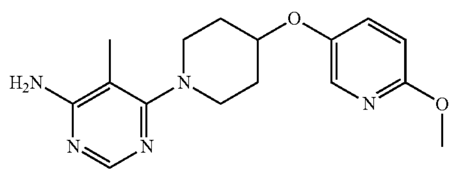 [SMILES: COc1ccc(OC2CCN(c3ncnc(N)c3C)CC2)cn1] | 6-(4-((6-methoxypyridin-3-yl)oxy)piperidin-1-yl)-5-methylpyrimidin-4-amine | 316 |
| 90 | 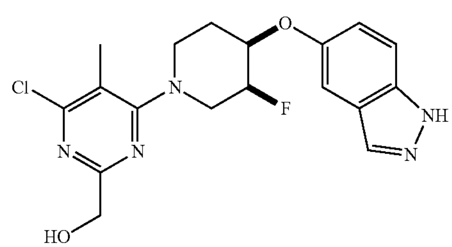 [SMILES: Cc1c(Cl)nc(CO)nc1N1CC[C@@H](Oc2ccc3[nH]ncc3c2)[C@@H](F)C1] | (4-((3S,4R)-4-((1H-indazol-5-yl)oxy)-3-fluoropiperidin-1-yl)-6-chloro-5-methylpyrimidin-2-yl)methanol | 392 |
| 91 | 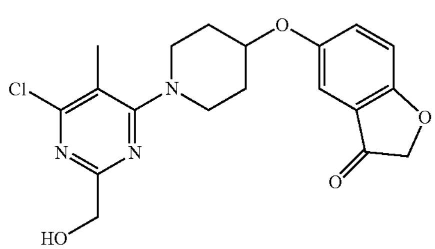 [SMILES: Cc1c(Cl)nc(CO)nc1N1CCC(Oc2ccc3c(c2)C(=O)CO3)CC1] | 5-((1-(6-chloro-2-(hydroxymethyl)-5-methylpyrimidin-4-yl)piperidin-4-yl)oxy)benzofuran-3(2H)-one | 390 |
| 92 | 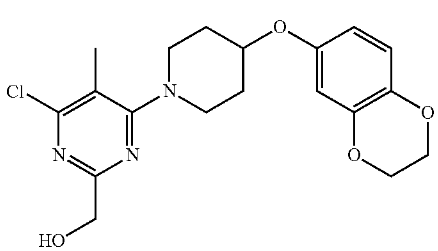 [SMILES: Cc1c(Cl)nc(CO)nc1N1CCC(Oc2ccc3c(c2)OCCO3)CC1] | (4-chloro-6-(4-((2,3-dihydrobenzo[b][1,4]dioxin-6-yl)oxy)piperidin-1-yl)-5-methylpyrimidin-2-yl)methanol | 392 |
| 93 | 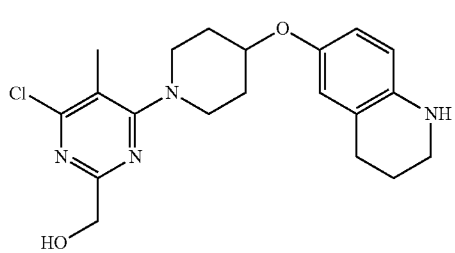 [SMILES: Cc1c(Cl)nc(CO)nc1N1CCC(Oc2ccc3c(c2)CCCN3)CC1] | (4-chloro-5-methyl-6-(4-((1,2,3,4-tetrahydroquinolin-6-yl)oxy)piperidin-1-yl)pyrimidin-2-yl)methanol | 389 |

TABLE 1-continued

| Example | Structure | Name | MS (M + 1) |
|---|---|---|---|
| 94 | 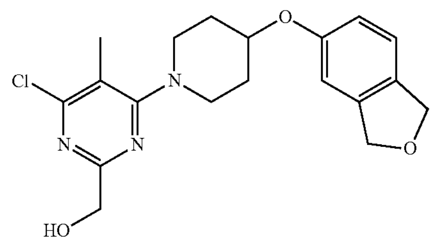 [SMILES: Cc1c(Cl)nc(CO)nc1N1CCC(Oc2ccc3c(c2)COC3)CC1] | (4-chloro-6-(4-((1,3-dihydroisobenzofuran-5-yl)oxy)piperidin-1-yl)-5-methylpyrimidin-2-yl)methanol | 376 |
| 95[3] | 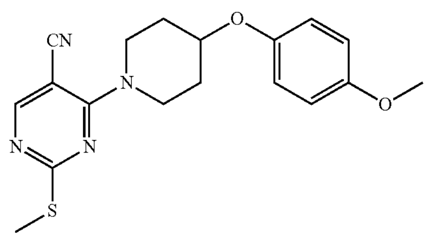 [SMILES: COc1ccc(OC2CCN(c3nc(SC)ncc3C#N)CC2)cc1] | 4-(4-(4-methoxyphenoxy)piperidin-1-yl)-2-(methylthio)pyrimidine-5-carbonitrile | 357 |
| 95A[3] | 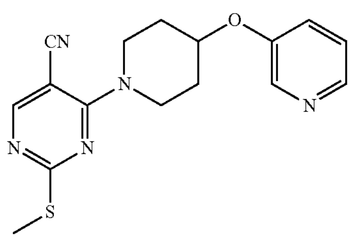 [SMILES: CSc1ncc(C#N)c(N2CCC(Oc3cccnc3)CC2)n1] | 2-(methylthio)-4-(4-(pyridin-3-yloxy)piperidin-1-yl)pyrimidine-5-carbonitrile | 328 |
| 95B[4] | 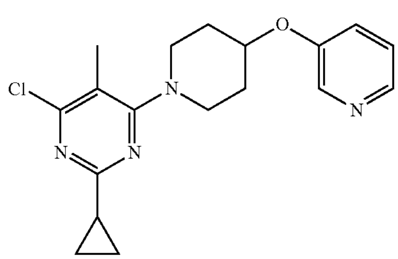 [SMILES: Cc1c(Cl)nc(C2CC2)nc1N1CCC(Oc2cccnc2)CC1] | 4-chloro-2-cyclopropyl-5-methyl-6-(4-(pyridin-3-yloxy)piperidin-1-yl)pyrimidine | 345 |
| 95C[4] | 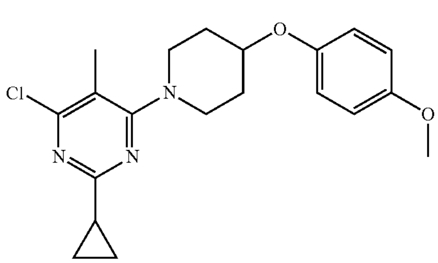 [SMILES: COc1ccc(OC2CCN(c3nc(C4CC4)nc(Cl)c3C)CC2)cc1] | 4-chloro-2-cyclopropyl-6-(4-(4-methoxyphenoxy)piperidin-1-yl)-5-methylpyrimidine | 374 |

TABLE 1-continued

| Example | Structure | Name | MS (M + 1) |
| --- | --- | --- | --- |
| 95D | 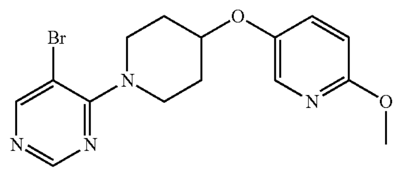 [SMILES: COc1ccc(OC2CCN(c3ncncc3Br)CC2)cn1] | 5-bromo-4-(4-((6-methoxypyridin-3-yl)oxy)piperidin-1-yl)pyrimidine | 365, 367 |

[1]Pyrazine starting materials may be prepared according to literature procedures, see e.g.: Al-Kamali, A. S. N. *Phos. Sul. Sil. Rel. Elem* 2009, 184, 1812-1824.
[2]Pyrimidine starting materials may be prepared according to literature procedures, see e.g.: Cai, D., et al. Preparation of (iso)quinolinyl pyridinamines, pyrimidinamines, pyrazinamines, pyridazinamines, and triazinamines as vanilloid-1 receptor antagonists for treating pain. Merck Sharp & Dohme Limited, UK; Merck & Co. Inc., PCT Patent Publication WO 2005047280, 26 May 2005.
[3]Pyrimidine starting materials may be prepared according to literature procedures, see e.g.: Yang, L. -L., et al. *Eur. J. Med. Chem.* 2012, 56, 30-38.
[4]Pyrimidine starting materials may be prepared according to literature procedures, see e.g.: Shipe, W. D., et al. *J. Med. Chem.* 2015, 58, 7888-7894.

Example 96

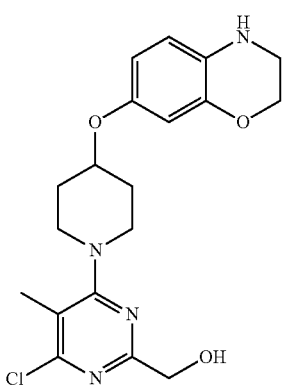 [SMILES: Cc1c(Cl)nc(CO)nc1N1CCC(Oc2ccc3c(c2)OCCN3)CC1]

(4-Chloro-6-(4-((3,4-dihydro-2H-benzo[b][1,4]oxazin-7-yl)oxy)piperidin-1-yl)-5-methylpyrimidin-2-yl)methanol (Scheme 2)

Step 1: tert-Butyl 7-((1-(6-chloro-2-(hydroxymethyl)-5-methylpyrimidin-4-yl)piperidin-4-yl)oxy)-2H-benzo[b][1,4]oxazine-4(3H)-carboxylate To a solution of tert-butyl 7-(piperidin-4-yloxy)-2H-benzo[b][1,4]oxazine-4(3H)-carboxylate (67 mg, 0.20 mmol) in dioxane (3 mL) was added (4,6-dichloro-5-methylpyrimidin-2-yl)methanol (intermediate B, 58.0 mg, 0.301 mmol) and DIPEA (0.035 mL, 0.20 mmol). The reaction mixture was stirred at RT for 24 h before partitioning with water (10 mL) and EtOAc (30 mL). The organic phase was washed with brine (10 mL), dried over anhydrous sodium sulfate, filtered and the filtrate was concentrated in vacuo to afford the title compound. MS: 491 (M+1).

Step 2: (4-Chloro-6-(4-((3,4-dihydro-2H-benzo[b][1,4]oxazin-7-yl)oxy)piperidin-1-yl)-5-methylpyrimidin-2-yl)methanol To a solution of tert-butyl 7-((1-(6-chloro-2-(hydroxymethyl)-5-methylpyrimidin-4-yl)piperidin-4-yl)oxy)-2H-benzo[b][1,4]oxazine-4(3H)-carboxylate (75 mg, 0.153 mmol) in DCM (2 mL) was added TFA (1 mL, 13.0 mmol). The reaction mixture was stirred at RT for 1 h before being was concentrated in vacuo. The residue was purified by reverse phase HPLC (ACN/water with 0.1% TFA modifier) to furnish the title compound. MS: 391 (M+1). $^1$H NMR (400 MHz, methanol-$d_4$): δ 7.17 (1H, d, J=8.8 Hz), 6.68-6.75 (2H, m), 4.52 (2H, s), 4.55-4.64 (1H, m), 4.52 (2H, s), 4.31-4.46 (2H, m), 3.74-3.77 (2H, m), 3.61-3.66 (2H, m), 3.40-3.46 (2H, m), 2.28 (3H, s), 2.05-2.12 (2H, m), 1.82-1.87 (2H, m).

The following examples in table 2 were prepared according to scheme 2 using the procedure outlined in the synthesis of Example 90 using known or prepared piperidines and halogenated heteroaromatic compounds in step 1.

TABLE 2

| Example | Structure | Name | MS (M + 1) |
| --- | --- | --- | --- |
| 97 | 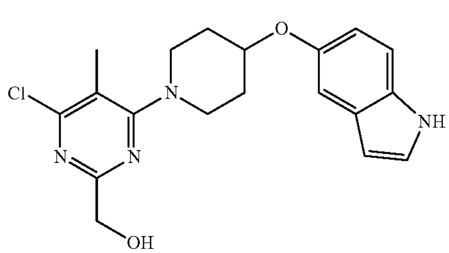 [SMILES: Cc1c(Cl)nc(CO)nc1N1CCC(Oc2ccc3[nH]ccc3c2)CC1] | (4-(4-((1H-indol-5-yl)oxy)piperidin-1-yl)-6-chloro-5-methylpyrimidin-2-yl)methanol | 373 |

TABLE 2-continued

| Example | Structure | Name | MS (M + 1) |
|---|---|---|---|
| 98 | 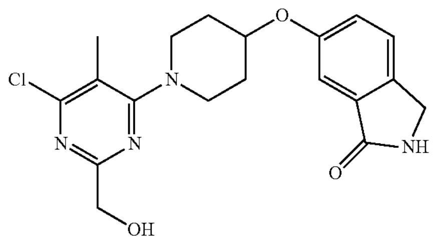 [SMILES: Cc1c(Cl)nc(CO)nc1N1CCC(Oc2ccc3c(c2)C(=O)NC3)CC1] | 6-((1-(6-chloro-2-(hydroxymethyl)-5-methylpyrimidin-4-yl)piperidin-4-yl)oxy)isoindolin-1-one | 389 |

Example 99

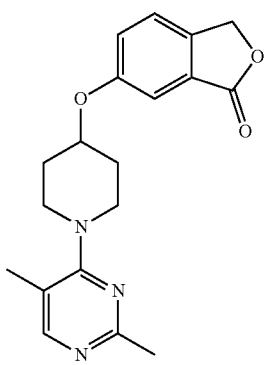 [SMILES: Cc1ncc(C)c(N2CCC(Oc3ccc4c(c3)C(=O)OC4)CC2)n1]

6-((1-(2,5-Dimethylpyrimidin-4-yl)piperidin-4-yl)oxy)isobenzofuran-1(3H-1)-one (Scheme 3)

Step 2: 1-(2,5-Dimethylpyrimidin-4-yl)piperidin-4-yl methanesulfonate

To a mixture of triethylamine (2.38 mL, 17.1 mmol) and 1-(2,5-dimethylpyrimidin-4-yl)piperidin-4-ol (intermediate X1, 1.77 g, 8.54 mmol) in DCM (50 mL) at 0° C. was added MsCl (1.0 mL, 12.8 mmol). The resulting mixture was stirred at 15° C. for 18 before being diluted with DCM (50 mL) and water (50 mL). The organic phase was washed with brine (50 mL), dried over anhydrous sodium sulfate and filtered. The filtrate was concentrated in vacuo afford the title compound. MS: 286 (M+1).

Step 3: 6-((1-(2,5-dimethylpyrimidin-4-yl)piperidin-4-yl)oxy)isobenzofuran-1(3H-1)-one A mixture of 1-(2,5-dimethylpyrimidin-4-yl)piperidin-4-yl methanesulfonate (62.7 mg, 0.22 mmol), 6-hydroxy-isobenzofuran-1(3H)-one (30 mg, 0.20 mmol) and potassium carbonate (41.4 mg, 0.30 mmol) in DMF (3 mL) was stirred for 16 h at 80° C. After cooling to RT, EtOAc (25 mL) and water (25 mL) were added and the organic phase was washed with brine (25 mL), dried over anhydrous sodium sulfate and filtered. The filtrate was concentrated in vacuo and the residue was purified by reverse phase HPLC (ACN/water with 0.1% TFA modifier) to furnish the title compound. MS: 340 (M+1). $^1$H NMR (400 MHz, methanol-$d_4$): δ: 7.95 (1H, s), 7.56 (1 H, d, J=6.8 Hz), 7.35-7.45 (2H, m), 5.36 (2H, s), 4.13-4.24 (2H, m), 4.02-4.08 (2H, m), 2.56 (3H, s), 2.35 (3H, s), 2.06-2.22 (2H, m), 1.96-2.02 (2H, m).

The following examples in table 3 were prepared according to scheme 3 using the procedure outlined in the synthesis of Example 99 using known or prepared phenols.

TABLE 3

| Example | Structure | Name | MS (M + 1) |
|---|---|---|---|
| 100 | 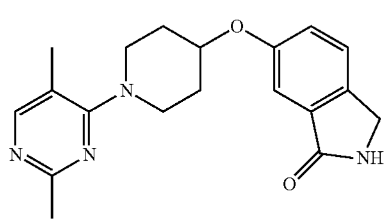 [SMILES: Cc1ncc(C)c(N2CCC(Oc3ccc4c(c3)C(=O)NC4)CC2)n1] | 6-((1-(2,5-dimethylpyrimidin-4-yl)piperidin-4-yl)oxy)isoindolin-1-one | 339 |

Example 101

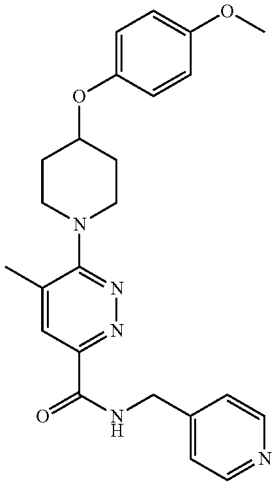 [SMILES: COc1ccc(OC2CCN(c3nnc(C(=O)NCc4ccncc4)cc3C)CC2)cc1]

6-(4-(4-Methoxyphenoxy)piperidin-1-yl)-5-methyl-
N-(pyridin-4-ylmethyl)pyridazine-3-carboxamide
(Scheme 4)

To a solution of 6-(4-hydroxypiperidin-1-yl)-5-methyl-N-(pyridin-4-ylmethyl)pyridazine-3-carboxamide (intermediate X3, 40 mg, 0.122 mmol), 4-methoxyphenol (16.68 mg, 0.134 mmol), Bu$_3$P (0.060 mL, 0.244 mmol) in THF (2 mL) was added a solution of (E)-diazene-1,2-diylbis(piperidin-1-ylmethanone) (61.7 mg, 0.244 mmol) in THF (0.5 mL) added dropwise at 0° C. The reaction mixture was stirred at 55° C. for 12 h before the volatiles were removed under reduced pressure. The residue was purified by prep-TLC (20:1 EtOAc:MeOH) to afford the title compound. MS: 434 (M+1). $^1$H (400 MHz, methanol-d$_4$): δ 8.47 (2H, d, J=4.8 Hz), 7.91 (1H, s), 7.43 (2H, d, J=4.8 Hz), 6.93 (2H, d, J=8.8 Hz), 6.85 (2H, d, J=9.2 Hz), 4.68 (2H, s), 4.50-4.53 (1H, m), 3.75 (3H, s), 3.65-3.70 (2H, m), 3.34-3.40 (2H, m), 2.41 (3H, s), 2.10-2.17 (2H, m), 1.90-1.95 (2H, m).

Example 102

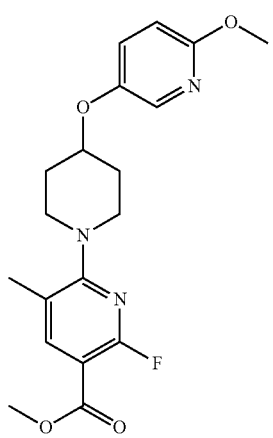

Methyl 2-fluoro-6-(4-((6-methoxypyridin-3-yl)oxy)
piperidin-1-yl)-5-methylnicotinate (Scheme 5)

Step 1: Methyl 2-fluoro-6-(4-((6-methoxypyridin-3-yl)oxy)piperidin-1-yl)nicotinate To a solution of methyl 2,6-difluoronicotinate (800 mg, 4.62 mmol) and DIPEA (4.0 mL, 23.1 mmol) in DMF (10 mL) was added 2-methoxy-5-(piperidin-4-yloxy)pyridine, HCl (1244 mg, 5.08 mmol) at RT. After stirring for 1 h, water (15 mL) was added and the mixture was extracted with EtOAc (20 mL×4). The combined organic fractions were washed with water (50 mL×3), dried over anhydrous sodium sulfate, filtered and concentrated. The crude product was purified by silica gel chromatography (0-30% EtOAc/petroleum ether) to give the title compound. MS: 362 (M+1).

Step 2: Methyl 5-bromo-2-fluoro-6-(4-((6-methoxypyridin-3-yl)oxy)piperidin-1-yl)nicotinate A solution of methyl 2-fluoro-6-(4-((6-methoxypyridin-3-yl)oxy)piperidin-1-yl)nicotinate (50 mg, 0.138 mmol) and NBS (24.6 mg, 0.138 mmol) in chloroform (5 mL) was stirred at 60° C. for 12 h. The reaction was cooled to RT and was diluted with water (10 mL) and extracted with DCM (10 mL×3). The organic layers were combined, washed with brine (10 mL), dried over magnesium sulfate, filtered, and concentrated in vacuo to provide the title compound. MS: 440, 442 (M+1).

Step 3: Methyl 2-fluoro-6-(4-((6-methoxypyridin-3-yl)oxy)piperidin-1-yl)-5-methylnicotinate To a solution of methyl 5-bromo-2-fluoro-6-(4-((6-methoxypyridin-3-yl)oxy)piperidin-1-yl)nicotinate (60 mg, 0.136 mmol) in toluene (5 mL) was added Pd(Ph$_3$P)$_4$ (31.5 mg, 0.027 mmol) and trimethylaluminum (2 M, 0.34 mL, 0.681 mmol). The mixture was stirred at 90° C. for 16 h under an inert nitrogen atmosphere. The mixture was cooled to RT then diluted with water (20 mL) and extracted with EtOAc (20 mL×3). The organic layers were combined, washed with brine (20 mL), dried over anhydrous magnesium sulfate, filtered, and concentrated. The residue was purified by prep-TLC (3:1 petroleum ether:EtOAc) to afford the title compound. MS: 376 (M+1). $^1$H NMR (400 MHz, CDCl$_3$): δ 7.98 (1H, d, J=9.2 Hz), 7.86 (1H, s), 7.30 (1H, dd, J=49.2, 2.8 Hz), 6.69 (1H, d, J=8.8 Hz), 4.36-4.40 (1H, m), 3.89 (6H, s), 3.61-3.67 (2H, m), 3.20-3.28 (2H, m), 2.26 (3H, s), 2.02-2.06 (2H, m), 1.86-1.93 (2H, m).

Example 103

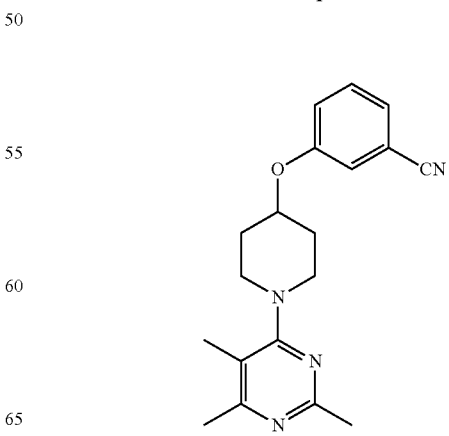

3-((1-(2,5,6-Trimethylpyrimidin-4-yl)piperidin-4-yl)oxy)benzonitrile (Scheme 5)

Step 1: 3-((1-(6-Chloro-2,5-dimethylpyrimidin-4-yl)piperidin-4-yl)oxy)benzonitrile 4,6-Dichloro-2,5-dimethylpyrimidine (212 mg, 1.20 mmol) and 3-(piperidin-4-yloxy)benzonitrile hydrochloride (239 mg, 1.0 mmol) were suspended in dioxane (5 mL).

(M+1). $^1$H NMR (500 MHz, CDCl$_3$): δ 7.38 (m, 1H), 7.24 (d, 1H), 7.16 (m, 2H), 4.53 (m, 1H), 3.56 (m, 2H), 3.19 (m, 2H), 2.52 (s, 3H), 2.38 (s, 3H), 2.13 (s, 3H), 2.09 (m, 2H), 1.91 (m, 2H). The following examples in table 5 were prepared according to scheme 5 using the procedure outlined in the synthesis of Example 102 and 103. In some cases, where there is an existing bromide or chloride at the 3-position, the bromination step maybe omitted as it was in the synthesis of Example 103.

TABLE 5

| Example | Structure | Name | MS (M + 1) |
| --- | --- | --- | --- |
| 104 | 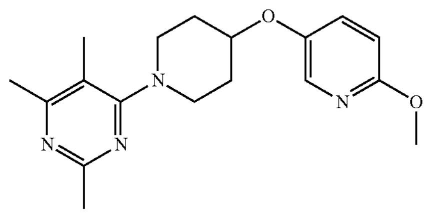 | 4-(4-((6-methoxypyridin-3-yl)oxy)piperidin-1-yl)-2,5,6,-trimethylpyrimidine | 329 |
| 105 | 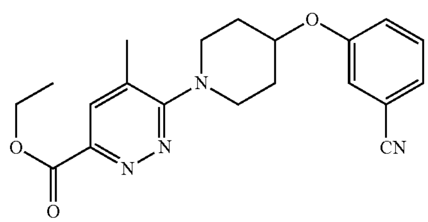 [SMILES: CCOC(=O)c1cc(C)c(N2CCC(Oc3cccc(C#N)c3)CC2)nn1] | ethyl 6-(4-(3-cyanophenoxy)piperidin-1-yl)-5-methylpyridazine-3-carboxylate | 367 |
| 105A | 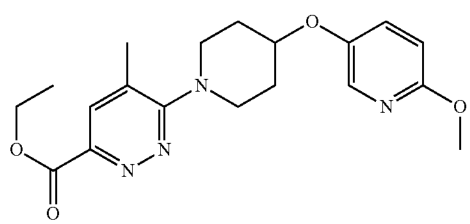 [SMILES: CCOC(=O)c1cc(C)c(N2CCC(Oc3ccc(OC)nc3)CC2)nn1] | ethyl 6-(4-((6-methoxypyridin-3-yl)oxy)piperidin-1-yl)-5-methylpyridazine-3-carboxylate | 373 |

DIPEA (873 μL, 5.00 mmol) and the reaction was stirred at RT for 6 h and then 50° C. for 15 h. The reaction was cooled to RT and was partitioned between ethyl acetate and aqueous ammonium chloride (staturated). The organics were washed with brine, then dried over anhydrous sodium sulfate, filtered and evaporated under reduced pressure. The residue was purified by silica gel chromatography (0-50% EtOAc/hexanes) to afford the title compound. MS: 343 (M+1).

Step 2: 3-((1-(2,5,6-Trimethylpyrimidin-4-yl)piperidin-4-yl)oxy)benzonitrile 3-((1-(6-Chloro-2,5-dimethylpyrimidin-4-yl)piperidin-4-yl)oxy)benzonitrile (0.064 g, 0.187 mmol) was mixed with dioxane (1.87 mL) and chloro(2-dicyclohexylphosphino-2',4',6'-triisopropyl-1,1'-biphenyl)[2-(2'-amino-1,1'-biphenyl)]palladium(II) (0.015 g, 0.019 mmol). Under an inert nitrogen atmosphere, methylzinc chloride (2 M, 0.19 mL, 0.373 mmol) was added to the mixture before heating to 150° C. under microwave irradiation for 30 min. The reaction was cooled to RT and partitioned between water and ethyl acetate. The organic was washed with brine, dried over anhydrous sodium sulfate, filtered and concentrated. The residue was purified by silica gel chromatography (15-60% acetone/hexanes) to afford the title compound. MS: 323

Example 106

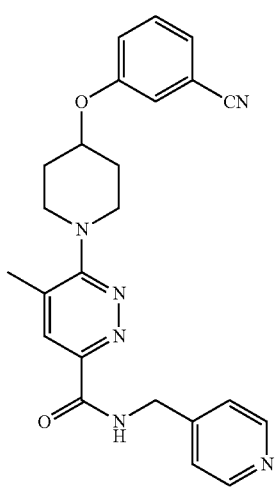 [SMILES: Cc1cc(C(=O)NCc2ccncc2)nnc1N1CCC(Oc2cccc(C#N)c2)CC1]

6-(4-(3-Cyanophenoxy)piperidin-1-yl)-5-methyl-N-(pyridin-4-ylmethyl)pyridazine-3-carboxamide (Scheme 6)

Step 1: Methyl 6-(4-(3-cyanophenoxy)piperidin-1-yl)-5-methylpyridazine-3-carboxylate A solution of methyl 6-bromo-5-methylpyridazine-3-carboxylate (intermediate H, 5.0 g, 21.6 mmol), Hûinig's Base (7.56 mL, 43.3 mmol) and 3-(piperidin-4-yloxy)benzonitrile (4.38 g, 21.6 mmol) in DMF (108 mL) was added heated to 80° C. for 15 h. The reaction was cooled to RT and was diluted with water and DCM. The organic separated, dried over anhydrous sodium sulfate, filtered and then concentrated to dryness. Cold ether was added to the crude material and the product was collected by filtration to afford the title compound. MS: 353 (M+1).

Step 2: 6-(4-(3-Cyanophenoxy)piperidin-1-yl)-5-methylpyridazine-3-carboxylic Acid To a solution of methyl 6-(4-(3-cyanophenoxy)piperidin-1-yl)-5-methylpyridazine-3-carboxylate (6.31 g, 17.9 mmol) in THF (53.7 mL) and MeOH (17.9 mL) was added a solution of LiOH (0.86 g, 35.8 mmol) in water (17.9 mL) at RT. The heterogeneous reaction was concentrated and the product was filtered off and washed with water and Et$_2$O and lyophilized to dryness to provide the title compound. MS: 339 (M+1).

Step 3: 6-(4-(3-Cyanophenoxy)piperidin-1-yl)-5-methyl-N-(pyridin-4-ylmethyl)pyridazine-3-carboxamide A solution of 6-(4-(3-cyanophenoxy)piperidin-1-yl)-5-methylpyridazine-3-carboxylic acid (5.0 g, 14.8 mmol), HATU (8.43 g, 22.2 mmol) and DIPEA (7.74 mL, 44.3 mmol) in DMAc (49.3 mL) was stirred for 10 min at RT before pyridin-4-ylmethanamine (1.92 g, 17.7 mmol) was added. After stirring for 18 h at RT, the mixture was partitioned by water and dichloromethane. The organic was separated, dried over anhydrous sodium sulfate, filtered, and concentrated under reduced pressure. The reaction was purified by reverse phase HPLC (10-50% MeCN/water with 0.1% TFA modifier) and then again by silica gel chromatography (15-80% 1:3 EtOH:EtOAc in hexanes with 0.1% NH$_3$OH) to afford the title compound. MS: 429 (M+1). $^1$H NMR (400 MHz, methanol-d$_4$) δ: 8.46 (1H, d, J=6.0 Hz), 7.91 (1H, s), 7.25-7.45 (6H, m), 4.74-4.89 (1H, m), 4.70 (2H, s), 3.62-3.68 (2H, m), 3.34-3.38 (2H, m), 2.40 (3H, s), 2.15-2.21 (2H, m), 1.91-1.96 (2H, m).

Example 106A

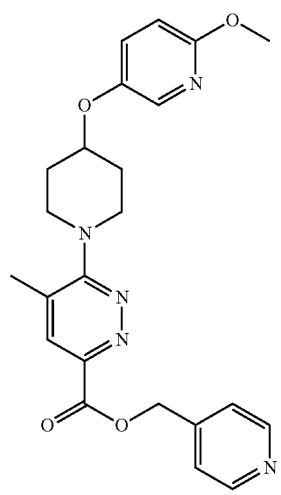 [SMILES: COc1ccc(OC2CCN(c3nnc(C(=O)OCc4ccncc4)cc3C)CC2)cn1]

Pyridin-4-ylmethyl 6-(4-((6-methoxypyridin-3-yl)oxy)piperidin-1-yl)-5-methylpyridazine-3-carboxylate (Scheme 6)

Step 1: Methyl 6-(4-((6-methoxypyridin-3-yl)oxy)piperidin-1-yl)-5-methylpyridazine-3-carboxylate To methyl 6-bromo-5-methylpyridazine-3-carboxylate (intermediate H, 1.2 g, 5.19 mmol) in DMF (20 mL) was added DIPEA (2.27 mL, 13.0 mmol) and 2-methoxy-5-(piperidin-4-yloxy)pyridine hydrochloride (1.27 g, 5.19 mmol). The reaction was heated to 80° C. for 15 h before cooling to RT and partitioning with water (100 mL) and DCM (20 mL×3). The organic was separated, dried over anhydrous sodium sulfate, filtered, and concentrated under reduced pressure. The residue was purified by silica gel column chromatography (10-50% 3:1 EtOAc:EtOH in hexanes) to afford the title compound. MS: 359 (M+1).

Step 2: 6-(4-((6-Methoxypyridin-3-yl)oxy)piperidin-1-yl)-5-methylpyridazine-3-carboxylic Acid To a solution of methyl 6-(4-((6-methoxypyridin-3-yl)oxy)piperidin-1-yl)-5-methylpyridazine-3-carboxylate (1.86 g, 5.19 mmol) was added lithium hydroxide (0.497 g, 20.76 mmol) in 2-propanol (13.8 mL) and water (3.46 mL). The reaction was heated to 45° C. for 15 h before cooling to RT and diluting with aqueous 1 M HCl and EtOAc/DCM. The title compound was collected by filtration (diethyl ether wash). MS: 345 (M+1).

The organic was separated, dried over sodium sulfate, filtered, and concentrated under reduced pressure to yield a crude oil 676 mg. This was made into a solution in DMAc and hunigs base for future coupling reactions.

Step 3: Pyridin-4-ylmethyl 6-(4-((6-methoxypyridin-3-yl)oxy)piperidin-1-yl)-5-methylpyridazine-3-carboxylate In a vial with 6-(4-((6-methoxypyridin-3-yl)oxy)piperidin-1-yl)-5-methylpyridazine-3-carboxylic acid (200 mg, 0.581 mmol) was added DMF (2.90 mL), triethylamine (243

μL, 1.74 mmol) and 4-(chloromethyl)pyridine hydrochloride (105 mg, 0.639 mmol). The reaction was stirred at 80° C. for 1 hr and additional triethylamine (243 μL, 1.74 mmol) and 4-(chloromethyl)pyridine hydrochloride (105 mg, 0.639 mmol) were added. The mixture was stirred for 15 h at 80° C. and was cooled to RT and diluted with water and DCM. The organic phase was separated, dried over anhydrous sodium sulfate, filtered, and concentrated under reduced pressure. The residue was purified by silica gel column chromatography (20-80% 3:1 EtOAc:EtOH in hexanes) to afford the title compound. MS: 436 (M+1). $^1$H NMR (500 MHz, CD$_3$OD) δ 8.56 (d, J=5.7 Hz, 2H), 7.99 (s, 1H), 7.56 (d, J=5.7 Hz, 2H), 7.47 (t, J=8.0 Hz, 1 H), 7.37 (s, 1H), 7.35-7.27 (m, 2H), 5.53 (s, 3H), 4.77 (tt, J=3.7, 7.4 Hz, 1H), 3.82-3.73 (m, 3H), 3.50-3.41 (m, 3H), 2.43 (s, 4H), 2.25-2.15 (m, 3H), 1.99-1.90 (m, 4H).

Example 107A and 107B

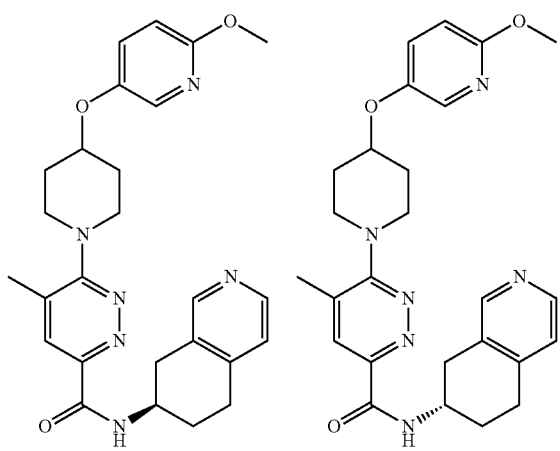

(R)-6-(4-((6-methoxypyridin-3-yl)oxy)piperidin-1-yl)-5-methyl-N-(5,6,7,8-tetrahydroisoquinolin-7-yl)pyridazine-3-carboxamide and (R)-6-(4-((6-methoxypyridin-3-yl)oxy)piperidin-1-yl)-5-methyl-N-(5,6,7,8-tetrahydroisoquinolin-7-yl)pyridazine-3-carboxamide (Scheme 6)

Step 1: Methyl 6-(4-((6-methoxypyridin-3-yl)oxy)piperidin-1-yl)-5-methylpyridazine-3-carboxylate To a solution for methyl 6-bromo-5-methylpyridazine-3-carboxylate (intermediate H, 1.2 g, 5.19 mmol) in DMF (20 mL) was added DIPEA (2.27 mL, 13.0 mmol) and 2-methoxy-5-(piperidin-4-yloxy)pyridine hydrochloride (1.27 g, 5.19 mmol). The reaction was heated to 80° C. for 15 h before it was cooled to RT and was diluted with water and DCM. The organic separated, dried over anhydrous sodium sulfate, filtered and then concentrated to dryness. The residue was purified by column chromatography on silica gel (10-50% 3:1 EtOAc:EtOH in hexanes) to yield the title compound. MS: 359 (M+1).

Step 2: 6-(4-((6-Methoxypyridin-3-yl)oxy)piperidin-1-yl)-5-methylpyridazine-3-carboxylic Acid A solution of methyl 6-(4-((6-methoxypyridin-3-yl)oxy)piperidin-1-yl)-5-methylpyridazine-3-carboxylate (1.86 g, 5.19 mmol) and lithium hydroxide (0.497 g, 20.8 mmol) in 2-propanol (13.8 mL) and water (3.50 mL) was stirred for 6 h at 45° C. The reaction mixture was cooled to RT and was diluted with 1 M HCl, EtOAc and DCM before the product was filtered off and washed with water and Et$_2$O and lyophilized to dryness to provide the title compound. MS: 345 (M+1).

Step 3: 6-(4-(3-Cyanophenoxy)piperidin-1-yl)-5-methyl-N-(pyridin-4-ylmethyl)pyridazine-3-carboxamide To a solution of 5,6,7,8-tetrahydroquinolin-6-amine (43 mg, 0.290 mmol), 6-(4-((6-methoxypyridin-3-yl)oxy)piperidin-1-yl)-5-methylpyridazine-3-carboxylic acid (50 mg, 0.145 mmol) in DMA (1 mL) was added HATU (83 mg, 0.218 mmol) and DIEA (0.072 ml, 0.436 mmol). The reaction mixture was stirred for 4 h at RT before direct purification by reverse phase HPLC (20-60% MeCN/water with 0.1% TFA modifier). The racemate was then purified by chiral SFC (OJ-H column, 40%/60% MeOH with 0.2% diethylamine modifier/CO$_2$) to afford intermediate 107A (faster eluting isomer): MS: 475 (M+1). $^1$H NMR (500 MHz, CDCl$_3$): δ 2.02-1.91 (4H, m), 2.22-2.14 (3H, m), 2.40 (3H, s), 2.80 (1H, dd, J=16.4, 8.4 Hz), 2.96 (2H, t, J=6.5 Hz) 3.33-3.22 (3H, m), 3.70 (1H, t, J=9.3 Hz), 3.92 (3H, s), 4.45-4.42 (1H, m), 4.52 (1H, t, J=7.7 Hz), 6.72 (1H, d, J=8.9 Hz), 7.05 (1H, s), 7.28 (2H, dd, J=13.0, 4.0 Hz), 7.89 (1H, d, J=3.0 Hz), 7.98 (1H, s), 8.11 (1H, d, J=8.0 Hz), 8.36 (2H, br s). Intermediate 107B (slower eluting isomer): MS: 475 (M+1). $^1$H NMR (500 MHz, CDCl$_3$): δ 2.02-1.91 (4H, m), 2.22-2.14 (3H, m), 2.40 (3H, s), 2.80 (1H, dd, J=16.4, 8.4 Hz), 2.96 (2H, t, J=6.5 Hz) 3.33-3.22 (3H, m), 3.70 (1H, t, J=9.3 Hz), 3.92 (3H, s), 4.45-4.42 (1H, m), 4.52 (1H, t, J=7.7 Hz), 6.72 (1H, d, J=8.9 Hz), 7.05 (1H, s), 7.28 (2H, dd, J=13.0, 4.0 Hz), 7.89 (1H, d, J=3.0 Hz), 7.98 (1H, s), 8.11 (1H, d, J=8.0 Hz), 8.36 (2H, br s).

The following examples in table 6 were prepared according to scheme 6 using the procedure outlined in the synthesis of Examples 106, 106A, 107A and 107B using known or commercially available amines (or in some cases ammonium chloride) or alkyl halides for step 3.

TABLE 6

| Example | Structure | Name | MS (M + 1) |
|---|---|---|---|
| 108 | 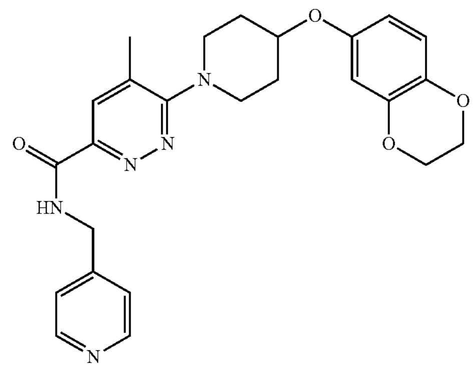 [SMILES: Cc1cc(C(=O)NCc2ccncc2)nnc1N1CCC(Oc2ccc3c(c2)OCCO3)CC1] | 6-[4-(2,3-dihydro-1,4-benzodioxin-6-yloxy)piperidin-1-yl]-5-methyl-N-(pyridin-4-ylmethyl)pyridazine-3-carboxamide | 462 |
| 109 | 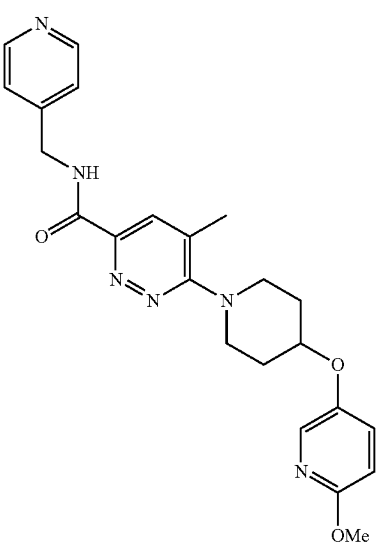 [SMILES: COc1ccc(OC2CCN(c3nnc(C(=O)NCc4ccncc4)cc3C)CC2)cn1] | 6-{4-[(6-methoxypyridin-3-yl)oxy]piperidin-1-yl}-5-methyl-N-(pyridin-4-ylmethyl)pyridazine-3-carboxamide | 435 |
| 110 | 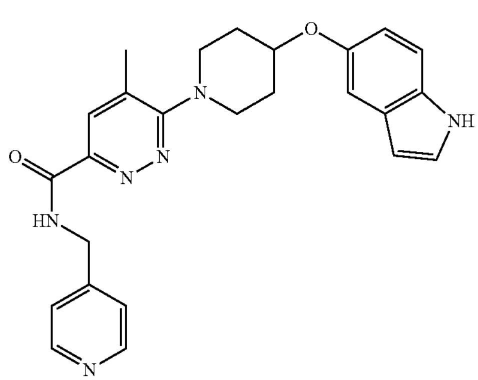 [SMILES: Cc1cc(C(=O)NCc2ccncc2)nnc1N1CCC(Oc2ccc3[nH]ccc3c2)CC1] | 6-[4-(1H-indol-5-yloxy)piperidin-1-yl]-5-methyl-N-(pyridin-4-ylmethyl)pyridazine-3-carboxamide | 443 |

TABLE 6-continued

| Example | Structure | Name | MS (M + 1) |
|---|---|---|---|
| 111 | 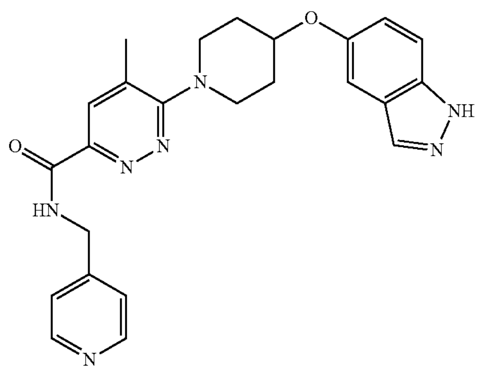 [SMILES: Cc1cc(C(=O)NCc2ccncc2)nnc1N1CCC(Oc2ccc3[nH]ncc3c2)CC1] | 6-[4-(1H-indazol-5-yloxy)piperidin-1-yl]-5-methyl-N-(pyridin-4-ylmethyl)pyridazine-3-carboxamide | 444 |
| 112 | 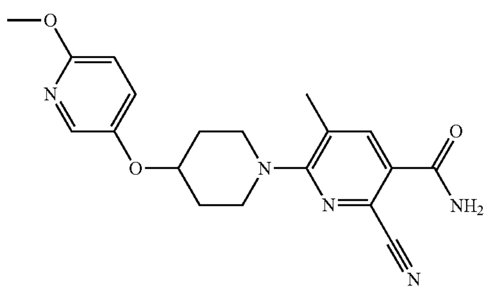 [SMILES: COc1ccc(OC2CCN(c3nc(C#N)c(C(N)=O)cc3C)CC2)cn1] | 2-cyano-6-{4-[(6-methoxypyridin-3-yl)oxy]piperidin-1-yl}-5-methylpyridine-3-carboxamide | 368 |
| 113 | 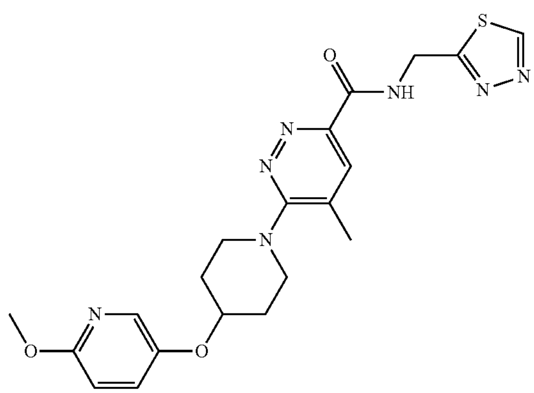 [SMILES: COc1ccc(OC2CCN(c3nnc(C(=O)NCc4nncs4)cc3C)CC2)cn1] | 6-{4-[(6-methoxypyridn-3-yl)oxy]piperidin-1-yl}-5-methyl-N-(1,3,4-thiadiazol-2-ylmethyl)pyridazine-3-carboxamide | 442 |
| 114 | 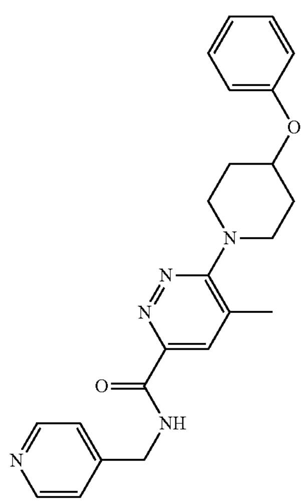 [SMILES: Cc1cc(C(=O)NCc2ccncc2)nnc1N1CCC(Oc2ccccc2)CC1] | 5-methyl-6-(4-phenoxypiperidin-1-yl)-N-(pyridin-4-ylmethyl)pyridazine-3-carboxamide | 404 |

TABLE 6-continued
| Example | Structure | Name | MS (M + 1) |
|---|---|---|---|
| 115 | 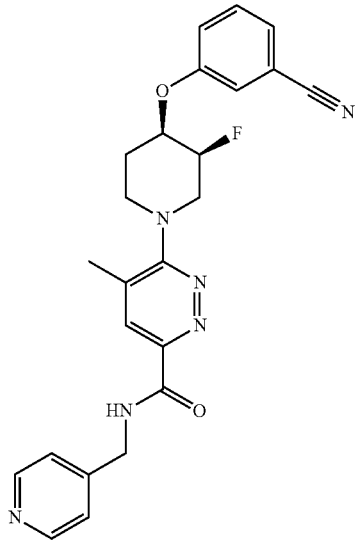 [SMILES: Cc1cc(C(=O)NCc2ccncc2)nnc1N1CC[C@@H](Oc2cccc(C#N)c2)[C@@H](F)C1] | 6-[(3S,4R)-4-(3-cyanophenoxy)-3-fluoropiperidin-1-yl]-5-methyl-N-(pyridin-4-ylmethyl)pyridazine-3-carboxamide | 447 |
| 116 | 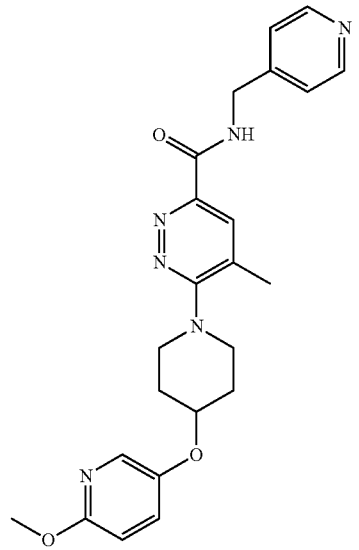 [SMILES: COc1ccc(OC2CCN(c3nnc(C(=O)NCc4ccncc4)cc3C)CC2)cn1] | 6-{4-[(6-methoxypyridin-3-yl)oxy]piperidin-1-yl}-5-methyl-N-(pyridin-4-ylmethyl)pyridazine-3-carboxamide | 435 |

TABLE 6-continued
| Example | Structure | Name | MS (M + 1) |
|---|---|---|---|
| 117 | 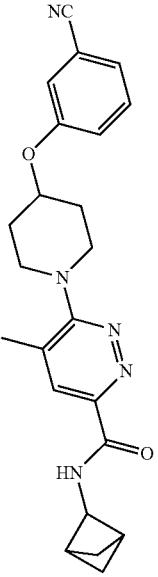 [SMILES: Cc1cc(C(=O)NC2C3CC2C3)nnc1N1CCC(Oc2cccc(C#N)c2)CC1] | N-bicyclo[1.1.1]pent-2-yl-6-[4-(3-cyanophenoxy)piperidin-1-yl]-5-methylpyridazine-3-carboxamide | 404 |
| 118 | 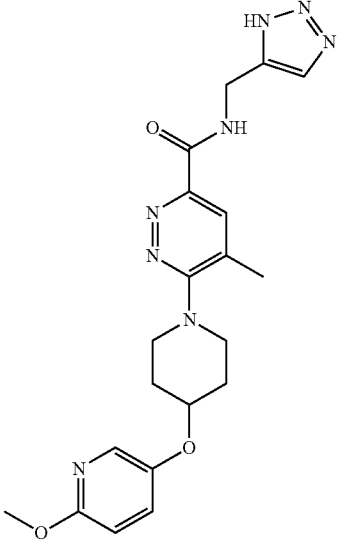 [SMILES: COc1ccc(OC2CCN(c3nnc(C(=O)NCc4cnn[nH]4)cc3C)CC2)cn1] | 6-{4-[(6-methoxypyridin-3-yl)oxy]piperidin-1-yl}-5-methyl-N-(1H-1,2,3-triazol-5-ylmethyl)pyridazine-3-carboxamide | 425 |

TABLE 6-continued

| Example | Structure | Name | MS (M + 1) |
|---|---|---|---|
| 119 | 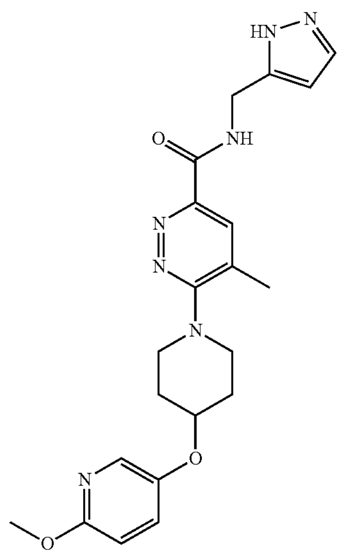 [SMILES: COc1ccc(OC2CCN(c3nnc(C(=O)NCc4ccn[nH]4)cc3C)CC2)cn1] | 6-{4-[(6-methoxypyridin-3-yl)oxy]piperidin-1-yl}-5-methyl-N-(1H-pyrazol-5-ylmethyl)pyridazine-3-carboxamide | 424 |
| 120 | 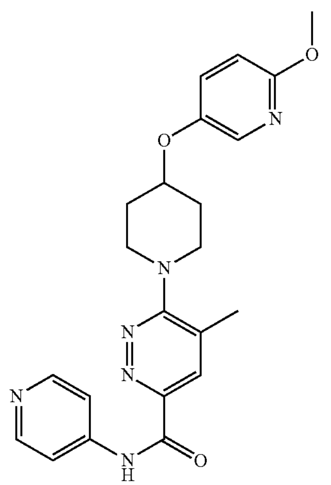 [SMILES: COc1ccc(OC2CCN(c3nnc(C(=O)Nc4ccncc4)cc3C)CC2)cn1] | 6-{4-[(6-methoxypyridin-3-yl)oxy]piperidin-1-yl}-5-methyl-N-pyridin-4-ylpyridazine-3-carboxamide | 421 |
| 121 | 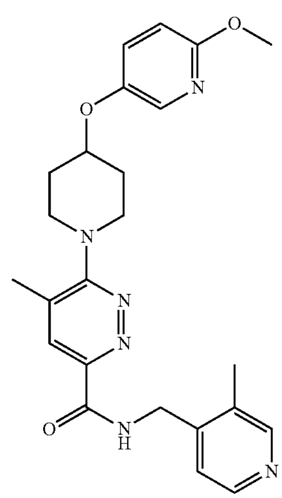 | 6-{4-[(6-methoxypyridin-3-yl)oxy]piperidin-1-yl}-5-methyl-N-[(3-methylpyridin-4-yl)methyl]pyridazine-3-carboxamide | 449 |

| Example | Structure | Name | MS (M + 1) |
|---|---|---|---|
| 122 | 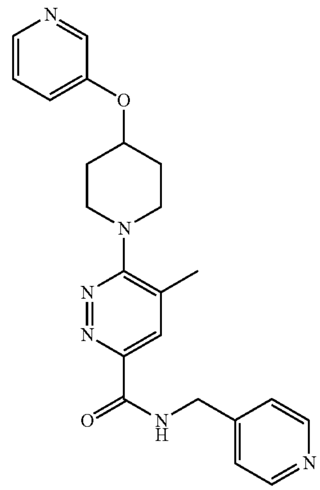 [SMILES: Cc1cc(C(=O)NCc2ccncc2)nnc1N1CCC(Oc2cccnc2)CC1] | 5-methyl-N-(pyridin-4-ylmethyl)-6-[4-(pyridin-3-yloxy)piperidin-1-yl]pyridazine-3-carboxamide | 405 |
| 123 | 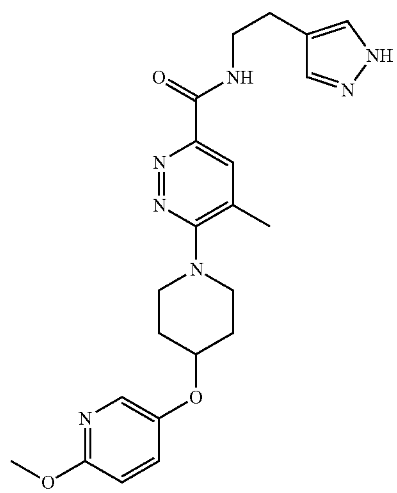 [SMILES: COc1ccc(OC2CCN(c3nnc(C(=O)NCCc4cn[nH]c4)cc3C)CC2)cn1] | 6-{4-[(6-methoxypyridin-3-yl)oxy]piperidin-1-yl}-5-methyl-N-[2-(1H-pyrazol-4-yl)ethyl]pyridazine-3-carboxamide | 438 |
| 124 | 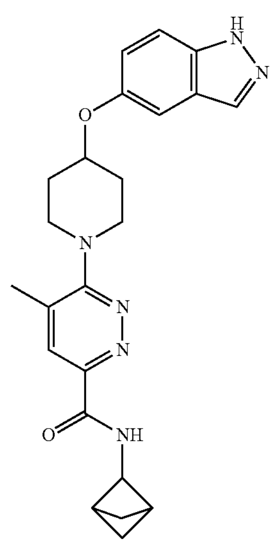 [SMILES: Cc1cc(C(=O)NC2C3CC2C3)nnc1N1CCC(Oc2ccc3[nH]ncc3c2)CC1] | N-bicyclo[1.1.1]pent-2-yl-6-[4-(1H-indazol-5-yloxy)piperidin-1-yl]-5-methylpyridazine-3-carboxamide | 419 |

TABLE 6-continued

| Example | Structure | Name | MS (M + 1) |
|---|---|---|---|
| 125 | 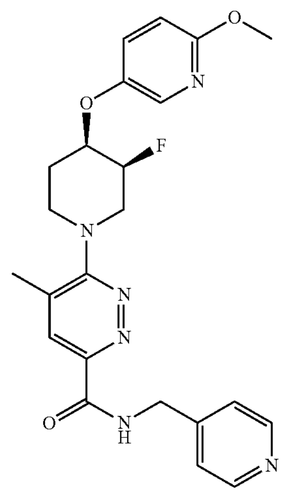 | 6-{(3S,4R)-3-fluoro-4-[(6-methoxypyridin-3-yl)oxy]piperidin-1-yl}-5-methyl-N-(pyridin-4-ylmethyl)pyridazine-3-carboxamide | 453 |
| 126A<br>126B | | (R)-6-{4-[(6-methoxypyridin-3-yl)oxy]piperidin-1-yl}-5-methyl-N-(5,6,7,8-tetrahydroquinolin-7-yl)pyridazine-3-carboxamide and (S)-6-{4-[(6-methoxypyridin-3-yl)oxy]piperidin-1-yl}-5-methyl-N-(5,6,7,8-tetrahydroquinolin-7-yl)pyridazine-3-carboxamide | 475<br>475 |
| 127 | 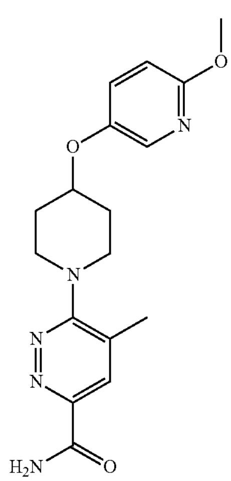 [SMILES: COc1ccc(OC2CCN(c3nnc(C(N)=O)cc3C)CC2)cn1] | 6-{4-[(6-methoxypyridin-3-yl)oxy]piperidin-1-yl}-5-methylpyridazine-3-carboxamide | 344 |

TABLE 6-continued

| Example | Structure | Name | MS (M + 1) |
|---|---|---|---|
| 128 | 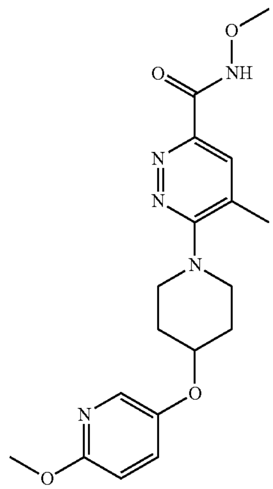 | N-methoxy-6-{4-[(6-methoxypyridin-3-yl)oxy]piperidin-1-yl}-5-methylpyridazine-3-carboxamide | 374 |
| 129 | 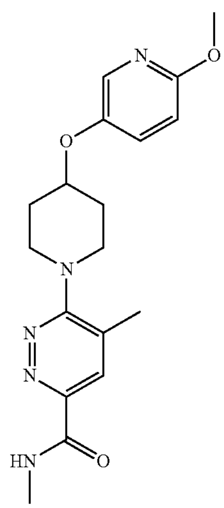 [SMILES: CNC(=O)c1cc(C)c(N2CCC(Oc3ccc(OC)nc3)CC2)nn1] | 6-{4-[(6-methoxypyridin-3-yl)oxy]piperidin-1-yl}-N,5-dimethylpyridazine-3-carboxamide | 358 |
| 130A 130B | | (S)-6-[4-(3-cyanophenoxy)piperidin-1-yl]-5-methyl-N-(5,6,7,8-tetrahydroquinolin-6-yl)pyridazine-3-carboxamide and (R)-6-[4-(3-cyanophenoxy)piperidin-1-yl]-5-methyl-N-(5,6,7,8-tetrahydroquinolin-6-yl)pyridazine-3-carboxamide | 469 469 |

TABLE 6-continued
| Example | Structure | Name | MS (M + 1) |
|---|---|---|---|
| 131 | 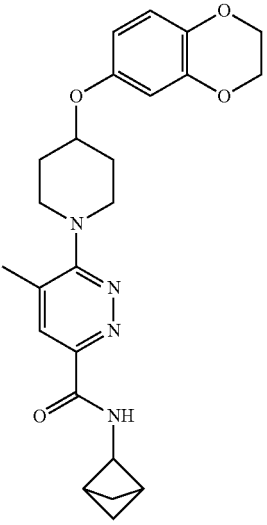 [SMILES: Cc1cc(C(=O)NC2C3CC2C3)nnc1N1CCC(Oc2ccc3c(c2)OCCO3)CC1] | N-bicyclo[1.1.1]pent-2-yl-6-[4-(2,3-dihydro-1,4-benzodioxin-6-yloxy)piperidin-1-yl]-5-methylpyridazine-3-carboxamide | 437 |
| 132 | 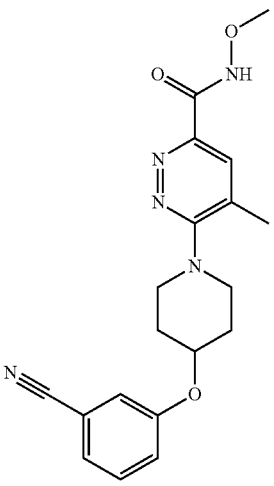 [SMILES: CONC(=O)c1cc(C)c(N2CCC(Oc3cccc(C#N)c3)CC2)nn1] | 6-[4-(3-cyanophenoxy)piperidin-1-yl]-N-methoxy-5-methypyridazine-3-carboxamide | 368 |
| 133 | 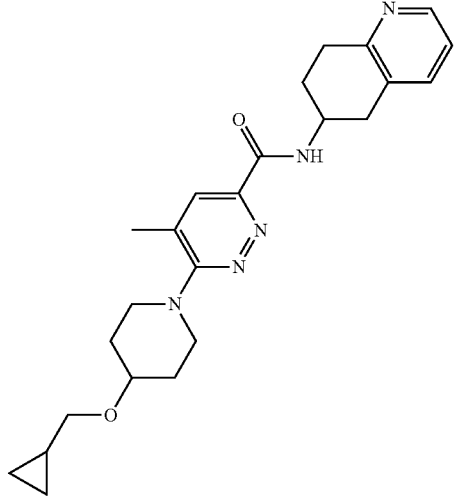 [SMILES: Cc1cc(C(=O)NC2CCc3ncccc3C2)nnc1N1CCC(OCC2CC2)CC1] | 6-[4-(cyclopropylmethoxy)piperidin-1-yl]-5-methyl-N-(5,6,7,8-tetrahydroquinolin-6-yl)pyridazine-3-carboxamide | 422 |

TABLE 6-continued

| Example | Structure | Name | MS (M + 1) |
|---|---|---|---|
| 134 | 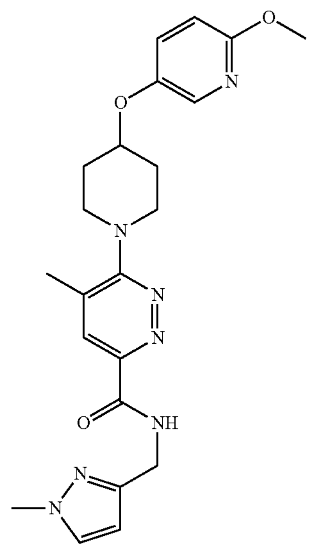 | 6-{4-[(6-methoxypyridin-3-yl)oxy]piperidin-1-yl}-5-methyl-N-[(1-methyl-1H-pyrazol-3-yl)methyl]pyridazine-3-carboxamide | 438 |
| 135 | 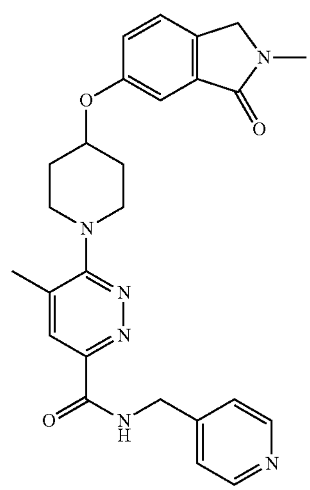 | 5-methyl-6-{4-[(2-methyl-3-oxo-2,3-dihydro-1H-isoindol-5-yl)oxy]piperidin-1-yl}-N-(pyridin-4-ylmethyl)pyridazine-3-carboxamide | 473 |
| 136 | 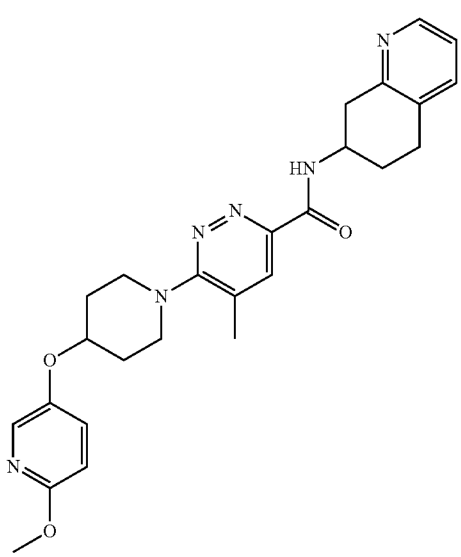 [SMILES: COc1ccc(OC2CCN(c3nnc(C(=O)NC4CCc5cccnc5C4)cc3C)CC2)cn1] | 6-{4-[(6-methoxypyridin-3-yl)oxy]piperidin-1-yl}-5-methyl-N-(5,6,7,8-tetrahydroquinolin-7-yl)pyridazine-3-carboxamide | 475 |

TABLE 6-continued

| Example | Structure | Name | MS (M + 1) |
|---|---|---|---|
| 137 | 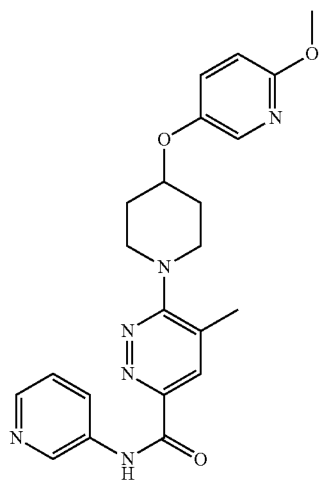 [SMILES: COc1ccc(OC2CCN(c3nnc(C(=O)Nc4cccnc4)cc3C)CC2)cn1] | 6-{4-[(6-methoxypyridin-3-yl)oxy]piperidin-1-yl}-5-methyl-N-pyridin-3-ylpyridazine-3-carboxamide | 421 |
| 138A 138B | | 6-((3S,4R)-3-fluoro-4-((6-methoxypyridin-3-yl)oxy)piperidin-1-yl)-5-methyl-N-((S)-5,6,7,8-tetrahydroquinolin-6-yl)pyridazine-3-carboxamide and 6-((3S,4R)-3-fluoro-4-((6-methoxypyridin-3-yl)oxy)piperidin-1-yl)-5-methyl-N-((R)-5,6,7,8-tetrahydroquinolin-6-yl)pyridazine-3-carboxamide | 493 493 |
| 139 | 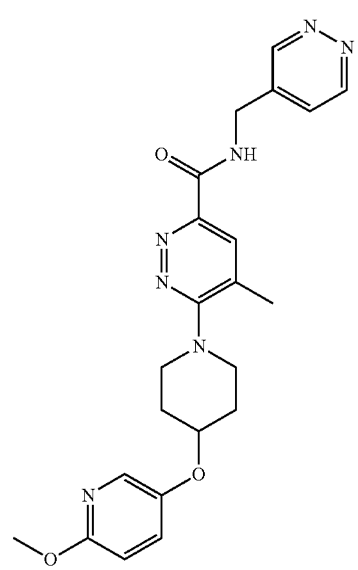 [SMILES: COc1ccc(OC2CCN(c3nnc(C(=O)NCc4ccnnc4)cc3C)CC2)cn1] | 6-{4-[(6-methoxypyridin-3-yl)oxy]piperidin-1-yl}-5-methyl-N-(pyridazin-4-ylmethyl)pyridazine-3-carboxamide | 436 |

TABLE 6-continued

| Example | Structure | Name | MS (M + 1) |
|---|---|---|---|
| 140 | 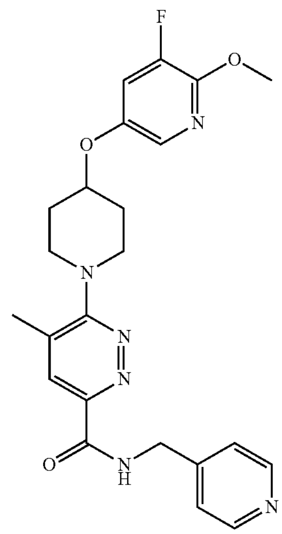 | 6-{4-[(5-fluoro-6-methoxypyridin-3-yl)oxy]piperidin-1-yl}-5-methyl-N-(pyridin-4-ylmethyl)pyridazine-3-carboxamide | 453 |
| 141A 141B | 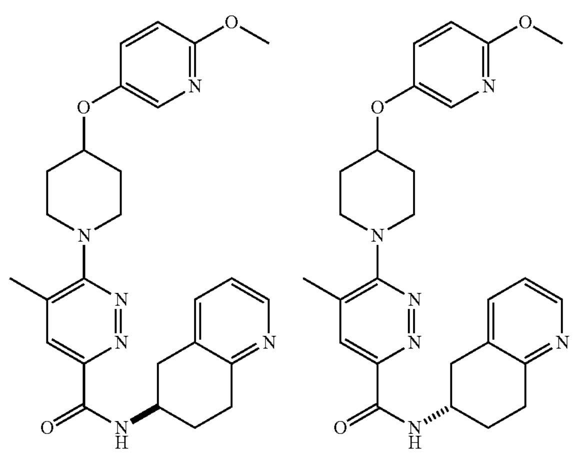 | (R)-6-(4-((6-methoxypyridin-3-yl)oxy)piperidin-1-yl)-5-methyl-N-(5,6,7,8-tetrahydroquinolin-6-yl)pyridazine-3-carboxamide compound and (S)-6-(4-((6-methoxypyridin-3-yl)oxy)piperidin-1-yl)-5-methyl-N-(5,6,7,8-tetrahydroquinolin-6-yl)pyridazine-3-carboxamide | 475 475 |
| 142 | 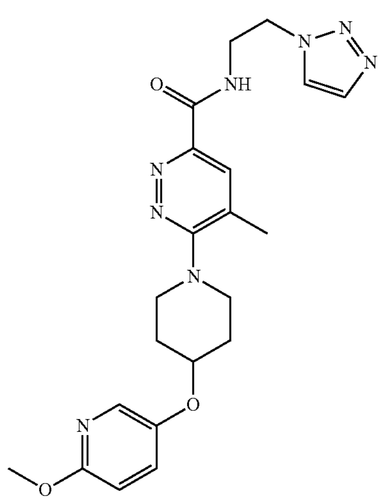 [SMILES: COc1ccc(OC2CCN(c3nnc(C(=O)NCCn4ccnn4)cc3C)CC2)cn1] | 6-{4-[(6-methoxypyridin-3-yl)oxy]piperidin-1-yl}-5-methyl-N-[2-(1H-1,2,3-triazol-1-yl)ethyl]pyridazine-3-carboxamide | 439 |

TABLE 6-continued

| Example | Structure | Name | MS (M + 1) |
|---|---|---|---|
| 143 | 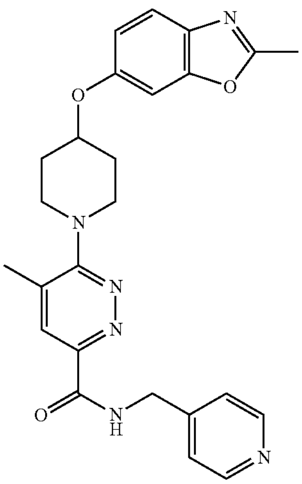 | 5-methyl-6-{4-[(2-methyl-1,3-benzoxazol-6-yl)oxy]piperidin-1-yl}-N-(pyridin-4-ylmethyl)pyridazine-3-carboxamide | 459 |
| 144 | 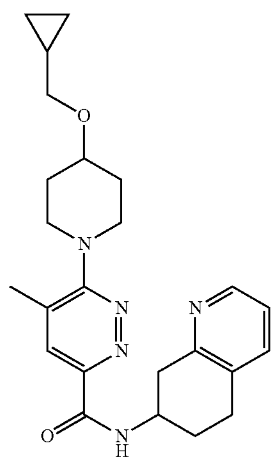 [SMILES: Cc1cc(C(=O)NC2CCc3cccnc3C2)nnc1N1CCC(OCC2CC2)CC1] | 6-[4-(cyclopropylmethoxy)piperidin-1-yl]-5-methyl-N-(5,6,7,8-tetrahydroquinolin-7-yl)pyridazine-3-carboxamide | 422 |
| 145 | 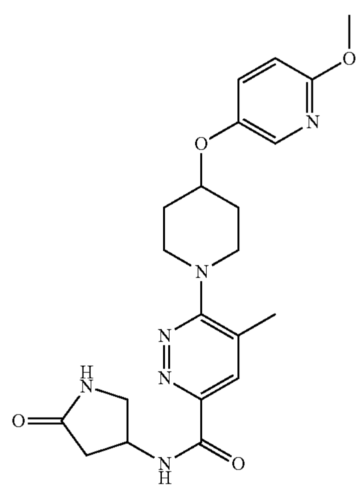 [SMILES: COc1ccc(OC2CCN(c3nnc(C(=O)NC4CNC(=O)C4)cc3C)CC2)cn1] | 6-{4-[(6-methoxypyridin-3-yl)oxy]piperidin-1-yl}-5-methyl-N-(5-oxopyrrolidin-3-yl)pyridazine-3-carboxamide | 427 |

TABLE 6-continued

| Example | Structure | Name | MS (M + 1) |
|---|---|---|---|
| 146[1] | 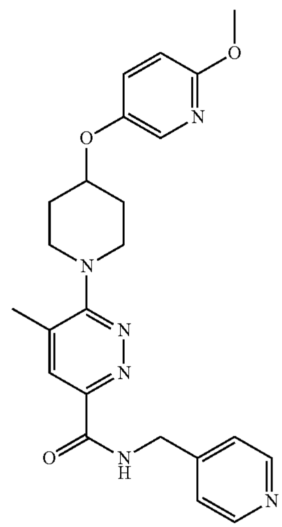 [SMILES: COc1ccc(OC2CCN(c3nnc(C(=O)NCc4ccncc4)cc3C)CC2)cn1] | 6-{4-[(6-methoxypyridin-3-yl)oxy]piperidin-1-yl}-5-methyl-N-(pyridin-4-ylmethyl)pyridine-3-carboxamide | 434 |
| 147 | 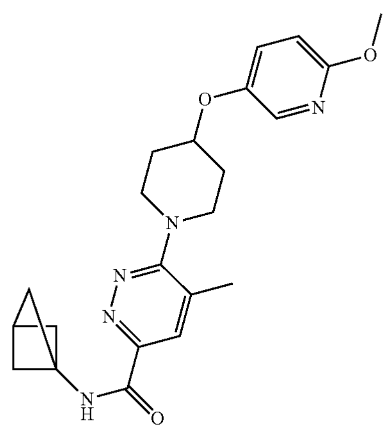 [SMILES: COc1ccc(OC2CCN(c3nnc(C(=O)NC45CC(C4)C5)cc3C)CC2)cn1] | N-bicyclo[1.1.1]pent-1-yl-6-{4-[(6-methoxypyridin-3-yl)oxy]piperidin-1-yl}-5-methylpyridazine-3-carboxamide | 410 |
| 148 | 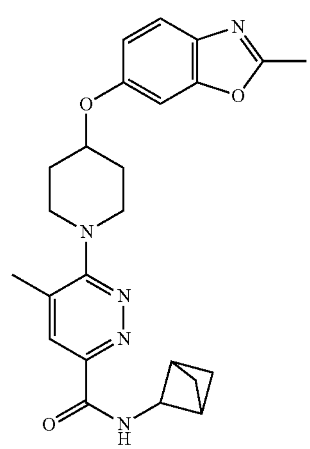 | N-bicyclo[1.1.1]pent-2-yl-5-methyl-6-{4-[(2-methyl-1,3-benzoxazol-6-yl)oxy]piperidin-1-yl}pyridazine-3-carboxamide | 434 |

TABLE 6-continued

| Example | Structure | Name | MS (M + 1) |
|---|---|---|---|
| 149 | 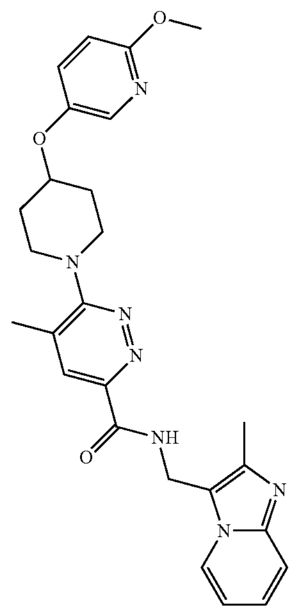 [SMILES: COc1ccc(OC2CCN(c3nnc(C(=O)NCc4c(C)nc5ccccn45)cc3C)CC2)cn1] | 6-{4-[(6-methoxypyridin-3-yl)oxy]piperidin-1-yl}-5-methyl-N-[(2-methylimidazo[1,2-a]pyridin-3-yl)methyl]pyridazine-3-carboxamide | 488 |
| 150 | 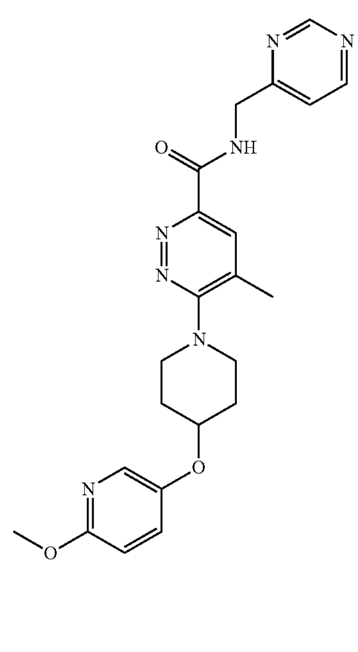 [SMILES: COc1ccc(OC2CCN(c3nnc(C(=O)NCc4ccncn4)cc3C)CC2)cn1] | 6-{4-[(6-methoxypyridin-3-yl)oxy]piperidin-1-yl}-5-methyl-N-(pyrimidin-4-ylmethyl)pyridazine-3-carboxamide | 436 |

TABLE 6-continued

| Example | Structure | Name | MS (M + 1) |
|---|---|---|---|
| 151 | 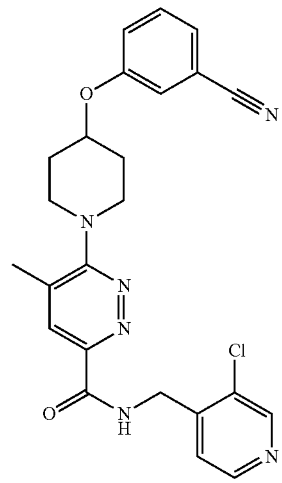 [SMILES: Cc1cc(C(=O)NCc2ccncc2Cl)nnc1N1CCC(Oc2cccc(C#N)c2)CC1] | N-[(3-chloropyridin-4-yl)methyl]-6-[4-(3-cyanophenoxy)piperidin-1-yl]-5-methylpyridazine-3-carboxamide | 463 |
| 152 | 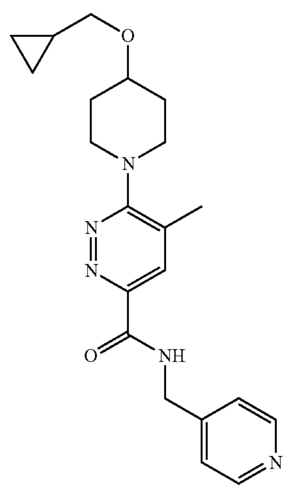 [SMILES: Cc1cc(C(=O)NCc2ccncc2)nnc1N1CCC(OCC2CC2)CC1] | 6-[4-(cyclopropylmethoxy)piperidin-1-yl]-6-methyl-N-(pyridin-4-ylmethyl)pyridazine-3-carboxamide | 382 |
| 153 | 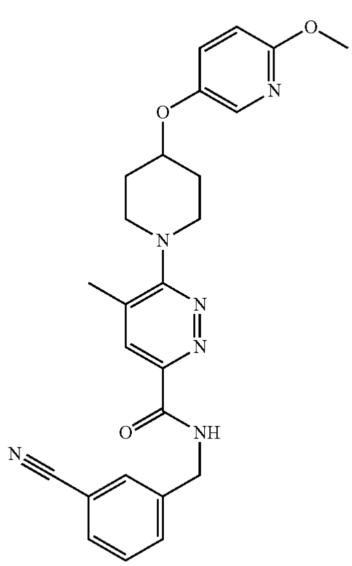 [SMILES: COc1ccc(OC2CCN(c3nnc(C(=O)NCc4cccc(C#N)c4)cc3C)CC2)cn1] | N-(3-cyanobenzyl)-6-{4-[(6-methoxypyridin-3-yl)oxy]piperidin-1-yl}-5-methylpyridazine-3-carboxamide | 459 |

TABLE 6-continued
| Example | Structure | Name | MS (M + 1) |
|---|---|---|---|
| 154 | 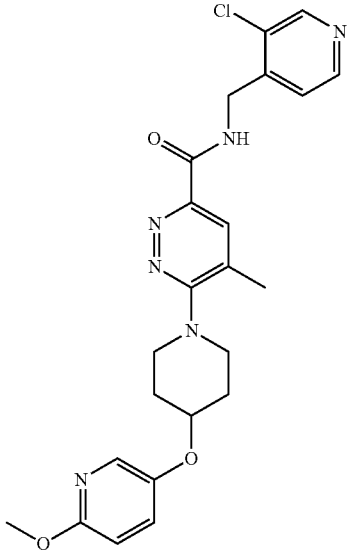 [SMILES: COc1ccc(OC2CCN(c3nnc(C(=O)NCc4ccncc4Cl)cc3C)CC2)cn1] | N-[(3-chloropyridin-4-yl)methyl]-6-{4-[(6-methoxypyridin-3-yl)oxy]piperidin-1-yl}-5-methylpyridazine-3-carboxamide | 469 |
| 155 | 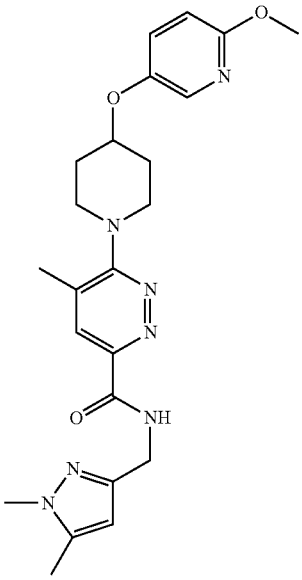 | N-[(1,5-dimethyl-1H-pyrazol-3-yl)methyl]-6-{4-[(6-methoxypyridin-3-yl)oxy]piperidin-1-yl}-5-methylpyridazine-3-carboxamide | 452 |

TABLE 6-continued

| Example | Structure | Name | MS (M + 1) |
|---|---|---|---|
| 156[2] | 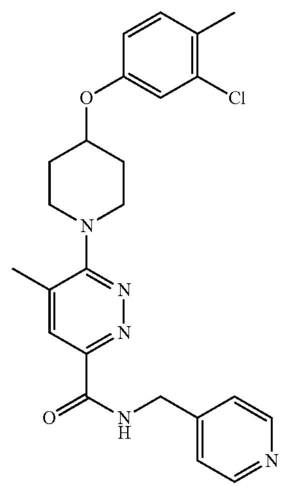 [SMILES: Cc1ccc(OC2CCN(c3nnc(C(=O)NCc4ccncc4)cc3C)CC2)cc1Cl] | 6-[4-(3-chloro-4-methylphenoxy)piperidin-1-yl]-5-methyl-N-(pyridin-4-ylmethyl)pyridazine-3-carboxamide | 452 |
| 157 | 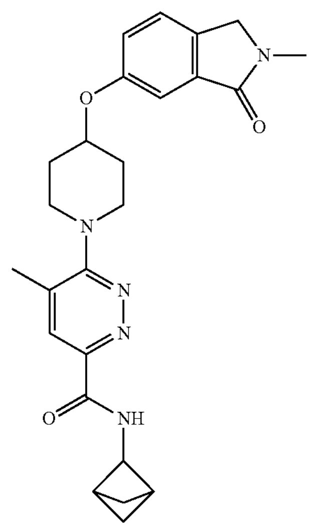 | N-bicyclo[1.1.1]pent-2-yl-5-methyl-6-{4-[(2-methyl-3-oxo-2,3-dihydro-1H-isoindol-5-yl)oxy]piperidin-1-yl}pyridazine-3-carboxamide | 448 |
| 158 | 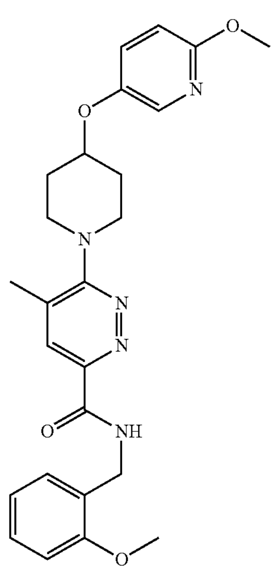 | N-(2-methoxybenzyl)-6-{4-[(6-methoxypyridin-3-yl)oxy]piperidin-1-yl}-5-methylpyridazine-3-carboxamide | 464 |

TABLE 6-continued

| Example | Structure | Name | MS (M + 1) |
|---|---|---|---|
| 159 | 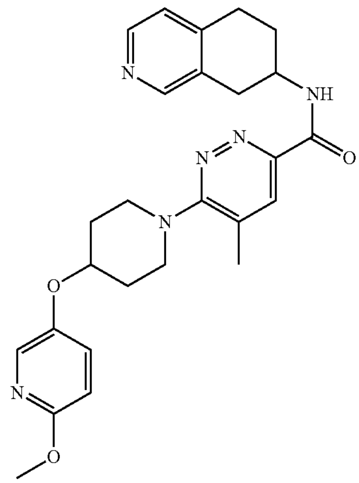 [SMILES: COc1ccc(OC2CCN(c3nnc(C(=O)NC4CCc5ccncc5C4)cc3C)CC2)cn1] | 6-{4-[(6-methoxypyridin-3-yl)oxy]piperidin-1-yl}-5-methyl-N-(5,6,7,8-tetrahydroisoquinolin-7-yl)pyridazine-3-carboxamide | 475 |
| 160 | 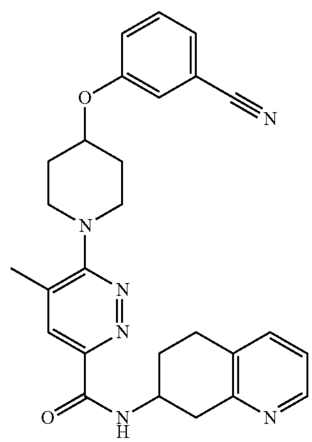 [SMILES: Cc1cc(C(=O)NC2CCc3cccnc3C2)nnc1N1CCC(Oc2cccc(C#N)c2)CC1] | 6-[4-(3-cyanophenoxy)piperidin-1-yl]-5-methyl-N-(5,6,7,8-tetrahydroquinolin-7-yl)pyridazine-3-carboxamide | 469 |
| 161 | 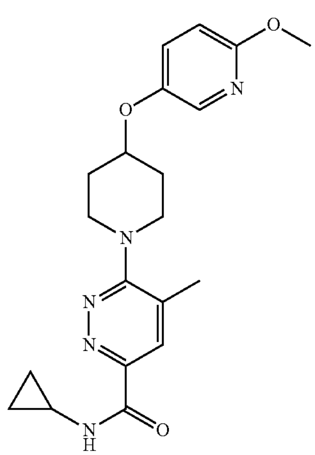 [SMILES: COc1ccc(OC2CCN(c3nnc(C(=O)NC4CC4)cc3C)CC2)cn1] | N-cyclopropyl-6-{4-[(6-methoxypyridin-3-yl)oxy]piperidin-1-yl}-5-methylpyridazine-3-carboxamide | 384 |

TABLE 6-continued

| Example | Structure | Name | MS (M + 1) |
|---|---|---|---|
| 162 | 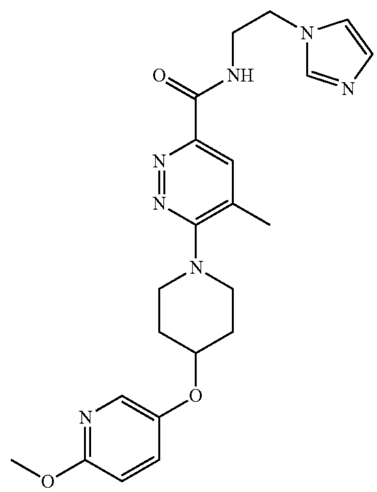 [SMILES: COc1ccc(OC2CCN(c3nnc(C(=O)NCCn4ccnc4)cc3C)CC2)cn1] | N-[2-(1H-imidazol-1-yl)ethyl]-6-{4-[(6-methoxypyridin-3-yl)oxy]piperidin-1-yl}-5-methylpyridazine-3-carboxamide | 438 |
| 163 | 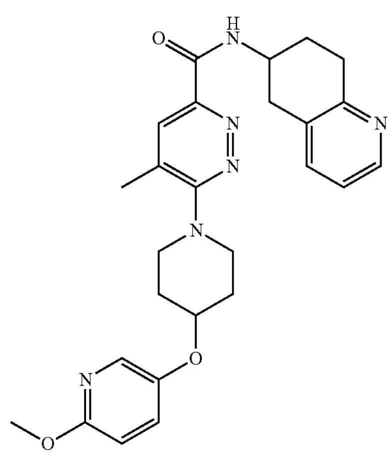 [SMILES: COc1ccc(OC2CCN(c3nnc(C(=O)NC4CCc5ncccc5C4)cc3C)CC2)cn1] | 6-{4-[(6-methoxypyridin-3-yl)oxy]piperidin-1-yl}-5-methyl-N-(5,6,7,8-tetrahydroquinolin-6-yl)pyridazine-3-carboxamide | 475 |
| 164A 164B | | (S)-6-[4-(3-cyanophenoxy)piperidin-1-yl]-5-methyl-N-(5,6,7,8-tetrahydroquinolin-7-yl)pyridazine-3-carboxamide and (R)-6-[4-(3-cyanophenoxy)piperidin-1-yl]-5-methyl-N-(5,6,7,8-tetrahydroquinolin-7-yl)pyridazine-3-carboxamide | 469 469 |

TABLE 6-continued

| Example | Structure | Name | MS (M + 1) |
|---|---|---|---|
| 165A 165B | | (R)-6-{4-[(6-methoxypyridin-3-yl)oxy]piperidin-1-yl}-5-methyl-N-(1,2,3,4-tetrahydronaphthalen-2-yl)pyridazine-3-carboxamide and (S)-6-{4-[(6-methoxypyridin-3-yl)oxy]piperidin-1-yl}-5-methyl-N-(1,2,3,4-tetrahydronapthalen-2-yl)pyridazine-3-carboxamide | 474 474 |
| 166 | 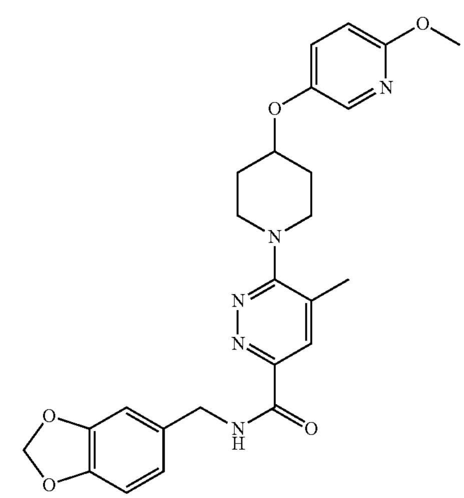 [SMILES: COc1ccc(OC2CCN(c3nnc(C(=O)NCc4ccc5c(c4)OCO5)cc3C)CC2)cn1] | N-(1,3-benzodioxol-5-ylmethyl)-6-{4-[(6-methoxypyridin-3-yl)oxy]piperidin-1-yl}-5-methylpyridazine-3-carboxamide | 478 |
| 167 | 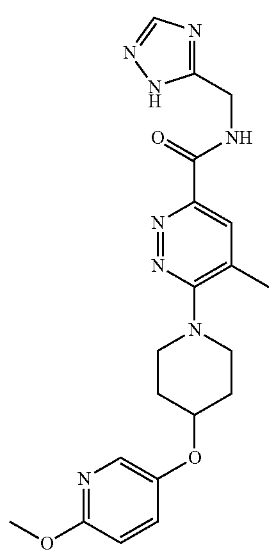 | 6-{4-[(6-methoxypyridin-3-yl)oxy]piperidin-1-yl}-5-methyl-N-(1H-1,2,4-triazol-5-ylmethyl)pyridazine-3-carboxamide | 425 |

TABLE 6-continued

| Example | Structure | Name | MS (M + 1) |
|---|---|---|---|
| 168 | 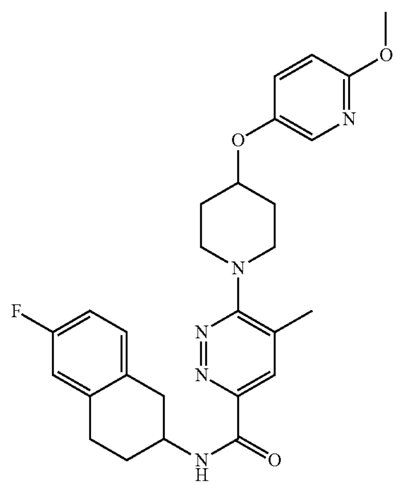 [SMILES: COc1ccc(OC2CCN(c3nnc(C(=O)NC4CCc5cc(F)ccc5C4)cc3C)CC2)cn1] | N-(6-fluoro-1,2,3,4-tetrahydronaphthalen-2-yl)-6-{4-[(6-methoxypyridin-3-yl)oxy]piperidin-1-yl}-5-methylpyridazine-3-carboxamide | 492 |
| 169 | 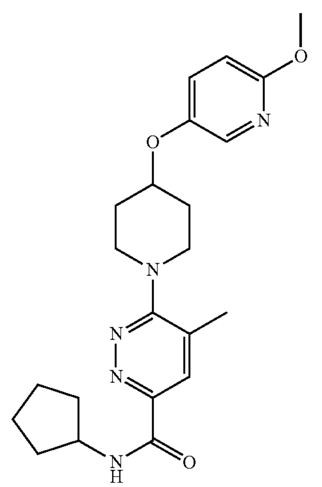 [SMILES: COc1ccc(OC2CCN(c3nnc(C(=O)NC4CCCC4)cc3C)CC2)cn1] | N-cyclopentyl-6-{4-[(6-methoxypyridin-3-yl)oxy]piperidin-1-yl}-5-methylpyridazine-3-carboxamide | 412 |
| 170 | 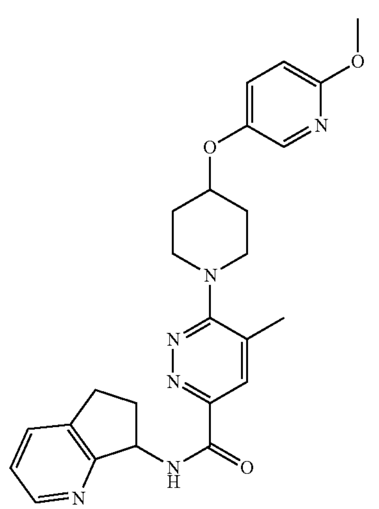 [SMILES: COc1ccc(OC2CCN(c3nnc(C(=O)NC4CCc5cccnc54)cc3C)CC2)cn1] | N-(6,7-dihdyro-5H-cyclopenta[b]pyridin-7-yl)-6-{4-[(6-methoxypyridin-3-yl)oxy]piperidin-1-yl}-5-methylpyridazine-3-carboxamide | 461 |

TABLE 6-continued

| Example | Structure | Name | MS (M + 1) |
|---|---|---|---|
| 171 | 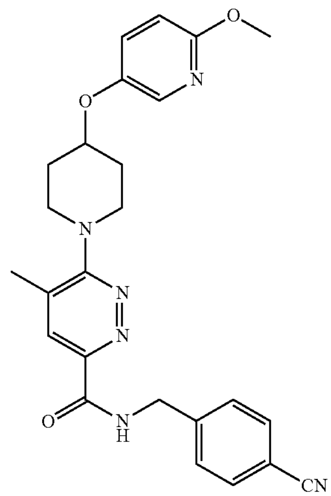 [SMILES: COc1ccc(OC2CCN(c3nnc(C(=O)NCc4ccc(C#N)cc4)cc3C)CC2)cn1] | N-(4-cyanobenzyl)-6-{4-[(6-methoxypyridin-3-yl)oxy]piperidin-1-yl}-5-methylpyridazine-3-carboxamide | 459 |
| 172 | 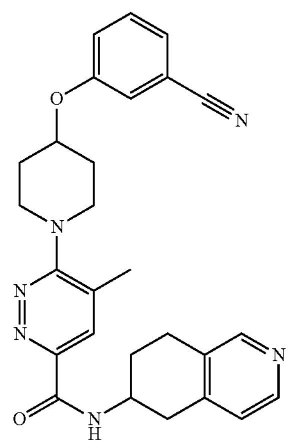 [SMILES: Cc1cc(C(=O)NC2CCc3cnccc3C2)nnc1N1CCC(Oc2cccc(C#N)c2)CC1] | 6-[4-(3-cyanophenoxy)piperidin-1-yl]-5-methyl-N-(5,6,7,8-tetrahydroisoquinolin-6-yl)pyridazine-3-carboxamide | 469 |
| 173 | 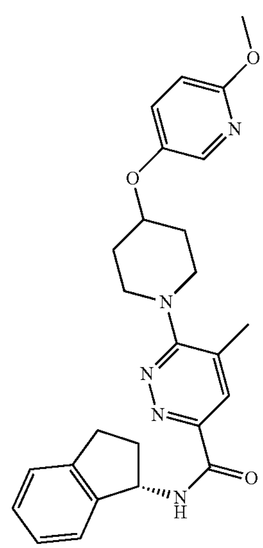 [SMILES: COc1ccc(OC2CCN(c3nnc(C(=O)N[C@H]4CCc5ccccc54)cc3C)CC2)cn1] | N-[(1S)-2,3-dihydro-1H-inden-1-yl]-6-{4-[(6-methoxypyridin-3-yl)oxy]piperidin-1-yl}-5-methylpyridazine-3-carboxamide | 460 |

TABLE 6-continued
| Example | Structure | Name | MS (M + 1) |
|---|---|---|---|
| 174 | 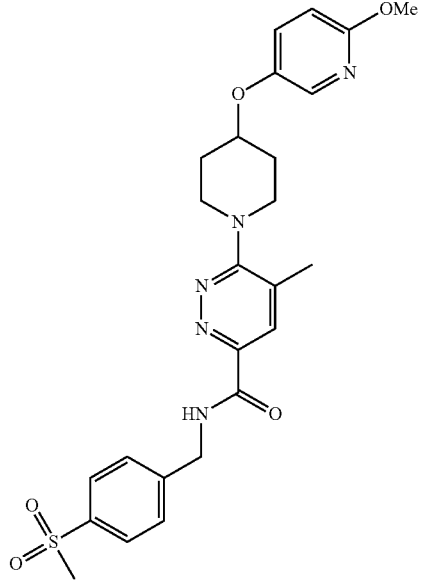 [SMILES: COc1ccc(OC2CCN(c3nnc(C(=O)NCc4ccc(S(C)(=O)=O)cc4)cc3C)CC2)cn1] | 6-{4-[(6-methoxypyridin-3-yl)oxy]piperidin-1-yl}-5-methyl-N-[4-(methylsulfonyl)benzyl]pyridazine-3-carboxamide | 512 |
| 175 | 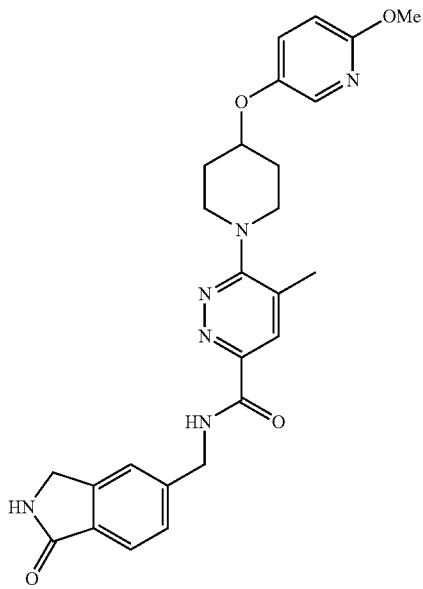 [SMILES: COc1ccc(OC2CCN(c3nnc(C(=O)NCc4ccc5c(c4)CNC5=O)cc3C)CC2)cn1] | 6-{4-[(6-methoxypyridin-3-yl)oxy]piperidin-1-yl}-5-methyl-N-[(1-oxo-2,3-dihydro-1H-isoindol-5-yl)methyl]pyridazine-3-carboxamide | 489 |

TABLE 6-continued

| Example | Structure | Name | MS (M + 1) |
|---|---|---|---|
| 176 | 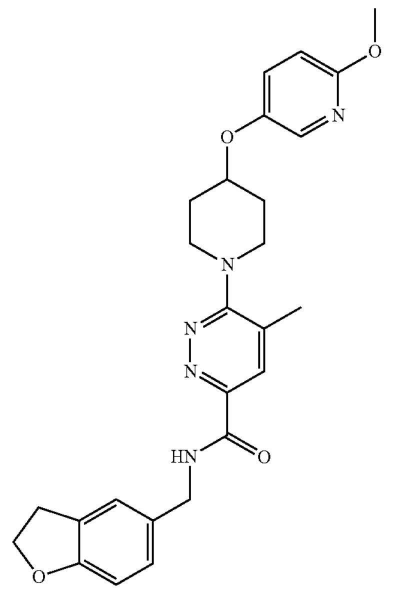 [SMILES: COc1ccc(OC2CCN(c3nnc(C(=O)NCc4ccc5c(c4)CCO5)cc3C)CC2)cn1] | N-(2,3-dihydro-1-benzofuran-5-ylmethyl)-6-{4-[(6-methoxypyridin-3-yl)oxy]piperidin-1-yl}-5-methylpyridazine-3-carboxamide | 476 |
| 177 | 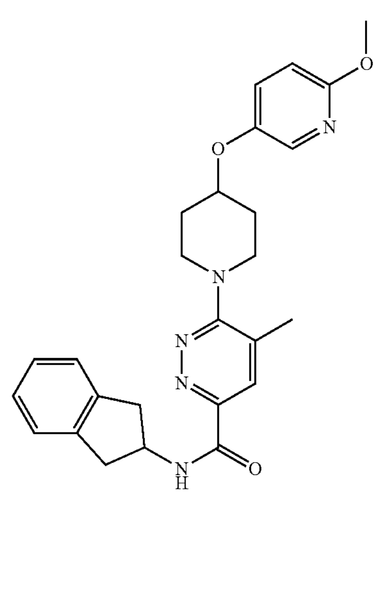 [SMILES: COc1ccc(OC2CCN(c3nnc(C(=O)NC4Cc5ccccc5C4)cc3C)CC2)cn1] | N-(2,3-dihydro-1H-inden-2-yl)-6-{4-[(6-methoxypyridin-3-yl)oxy]piperidin-1-yl}-5-methylpyridazine-3-carboxamide | 460 |

TABLE 6-continued

| Example | Structure | Name | MS (M + 1) |
|---|---|---|---|
| 178 | 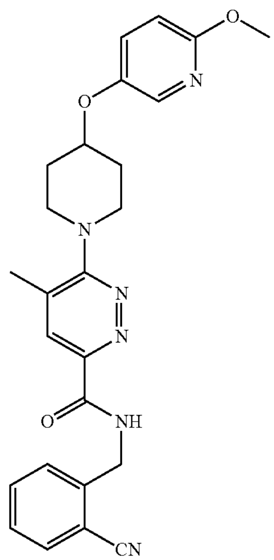 | N-(2-cyanobenzyl)-6-{4-[(6-methoxypyridin-3-yl)oxy]piperidin-1-yl}-5-methylpyridazine-3-carboxamide | 459 |
| 179 | 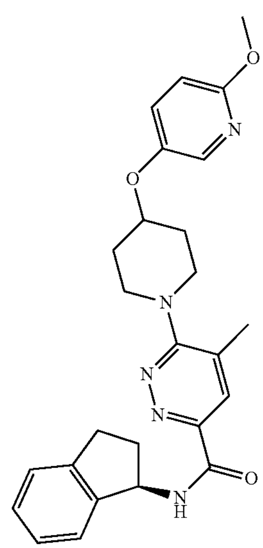 [SMILES: COc1ccc(OC2CCN(c3nnc(C(=O)N[C@@H]4CCc5ccccc54)cc3C)CC2)cn1] | N-[(1R)-2,3-dihydro-1H-inden-1-yl]-6-{4-[(6-methoxypyridin-3-yl)oxy]piperidin-1-yl}-5-methylpyridazine-3-carboxamide | 460 |

TABLE 6-continued

| Example | Structure | Name | MS (M + 1) |
|---|---|---|---|
| 180 | 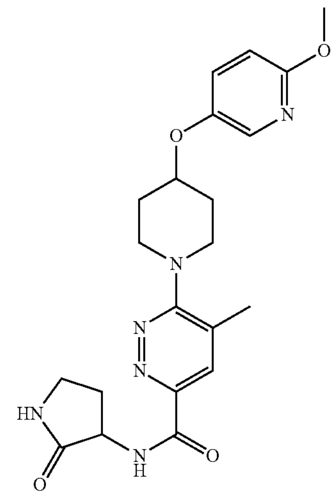 [SMILES: COc1ccc(OC2CCN(c3nnc(C(=O)NC4CCNC4=O)cc3C)CC2)cn1] | 6-{4-[(6-methoxypyridin-3-yl)oxy]piperidin-1-yl}-5-methyl-N-(2-oxopyrrolidin-3-yl)pyridazine-3-carboxamide | 427 |
| 181 | 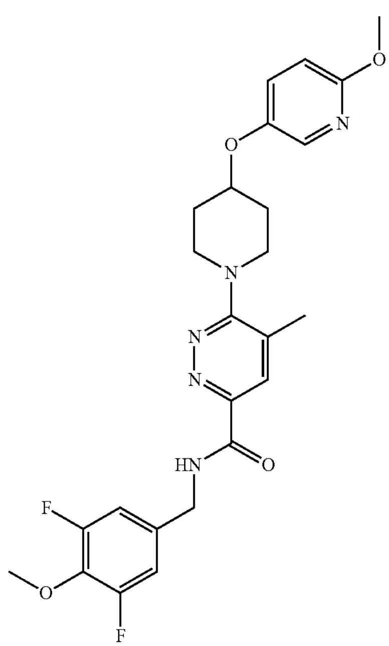 | N-(3,5-difluoro-4-methoxybenzyl)-6-{4-[(6-methoxypyridin-3-yl)oxy]piperidin-1-yl}-5-methylpyridazine-3-carboxamide | 500 |

TABLE 6-continued
| Example | Structure | Name | MS (M + 1) |
|---|---|---|---|
| 182 | 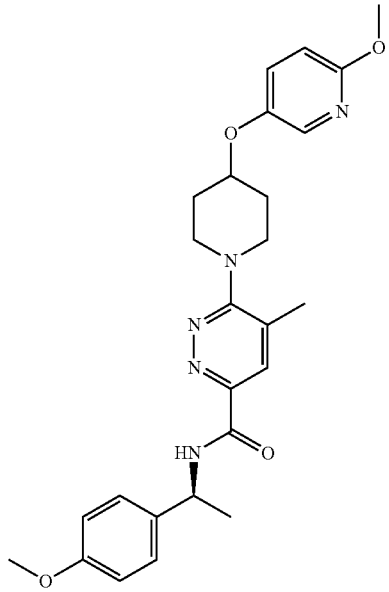 | N-[(1S)-1-(4-methoxyphenyl)ethyl]-6-{4-[(6-methoxypyridin-3-yl)oxy]piperidin-1-yl}-5-methylpyridazine-3-carboxamide | 478 |
| 183 | 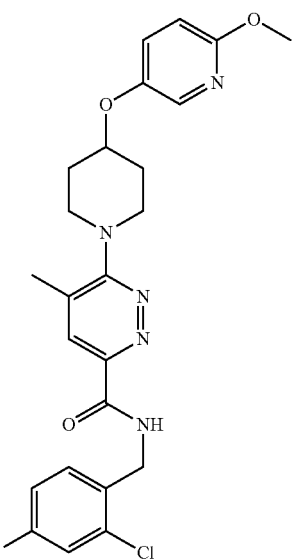 | N-(2-chloro-4-fluorobenzyl)-6-{4-[(6-methoxypyridin-3-yl)oxy]piperidin-1-yl}-5-methylpyridazine-3-carboxamide | 486 |

TABLE 6-continued
| Example | Structure | Name | MS (M + 1) |
|---|---|---|---|
| 184A 184B | 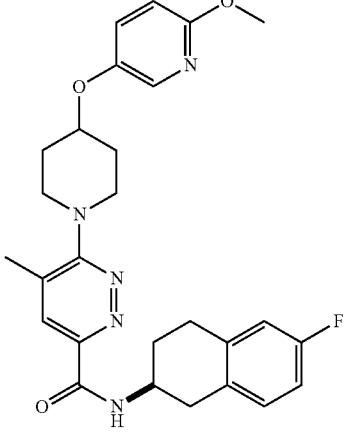 | (S)-N-(6-fluoro-1,2,3,4-tetrahydronaphthalen-2-yl)-6-{4-[(6-methoxypyridin-3-yl)oxy]piperidin-1-yl}-5-methylpyridazine-3-carboxamide and (R)-N-(6-fluoro-1,2,3,4-tetrahydronaphthalen-2-yl)-6-{4-[(6-methoxypyridin-3-yl)oxy]piperidin-1-yl}-5-methylpyridazine-3-carboxamide | 492 492 |
| 185 | 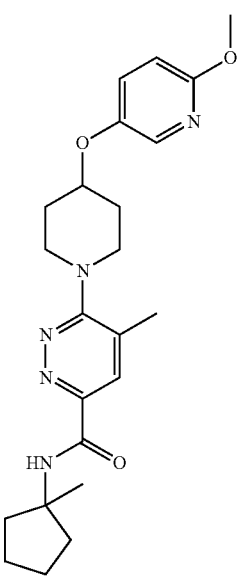 [SMILES: COc1ccc(OC2CCN(c3nnc(C(=O)NC4(C)CCCC4)cc3C)CC2)cn1] | 6-{4-[(6-methoxypyridin-3-yl)oxy]piperidin-1-yl}-5-methyl-N-(1-methylcyclopentyl)pyridazine-3-carboxamide | 426 |

TABLE 6-continued

| Example | Structure | Name | MS (M + 1) |
|---|---|---|---|
| 186 | 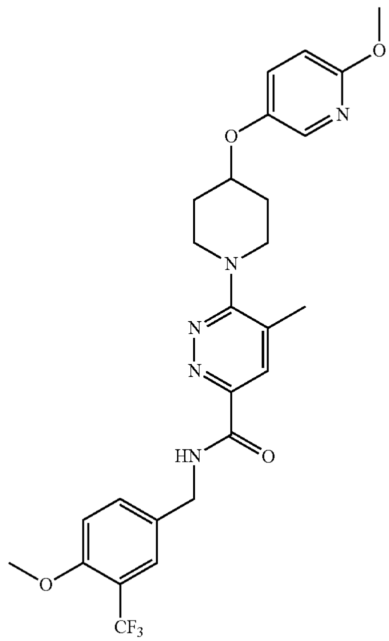 | 6-{4-[(6-methoxypyridin-3-yl)oxy]piperidin-1-yl}-N-[4-methoxy-3-(trifluoromethyl)benzyl]-5-methylpyridazine-3-carboxamide | 532 |
| 187 | 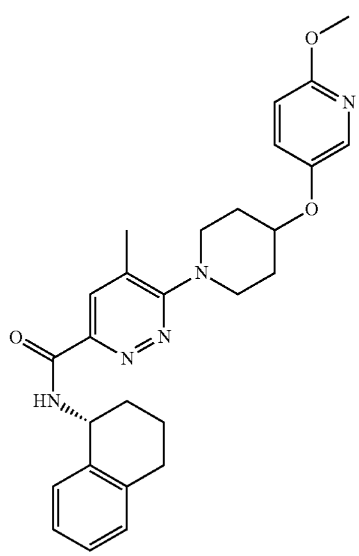 [SMILES: COc1ccc(OC2CCN(c3nnc(C(=O)N[C@@H]4CCCc5ccccc54)cc3C)CC2)cn1] | 6-{4-[(6-methoxypyridin-3-yl)oxy]piperidin-1-yl}-5-methyl-N-[(1R)-1,2,3,4-tetrahydronaphthalen-1-yl]pyridazine-3-carboxamide | 474 |

TABLE 6-continued

| Example | Structure | Name | MS (M + 1) |
|---|---|---|---|
| 188 | 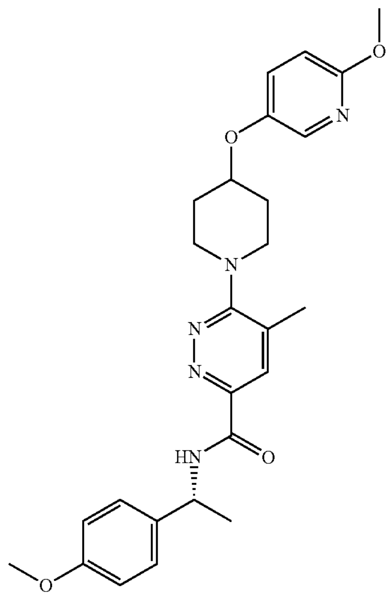 | N-[(1R)-1-(4-methoxyphenyl)ethyl]-6-{4-[(6-methoxypyridin-3-yl)oxy]piperidin-1-yl}-5-methylpyridazine-3-carboxamide | 478 |
| 189 | 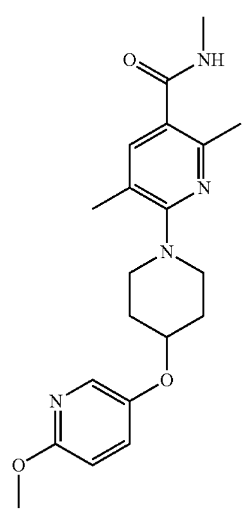 | 6-{4-[(6-methoxypyridin-3-yl)oxy]piperidin-1-yl}-N,2,5-trimethylpyridine-3-carboxamide | 371 |

TABLE 6-continued
| Example | Structure | Name | MS (M + 1) |
|---|---|---|---|
| 190 | 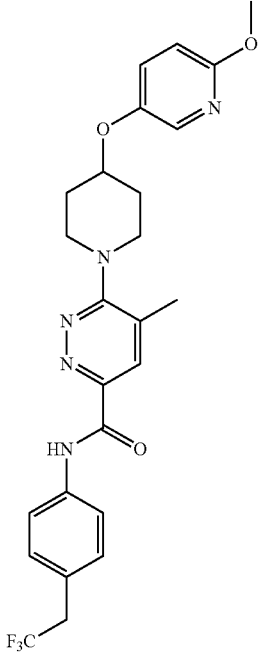 [SMILES: COc1ccc(OC2CCN(c3nnc(C(=O)Nc4ccc(CC(F)(F)F)cc4)cc3C)CC2)cn1] | 6-{4-[(6-methoxypyridin-3-yl)oxy]piperidin-1-yl}-5-methyl-N-[4-(2,2,2-trifluoroethyl)phenyl]pyridazine-3-carboxamide | 502 |
| 191 | 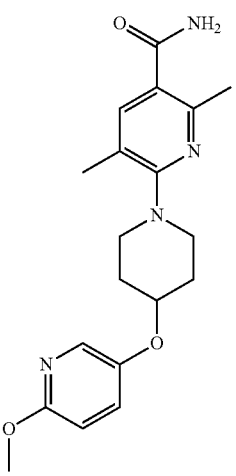 [SMILES: COc1ccc(OC2CCN(c3nc(C)c(C(N)=O)cc3C)CC2)cn1] | 6-{4-[(6-methoxypyridin-3-yl)oxy]piperidin-1-yl}-2,5-dimethypyridine-3-carboxamide | 357 |

TABLE 6-continued

| Example | Structure | Name | MS (M + 1) |
|---|---|---|---|
| 192 | 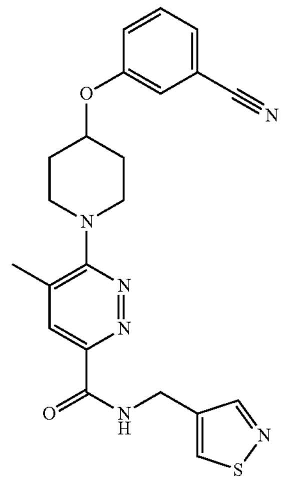 [SMILES: Cc1cc(C(=O)NCc2cnsc2)nnc1N1CCC(Oc2cccc(C#N)c2)CC1] | 6-[4-(3-cyanophenoxy)piperidin-1-yl]-N-(isothiazol-4-ylmethyl)-5-methypyridazine-3-carboxamide | 435 |
| 193 | 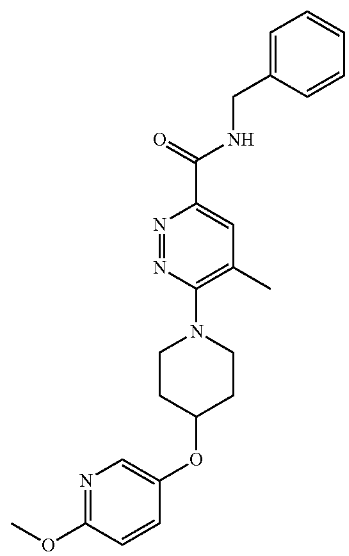 [SMILES: COc1ccc(OC2CCN(c3nnc(C(=O)NCc4ccccc4)cc3C)CC2)cn1] | N-benzyl-6-{4-[(6-methoxypyridin-3-yl)oxy]piperidin-1-yl}-5-methylpyridazine-3-carboxamide | 434 |
| 194 | 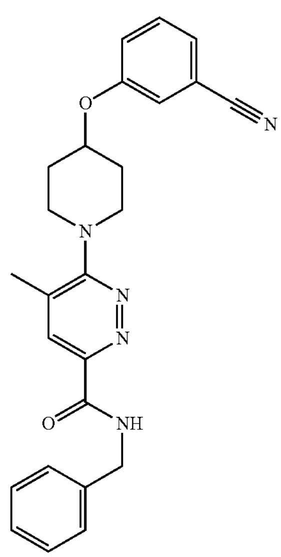 [SMILES: Cc1cc(C(=O)NCc2ccccc2)nnc1N1CCC(Oc2cccc(C#N)c2)CC1] | N-benzyl-6-[4-(3-cyanophenoxy)piperidin-1-yl]-5-methylpyridazine-3-carboxamide | 428 |

TABLE 6-continued
| Example | Structure | Name | MS (M + 1) |
|---|---|---|---|
| 195 | 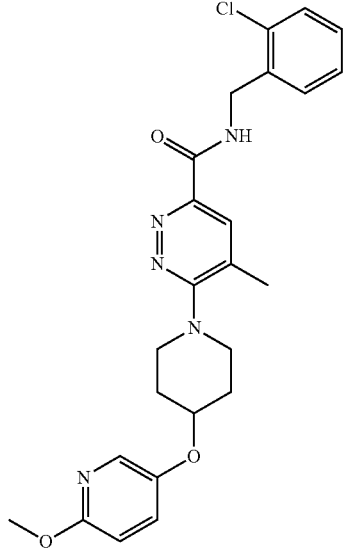 [SMILES: COc1ccc(OC2CCN(c3nnc(C(=O)NCc4ccccc4Cl)cc3C)CC2)cn1] | N-(2-chlorobenzyl)-6-{4-[(6-methoxypyridin-3-yl)oxy]piperidin-1-yl}-5-methylpyridazine-3-carboxamide | 468 |
| 196 | 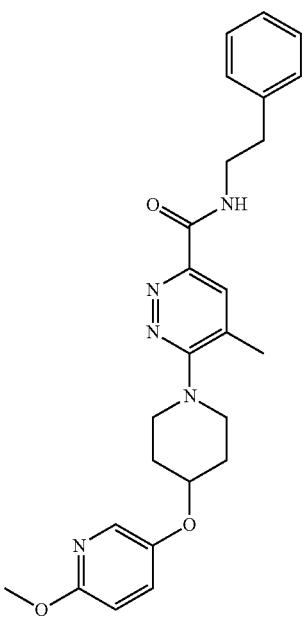 [SMILES: COc1ccc(OC2CCN(c3nnc(C(=O)NCCc4ccccc4)cc3C)CC2)cn1] | 6-{4-[(6-methoxypyridin-3-yl)oxy]piperidin-1-yl}-5-methyl-N-(2-phenylethyl)pyridazine-3-carboxamide | 448 |

TABLE 6-continued
| Example | Structure | Name | MS (M + 1) |
|---|---|---|---|
| 197 | 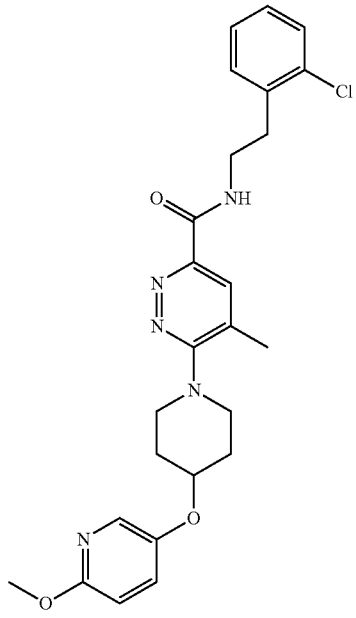 [SMILES: COc1ccc(OC2CCN(c3nnc(C(=O)NCCc4ccccc4Cl)cc3C)CC2)cn1] | N-[2-(2-chlorophenyl)ethyl]-6-{4-[(6-methoxypyridin-3-yl)oxy]piperidin-1-yl}-5-methylpyridazine-3-carboxamide | 482 |
| 199 | 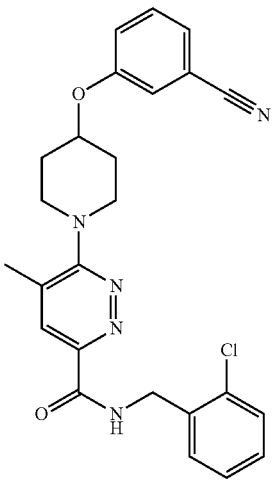 [SMILES: Cc1cc(C(=O)NCc2ccccc2Cl)nnc1N1CCC(Oc2cccc(C#N)c2)CC1] | N-(2-chlorobenzyl)-6-[4-(3-cyanophenoxy)piperidin-1-yl]-5-methylpyridazine-3-carboxamide | 462 |

TABLE 6-continued

| Example | Structure | Name | MS (M + 1) |
| --- | --- | --- | --- |
| 200 | 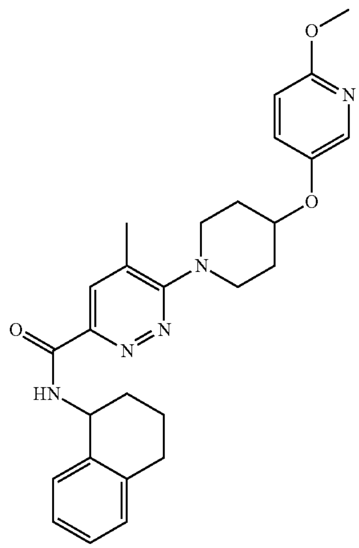 [SMILES: COc1ccc(OC2CCN(c3nnc(C(=O)NC4CCCc5ccccc54)cc3C)CC2)cn1] | 6-{4-[(6-methoxypyridin-3-yl)oxy]piperidin-1-yl}-5-methyl-N-(1,2,3,4-tetrahydronaphthalen-1-yl)pyridazine-3-carboxamide | 474 |
| 201 | 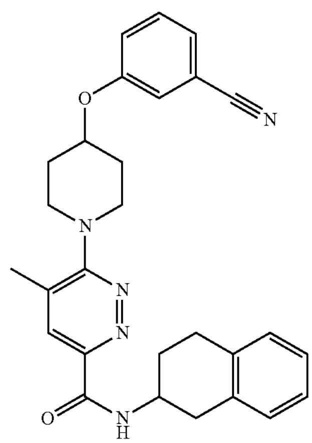 | 6-[4-(3-cyanophenoxy)piperidin-1-yl]-5-methyl-N-(1,2,3,4-tetrahydronaphthalen-2-yl)pyridazine-3-carboxamide | 468 |
| 202 | 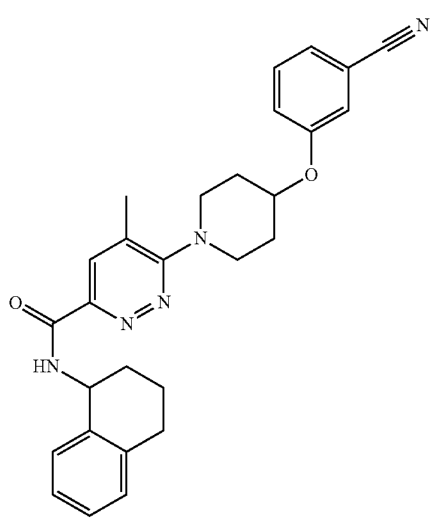 [SMILES: Cc1cc(C(=O)NC2CCCc3ccccc32)nnc1N1CCC(Oc2cccc(C#N)c2)CC1] | 6-[4-(3-cyanophenoxy)piperidin-1-yl]-5-methyl-N-(1,2,3,4-tetrahydronaphthalne-1-yl)pyridazine-3-carboxamide | 468 |

TABLE 6-continued
| Example | Structure | Name | MS (M + 1) |
|---|---|---|---|
| 203 | 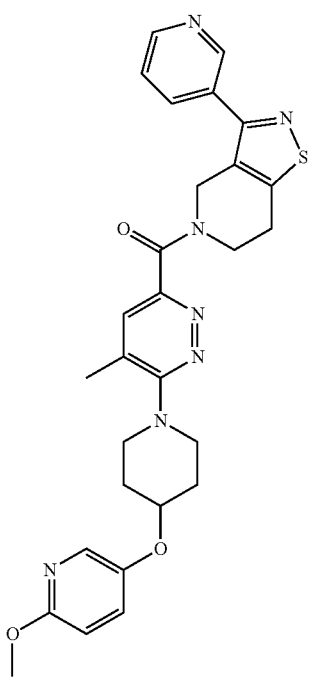 [SMILES: COc1ccc(OC2CCN(c3nnc(C(=O)N4CCc5snc(-c6cccnc6)c5C4)cc3C)CC2)cn1] | 5-[(6-{4-[(6-methoxypyridin-3-yl)oxy]piperidin-1-yl}-5-methylpyridazin-3-yl)carbonyl]-3-pyridin-3-yl-4,5,6,7-tetrahydroisothiazolo[4,5-c]pyridine | 544 |
| 204 | 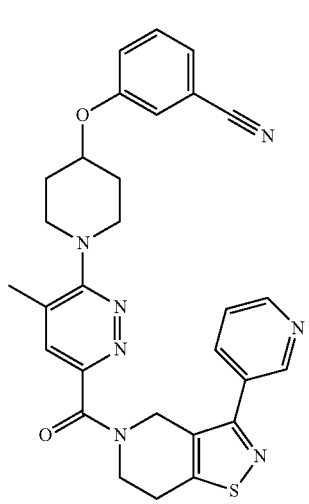 [SMILES: Cc1cc(C(=O)N2CCc3snc(-c4cccnc4)c3C2)nnc1N1CCC(Oc2cccc(C#N)c2)CC1] | 3-[(1-{4-methyl-6-[(3-pyridin-3-yl-6,7-dihydroisothiazolo[4,5-c]pyridin-5(4H)-yl)carbonyl]pyridazin-3-yl}piperidin-4-yl)oxy]benzonitrile | 538 |

TABLE 6-continued

| Example | Structure | Name | MS (M + 1) |
|---|---|---|---|
| 204A | 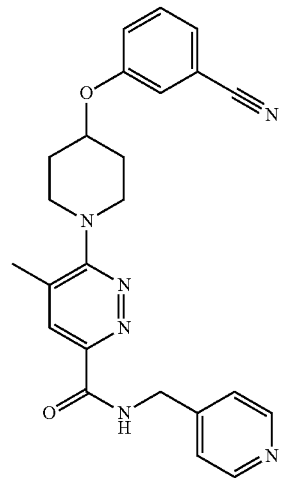 [SMILES: Cc1cc(C(=O)NCc2ccncc2)nnc1N1CCC(Oc2cccc(C#N)c2)CC1] | 6-(4-(3-cyanophenoxy)piperidin-1-yl)-5-methyl-N-(pyridin-4-ylmethyl)pyridazine-3-carboxamide | 430 |

[1] Pyridine starting materials may be prepared according to literature procedures, see e.g.: Kawamura, K., et al. Pyrrolopyridinone derivatives as TTX-S blockers and their preparation. RaQualia Pharma Inc., Japan, PCT Patent Publication WO 2013161312, 31 Oct. 2013.
[2] Piperidine starting materials may be prepared according to literature procedures, see e.g.: Lawrence, L., et al. Synthesis of substituted bipiperidines and their use as H1 antagonists. AstraZeneca AB, PCT Patent Publication WO 2001077101, 18 Oct. 2001

Example 205

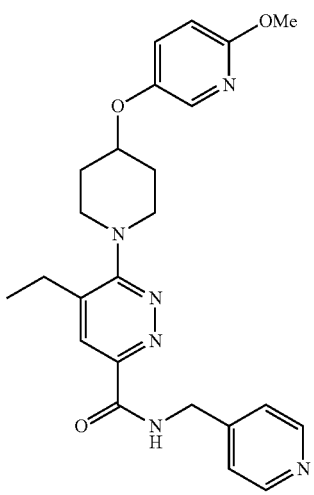 [SMILES: CCc1cc(C(=O)NCc2ccncc2)nnc1N1CCC(Oc2ccc(OC)nc2)CC1]

5-Ethyl-6-(4-(((6-methoxypyridin-3-yl)oxy)piperidin-1-yl)-N-(pyridin-4-ylmethyl)pyridazine-3-carboxamide (Scheme 7)

Step 1: 5-Ethyl-6-(4-(((6-methoxypyridin-3-yl)oxy)piperidin-1-yl)pyridazine-3-carboxylic Acid To a solution of methyl 5-ethyl-6-(4-(((6-methoxypyridin-3-yl)oxy)piperidin-1-yl)pyridazine-3-carboxylate (intermediate X2, 10 mg, 0.027 mmol) in MeOH (2 mL) and water (1 mL) was added LiOH (1.93 mg, 0.081 mmol). The resulting mixture was stirred at RT for 16 h before the volatiles were removed under reduced pressure to afford the title compound. MS: 359 (M+1).

Step 2: 5-Ethyl-6-(4-(((6-methoxypyridin-3-yl)oxy)piperidin-1-yl)-N-(pyridin-4-ylmethyl)pyridazine-3-carboxamide To a solution of 5-ethyl-6-(4-(((6-methoxypyridin-3-yl)oxy)piperidin-1-yl)pyridazine-3-carboxylic acid (12 mg, 0.033 mmol) and HATU (15.28 mg, 0.040 mmol) in DMF (1 mL) was added TEA (0.014 mL, 0.10 mmol) and pyridin-4-ylmethanamine (3.62 mg, 0.033 mmol). The reaction mixture was stirred at RT for 16 h before direct purification by reverse phase HPLC (ACN/water with 0.1% TFA modifier) to yield the title compound. MS: 449 (M+1). $^1$H NMR (400 MHz, methanol-$d_4$): δ 8.76 (2H, d, J=6.0 Hz), 7.95-8.05 (3H, m), 7.86 (1H, d, J=2.8 Hz), 7.46 (1H, dd, J=8.8, 2.8 Hz), 6.78 (1H, d, J=8.8 Hz), 4.89 (2H, s), 4.55-4.58 (1H, m), 3.87 (3H, s), 3.62-3.69 (2H, m), 3.20-3.29 (2H, m), 2.72-2.80 (2H, q, J=7.2 Hz), 2.15-2.20 (2H, m), 1.94-1.99 (2H, m), 1.33 (3H, t, J=7.6 Hz).

The following examples in table 7 were prepared according to scheme 7 using the procedure outlined in the synthesis of Example 205. In cases where there saponification is not necessary, the first step is omitted. Commercially available amines or ammonium chloride are employed in step 2.

TABLE 7

| Example | Structure | Name | MS (M + 1) |
|---|---|---|---|
| 206 | 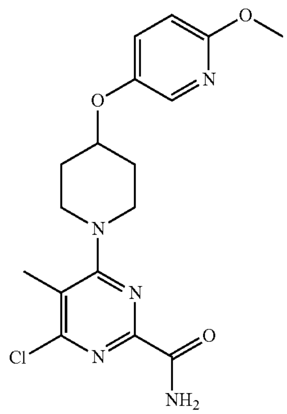 | 4-chloro-6-(4-((6-methoxypyridin-3-yl)oxy)piperidin-1-yl)-5-methylpyrimidine-2-carboxamide | 378 |
| 207 | 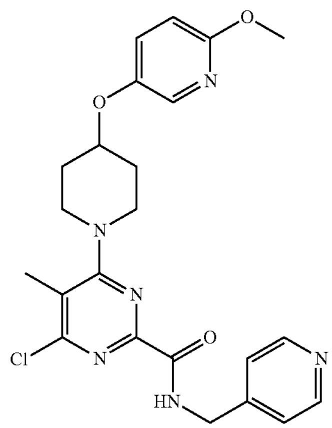 [SMILES: COc1ccc(OC2CCN(c3nc(C(=O)NCc4ccncc4)nc(Cl)c3C)CC2)cn1] | 4-chloro-6-(4-((6-methoxypyridin-3-yl)oxy)piperidin-1-yl)-5-methyl-N-(pyridin-4-ylmethyl)pyrimidine-2-carboxamide | 469 |
| 208 | 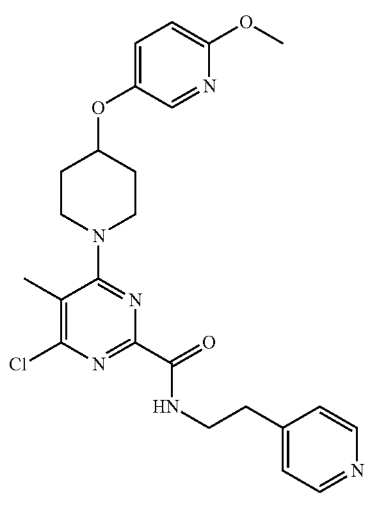 [SMILES: COc1ccc(OC2CCN(c3nc(C(=O)NCCc4ccncc4)nc(Cl)c3C)CC2)cn1] | 4-chloro-6-(4-((6-methoxypyridin-3-yl)oxy)piperidin-1-yl)-5-methyl-N-(2-(pyridin-4-yl)ethyl)pyrimidine-2-carboxamide | 483 |

TABLE 7-continued

| Example | Structure | Name | MS (M + 1) |
|---|---|---|---|
| 209 | 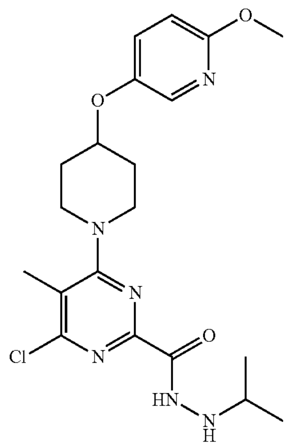 [SMILES: COc1ccc(OC2CCN(c3nc(C(=O)NNC(C)C)nc(Cl)c3C)CC2)cn1] | 4-chloro-N'-isopropyl-6-(4-((6-methoxypyridin-3-yl)oxy)piperidin-1-yl)-5-methylpyrimidine-2-carbohydrazide | 483 |
| 210 | 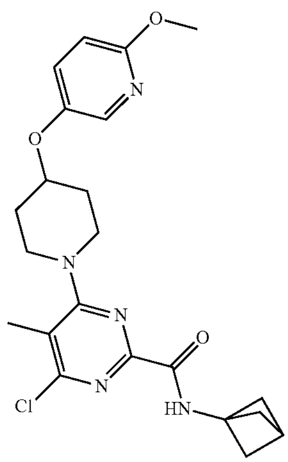 [SMILES: COc1ccc(OC2CCN(c3nc(C(=O)NC45CC(C4)C5)nc(Cl)c3C)CC2)cn1] | N-(bicyclo[1.1.1]pentan-1-yl)-4-chloro-6-(4-((6-methoxypyridin-3-yl)oxy)piperidin-1-yl)-5-methylpyrimidine-2-carboxamide | 444 |
| 211 | 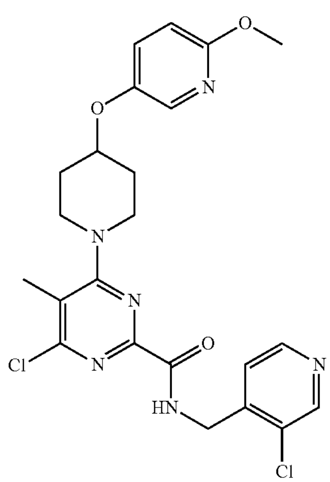 [SMILES: COc1ccc(OC2CCN(c3nc(C(=O)NCc4ccncc4Cl)nc(Cl)c3C)CC2)cn1] | 4-chloro-N-((3-chloropyridin-4-yl)methyl)-6-(4-((6-methoxypyridin-3-yl)oxy)piperidin-1-yl)-5-methylpyrimidine-2-carboxamide | 503 |

TABLE 7-continued

| Example | Structure | Name | MS (M + 1) |
|---|---|---|---|
| 212 | 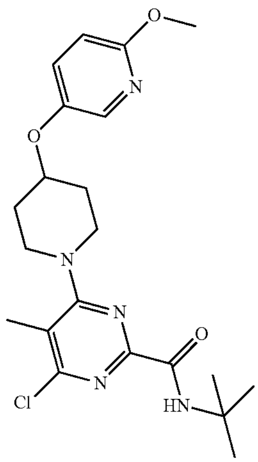 [SMILES: COc1ccc(OC2CCN(c3nc(C(=O)NC(C)(C)C)nc(Cl)c3C)CC2)cn1] | N-(bicyclo[1.1.1]pentan-1-yl)-4-chloro-6-(4-((6-methoxypyridin-3-yl)oxy)piperidin-1-yl)-5-methylpyrimidine-2-carboxamide | 434 |
| 213 | 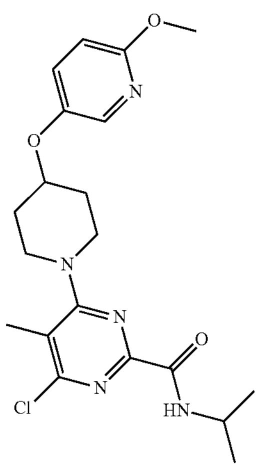 [SMILES: COc1ccc(OC2CCN(c3nc(C(=O)NC(C)C)nc(Cl)c3C)CC2)cn1] | 4-chloro-N-isopropyl-6-(4-((6-methoxypyridin-3-yl)oxy)piperidin-1-yl)-5-methylpyrimidine-2-carboxamide | 420 |
| 214 | 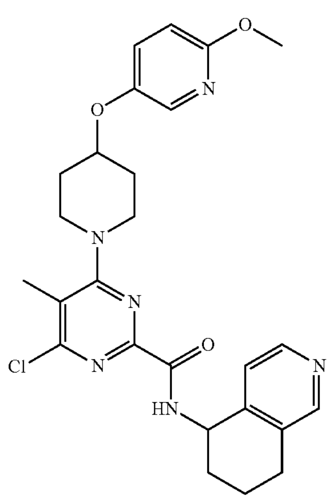 [SMILES: COc1ccc(OC2CCN(c3nc(C(=O)NC4CCCc5cnccc54)nc(Cl)c3C)CC2)cn1] | 4-chloro-6-(4-((6-methoxypyridin-3-yl)oxy)piperidin-1-yl)-5-methyl-N-(5,6,7,8-tetrahydroisoquinolin-5-yl)pyrimidine-2-carboxamide | 509 |

TABLE 7-continued

| Example | Structure | Name | MS (M + 1) |
|---|---|---|---|
| 215 | 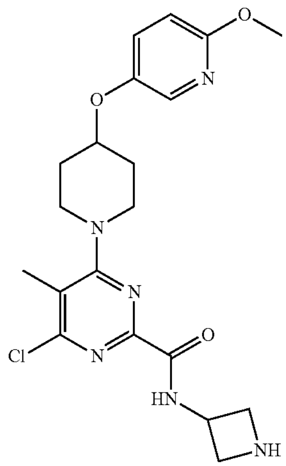 | N-(azetidin-3-yl)-4-chloro-6-(4-((6-methoxypyridin-3-yl)oxy)piperidin-1-yl)-5-methylpyrimidine-2-carboxamide | 509 |
| 216 | 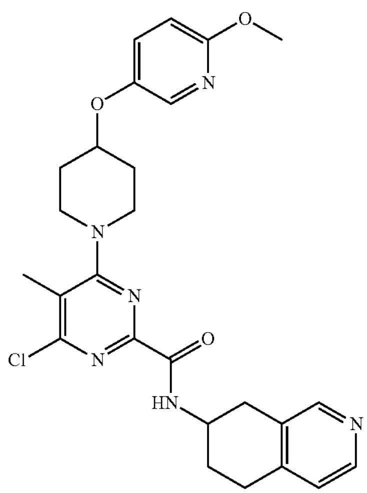 [SMILES: COc1ccc(OC2CCN(c3nc(C(=O)NC4CCc5ccncc5C4)nc(Cl)c3C)CC2)cn1] | 4-chloro-6-(4-((6-methoxypyridin-3-yl)oxy)piperidin-1-yl)-5-methyl-N-(5,6,7,8-tetrahydroisoquinolin-7-yl)pyrimidine-2-carboxamide | 509 |
| 217 | 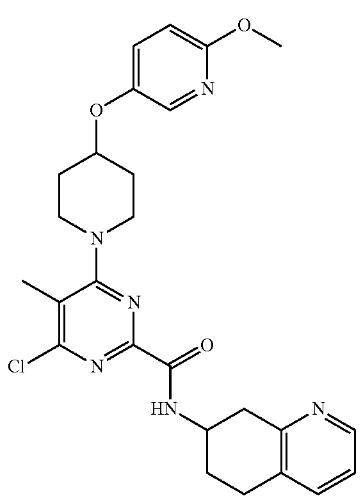 [SMILES: COc1ccc(OC2CCN(c3nc(C(=O)NC4CCc5cccnc5C4)nc(Cl)c3C)CC2)cn1] | 4-chloro-6-(4-((6-methoxypyridin-3-yl)oxy)piperidin-1-yl)-5-methyl-N-(5,6,7,8-tetrahydroquinolin-7-yl)pyrimidine-2-carboxamide | 509 |

TABLE 7-continued

| Example | Structure | Name | MS (M + 1) |
|---|---|---|---|
| 218 | 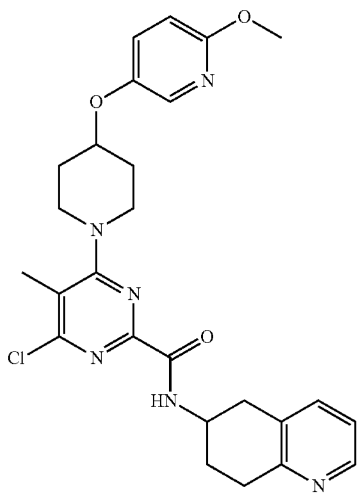 [SMILES: COc1ccc(OC2CCN(c3nc(C(=O)NC4CCc5ncccc5C4)nc(Cl)c3C)CC2)cn1] | 4-chloro-6-(4-((6-methoxypyridin-3-yl)oxy)piperidin-1-yl)-5-methyl-N-(5,6,7,8-tetrahydroquinolin-6-yl)pyrimidine-2-carboxamide | 509 |
| 219 | 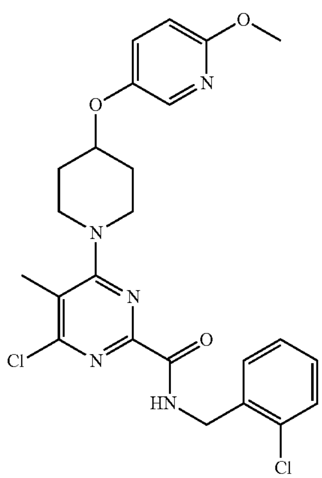 [SMILES: COc1ccc(OC2CCN(c3nc(C(=O)NCc4ccccc4Cl)nc(Cl)c3C)CC2)cn1] | 4-chloro-N-(2-chlorobenzyl)-6-(4-((6-methoxypyridin-3-yl)oxy)piperidin-1-yl)-5-methylpyrimidine-2-carboxamide | 502 |
| 220 | 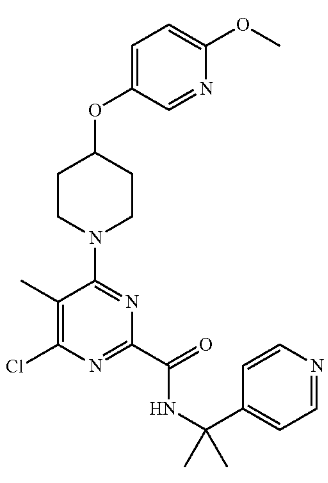 [SMILES: COc1ccc(OC2CCN(c3nc(C(=O)NC(C)(C)c4ccncc4)nc(Cl)c3C)CC2)cn1] | 4-chloro-6-(4-((6-methoxypyridin-3-yl)oxy)piperidin-1-yl)-5-methyl-N-(2-(pyridin-4-yl)propan-2-yl)pyrimidine-2-carboxamide | 502 |

TABLE 7-continued

| Example | Structure | Name | MS (M + 1) |
|---|---|---|---|
| 221 | 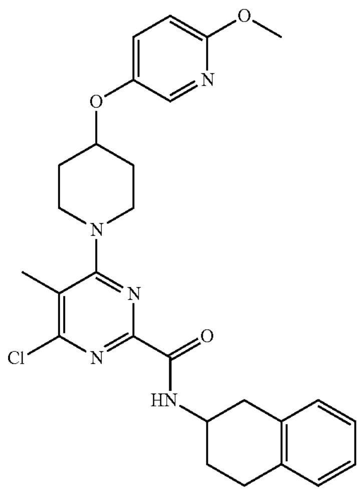 [SMILES: COc1ccc(OC2CCN(c3nc(C(=O)NC4CCc5ccccc5C4)nc(Cl)c3C)CC2)cn1] | 4-chloro-6-(4-((6-methoxypyridin-3-yl)oxy)piperidin-1-yl)-5-methyl-N-(1,2,3,4-tetrahydronaphthalen-2-yl)pyrimidine-2-carboxamide | 508 |
| 222 | 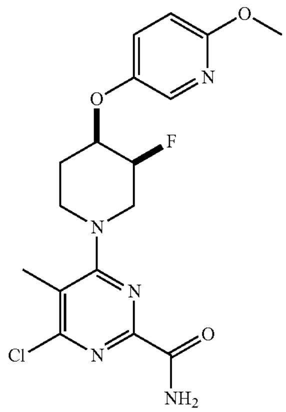 | 4-chloro-6-((3S,4R)-3-fluoro-4-((6-methoxypyridin-3-yl)oxy)piperidin-1-yl)-5-methylpyrimidine-2-carboxamide | 508 |
| 223 | 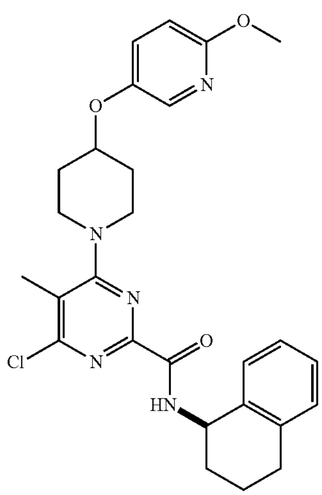 | (R)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide | 508 |

TABLE 7-continued

| Example | Structure | Name | MS (M + 1) |
|---|---|---|---|
| 224 | 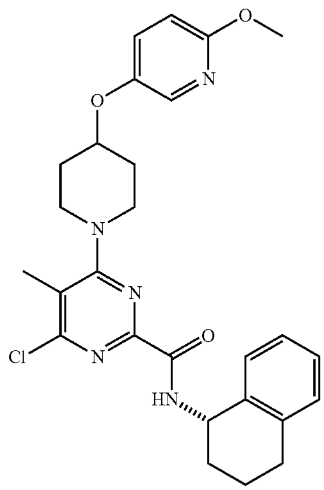 | (S)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide | 508 |
| 225 | 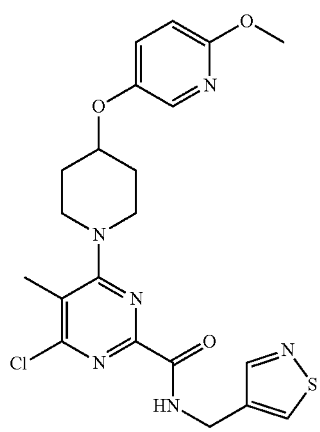 [SMILES: COc1ccc(OC2CCN(c3nc(C(=O)NCc4cnsc4)nc(Cl)c3C)CC2)cn1] | 4-chloro-N-(isothiazol-4-ylmethyl)-6-(4-((6-methoxypyridin-3-yl)oxy)piperidin-1-yl)-5-methylpyrimidine-2-carboxamide | 475 |
| 225A | 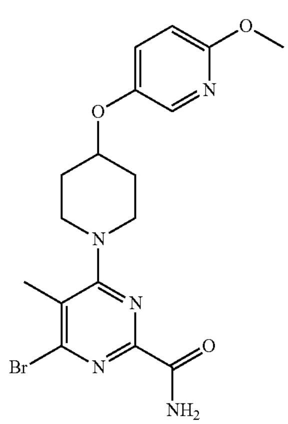 | 4-bromo-6-(4-((6-methoxypyridin-3-yl)oxy)piperidin-1-yl)-5-methylpyrimidine-2-carboxamide | 422, 424 |

Example 226

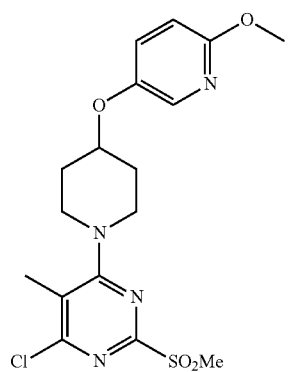

4-Chloro-6-(4-((6-methoxypyridin-3-yl)oxy)piperidin-1-yl)-5-methyl-2-(methylsulfonyl)pyrimidine (Scheme 8)

To 4-chloro-6-(4-((6-methoxypyridin-3-yl)oxy)piperidin-1-yl)-5-methyl-2-(methylthio)pyrimidine (1.5 g, 3.94 mmol) in DCM (19.7 mL) at 0° C. was added m-CPBA (2.21 g, 9.85 mmol) portionwise. After 1 h, the reaction mixture was diluted with DCM and the organic phase was separated then washed with aqueous NaHCO$_3$ (saturated) and brine. The mixture was dried over anhydrous magnesium sulfate, filtered, and concentrated in vacuo. The residue was purified by silica gel chromatography (10-60% acetone/hexanes) to afford the title compound. MS: 413 (M+1). $^1$H NMR (500 MHz, C$_D$C13) δ 7.88 (d, J=3.0 Hz, 1H), 7.30-7.24 (m, 1H), 6.74 (d, J=8.9 Hz, 1H), 4.49 (tt, J=3.5, 6.7 Hz, 1H), 3.93 (s, 2H), 3.81 (ddd, J=3.4, 8.4, 12.5 Hz, 2H), 3.56 (ddd, J=3.7, 7.0, 13.5 Hz, 2H), 3.32 (s, 3H), 2.35 (s, 3H), 2.14-2.04 (m, 2H), 2.02-1.92 (m, 2H).

Example 227

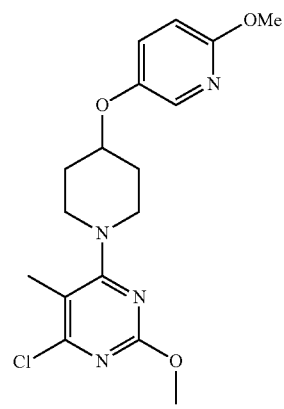 [SMILES: COc1ccc(OC2CCN(c3nc(OC)nc(Cl)c3C)CC2)cn1]

4-Chloro-2-methoxy-6-(4-((6-methoxypyridin-3-yl)oxy)piperidin-1-yl)-5-methylpyrimidine (Scheme 9)

A solution of 4-chloro-6-(4-((6-methoxypyridin-3-yl)oxy)piperidin-1-yl)-5-methyl-2-(methylsulfonyl)pyrimidine (80 mg, 0.194 mmol) in THF (969 pi) was added a premixed solution of LiHMDS (1 M in THF, 291 μL, 0.291 mmol) and methanol (β9.2 μL, 0.969 mmol). This was stirred for 1 h at RT before being partitioned with aqueous ammonium chloride (saturated) and DCM. The organic was separated, dried over anhydrous sodium sulfate, filtered, and concentrated under reduced pressure. The residue was purified by mass directed HPLC (ACN/water with 0.1% NH$_3$OH modifier) to afford the title compound. MS: 365 (M+1). $^1$H NMR (500 MHz, C$_D$C13) δ 7.88 (d, J=3.0 Hz, 1H), 7.27 (dd, J=3.0, 8.9 Hz, 1H), 6.73 (d, J=8.9 Hz, 1H), 4.42 (tt, J=3.7, 7.3 Hz, 1H), 3.94 (d, J=17.8 Hz, 5H), 3.75-3.66 (m, 2H), 3.37-3.28 (m, 2H), 2.22 (s, 3H), 2.13-2.05 (m, 2H), 1.97-1.86 (m, 2H).

Example 228

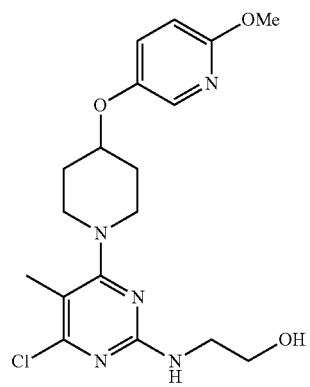 [SMILES: COc1ccc(OC2CCN(c3nc(NCCO)nc(Cl)c3C)CC2)cn1]

2-((4-Chloro-6-(4-((6-methoxypyridin-3-yl)oxy)piperidin-1-yl)-5-methylpyrimidin-2-yl)amino)ethan-1-ol (Scheme 9)

To 4-chloro-6-(4-((6-methoxypyridin-3-yl)oxy)piperidin-1-yl)-5-methyl-2-(methylsulfonyl)pyrimidine (Example 226, 100 mg, 0.242 mmol) in butan-1-ol (2.4 mL) was added ethanolamine (16 μL, 0.266 mmol) and DIPEA (169 μL, 0.969 mmol). The reaction was heated in for 2 h under microwave irradiation at 150° C. The mixture was partitioned with water and extracted with DCM. The organic phase was dried over anhydrous sodium sulfate and concentrated to dryness. The residue was purified by mass directed HPLC (ACN/water with 0.1% NH$_3$OH modifier) to afford the title compound. MS: 394 (M+1). $^1$H NMR (500 MHz, CDCl$_3$): δ 7.88 (d, J=3.0 Hz, 1H), 7.27 (dd, J=3.0, 8.9 Hz, 1H), 6.73 (d, J=8.9 Hz, 1H), 5.33 (s, 1H), 4.40 (tt, J=3.6, 7.3 Hz, 1H), 3.83 (dd, J=4.3, 5.4 Hz, 2H), 3.67-3.60 (m, 2H), 3.60-3.54 (m, 2H), 3.27-3.18 (m, 2H), 2.15 (s, 3H), 2.12-2.03 (m, 1H), 1.95-1.85 (m, 2H).

The following examples in table 9 were prepared according to scheme 9 using the procedure outlined in the synthesis of Examples 227 and 228 using prepared intermediates and commercially available amines, alcohols and in some cases, sodium hydroxide.

TABLE 9

| Example | Structure | Name | MS (M + 1) |
|---|---|---|---|
| 229 | 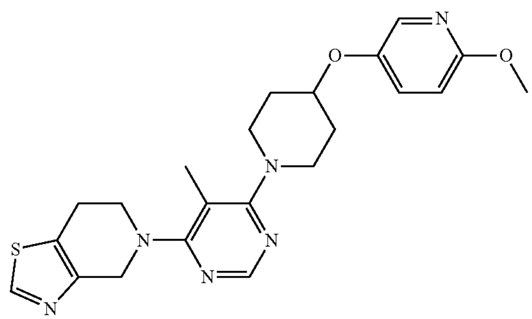 [SMILES: COc1ccc(OC2CCN(c3ncnc(N4CCc5scnc5C4)c3C)CC2)cn1] | 5-(6-(4-((6-methoxypyridin-3-yl)oxy)piperidin-1-yl)-5-methylpyrimidin-4-yl)-4,5,6,7-tetrahydrothiazolo[4,5-c]pyridine | 439 |
| 230 | 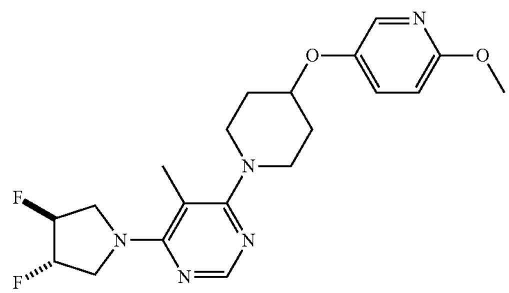 [SMILES: COc1ccc(OC2CCN(c3ncnc(N4C[C@H](F)[C@@H](F)C4)c3C)CC2)cn1] | 4-((3S,4S)-3,4-difluoropyrrolidin-1-yl)-6-(4-((6-methoxypyridin-3-yl)oxy)piperidin-1-yl)-5-methylpyrimidine | 406 |
| 231 | 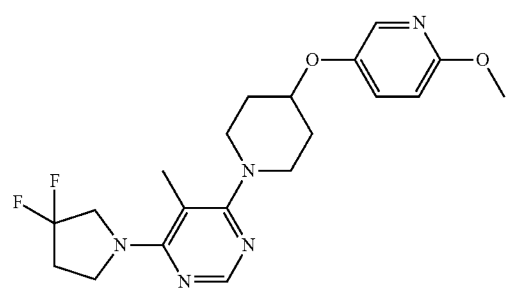 [SMILES: COc1ccc(OC2CCN(c3ncnc(N4CCC(F)(F)C4)c3C)CC2)cn1] | 4-(3,3-difluoropyrrolidin-1-yl)-6-(4-((6-methoxypyridin-3-yl)oxy)piperidin-1-yl)-5-methylpyrimidine | 406 |
| 232 | 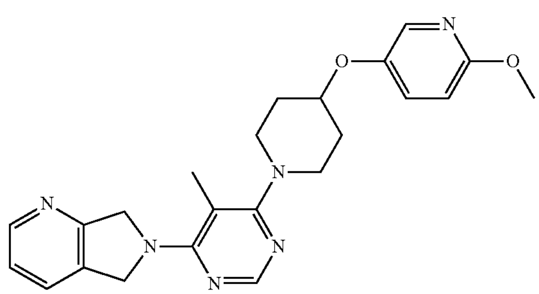 [SMILES: COc1ccc(OC2CCN(c3ncnc(N4Cc5cccnc5C4)c3C)CC2)cn1] | 6-(6-(4-((6-methoxypyridin-3-yl)oxy)piperidin-1-yl)-5-methylpyrimidin-4-yl)-6,7-dihydro-5H-pyrrolo[3,4-b]pyridine | 419 |
| 233 | 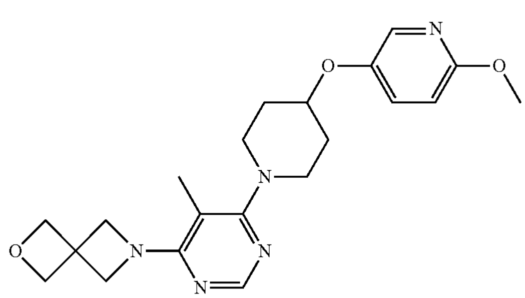 [SMILES: COc1ccc(OC2CCN(c3ncnc(N4CC5(COC5)C4)c3C)CC2)cn1] | 6-(6-(4-((6-methoxypyridin-3-yl)oxy)piperidin-1-yl)-5-methylpyrimidin-4-yl)-2-oxa-6-azaspiro[3.3]heptane | 398 |

TABLE 9-continued

| Example | Structure | Name | MS (M + 1) |
|---|---|---|---|
| 234 | 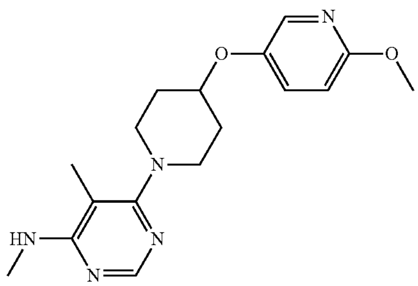 | 6-(4-((6-methoxypyridin-3-yl)oxy)piperidin-1-yl)-N,5-dimethylpyrimidin-4-amine | 364 |
| 235 | 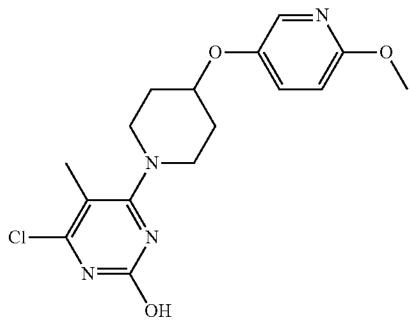 [SMILES: COc1ccc(OC2CCN(c3nc(O)nc(Cl)c3C)CC2)cn1] | 4-chloro-6-(4-((6-methoxypyridin-3-yl)oxy)piperidin-1-yl)-5-methylpyrimidin-2-ol | 351 |
| 236 | 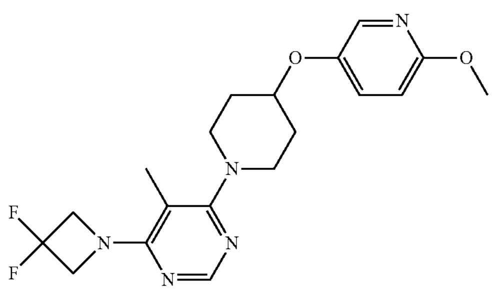 [SMILES: COc1ccc(OC2CCN(c3ncnc(N4CC(F)(F)C4)c3C)CC2)cn1] | 4-(3,3-difluoroazetidin-1-yl)-6-(4-((6-methoxypyridin-3-yl)oxy)piperidin-1-yl)-5-methylpyrimidine | 392 |
| 237 | 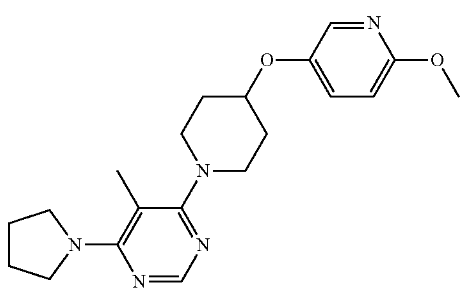 [SMILES: COc1ccc(OC2CCN(c3ncnc(N4CCCC4)c3C)CC2)cn1] | 4-(4-((6-methoxypyridin-3-yl)oxy)piperidin-1-yl)-5-methyl-6-(pyrrolidin-1-yl)pyrimidine | 370 |
| 238 | 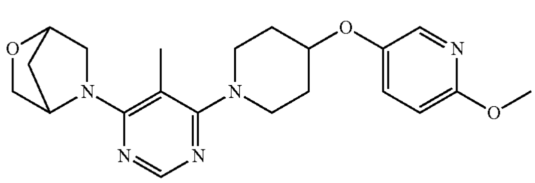 [SMILES: COc1ccc(OC2CCN(c3ncnc(N4CC5CC4CO5)c3C)CC2)cn1] | 5-(6-(4-((6-methoxypyridin-3-yl)oxy)piperidin-1-yl)-5-methylpyrimidin-4-yl)-2-oxa-5-azabicyclo[2.2.1]heptane | 398 |

TABLE 9-continued

| Example | Structure | Name | MS (M + 1) |
|---|---|---|---|
| 239 | 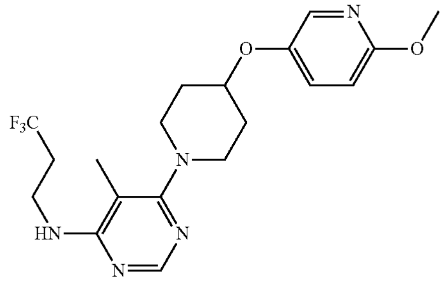 [SMILES: COc1ccc(OC2CCN(c3ncnc(NCCC(F)(F)F)c3C)CC2)cn1] | 6-(4-((6-methoxypyridin-3-yl)oxy)piperidin-1-yl)-5-methyl-N-(3,3,3-trifluoropropyl)pyrimidin-4-amine | 412 |
| 240 | 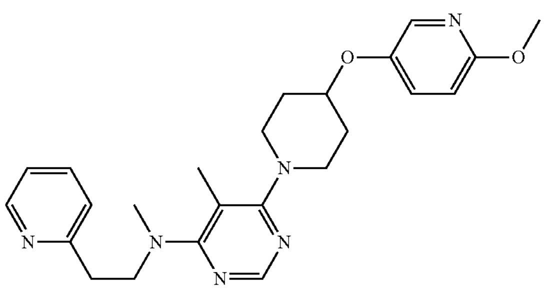 [SMILES: COc1ccc(OC2CCN(c3ncnc(N(C)CCc4ccccn4)c3C)CC2)cn1] | 6-(4-((6-methoxypyridin-3-yl)oxy)piperidin-1-yl)-N,5-dimethyl-N-(2-(pyridin-2-yl)ethyl)pyrimidin-4-amine | 435 |

Example 241

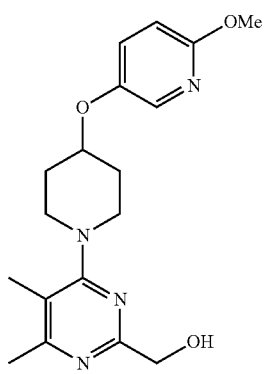 [SMILES: COc1ccc(OC2CCN(c3nc(CO)nc(C)c3C)CC2)cn1]

(4-(4-((6-Methoxypyridin-3-yl)oxy)piperidin-1-yl)-5,6-dimethylpyrimidin-2-yl)methanol (Scheme 10)

To (4-chloro-6-(4-((6-methoxypyridin-3-yl)oxy)piperidin-1-yl)-5-methylpyrimidin-2-yl)methanol (Example 68, 100 mg, 0.274 mmol) was added dioxane (1.4 mL), trimethylboroxine (41.3 mg, 0.329 mmol), and $Cs_2CO_3$ (268 mg, 0.822 mmol). The system was purged and flushed with nitrogen before adding $Pd(Ph_3P)_4$ (31.7 mg, 0.027 mmol) and the reaction was heated to 150° C. by microwave irradiation for 20 min. The reaction was diluted water and DCM and the organic phase was dried over anhydrous sodium sulfate, filtered through celite and concentrated to dryness. The residue was purified by mass directed HPLC purification (ACN/water with 0.1% $NH_3OH$) to afford the title compound. MS: 345 (M+1). 1H NMR (500 MHz, $CD_3OD$) δ 7.83 (d, J=3.0 Hz, 1H), 7.42 (dd, J=3.0, 8.9 Hz, 1H), 6.76 (d, J=8.9 Hz, 1 H), 4.55 (s, 2H), 4.52 (tt, J=3.7, 7.5 Hz, 1H), 3.86 (s, 3H), 3.74 (ddd, J=3.6, 7.3, 13.2 Hz, 2 H), 3.37 (ddd, J=3.4, 8.3, 13.2 Hz, 2H), 3.31 (s, 1H), 2.42 (s, 3H), 2.20 (s, 3H), 2.15-2.05 (m, 2H), 1.91-1.81 (m, 2H).

The following examples in table 10 were prepared according to scheme 10 using the procedure outlined in the synthesis of Example 240 using commercially available boronic acids and esters.

TABLE 10
| Example | Structure | Name | MS (M + 1) |
|---|---|---|---|
| 242 | 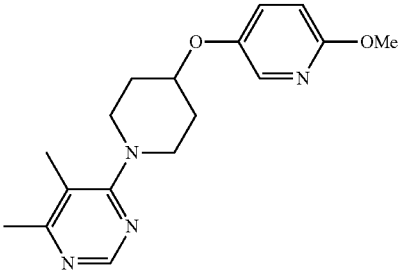 [SMILES: COc1ccc(OC2CCN(c3ncnc(C)c3C)CC2)cn1] | 4-(4-((6-methoxypyridin-3-yl)oxy)piperidin-1-yl)-5,6-dimethylpyrimidine | 315 |
| 243 | 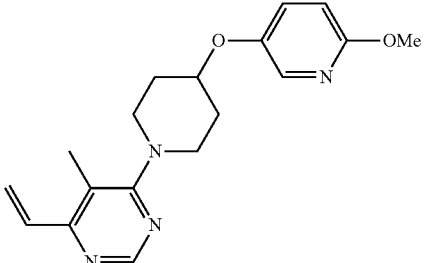 | 4-(4-((6-methoxypyridin-3-yl)oxy)piperidin-1-yl)-5-methyl-6-vinylpyrimidine | 327 |
| 244 | 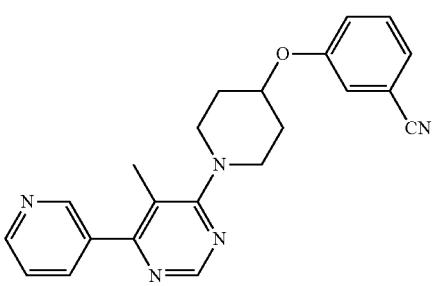 [SMILES: Cc1c(-c2cccnc2)ncnc1N1CCC(Oc2cccc(C#N)c2)CC1] | 3-((1-(5-methyl-6-(pyridin-3-yl)pyrimidin-4-yl)piperidin-4-yl)oxy)benzonitrile | 372 |
| 245 | 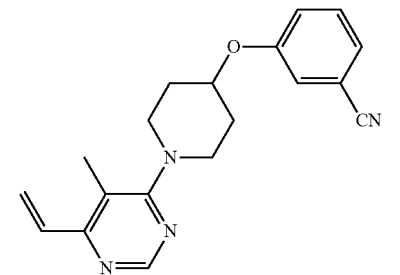 [SMILES: C=Cc1ncnc(N2CCC(Oc3cccc(C#N)c3)CC2)c1C] | 3-((1-(5-methyl-6-vinylpyrimidin-4-yl)piperidin-4-yl)oxy)benzonitrile | 321 |
| 246 | 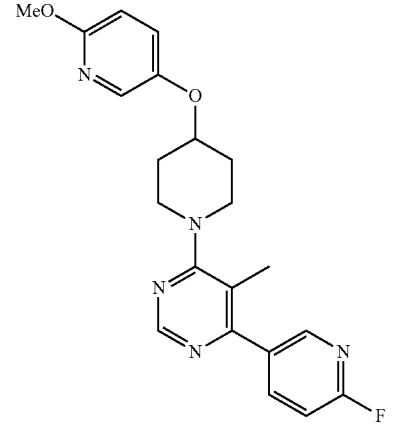 [SMILES: COc1ccc(OC2CCN(c3ncnc(-c4ccc(F)nc4)c3C)CC2)cn1] | 4-(6-fluoropyridin-3-yl)-6-(4-((6-methoxypyridin-3-yl)oxy)piperidin-1-yl)-5-methylpyrimidine | 396 |

TABLE 10-continued

| Example | Structure | Name | MS (M + 1) |
|---|---|---|---|
| 247 | 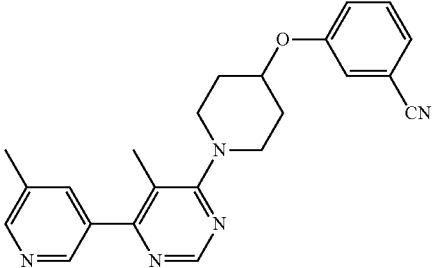 [SMILES: Cc1cncc(-c2ncnc(N3CCC(Oc4cccc(C#N)c4)CC3)c2C)c1] | 3-((1-(5-methyl-6-(5-methylpyridin-3-yl)pyrimidin-4-yl)piperidin-4-yl)oxy)benzonitrile | 386 |
| 248 | 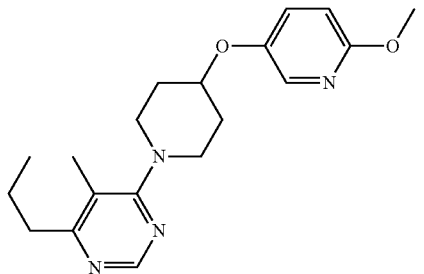 [SMILES: CCCc1ncnc(N2CCC(Oc3ccc(OC)nc3)CC2)c1C] | 4-(4-((6-methoxypyridin-3-yl)oxy)piperidin-1-yl)-5-methyl-6-propylpyrimidine | 343 |
| 249 | 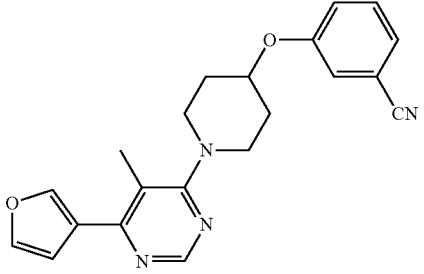 [SMILES: Cc1c(-c2ccoc2)ncnc1N1CCC(Oc2cccc(C#N)c2)CC1] | 3-((1-(6-(furan-3-yl)-5-methylpyrimidin-4-yl)piperidin-4-yl)oxy)benzonitrile | 361 |
| 250 | 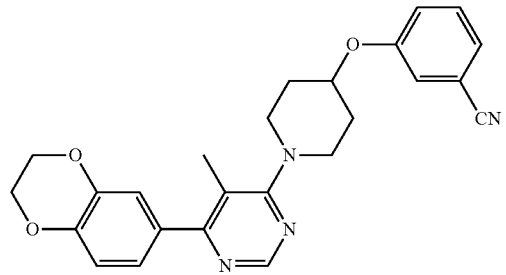 [SMILES: Cc1c(-c2ccc3c(c2)OCCO3)ncnc1N1CCC(Oc2cccc(C#N)c2)CC1] | 3-((1-(6-(2,3-dihydrobenzo[b][1,4]dioxin-6-yl)-5-methylpyrimidin-4-yl)piperidin-4-yl)oxy)benzonitrile | 429 |
| 251 | 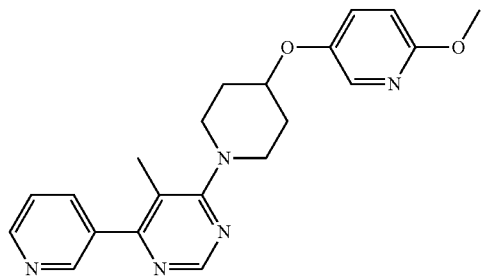 [SMILES: COc1ccc(OC2CCN(c3ncnc(-c4cccnc4)c3C)CC2)cn1] | 4-(4-((6-methoxypyridin-3-yl)oxy)piperidin-1-yl)-5-methyl-6-(pyridin-3-yl)pyrimidine | 378 |

TABLE 10-continued

| Example | Structure | Name | MS (M + 1) |
|---|---|---|---|
| 252 | 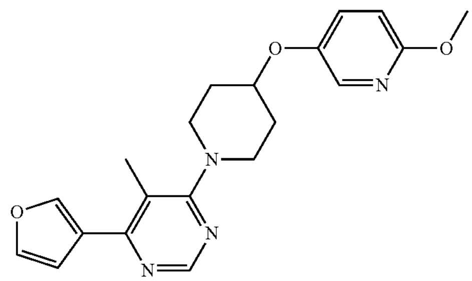 [SMILES: COc1ccc(OC2CCN(c3ncnc(-c4ccoc4)c3C)CC2)cn1] | 4-(furan-3-yl)-6-(4-((6-methoxypyridin-3-yl)oxy)piperidin-1-yl)-5-methylpyrimidine | 367 |
| 253 | 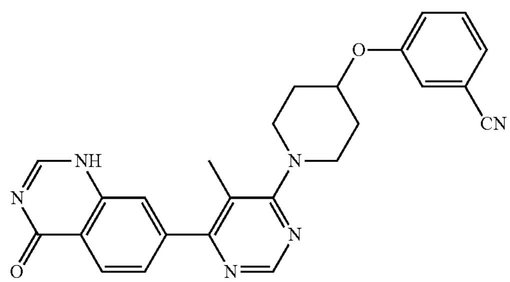 [SMILES: Cc1c(-c2ccc3c(=O)nc[nH]c3c2)ncnc1N1CCC(Oc2cccc(C#N)c2)CC1] | 3-((1-(5-methyl-6-(4-oxo-1,4-dihydroquinazolin-7-yl)pyrimidin-4-yl)piperidin-4-yl)oxy)benzonitrile | 439 |
| 254 | 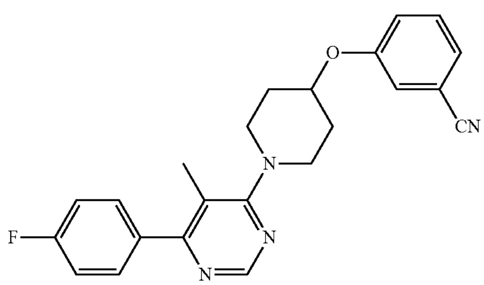 [SMILES: Cc1c(-c2ccc(F)cc2)ncnc1N1CCC(Oc2cccc(C#N)c2)CC1] | 3-((1-(6-(4-fluorophenyl)-5-methylpyrimidin-4-yl)piperidin-4-yl)oxy)benzonitrile | 389 |
| 255 | 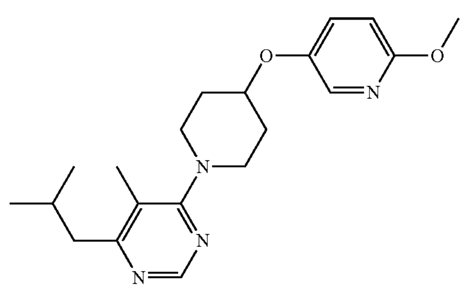 [SMILES: COc1ccc(OC2CCN(c3ncnc(CC(C)C)c3C)CC2)cn1] | 4-isobutyl-6-(4-((6-methoxypyridin-3-yl)oxy)piperidin-1-yl)-5-methylpyrimidine | 357 |
| 256 | 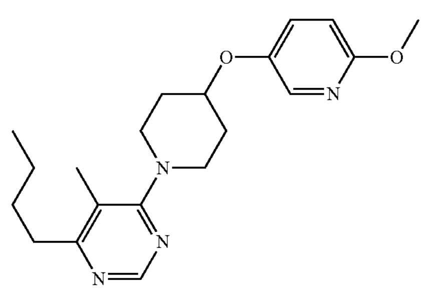 [SMILES: CCCCc1ncnc(N2CCC(Oc3ccc(OC)nc3)CC2)c1C] | 4-butyl-6-(4-((6-methoxypyridin-3-yl)oxy)piperidin-1-yl)-5-methylpyrimidine | 357 |

TABLE 10-continued

| Example | Structure | Name | MS (M + 1) |
|---|---|---|---|
| 257 | 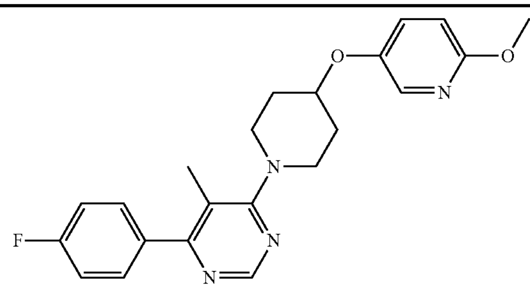 | 4-(4-fluorophenyl)-6-(4-((6-methoxypyridin-3-yl)oxy)piperidin-1-yl)-5-methylpyrimidine | 395 |

Example 258

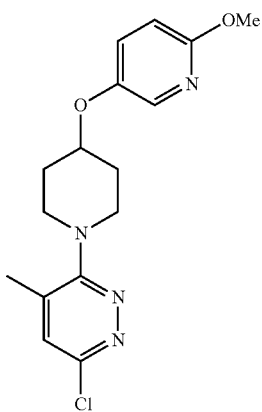 [SMILES: COc1ccc(OC2CCN(c3nnc(Cl)cc3C)CC2)cn1]

6-(4-((6-Methoxypyridin-3-yl)oxy)piperidin-1-yl)-5-methylpyridazine-3-carbonitrile (Scheme 11)

Step 1: 6-chloro-3-(4-((6-methoxypyridin-3-yl)oxy)piperidin-1-yl)-4-methylpyridazine To a solution of 3,6-dichloro-4-methylpyridazine (200 mg, 1.227 mmol) in dioxane (6 mL) was added 2-methoxy-5-(piperidin-4-yloxy)pyridine (268 mg, 1.29 mmol), DIPEA (0.643 mL, 3.68 mmol). The reaction was stirred at 110° C. for 8 h before being cooled to RT and diluted with water (10 mL) and extracting with EtOAc (8 mL×3). The combined organic layers were washed with water (15 mL) and brine (15 mL), dried over anhydrous sodium sulfate, filtered and concentrated. The crude product was purified by prep-TLC (2:1 petroleum ether:EtOAc) to afford the title compound. MS: 335 (M+1).

Step 2: 6-(4-((6-methoxypyridin-3-yl)oxy)piperidin-1-yl)-5-methylpyridazine-3-carbonitrile To a solution of 6-chloro-3-(4-((6-methoxypyridin-3-yl)oxy)piperidin-1-yl)-4-methylpyridazine (56 mg, 0.167 mmol) in DMF (5 mL) was added zinc cyanide (19.6 mg, 0.167 mmol), PdCl$_2$(dppf) (12.2 mg, 0.017 mmol), zinc (1 mg, 0.017 mmol) under an inert nitrogen atmosphere. The reaction was stirred at 160° C. for 4 h and then cooled to RT. The mixture was partitioned with water (8 mL) and EtOAc (8 mL) and the organic phase was washed with brine (8 mL), dried over anhydrous Na$_2$SO$_4$, filtered and concentrated under reduced pressure. The residue was purified by reverse phase HPLC (ACN/water with 0.1% NH$_3$OH) to afford the title compound. MS: 345 (M+1). $^1$H NMR (400 MHz, methanol-d$_4$): δ 7.85 (1H, d, J=2.0 Hz), 7.70 (1H, s), 7.49 (1H, dd, J=8.8, 2.8 Hz), 6.81 (1H, d, J=8.8 Hz), 4.55-4.58 (1H, m), 3.86 (3H, s), 3.72-3.77 (2H, m), 3.39-3.42 (2H, m), 2.36 (3H, s), 2.10-2.15 (2H, m), 1.88-1.91 (2H, m).

The following examples in table 11 were prepared according to scheme 11 using the procedure outlined in the synthesis of Example 258.

TABLE 11

| Example | Structure | Name | MS (M + 1) |
|---|---|---|---|
| 259 | 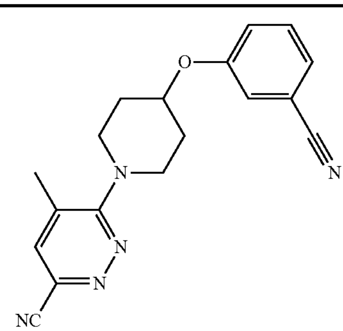 | 6-(4-(3-cyanophenoxy)piperidin-1-yl)-5-methylpyridazine-3-carbonitrile | 320 |

TABLE 11-continued

| Example | Structure | Name | MS (M + 1) |
|---|---|---|---|
| 260 | 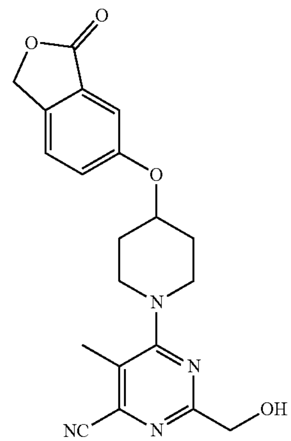 [SMILES: Cc1c(C#N)nc(CO)nc1N1CCC(Oc2ccc3c(c2)C(=O)OC3)CC1] | 2-(hydroxymethyl)-5-methyl-6-(4-((3-oxo-1,3-dihydroisobenzofuran-5-yl)oxy)piperidin-1-yl)pyrimidine-4-carbonitrile | 381 |

Example 261

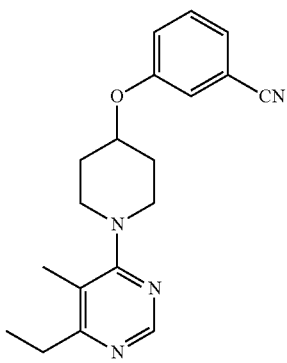 [SMILES: CCc1ncnc(N2CCC(Oc3cccc(C#N)c3)CC2)c1C]

3-((1-(6-Ethyl-5-methylpyrimidin-4-yl)piperidin-4-yl)oxy)benzonitrile (Scheme 12)

3-((1-(5-Methyl-6-vinylpyrimidin-4-yl)piperidin-4-yl)oxy)benzonitrile (26.6 mg, 0.083 mmol) was dissolved in methanol (1.0 mL) and ethyl acetate (0.5 mL). Pd—C(10 wt %, 6.63 mg, 6.23 μmop was added under an inert atmosphere before stirring at RT for 3 h under a hydrogen atmosphere. The mixture was filtered over celite (EtOAc wash) and the filtrate was concentrated to dryness. The residue was purified by silica gel chromatography (0-70% EtOAc/hexanes) to affor the title compound. MS: 323 (M+1). $^1$H NMR (500 MHz, CDCl$_3$): δ 8.61 (s, 1H), 7.38 (m, 1H), 7.26 (m, 1H+CHCl$_3$), 7.17 (m, 2H), 4.55 (m, 1H), 3.57 (m, 2H), 3.21 (m, 2H), 2.72 (q, 2H), 2.19 (s, 3H), 2.11 (m, 2H), 1.94 (m, 2H), 1.27 (t, 3H).

The following examples in table 11 were prepared according to scheme 12 using the procedure outlined in the synthesis of Example 261.

TABLE 12

| Example | Structure | Name | MS (M + 1) |
|---|---|---|---|
| 262 | 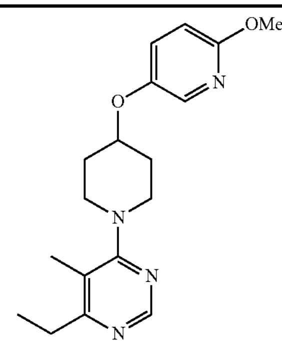 | 6-(4-(3-cyanophenoxy)piperidin-1-yl)-5-methylpyridazine-3-carbonitrile | 329 |

Example 263

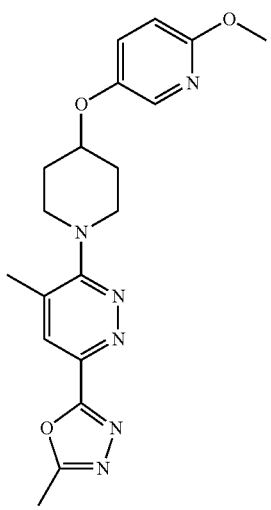

2-(6-(4-((6-Methoxypyridin-3-yl)oxy)piperidin-1-yl)-5-methylpyridazin-3-yl)-5-methyl-1,3,4-oxadiazole (Scheme 13)

N-Acetyl-6-(4-((6-methoxypyridin-3-yl)oxy)piperidin-1-yl)-5-methylpyridazine-3-carbohydrazide (intermediate LB1.30 mg, 0.075 mmol) was dissolved in POCl$_3$ (698 μL, 7.49 mmol) and was stirred at 90° C. and stirred for 8 h. The reaction was cooled to RT and the volatiles were removed under reduced pressure. The residue was partitioned with water (10 mL) and then with aqueous NaHCO$_3$ (saturated) until pH-9 and was extracted with ethyl acetate (15 mL×3). The combined organic phases were dried over anhydrous sodium sulfate, filtered and the filtrate was concentrated in vacuo. The crude material was purified by reverse phase HPLC
(ACN/water with 0.1% ammonium hydroxide modifier) to afford the title compound. MS: 383 (M+1). $^1$H NMR (400 MHz, methanol-d$_4$) δ: 8.07 (1H, s), 7.89 (1H, s), 7.46 (1H, dd, J=8.8, 2.8 Hz), 6.78 (1H, d, J=9.2 Hz), 4.56-4.61 (1H, m), 3.88 (3H, s), 3.72-3.76 (2H, m), 3.39-3.43 (2H, m), 2.69 (3H, s), 2.48 (3H, s), 2.16-2.22 (2H, m), 1.94-1.99 (2H, m).

Example 264

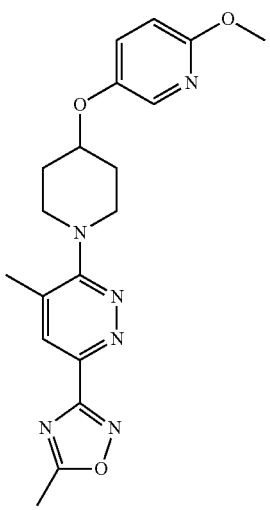

3-(6-(4-((6-Methoxypyridin-3-yl)oxy)piperidin-1-yl)-5-methylpyridazin-3-yl)-5-methyl-1,2,4-oxadiazole (Scheme 14)

Step 1: 6-(4-((6-Methoxypyridin-3-yl)oxy)piperidin-1-yl)-5-methylpyridazine-3-carbonitrile To a solution of 6-(4-((6-methoxypyridin-3-yl)oxy)piperidin-1-yl)-5-methylpyridazine-3-carboxamide (80 mg, 0.233 mmol) and TEA (0.162 mL, 1.165 mmol) in DCM (5 mL) was added TFAA (0.132 mL, 0.932 mmol) at 0° C. The reaction was stirred at 25° C. for 20 min before a quench with water (20 mL). The mixture extracted with EtOAc (20 mL×3) and the combined organic layers were dried over anhydrous sodium sulfate, filtered and concentrated to yield the title compound. MS: 326 (M+1).

Step 2: (E)-N-hydroxy-6-(4-((6-methoxypyridin-3-yl)oxy)piperidin-1-yl)-5-methylpyridazine-3-carboximidamide To a solution of 6-(4-((6-methoxypyridin-3-yl)oxy)piperidin-1-yl)-5-methylpyridazine-3-carbonitrile (70 mg, 0.215 mmol) in EtOH (3 mL) and DCM (0.25 mL) was added hydroxylamine hydrochloride (22.43 mg, 0.323 mmol) and TEA (0.060 mL, 0.430 mmol). The mixture was stirred at RT for 8 h before being diluted with water (20 mL) and extracted with EtOAc (20 mL×3). The combined organic phases were dried over anhydrous sodium sulfate, filtered and the filtrate was concentrated in vacuo to afford the title compound. MS: 359 (M+1).

Step 3: 3-(6-(4-((6-Methoxypyridin-3-yl)oxy)piperidin-1-yl)-5-methylpyridazin-3-yl)-5-methyl-1,2,4-oxadiazole (E)-N-hydroxy-6-(4-((6-methoxypyridin-3-yl)oxy)piperidin-1-yl)-5-methylpyridazine-3-carboximidamide (27 mg, 0.075 mmol), pyridine (2 mL) and acetic anhydride (15.4 mg, 0.151 mmol) was stirred under a nitrogen atmosphere for 8 h at 100° C. After cooling to RT, the mixture was diluted with water (7 mL) and extracted with EtOAc (8 mL×3). The combined organic layers were washed with brine (8 mL), dried over anhydrous sodium sulfate, filtered and concentrated under reduced pressure. The residue was purified by reverse phase HPLC (ACN/water with 0.1% ammonium hydroxide modifier) to afford the title compound. MS: 383 (M+1). $^1$H NMR (400 MHz, methanol-d$_4$): δ 7.98 (1H, s), 7.85 (1H, d, J=2.4 Hz), 7.44 (1H, dd, J=8.8, 2.4 Hz), 6.76 (1H, d, J=9.2 Hz), 4.53-4.56 (1H, m), 3.86 (3H, s), 3.68-3.73 (2H, m), 3.36-3.38 (2H, m), 2.69 (3H, s), 2.44 (3H, s), 2.08-2.16 (2H, m), 1.92-1.98 (2H, m).

Example 265

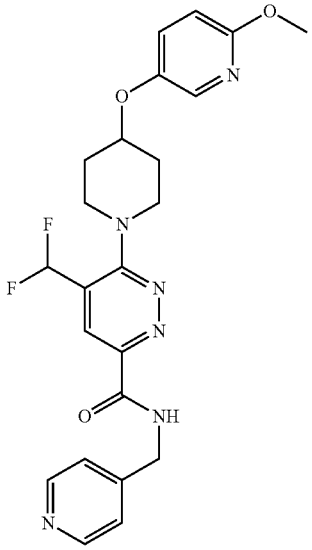 [SMILES: COc1ccc(OC2CCN(c3nnc(C(=O)NCc4ccncc4)cc3C(F)F)CC2)cn1]

5-(Difluoromethyl)-6-(4-((6-methoxypyridin-3-yl)oxy)piperidin-1-yl)-N-(pyridin-4-ylmethyl)pyridazine-3-carboxamide (Scheme 15)

Step 1: 6-(4-((6-Methoxypyridin-3-yl)oxy)piperidin-1-yl)-5-methylpyridazine-3-carbonitrile To a solution of methyl 3,6-dichloropyridazine-4-carboxylate (1.18 g, 5.70 mmol) in dioxane (30 mL) was added 2-methoxy-5-(piperidin-4-yloxy)pyridine hydrochloride (1604 mg, 6.56 mmol) and DIPEA (2.99 mL, 17.1 mmol). The reaction mixture was stirred for 2.5 h at 110° C. before cooling to RT. The mixture was concentrated in vacuo and the residue was purified by silica gel chromatography (0-30% EtOAc/petroleum ether) to afford the title compound. MS: 379 (M+1).

Step 2: (6-Chloro-3-(4-((6-methoxypyridin-3-yl)oxy)piperidin-1-yl)pyridazin-4-yl)methanol To a solution of ethyl 6-chloro-3-(4-((6-methoxypyridin-3-yl)oxy)piperidin-1-yl)pyridazine-4-carboxylate (500 mg, 1.32 mmol) in THF (20 mL) was added sodium borohydride (100 mg, 2.64 mmol) at 0° C. The reaction was stirred for 3 h and was diluted with water (20 mL) and extracted with EtOAc (10 mL×3). The combined organic layers were dried over anhydrous sodium sulfate, filtered and the filtrate was concentrated. The resultant residue was purified by silica gel chromatography (0-40% EtOAc/petroleum ether) to give the title compound. MS: 351 (M+1).

Step 3: 6-Chloro-3-(4-((6-methoxypyridin-3-yl)oxy)piperidin-1-yl)pyridazine-4-carbaldehyde To a solution of (6-chloro-3-(4-((6-methoxypyridin-3-yl)oxy)piperidin-1-yl)pyridazin-4-yl)methanol (200 mg, 0.570 mmol) in DCM (15 mL) was added manganese(IV) oxide (991 mg, 11.4 mmol). The reaction was stirred for 2 h at RT and was filtered before the filtrate was concentrated in vacuo. The residue was purified by silica gel chromatography (0-20% EtOAc/petroleum ether) to afford the title compound. MS: 349 (M+1).

Step 4: 6-Chloro-4-(difluoromethyl)-3-(4-((6-methoxypyridin-3-yl)oxy)piperidin-1-yl)pyridazine To a solution of 6-chloro-3-(4-((6-methoxypyridin-3-yl)oxy)piperidin-1-yl)pyridazine-4-carbaldehyde (170 mg, 0.487 mmol) in DCM (10 mL) was added DAST (0.193 mL, 1.462 mmol) at 0° C. After 2 h, aqueous NaHCO$_3$ (saturated) was added to adjust the pH-8-9. The mixture was partitioned with water (30 mL) and extracted with DCM (15 mL×3) and the combined organic layers were dried over anhydrous sodium sulfate, filtered and the filtrated was concentrated. The material was purified by silica gel chromatography (3:1 petroleum ether/EtOAc) to afford the title compound. MS: 371 (M+1).

Step 5: Methyl 5-(difluoromethyl)-6-(4-((6-methoxypyridin-3-yl)oxy)piperidin-1-yl)pyridazine-3-carboxylate A mixture of 6-chloro-4-(difluoromethyl)-3-(4-((6-methoxypyridin-3-yl)oxy)piperidin-1-yl)pyridazine (125 mg, 0.337 mmol), triethylamine (102 mg, 1.011 mmol) and [1,1'-bis(diphenylphosphine)ferrocene]dichloropalladium(II) (24.67 mg, 0.034 mmol) in MeOH (25 mL) was stirred under 50 psi of CO at 50° C. for 2 h. The reaction was filtered and the filtrate was concentrated in vacuo and the residue was purified silica gel chromatography (1/1 petroleum ether/EtOAc) to give the title compound. MS: 395 (M+1).

Step 6: 5-(Difluoromethyl)-6-(4-((6-methoxypyridin-3-yl)oxy)piperidin-1-yl)pyridazine-3-carboxylic Acid To a solution of methyl 5-(difluoromethyl)-6-(4-((6-methoxypyridin-3-yl)oxy)piperidin-1-yl)pyridazine-3-carboxylate (50 mg, 0.127 mmol) in MeOH (3 mL) and water (0.1 mL) was added sodium hydroxide (15.21 mg, 0.380 mmol). The reaction was stirred for 2 h at 30° C. before the volatiles were removed under in vacuo. The crude material was diluted with water (10 mL) and aqueous HCl (4 N) was used to adjust the pH-3-4 and EtOAc (10 mL×3) was used to extract the product. The combined organic layers were dried over anhydrous sodium sulfate, filtered and then concentrated to afford the title compound. MS: 381 (M+1).

Step 7: 5-(Difluoromethyl)-6-(4-((6-methoxypyridin-3-yl)oxy)piperidin-1-yl)-N-(pyridin-4-ylmethyl)pyridazine-3-carboxamide A mixture of 5-(difluoromethyl)-6-(4-((6-methoxypyridin-3-yl)oxy)piperidin-1-yl)pyridazine-3-carboxylic acid (45 mg, 0.118 mmol), HATU (49.5 mg, 0.130 mmol), pyridin-4-ylmethanamine (25.6 mg, 0.237 mmol) and triethylamine (0.049 mL, 0.355 mmol) in DMF (3 mL) was stirred for 2 h at RT. The mixture was concentrated and directly purified by silica gel chromatography (1/1 petroleum ether/EtOAc) to give the title compound. MS: 471 (M+1). $^1$H NMR (400 MHz, methanol-d$_4$): δ 8.48 (2H, d, J=5.2 Hz), 8.23 (1H, s), 7.85 (1H, d, J=2.4 Hz), 7.42-7.45 (3H, m), 7.02 (1H, t, J=54.0 Hz), 6.76 (1H, d, J=9.2 Hz), 4.71 (2H, s), 4.54-4.59 (1H, m), 3.85 (3H, s), 3.81-3.84 (2H, m), 3.51-3.55 (2H, m), 2.14-2.19 (2H, m), 1.92-1.99 (2H, m).

Example 266

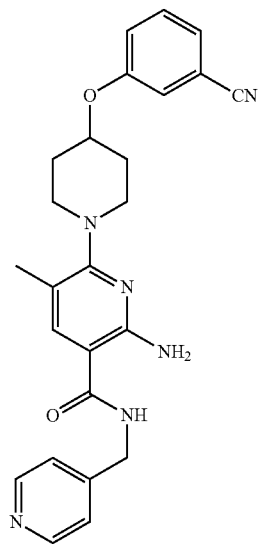 [SMILES: Cc1cc(C(=O)NCc2ccncc2)c(N)nc1N1CCC(Oc2cccc(C#N)c2)CC1]

2-Amino-6-(4-(3-cyanophenoxy)piperidin-1-yl)-5-methyl-N-(pyridin-4-ylmethyl)nicotinamide (Scheme 16)

Step 1: 2-Amino-6-(4-(3-cyanophenoxy)piperidin-1-yl)-N-(pyridin-4-ylmethyl)nicotinamide A mixture 6-(4-(3-cyanophenoxy)piperidin-1-yl)-2-fluoro-N-(pyridin-4-ylmethyl)nicotinamide (300 mg, 0.696 mmol) and ammonia (4 N in THF, 60 mL) was stirred in a sealed tube for 40 h at 120° C. The reaction was cooled to RT and concentrated in vacuo before purification by silica gel chromatography (1/2 petroleum ether/EtOAc) to afford the title compound. MS: 429 (M+1).

Step 2: 2-Amino-5-bromo-6-(4-(3-cyanophenoxy)piperidin-1-yl)-N-(pyridin-4-ylmethyl)nicotinamide To a solution of 2-amino-6-(4-(3-cyanophenoxy)piperidin-1-yl)-N-(pyridin-4-ylmethyl)nicotinamide 220 mg, 0.51 mmol) was added NMB (120 mg, 0.62 mmol) at RT. After stirring the reaction for 1 h, water (20 mL) was added to the mixture and it was extracted with DCM (20 mL×3). The organic phase was dried over anhydrous sodium sulfate, filtered and concentrated before purification by silica gel chromatography (1/2 petroleum ether/EtOAc) to afford the title compound. MS: 507, 509 (M+1).

Step 3: 2-Amino-6-(4-(3-cyanophenoxy)piperidin-1-yl)-5-methyl-N-(pyridin-4-ylmethyl)nicotinamide To a solution of 2-amino-5-bromo-6-(4-(3-cyanophenoxy)piperidin-1-yl)-N-(pyridin-4-ylmethyl)nicotinamide in DMF (3 mL) was added tetramethyltin (1 mL) and Pd(PPh$_3$)$_4$ (5 mg) under an inert nitrogen atmosphere at RT. The reaction was stirred at 140° C. funder microwave irradiation for 30 min. The reaction was filtered and directly purified by reverse phase HPLC (ACN/water with 0.1% TFA modifier) to afford the title compound. MS: 443 (M+1). $^1$H NMR (400 MHz, methanol-d$_4$): δ 8.72 (2H, d, J=6.4 Hz), 8.05 (1H, s), 7.92 (2H, d, J=6.4 Hz), 7.47 (1H, m), 7.30-7.36 (3H, m), 4.75 (3H, s), 3.64-3.69 (2H, m), 3.40-3.43 (2H, m), 2.27 (3H, s), 2.14-2.19 (2H, m), 1.96-1.97 (2H, m).

Example 267

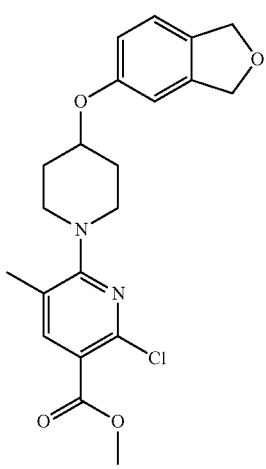 [SMILES: COC(=O)c1cc(C)c(N2CCC(Oc3ccc4c(c3)COC4)CC2)nc1Cl]

Methyl 2-chloro-6-(4-((1,3-dihydroisobenzofuran-5-yl)oxy)piperidin-1-yl)-5-methylnicotinate (Scheme 17)

Step 1: Methyl 6-(4-((1,3-dihydroisobenzofuran-5-yl)oxy)piperidin-1-yl)-2-iodo-5-methylnicotinate To a solution of 4-((1,3-dihydroisobenzofuran-5-yl)oxy) piperidine hydrochloride (20 mg, 78.4 μmop and methyl 6-chloro-2-iodo-5-methylnicotinate (29.2 mg, 93.3 μmop in DMF (3 mL) was added DIPEA (50.5 mg, 391 μmop. The reaction was stirred for 15 h at 80° C. and after cooling to RT water (5 mL) was added and EtOAc (3 mL×3) was used to extract the crude material. The organic phases were separated and dried over anhydrous sodium sulfate, filtered and concentrated to dryness. The residue was purified by silica gel chromatography (5/1 petroleum ether/EtOAc) to afford the title compound. MS: 495 (M+1).

Step 2: Methyl 2-chloro-6-(4-((1,3-dihydroisobenzofuran-5-yl)oxy)piperidin-1-yl)-5-methylnicotinate To a solution of methyl 6-(4-((1,3-dihydroisobenzofuran-5-yl)oxy)piperidin-1-yl)-2-iodo-5-methylnicotinate (13 mg, 26.3 μmol) and tetraethylammonium chloride (7.19 mg, 52.6 μmol) in EtOH (3 mL) was added copper(I) oxide (376 μL, 2.63 μmop and L-proline (606 μg, 5.26 μmop. The reaction was stirred for 16 h in a sealed tube at 110° C. The reaction was concentrated and the residue was purified by reverse phase HPLC (ACN/water with 0.1% TFA modifier) to afford the title compound. MS: 403 (M+1). $^1$H NMR (400 MHz, methanol-d$_4$): δ 7.94 (1H, s), 7.16 (1H, d, J=8.0 Hz), 6.90 (2H, d, J=9.6 Hz), 5.00 (4H, d, J=8.4 Hz), 4.58-4.60 (1H, m), 3.86 (3H, s), 3.61-3.66 (3H, m), 3.24-3.26 (1H, m), 2.29 (3H, s), 2.02-2.12 (2H, m), 1.72-1.87 (2H, m).

ASSAY PROTOCOL

The utility of the compounds as M4 muscarinic receptor allosteric modulators may be demonstrated by methodology known in the art, including by the assay described herein.

CHO-K1 cells stably transfected with human M4 receptor and chimeric G-protein Gαqi5 are thawed from liquid N$_2$ storage, resuspended in growth medium, plated in black, clear bottom 384 well plates, and incubated 16-20 hours at 37° C., 5% CO$_2$.

On the day of assay, growth medium is removed, the cells are washed 2 times with wash buffer, and cells are incubated in dye loading buffer at 37° C., 5% CO$_2$ for ~1 h. Following dye loading the cell plates are placed in a FLIPR Tetra instrument and while monitoring dye fluorescence (excitation 470-495 nM/emission 515-575 nM), 10 uL of test substance at increasing concentrations is added, and fluorescence values are recorded for 4 min. Next, 10 uL of acetylcholine is added (final concentration calculated so as to achieve 20% of the maximum acetycholine response), and the fluorescence reading is continued for 3.5 min. In some cases, a third addition of acetylcholine (final concentration calculated to achieve 70% of the maximal acetylcholine response) is performed.

The following table shows representative data for the compounds of the Examples as modulators of the M4 muscarinic acetylcholine receptor as determined by the assays described herein. Such results are indicative of the intrinsic activity of the compounds for use as allosteric modulators of the M4 muscarinic acetylcholine receptor.

TABLE 18

| Example | M4 PAM IP (nM) |
|---|---|
| 1 | 191 |
| 2 | 427 |
| 3 | 452 |
| 4 | 533 |
| 5 | 766 |
| 6 | 976 |
| 7 | 1245 |
| 8 | 1365 |
| 9 | 2490 |
| 10 | 82 |
| 11 | 1131 |
| 12 | 292 |
| 13 | 110 |
| 14 | 609 |
| 15 | 745 |
| 16 | 1830 |
| 17 | 2671 |
| 18 | 1890 |
| 19 | 2921 |
| 20 | 3058 |
| 21 | 57 |
| 22 | 74 |
| 23 | 75 |
| 24 | 77 |
| 25 | 78 |
| 26 | 85 |
| 27 | 112 |
| 28 | 119 |
| 29 | 126 |
| 30 | 140 |
| 31 | 157 |
| 32 | 185 |
| 33 | 210 |
| 34 | 217 |
| 35 | 220 |
| 36 | 222 |
| 37 | 225 |
| 38 | 252 |
| 39 | 278 |
| 40 | 290 |
| 41 | 322 |
| 42 | 325 |
| 43 | 378 |
| 44 | 446 |
| 45 | 493 |
| 46 | 939 |
| 47 | 25 |
| 48 | 44 |
| 49 | 44 |
| 50 | 49 |
| 51 | 51 |
| 52 | 53 |
| 53 | 53 |
| 54 | 55 |
| 55 | 59 |
| 56 | 60 |
| 57 | 61 |
| 58 | 64 |
| 59 | 66 |
| 60 | 67 |
| 61 | 84 |
| 62 | 94 |
| 63 | 99 |
| 64 | 99 |
| 65 | 100 |
| 66 | 106 |
| 67 | 108 |
| 68 | 126 |
| 69 | 126 |
| 70 | 129 |
| 71 | 135 |
| 72 | 140 |
| 73 | 141 |
| 74 | 155 |
| 75 | 156 |
| 76 | 172 |
| 77 | 177 |
| 78 | 187 |
| 79 | 235 |
| 80 | 257 |
| 81 | 293 |
| 82 | 385 |
| 83 | 475 |
| 84 | 574 |
| 85 | 1154 |
| 86 | 1174 |
| 87 | 1498 |
| 88 | 1534 |
| 89 | 1612 |
| 90 | 20 |
| 91 | 27 |
| 92 | 29 |
| 93 | 33 |
| 94 | 34 |
| 95 | 803 |
| 95A | 4938 |
| 95B | 435 |
| 95C | 846 |
| 95D | 928 |
| 96 | 37 |
| 97 | 68 |
| 98 | 184 |
| 99 | 319 |
| 100 | 674 |
| 101 | 129 |
| 102 | 378 |
| 103 | 61 |
| 104 | 91 |
| 105 | 58 |
| 105A | 170 |
| 106 | 33 |
| 106A | 85 |
| 107A | 182 |
| 107B | 107 |
| 108 | 18 |
| 109 | 34 |
| 110 | 35 |
| 111 | 40 |
| 112 | 41 |
| 113 | 44 |
| 114 | 53 |
| 115 | 61 |
| 116 | 79 |
| 117 | 85 |
| 118 | 86 |
| 119 | 95 |
| 120 | 96 |
| 121 | 99 |
| 122 | 101 |
| 123 | 101 |
| 124 | 101 |
| 125 | 102 |
| 126A | 110 |
| 126B | 159 |
| 127 | 114 |
| 128 | 121 |
| 129 | 121 |
| 130A | 125 |
| 130B | 254 |
| 131 | 127 |
| 132 | 139 |
| 133 | 142 |
| 134 | 151 |
| 135 | 158 |
| 136 | 173 |
| 137 | 175 |
| 138A | 177 |
| 138B | 243 |
| 139 | 177 |
| 140 | 179 |
| 141A | 57 |
| 141B | 173 |
| 142 | 185 |
| 143 | 193 |
| 144 | 193 |
| 145 | 194 |

TABLE 18-continued

| Example | M4 PAM IP (nM) |
|---|---|
| 146 | 208 |
| 147 | 209 |
| 148 | 221 |
| 149 | 228 |
| 150 | 233 |
| 151 | 241 |
| 152 | 259 |
| 153 | 261 |
| 154 | 262 |
| 155 | 265 |
| 156 | 272 |
| 157 | 277 |
| 158 | 282 |
| 159 | 293 |
| 160 | 295 |
| 161 | 302 |
| 162 | 306 |
| 163 | 325 |
| 164A | 434 |
| 164B | 338 |
| 165A | 344 |
| 165B | 527 |
| 166 | 400 |
| 167 | 417 |
| 168 | 446 |
| 169 | 459 |
| 170 | 465 |
| 171 | 471 |
| 172 | 508 |
| 173 | 552 |
| 174 | 563 |
| 175 | 573 |
| 176 | 629 |
| 177 | 693 |
| 178 | 724 |
| 179 | 793 |
| 180 | 808 |
| 181 | 871 |
| 182 | 893 |
| 183 | 915 |
| 184A | 427 |
| 184B | 1006 |
| 185 | 1036 |
| 186 | 1251 |
| 187 | 1334 |
| 188 | 1514 |
| 189 | 1867 |
| 190 | 1999 |
| 191 | 2958 |
| 192 | 22 |
| 193 | 35 |
| 194 | 51 |
| 195 | 57 |
| 196 | 74 |
| 197 | 91 |
| 199 | 118 |
| 200 | 218 |
| 201 | 272 |
| 202 | 473 |
| 203 | 504 |
| 204 | 1152 |
| 204A | 99 |
| 205 | 97 |
| 206 | 168 |
| 207 | 224 |
| 208 | 491 |
| 209 | 533 |
| 210 | 592 |
| 211 | 635 |
| 212 | 705 |
| 213 | 729 |
| 214 | 770 |
| 215 | 835 |
| 216 | 997 |
| 217 | 1019 |
| 218 | 1055 |
| 219 | 1093 |
| 220 | 1428 |

TABLE 18-continued

| Example | M4 PAM IP (nM) |
|---|---|
| 221 | 1827 |
| 222 | 141 |
| 223 | 3410 |
| 224 | 4846 |
| 225 | 321 |
| 225A | 62 |
| 226 | 231 |
| 227 | 55 |
| 228 | 156 |
| 229 | 807 |
| 230 | 1044 |
| 231 | 1092 |
| 232 | 1491 |
| 233 | 2095 |
| 234 | 134 |
| 235 | 248 |
| 236 | 228 |
| 237 | 1821 |
| 238 | 3062 |
| 239 | 3200 |
| 240 | 413 |
| 241 | 42 |
| 242 | 143 |
| 243 | 342 |
| 244 | 461 |
| 245 | 484 |
| 246 | 633 |
| 247 | 1133 |
| 248 | 1554 |
| 249 | 925 |
| 250 | 1132 |
| 251 | 1443 |
| 252 | 1712 |
| 253 | 1738 |
| 254 | 2468 |
| 255 | 2523 |
| 256 | 2628 |
| 257 | 2702 |
| 258 | 73 |
| 259 | 62 |
| 260 | 2561 |
| 261 | 425 |
| 262 | 824 |
| 263 | 251 |
| 264 | 399 |
| 265 | 585 |
| 266 | 4289 |
| 267 | 2572 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:
1. A compound of the formula I:

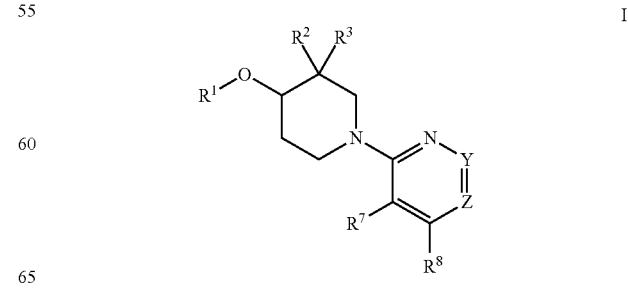

or a pharmaceutically acceptable salt thereof;

wherein:
the group:

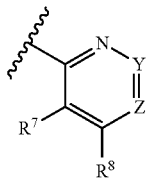

is selected from the group consisting of:

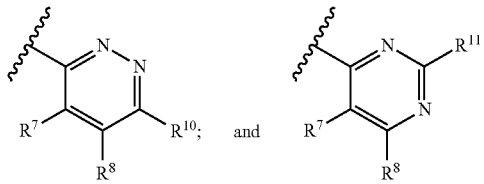

$R^1$ is selected from the group consisting of: benzodioxolyl, benzoimidazolyl, benzoxazoly, benzooxazinone, benzooxazolone, benzothiazolyl, chromanyl, cyclopentapyridinyl, dihydrobenzo[1,4]dioxinyl, dihydrobenzofuranyl, dihydrobenzo[1,4]oxazinyl, dihydrofuropyridinyl, dihydroisobenzofuranyl, dihydroisoquinolinone, dihydropyranopyridinyl, dihydroimidazopyridine, dihydropyrido[1,4]oxazinyl, dihydroquinolinone, indazolyl, indanyl, indolyl, isochromanone, isobenzofuranone, isochromanyl, isoindolinyl, isoxazolyl, oxoisoindolinyl, phenyl, pyrazolopyridinyl, pyrazolyl, pyridyl, pyrrolopyridinyl, pyrimidinyl, quinolinone, quinolinyl, tetrahydrofuranyl, tetrahydroisoquinolinyl, tetrahydroquinolinyl, and tetrahydropyranyl, which is substituted with one or more $R^{1a}$, $R^{1b}$ and $R^{1c}$, wherein $R^{1a}$, $R^{1b}$ and $R^{1c}$ are independently selected from the group consisting of:
(a) hydrogen,
(b) halogen,
(c) $C_{1-6}$alkyl, which is unsubstituted or substituted with substituents selected from the group consisting of: hydroxyl, fluoro and —$NH_2$,
(d) —O—$C_{1-6}$alkyl, which is unsubstituted or substituted with substituents selected from the group consisting of: fluoro and —$NH_2$,
(e) $C_{3-6}$cycloalkyl,
(f) —$SO_2$—$C_{1-6}$alkyl, and
(g) —CN;
$R^2$ and $R^3$ are independently selected from the group consisting of:
(1) hydrogen, and
(2) fluoro;
$R^7$ is selected from the group consisting of:
(1) halogen,
(2) $C_{1-6}$alkyl, which is unsubstituted or substituted with hydroxy, methoxy, fluoro or —(C=O)O—$C_{1-6}$alkyl,
(3) —CN, and
(4) —(C=O)O—$C_{1-6}$alkyl;
$R^8$ is selected from the group consisting of:
(1) methyl,
(2) ethyl,
(3) -fluoro, and
(4) -chloro;

each of $R^{10}$ and $R^{11}$ is independently selected from the group consisting of:
(1) hydrogen,
(2) halogen,
(3) hydroxy,
(4) —$C_{1-6}$alkyl, which is unsubstituted or substituted with substituents selected from the group consisting of: hydroxy, methoxy, or fluoro,
(5) —$C_{2-4}$alkenyl,
(6) —O—$C_{1-6}$alkyl, which is unsubstituted or substituted with substituents selected from the group consisting of: methoxy or fluoro,
(7) —$C_{3-6}$cycloalkyl, which is unsubstituted or substituted with fluoro,
(8) —(C=O)O—$C_{1-6}$alkyl,
(9) —(C=O)$NH_2$,
(10) —(C=O)—NH—$C_{3-6}$cycloalkyl, which is unsubstituted or substituted with phenyl, pyridinyl, fluoro, chloro, —$C_{1-6}$alkyl or —O—$C_{1-6}$alkyl,
(11) —(C=O)—NH—$C_{1-6}$alkyl, which is unsubstituted or substituted with benzodioxolyl, benzofuranyl, bicyclopentyl, imidazolyl, imidazolopyridinyl, indenyl, isothiazolyl, oxoisoindolinyl, oxopyrrolidinyl, phenyl, pyrrolidinonyl, pyrazolyl, pyridyl, pyridinyl, pyridazinyl, pyrimidinyl, tetrahydroquinolinyl, tetrahydroisoquinolinyl, thiadiazolyl, thiazolyl, triazolyl, which is unsubstituted or substituted with fluoro, chloro, —$C_{1-6}$alkyl, —$CF_3$, —CN, —($SO_2$)—$C_{1-6}$alkyl, —O—$C_{1-6}$alkyl, phenyl, or pyridyl;
(12) —(C=O)—NH-heteroaryl or —(C=O)—NH-heterocyclyl, wherein the heteroaryl or heterocyclyl is selected from the group consisting of benzodioxolyl, benzofuranyl, bicyclopentyl, imidazolyl, imidazolopyridinyl, indenyl, isothiazolyl, oxoisoindolinyl, oxopyrrolidinyl, pyrrolidinonyl, pyrazolyl, pyridyl, pyridinyl, pyridazinyl, pyrimidinyl, tetrahydroquinolinyl, tetrahydroisoquinolinyl, thiadiazolyl, thiazolyl, triazolyl, which is unsubstituted or substituted with fluoro, chloro, —$C_{1-6}$alkyl, —$CF_3$, —CN, —($SO_2$)—$C_{1-6}$alkyl, —O—$C_{1-6}$alkyl, phenyl, or pyridyl;
(13) —(C=O)—NH—O—$C_{1-6}$alkyl,
(14) —(C=O)—NH—NH—$C_{1-6}$alkyl,
(15) pyridyl,
(16) oxadiazolyl,
(17) —$NH_2$,
(18) —NH—$C_{1-6}$alkyl or —N($C_{1-6}$alkyl)$_2$, which is unsubstituted or substituted with fluoro, hydroxyl, phenyl, or pyridyl,
(19) —CN,
(20) —S—$C_{1-6}$alkyl, and
(21) —($SO_2$)—$C_{1-6}$alkyl.

2. The compound of claim 1, or a pharmaceutically acceptable salt thereof, wherein $R^1$ is phenyl, which is unsubstituted or substituted with —CN.

3. The compound of claim 1, or a pharmaceutically acceptable salt thereof, wherein $R^1$ is pyridyl, which is unsubstituted or substituted with —$OCH_3$.

4. The compound of claim 1, or a pharmaceutically acceptable salt thereof, wherein $R^2$ is hydrogen and $R^3$ is hydrogen.

5. The compound of claim 1, or a pharmaceutically acceptable salt thereof, wherein $R^7$ is selected from the group consisting of:
(1) methyl,
(2) ethyl,
(3) —$CHF_2$, (4) -fluoro,
(5) -chloro,
(6) -bromo,
(7) —CN,
(8) —(C=O)O-methyl, and
(9) —CH$_2$(C=O)O-methyl.

6. The compound of claim 1, or a pharmaceutically acceptable salt thereof, wherein each of R$^{10}$ and R$^{11}$ is independently selected from the group consisting of:
(1) hydrogen,
(2) fluoro,
(3) chloro,
(4) hydroxy,
(5) —CH$_3$,
(6) —CF$_3$,
(7) —CH$_2$OH,
(8) —CH$_2$CH$_2$OH,
(9) —C(CH$_3$)$_2$OH,
(10) —S—CH$_3$,
(11) —CH$_2$OCH$_3$,
(12) cyclopropyl,
(13) —(C=O)O—CH$_3$,
(14) —(C=O)O—CH$_2$CH$_3$,
(15) —(C=O)—NH-tetrahydroquinolinyl,
(16) —(C=O)—NH—CH$_2$-pyridyl, and
(17) —(C=O)—NH—CH$_2$-tetrahydroquinolinyl.

7. The compound of claim 1, or a pharmaceutically acceptable salt thereof, wherein each of R$^{10}$ and R$^{11}$ is independently selected from the group consisting of:
(1) hydrogen, and
(2) —C$_{1-6}$alkyl, which is unsubstituted or substituted with hydroxy, methoxy, 1-3 fluoro.

8. A compound which is selected from the group consisting of:
4-chloro-6-(4-((6-methoxypyridin-3-yl)oxy)piperidin-1-yl)-2,5-dimethylpyrimidine;
(4-chloro-6-(4-(3-chloro-4-methylphenoxy)piperidin-1-yl)-5-methylpyrimidin-2-yl)methanol;
3-(4-(3-cyanophenoxy)piperidin-1-yl)-5,6-dimethylpyridazine-4-carbonitrile;
4-chloro-2,5-dimethyl-6-(4-(pyridin-3-yloxy)piperidin-1-yl)pyrimidine;
4-chloro-6-((cis)-3-fluoro-4-(4-methoxyphenoxy)piperidin-1-yl)-5-methylpyrimidine;
4-chloro-5-methyl-6-(4-(pyridin-3-yloxy)piperidin-1-yl)pyrimidine;
4-chloro-5-methyl-2-(methylthio)-6-(4-(pyridin-3-yloxy)piperidin-1-yl)pyrimidine;
4-chloro-6-(4-(4-methoxyphenoxy)piperidin-1-yl)-5-methyl-2-(methylthio)pyrimidine;
methyl 2-(4-chloro-6-(4-(4-methoxyphenoxy)piperidin-1-yl)pyrimidin-5-yl)acetate;
3-((1-(6-chloro-2-(hydroxymethyl)-5-methylpyrimidin-4-yl)-3,3-difluoropiperidin-4-yl)oxy)benzonitrile;
(4-chloro-6-(4-(4-methoxyphenoxy)piperidin-1-yl)-5-methylpyrimidin-2-yl)methanol;
5-((1-(6-chloro-2-(hydroxymethyl)-5-methylpyrimidin-4-yl)piperidin-4-yl)oxy)-2-methoxybenzonitrile;
4-chloro-6-(4-((6-methoxypyridin-3-yl)oxy)piperidin-1-yl)-5-methylpyrimidine;
3-((1-(6-chloro-5-methylpyrimidin-4-yl)piperidin-4-yl)oxy)benzonitrile;
3-((1-(6-chloro-2-(hydroxymethyl)-5-methylpyrimidin-4-yl)piperidin-4-yl)oxy)benzonitrile;
(4-chloro-6-(4-((5-fluoro-6-methoxypyridin-3-yl)oxy)piperidin-1-yl)-5-methylpyrimidin-2-yl)methanol;
3-((1-(6-chloro-2,5-dimethylpyrimidin-4-yl)piperidin-4-yl)oxy)benzonitrile;
4-chloro-6-(4-(4-methoxyphenoxy)piperidin-1-yl)-5-methylpyrimidine;
4-chloro-2-(methoxymethyl)-6-(4-(4-methoxyphenoxy)piperidin-1-yl)-5-methylpyrimidine;
4-chloro-6-(4-(4-methoxyphenoxy)piperidin-1-yl)-2,5-dimethylpyrimidine;
(4-chloro-6-(4-((5-chloro-6-methoxypyridin-3-yl)oxy)piperidin-1-yl)-5-methylpyrimidin-2-yl)methanol;
(4-chloro-6-(4-((6-methoxypyridin-3-yl)oxy)piperidin-1-yl)-5-methylpyrimidin-2-yl)methanol;
4-chloro-6-(4-(4-methoxyphenoxy)piperidin-1-yl)-5-methyl-2-(methyl sulfonyl)pyrimidine;
2,4-dichloro-6-(4-(4-methoxyphenoxy)piperidin-1-yl)-5-methylpyrimidine;
4-chloro-2-(methoxymethyl)-6-(4-((6-methoxypyridin-3-yl)oxy)piperidin-1-yl)-5-methylpyrimidine;
4-chloro-6-(4-((6-methoxypyridin-3-yl)oxy)piperidin-1-yl)-5-methyl-2-(methylthio)pyrimidine;
3-(4-((6-methoxypyridin-3-yl)oxy)piperidin-1-yl)-5,6-dimethylpyridazine-4-carbonitrile;
6-(4-((6-methoxypyridin-3-yl)oxy)piperidin-1-yl)-2,5-dimethylpyrimidin-4-amine;
6-(4-((6-methoxypyridin-3-yl)oxy)piperidin-1-yl)-5-methylpyrimidin-4-amine;
4-chloro-2-cyclopropyl-5-methyl-6-(4-(pyridin-3-yloxy)piperidin-1-yl)pyrimidine;
4-chloro-2-cyclopropyl-6-(4-(4-methoxyphenoxy)piperidin-1-yl)-5-methylpyrimidine;
3-((1-(2,5,6-Trimethylpyrimidin-4-yl)piperidin-4-yl)oxy)benzonitrile;
4-(4-((6-methoxypyridin-3-yl)oxy)piperidin-1-yl)-2,5,6-trimethylpyrimidine;
4-chloro-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(pyridin-4-ylmethyl)pyrimidine-2-carboxamide;
4-chloro-6-(4-((6-methoxypyridin-3-yl)oxy)piperidin-1-yl)-5-methyl-N-(2-(pyridin-4-yl)ethyl)pyrimidine-2-carboxamide;
4-chloro-N'-isopropyl-6-(4-((6-methoxypyridin-3-yl)oxy)piperidin-1-yl)-5-methylpyrimidine-2-carbohydrazide;
N-(bicyclo[1.1.1]pentan-1-yl)-4-chloro-6-(4-((6-methoxypyridin-3-yl)oxy)piperidin-1-yl)-5-methylpyrimidine-2-carboxamide;
4-chloro-N-((3-chloropyridin-4-yl)methyl)-6-(4-((6-methoxypyridin-3-yl)oxy)piperidin-1-yl)-5-methylpyrimidine-2-carboxamide;
N-(tert-butyl)-4-chloro-6-(4-((6-methoxypyridin-3-yl)oxy)piperidin-1-yl)-5-methylpyrimidine-2-carboxamide;
4-chloro-N-isopropyl-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(5,6,7,8-tetrahydroisoquinolin-5-yl)pyrimidine-2-carboxamide;
N-(azetidin-3-yl)-4-chloro-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(5,6,7,8-tetrahydroisoquinolin-7-yl)pyrimidine-2-carboxamide;

4-chloro-6-(4-((6-methoxypyridin-3-yl)oxy)piperidin-1-yl)-5-methyl-N-(5,6,7,8-tetrahydroquinolin-7-yl)pyrimidine-2-carboxamide;
4-chloro-6-(4-((6-methoxypyridin-3-yl)oxy)piperidin-1-yl)-5-methyl-N-(5,6,7,8-tetrahydroquinolin-6-yl)pyrimidine-2-carboxamide;
4-chloro-N-(2-chlorobenzyl)-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(2-(pyridin-4-yl)propan-2-yl)pyrimidine-2-carboxamide;
4-chloro-6-(4-((6-methoxypyridin-3-yl)oxy)piperidin-1-yl)-5-methyl-N-(1,2,3,4-tetrahydronaphthalen-2-yl)pyrimidine-2-carboxamide;
4-chloro-6-((3 S,4R)-3-fluoro-4-((6-methoxypyri din-3-yl)oxy)piperidin-1-yl)-5-methylpyrimidine-2-carboxamide;
(R)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide;
(S)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide;
4-chloro-N-(isothiazol-4-ylmethyl)-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-2-(methylsulfonyl)pyrimidine;
4-chloro-2-methoxy-6-(4-((6-methoxypyridin-3-yl)oxy)piperidin-1-yl)-5-methylpyrimidine;
2-((4-chloro-6-(4-((6-methoxypyridin-3-yl)oxy)piperidin-1-yl)-5-methylpyrimidin-2-yl)amino)ethan-1-ol;
4-chloro-6-(4-((6-methoxypyridin-3-yl)oxy)piperidin-1-yl)-5-methylpyrimidin-2-ol;
(4-(4-((6-methoxypyridin-3-yl)oxy)piperidin-1-yl)-5,6-dimethylpyrimidin-2-yl)methanol;
4-(4-((6-methoxypyridin-3-yl)oxy)piperidin-1-yl)-5,6-dimethylpyrimidine;
3-((1-(6-ethyl-5-methylpyrimidin-4-yl)piperidin-4-yl)oxy)benzonitrile; and
4-ethyl-6-(4-((6-methoxypyridin-3-yl)oxy)piperidin-1-yl)-5-methylpyrimidine;
or a pharmaceutically acceptable salt thereof.

9. A pharmaceutical composition which comprises an inert carrier and a compound of claim 1 or a pharmaceutically acceptable salt thereof.

10. A method for the treatment of a neurological and/or psychiatric disorder associated with muscarinic acetylcholine receptor dysfunction in a mammal comprising the step of administering at least one compound of claim 1, or a pharmaceutically acceptable salt of said compound, to a patient in need thereof in an amount effective to treat said disorder.

11. The method of claim 10, wherein the mammal has been diagnosed with a need for treatment of the disorder prior to the administering step.

12. The method of claim 10, wherein the disorder is a neurological and/or psychiatric disorder associated with mAChR M4 dysfunction.

13. The method of claim 10, wherein the disorder is a psychotic disorder.

14. The method of claim 13, wherein the psychotic disorder is selected from schizophrenia, brief psychotic disorder, schizophreniform disorder, schizoaffective disorder, delusional disorder, shared psychotic disorder, catastrophic schizophrenia, postpartum psychosis, psychotic depression, psychotic break, tardive psychosis, myxedematous psychosis, occupational psychosis, menstrual psychosis, secondary psychotic disorder, bipolar I disorder with psychotic features, and substance-induced psychotic disorder.

15. The compound of claim 1, wherein $R^1$ is selected from the group consisting of phenyl and pyridyl, which is substituted with one or more $R^{1a}$, $R^{1b}$ and $R^{1c}$.

16. The compound of claim 15, which is selected from the group consisting of:
4-chloro-6-(4-((6-methoxypyridin-3-yl)oxy)piperidin-1-yl)-2,5-dimethylpyrimidine;
(4-chloro-6-(4-(3-chloro-4-methylphenoxy)piperidin-1-yl)-5-methylpyrimidin-2-yl)methanol;
3-(4-(3-cyanophenoxy)piperidin-1-yl)-5,6-dimethylpyridazine-4-carbonitrile;
4-chloro-2,5-dimethyl-6-(4-(pyridin-3-yloxy)piperidin-1-yl)pyrimidine;
4-chloro-6-((cis)-3-fluoro-4-(4-methoxyphenoxy)piperidin-1-yl)-5-methylpyrimidine;
4-chloro-5-methyl-6-(4-(pyridin-3-yloxy)piperidin-1-yl)pyrimidine;
4-chloro-5-methyl-2-(methylthio)-6-(4-(pyridin-3-yloxy)piperidin-1-yl)pyrimidine;
4-chloro-6-(4-(4-methoxyphenoxy)piperidin-1-yl)-5-methyl-2-(methylthio)pyrimidine;
methyl 2-(4-chloro-6-(4-(4-methoxyphenoxy)piperidin-1-yl)pyrimidin-5-yl)acetate;
3-((1-(6-chloro-2-(hydroxymethyl)-5-methylpyrimidin-4-yl)-3,3-difluoropiperidin-4-yl)oxy)benzonitrile;
(4-chloro-5-methyl-6-(4-(3-(methylsulfonyl)phenoxy)piperidin-1-yl)pyrimidin-2-yl)methanol;
(4-chloro-6-(4-(4-methoxyphenoxy)piperidin-1-yl)-5-methylpyrimidin-2-yl)methanol;
5-((1-(6-chloro-2-(hydroxymethyl)-5-methylpyrimidin-4-yl)piperidin-4-yl)oxy)-2-methoxybenzonitrile;
4-chloro-6-(4-((6-methoxypyridin-3-yl)oxy)piperidin-1-yl)-5-methylpyrimidine;
3-((1-(6-chloro-5-methylpyrimidin-4-yl)piperidin-4-yl)oxy)benzonitrile;
3-((1-(6-chloro-2-(hydroxymethyl)-5-methylpyrimidin-4-yl)piperidin-4-yl)oxy)benzonitrile;
(4-chloro-6-(4-((5-fluoro-6-methoxypyridin-3-yl)oxy)piperidin-1-yl)-5-methylpyrimidin-2-yl)methanol;
3-((1-(6-chloro-2,5-dimethylpyrimidin-4-yl)piperidin-4-yl)oxy)benzonitrile;
4-chloro-6-(4-(4-methoxyphenoxy)piperidin-1-yl)-5-methylpyrimidine;
4-chloro-2-(methoxymethyl)-6-(4-(4-methoxyphenoxy)piperidin-1-yl)-5-methylpyrimidine;
4-chloro-6-(4-(4-methoxyphenoxy)piperidin-1-yl)-2,5-dimethylpyrimidine;
(4-chloro-6-(4-((5-chloro-6-methoxypyridin-3-yl)oxy)piperidin-1-yl)-5-methylpyrimidin-2-yl)methanol;
(4-chloro-6-(4-((6-methoxypyridin-3-yl)oxy)piperidin-1-yl)-5-methylpyrimidin-2-yl)methanol;
4-chloro-6-(4-(4-methoxyphenoxy)piperidin-1-yl)-5-methyl-2-(methylsulfonyl)pyrimidine;
2,4-dichloro-6-(4-(4-methoxyphenoxy)piperidin-1-yl)-5-methylpyrimidine;
4-chloro-2-(methoxymethyl)-6-(4-((6-methoxypyridin-3-yl)oxy)piperidin-1-yl)-5-methylpyrimidine;
4-chloro-6-(4-((6-methoxypyridin-3-yl)oxy)piperidin-1-yl)-5-methyl-2-(methylthio)pyrimidine;
3-(4-((6-methoxypyridin-3-yl)oxy)piperidin-1-yl)-5,6-dimethylpyridazine-4-carbonitrile;

6-(4-(((6-methoxypyridin-3-yl)oxy)piperidin-1-yl)-2,5-dimethylpyrimidin-4-amine;
6-(4-(((6-methoxypyridin-3-yl)oxy)piperidin-1-yl)-5-methylpyrimidin-4-amine;
4-chloro-2-cyclopropyl-5-methyl-6-(4-(pyridin-3-yloxy)piperidin-1-yl)pyrimidine;
4-chloro-2-cyclopropyl-6-(4-(4-methoxyphenoxy)piperidin-1-yl)-5-methylpyrimidine;
3-((1-(2,5,6-Trimethylpyrimidin-4-yl)piperidin-4-yl)oxy)benzonitrile;
4-(4-(((6-methoxypyridin-3-yl)oxy)piperidin-1-yl)-2,5,6-trimethylpyrimidine;
4-chloro-6-(4-(((6-methoxypyridin-3-yl)oxy)piperidin-1-yl)-5-methylpyrimidine-2-carboxamide;
4-chloro-6-(4-(((6-methoxypyridin-3-yl)oxy)piperidin-1-yl)-5-methyl-N-(pyridin-4-ylmethyl)pyrimidine-2-carboxamide;
4-chloro-6-(4-(((6-methoxypyridin-3-yl)oxy)piperidin-1-yl)-5-methyl-N-(2-(pyridin-4-yl)ethyl)pyrimidine-2-carboxamide;
4-chloro-N'-isopropyl-6-(4-(((6-methoxypyridin-3-yl)oxy)piperidin-1-yl)-5-methylpyrimidine-2-carbohydrazide;
N-(bicyclo[1.1.1]pentan-1-yl)-4-chloro-6-(4-(6-methoxypyridin-3-yl)oxy)piperidin-1-yl)-5-methylpyrimidine-2-carb oxamide;
4-chloro-N-((3-chloropyridin-4-yl)methyl)-6-(4-(((6-methoxypyridin-3-yl)oxy)piperidin-1-yl)-5-methylpyrimidine-2-carboxamide;
N-(tert-butyl)-4-chloro-6-(4-(((6-methoxypyridin-3-yl)oxy)piperidin-1-yl)-5-methylpyrimidine-2-carboxamide;
4-chloro-N-isopropyl-6-(4-(((6-methoxypyridin-3-yl)oxy)piperidin-1-yl)-5-methylpyrimidine-2-carboxamide;
4-chloro-6-(4-(((6-methoxypyridin-3-yl)oxy)piperidin-1-yl)-5-methyl-N-(5,6,7,8-tetrahydroisoquinolin-5-yl)pyrimidine-2-carboxamide;
N-(azetidin-3-yl)-4-chloro-6-(4-(((6-methoxypyridin-3-yl)oxy)piperidin-1-yl)-5-methylpyrimidine-2-carb oxamide;
4-chloro-6-(4-(((6-methoxypyridin-3-yl)oxy)piperidin-1-yl)-5-methyl-N-(5,6,7,8-tetrahydroisoquinolin-7-yl)pyrimidine-2-carboxamide;
4-chloro-6-(4-(((6-methoxypyridin-3-yl)oxy)piperidin-1-yl)-5-methyl-N-(5,6,7,8-tetrahydroquinolin-7-yl)pyrimidine-2-carboxamide;
4-chloro-6-(4-(((6-methoxypyridin-3-yl)oxy)piperidin-1-yl)-5-methyl-N-(5,6,7,8-tetrahydroquinolin-6-yl)pyrimidine-2-carboxamide;
4-chloro-N-(2-chlorobenzyl)-6-(4-(((6-methoxypyridin-3-yl)oxy)piperidin-1-yl)-5-methylpyrimidine-2-carb oxamide;
4-chloro-6-(4-(((6-methoxypyridin-3-yl)oxy)piperidin-1-yl)-5-methyl-N-(2-(pyridin-4-yl)propan-2-yl)pyrimidine-2-carboxamide;
4-chloro-6-(4-(((6-methoxypyridin-3-yl)oxy)piperidin-1-yl)-5-methyl-N-(1,2,3,4-tetrahydronaphthalen-2-yl)pyrimidine-2-carboxamide;
4-chloro-6-((3 S,4R)-3-fluoro-4-((6-methoxypyri din-3-yl)oxy)piperidin-1-yl)-5-methylpyrimidine-2-carb oxamide;
(R)-4-chloro-6-(4-(((6-methoxypyridin-3-yl)oxy)piperidin-1-yl)-5-methyl-N-(1,2,3,4-tetrahydronaphthalen-1-yl)pyrimidine-2-carboxamide;
(S)-4-chloro-6-(4-(((6-methoxypyridin-3-yl)oxy)piperidin-1-yl)-5-methyl-N-(1,2,3,4-tetrahydronaphthalen-1-yl)pyrimidine-2-carboxamide;

4-chloro-N-(isothiazol-4-ylmethyl)-6-(4-(((6-methoxypyridin-3-yl)oxy)piperidin-1-yl)-5-methylpyrimidine-2-carboxamide;
4-chloro-6-(4-(((6-methoxypyridin-3-yl)oxy)piperidin-1-yl)-5-methyl-2-(methylsulfonyl)pyrimidine;
4-chloro-2-methoxy-6-(4-(((6-methoxypyridin-3-yl)oxy)piperidin-1-yl)-5-methylpyrimidine;
2-((4-chloro-6-(4-(((6-methoxypyridin-3-yl)oxy)piperidin-1-yl)-5-methylpyrimidin-2-yl)amino)ethan-1-ol;
4-chloro-6-(4-(((6-methoxypyridin-3-yl)oxy)piperidin-1-yl)-5-methylpyrimidin-2-ol;
(4-(4-(((6-methoxypyridin-3-yl)oxy)piperidin-1-yl)-5,6-dimethylpyrimidin-2-yl)methanol;
4-(4-(((6-methoxypyridin-3-yl)oxy)piperidin-1-yl)-5,6-dimethylpyrimidine;
3-((1-(6-ethyl-5-methylpyrimidin-4-yl)piperidin-4-yl)oxy)benzonitrile;
4-ethyl-6-(4-(((6-methoxypyridin-3-yl)oxy)piperidin-1-yl)-5-methylpyrimidine;
or a pharmaceutically acceptable salt thereof.

17. The compound of claim 2, which is selected from the group consisting of:
3-(4-(3-cyanophenoxy)piperidin-1-yl)-5,6-dimethylpyridazine-4-carbonitrile;
3-((1-(6-chloro-2-(hydroxymethyl)-5-methylpyrimidin-4-yl)-3,3-difluoropiperidin-4-yl)oxy)benzonitrile;
3-((1-(6-chloro-5-methylpyrimidin-4-yl)piperidin-4-yl)oxy)benzonitrile;
3-((1-(6-chloro-2-(hydroxymethyl)-5-methylpyrimidin-4-yl)piperidin-4-yl)oxy)benzonitrile;
3-((1-(6-chloro-2,5-dimethylpyrimidin-4-yl)piperidin-4-yl)oxy)benzonitrile;
3-((1-(2,5,6-trimethylpyrimidin-4-yl)piperidin-4-yl)oxy)benzonitrile;
3-((1-(6-ethyl-5-methylpyrimidin-4-yl)piperidin-4-yl)oxy)benzonitrile; and
4-ethyl-6-(4-(((6-methoxypyridin-3-yl)oxy)piperidin-1-yl)-5-methylpyrimidine;
or a pharmaceutically acceptable salt thereof.

18. The compound of claim 3, which is selected from the group consisting of:
4-chloro-6-(4-(((6-methoxypyridin-3-yl)oxy)piperidin-1-yl)-2,5-dimethylpyrimidine;
4-chloro-2,5-dimethyl-6-(4-(pyridin-3-yloxy)piperidin-1-yl)pyrimidine;
4-chloro-5-methyl-6-(4-(pyridin-3-yloxy)piperidin-1-yl)pyrimidine;
4-chloro-5-methyl-2-(methylthio)-6-(4-(pyridin-3-yloxy)piperidin-1-yl)pyrimidine;
4-chloro-6-(4-(((6-methoxypyridin-3-yl)oxy)piperidin-1-yl)-5-methylpyrimidine;
(4-chloro-6-(4-(((6-methoxypyridin-3-yl)oxy)piperidin-1-yl)-5-methylpyrimidin-2-yl)methanol;
4-chloro-2-(methoxymethyl)-6-(4-(((6-methoxypyridin-3-yl)oxy)piperidin-1-yl)-5-methylpyrimidine;
4-chloro-6-(4-(((6-methoxypyridin-3-yl)oxy)piperidin-1-yl)-5-methyl-2-(methylthio)pyrimidine;
3-(4-((6-methoxypyridin-3-yl)oxy)piperidin-1-yl)-5,6-dimethylpyridazine-4-carbonitrile;
6-(4-(((6-methoxypyridin-3-yl)oxy)piperidin-1-yl)-2,5-dimethylpyrimidin-4-amine;
6-(4-(((6-methoxypyridin-3-yl)oxy)piperidin-1-yl)-5-methylpyrimidin-4-amine;
4-chloro-2-cyclopropyl-5-methyl-6-(4-(pyridin-3-yloxy)piperidin-1-yl)pyrimidine;
4-(4-(((6-methoxypyridin-3-yl)oxy)piperidin-1-yl)-2,5,6-trimethylpyrimidine;

4-chloro-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(pyridin-4-ylmethyl)pyrimidine-2-carboxamide;
4-chloro-6-(4-((6-methoxypyridin-3-yl)oxy)piperidin-1-yl)-5-methyl-N-(2-(pyridin-4-yl)ethyl)pyrimidine-2-carboxamide;
4-chloro-N-isopropyl-6-(4-((6-methoxypyridin-3-yl)oxy)piperidin-1-yl)-5-methylpyrimidine-2-carbohydrazide;
N-(bicyclo[1.1.1]pentan-1-yl)-4-chloro-6-(4-(6-methoxypyridin-3-yl)oxy)piperidin-1-yl)-5-methylpyrimidine-2-carb oxamide;
4-chloro-N-((3-chloropyridin-4-yl)methyl)-6-(4-((6-methoxypyridin-3-yl)oxy)piperidin-1-yl)-5-methylpyrimidine-2-carb oxamide;
N-(tert-butyl)-4-chloro-6-(4-((6-methoxypyridin-3-yl)oxy)piperidin-1-yl)-5-methylpyrimidine-2-carboxamide;
4-chloro-N-isopropyl-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(5,6,7,8-tetrahydroisoquinolin-5-yl)pyrimidine-2-carboxamide;
N-(azetidin-3-yl)-4-chloro-6-(4-((6-methoxypyridin-3-yl)oxy)piperidin-1-yl)-5-methylpyrimidine-2-carb oxamide;
4-chloro-6-(4-((6-methoxypyridin-3-yl)oxy)piperidin-1-yl)-5-methyl-N-(5,6,7,8-tetrahydroisoquinolin-7-yl)pyrimidine-2-carboxamide;
4-chloro-6-(4-((6-methoxypyridin-3-yl)oxy)piperidin-1-yl)-5-methyl-N-(5,6,7,8-tetrahydroquinolin-7-yl)pyrimidine-2-carboxamide;
4-chloro-6-(4-((6-methoxypyridin-3-yl)oxy)piperidin-1-yl)-5-methyl-N-(5,6,7,8-tetrahydroquinolin-6-yl)pyrimidine-2-carboxamide;
4-chloro-N-(2-chlorobenzyl)-6-(4-((6-methoxypyridin-3-yl)oxy)piperidin-1-yl)-5-methylpyrimidine-2-carb oxamide;
4-chloro-6-(4-((6-methoxypyridin-3-yl)oxy)piperidin-1-yl)-5-methyl-N-(2-(pyridin-4-yl)propan-2-yl)pyrimidine-2-carboxamide;
4-chloro-6-(4-((6-methoxypyridin-3-yl)oxy)piperidin-1-yl)-5-methyl-N-(1,2,3,4-tetrahydronaphthalen-2-yl)pyrimidine-2-carboxamide;
4-chloro-6-((3S,4R)-3-fluoro-4-((6-methoxypyridin-3-yl)oxy)piperidin-1-yl)-5-methylpyrimidine-2-carb oxamide;
(R)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide;
(S)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide;
4-chloro-N-(isothiazol-4-ylmethyl)-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-2-(methylsulfonyl)pyrimidine;
4-chloro-2-methoxy-6-(4-((6-methoxypyridin-3-yl)oxy)piperidin-1-yl)-5-methylpyrimidine;
2-((4-chloro-6-(4-((6-methoxypyridin-3-yl)oxy)piperidin-1-yl)-5-methylpyrimidin-2-yl)amino)ethan-1-ol;
4-chloro-6-(4-((6-methoxypyridin-3-yl)oxy)piperidin-1-yl)-5-methylpyrimidin-2-ol;
(4-(4-((6-methoxypyridin-3-yl)oxy)piperidin-1-yl)-5,6-dimethylpyrimidin-2-yl)methanol;
4-(4-((6-methoxypyridin-3-yl)oxy)piperidin-1-yl)-5,6-dimethylpyrimidine; and
4-ethyl-6-(4-((6-methoxypyridin-3-yl)oxy)piperidin-1-yl)-5-methylpyrimidine;
or a pharmaceutically acceptable salt thereof.

19. The compound of claim 1, which is selected from the group consisting of:
4-chloro-6-(4-((6-methoxypyridin-3-yl)oxy)piperidin-1-yl)-2,5-dimethylpyrimidine;
4-chloro-2,5-dimethyl-6-(4-(pyridin-3-yloxy)piperidin-1-yl)pyrimidine;
4-chloro-5-methyl-6-(4-(pyridin-3-yloxy)piperidin-1-yl)pyrimidine;
4-chloro-5-methyl-2-(methylthio)-6-(4-(pyridin-3-yloxy)piperidin-1-yl)pyrimidine;
4-chloro-6-(4-((6-methoxypyridin-3-yl)oxy)piperidin-1-yl)-5-methylpyrimidine;
(4-chloro-6-(4-((5-fluoro-6-methoxypyridin-3-yl)oxy)piperidin-1-yl)-5-methylpyrimidin-2-yl)methanol;
(4-chloro-6-(4-((5-chloro-6-methoxypyridin-3-yl)oxy)piperidin-1-yl)-5-methylpyrimidin-2-yl)methanol
(4-chloro-6-(4-((6-methoxypyridin-3-yl)oxy)piperidin-1-yl)-5-methylpyrimidin-2-yl)methanol;
4-chloro-2-(methoxymethyl)-6-(4-((6-methoxypyridin-3-yl)oxy)piperidin-1-yl)-5-methylpyrimidine;
4-chloro-6-(4-((6-methoxypyridin-3-yl)oxy)piperidin-1-yl)-5-methyl-2-(methylthio)pyrimidine;
3-(4-((6-methoxypyridin-3-yl)oxy)piperidin-1-yl)-5,6-dimethylpyridazine-4-carbonitrile;
6-(4-((6-methoxypyridin-3-yl)oxy)piperidin-1-yl)-2,5-dimethylpyrimidin-4-amine;
6-(4-((6-methoxypyridin-3-yl)oxy)piperidin-1-yl)-5-methylpyrimidin-4-amine;
4-chloro-2-cyclopropyl-5-methyl-6-(4-(pyridin-3-yloxy)piperidin-1-yl)pyrimidine;
4-(4-((6-methoxypyridin-3-yl)oxy)piperidin-1-yl)-2,5,6-trimethylpyrimidine;
4-chloro-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(pyridin-4-ylmethyl)pyrimidine-2-carboxamide;
4-chloro-6-(4-((6-methoxypyridin-3-yl)oxy)piperidin-1-yl)-5-methyl-N-(2-(pyridin-4-yl)ethyl)pyrimidine-2-carboxamide;
4-chloro-N-isopropyl-6-(4-((6-methoxypyridin-3-yl)oxy)piperidin-1-yl)-5-methylpyrimidine-2-carbohydrazide;
N-(bicyclo[1.1.1]pentan-1-yl)-4-chloro-6-(4-(6-methoxypyridin-3-yl)oxy)piperidin-1-yl)-5-methylpyrimidine-2-carb oxamide;
4-chloro-N-((3-chloropyridin-4-yl)methyl)-6-(4-((6-methoxypyridin-3-yl)oxy)piperidin-1-yl)-5-methylpyrimidine-2-carb oxamide;
N-(tert-butyl)-4-chloro-6-(4-((6-methoxypyridin-3-yl)oxy)piperidin-1-yl)-5-methylpyrimidine-2-carboxamide;
4-chloro-N-isopropyl-6-(4-((6-methoxypyridin-3-yl)oxy)piperidin-1-yl)-5-methylpyrimidine-2-carboxamide;
4-chloro-6-(4-((6-methoxypyridin-3-yl)oxy)piperidin-1-yl)-5-methyl-N-(5,6,7,8-tetrahydroisoquinolin-5-yl)pyrimidine-2-carboxamide;
N-(azetidin-3-yl)-4-chloro-6-(4-((6-methoxypyridin-3-yl)oxy)piperidin-1-yl)-5-methylpyrimidine-2-carb oxamide;
4-chloro-6-(4-((6-methoxypyridin-3-yl)oxy)piperidin-1-yl)-5-methyl-N-(5,6,7,8-tetrahydroisoquinolin-7-yl)pyrimidine-2-carboxamide;

4-chloro-6-(4-((6-methoxypyridin-3-yl)oxy)piperidin-1-yl)-5-methyl-N-(5,6,7,8-tetrahydroquinolin-7-yl)pyrimidine-2-carboxamide;

4-chloro-6-(4-((6-methoxypyridin-3-yl)oxy)piperidin-1-yl)-5-methyl-N-(5,6,7,8-tetrahydroquinolin-6-yl)pyrimidine-2-carboxamide;

4-chloro-N-(2-chlorobenzyl)-6-(4-((6-methoxypyridin-3-yl)oxy)piperidin-1-yl)-5-methylpyrimidine-2-carboxamide;

4-chloro-6-(4-((6-methoxypyridin-3-yl)oxy)piperidin-1-yl)-5-methyl-N-(2-(pyridin-4-yl)propan-2-yl)pyrimidine-2-carboxamide;

4-chloro-6-(4-((6-methoxypyridin-3-yl)oxy)piperidin-1-yl)-5-methyl-N-(1,2,3,4-tetrahydronaphthalen-2-yl)pyrimidine-2-carboxamide;

4-chloro-6-((3S,4R)-3-fluoro-4-((6-methoxypyridin-3-yl)oxy)piperidin-1-yl)-5-methylpyrimidine-2-carboxamide;

(R)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide;

(S)-4-chloro-6-(4-((6-methoxypyridin-3-yl)oxy)piperidin-1-yl)-5-methyl-N-(1,2,3,4-tetrahydronaphthalen-1-yl)pyrimidine-2-carboxamide;

4-chloro-N-(isothiazol-4-ylmethyl)-6-(4-((6-methoxypyridin-3-yl)oxy)piperidin-1-yl)-5-methylpyrimidine-2-carboxamide;

4-chloro-6-(4-((6-methoxypyridin-3-yl)oxy)piperidin-1-yl)-5-methyl-2-(methylsulfonyl)pyrimidine;

4-chloro-2-methoxy-6-(4-((6-methoxypyridin-3-yl)oxy)piperidin-1-yl)-5-methylpyrimidine;

2-((4-chloro-6-(4-((6-methoxypyridin-3-yl)oxy)piperidin-1-yl)-5-methylpyrimidin-2-yl)amino)ethan-1-ol;

4-chloro-6-(4-((6-methoxypyridin-3-yl)oxy)piperidin-1-yl)-5-methylpyrimidin-2-ol;

(4-(4-((6-methoxypyridin-3-yl)oxy)piperidin-1-yl)-5,6-dimethylpyrimidin-2-yl)methanol;

4-(4-((6-methoxypyridin-3-yl)oxy)piperidin-1-yl)-5,6-dimethylpyrimidine; and 4-ethyl-6-(4-((6-methoxypyridin-3-yl)oxy)piperidin-1-yl)-5-methylpyrimidine;

or a pharmaceutically acceptable salt thereof.

20. The compound of claim 1, which is:

(4-chloro-6-(4-((5-fluoro-6-methoxypyridin-3-yl)oxy)piperidin-1-yl)-5-methylpyrimidin-2-yl)methanol or a pharmaceutically acceptable salt thereof.

* * * * *